United States Patent [19]
Duggan et al.

[11] Patent Number: 5,854,245
[45] Date of Patent: Dec. 29, 1998

[54] FIBRINOGEN RECEPTOR ANTAGONISTS

[75] Inventors: Mark E. Duggan, Schwenksville; Melissa S. Egbertson, Ambler; George D. Hartman; Steven D. Young, both of Lansdale, all of Pa.; Nathan C. Ihle, Seattle, Wash.

[73] Assignee: Merck & Co., Inc., Rahway, N.J.

[21] Appl. No.: 883,108

[22] Filed: Jun. 26, 1997

Related U.S. Application Data

[60] Provisional application No. 60/020,975 Jun. 28, 1996.

[51] Int. Cl.$^6$ ...................... A61K 31/495; A61K 31/435; C07D 241/38; C07D 241/04
[52] U.S. Cl. ...................... 514/250; 514/252; 514/253; 514/255; 514/291; 514/292; 544/344; 544/360; 544/379; 544/393; 546/85; 546/89
[58] Field of Search ...................... 544/360, 393, 544/344, 379; 514/252, 255, 280, 418, 428, 316, 317, 323, 326, 329, 330, 331, 292, 291, 253; 546/187, 190, 194, 201, 208, 223, 224, 234, 85, 89; 548/571, 486

[56] References Cited

U.S. PATENT DOCUMENTS 5,652,242  7/1997  Wayne ...................... 514/255

FOREIGN PATENT DOCUMENTS

| | | |
|---|---|---|
| 659 743 A1 | 6/1995 | European Pat. Off. . |
| 718 287 A2 | 12/1995 | European Pat. Off. . |
| 4241632 | 6/1994 | Germany . |
| 44 46 301 A1 | 12/1994 | Germany . |
| WO 94 22834 | 10/1994 | WIPO . |

OTHER PUBLICATIONS

Kaljuste K and Unden A. Tetrahedron Lett. 36 (50), 9211–14, 1995.

*Primary Examiner*—Evelyn Huang
*Attorney, Agent, or Firm*—Richard S. Parr; Melvin Winokur

[57] ABSTRACT

Fibrinogen receptor antagonists having the structure

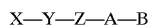

and pharmaceutically acceptable salts, wherein X is a 5, 6 or 7 membered aromatic or nonaromatic ring, and Y is a 5 or 6 membered aromatic ring, e.g.,

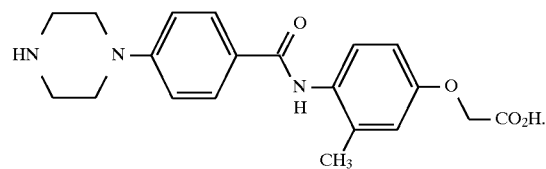

10 Claims, No Drawings

FIBRINOGEN RECEPTOR ANTAGONISTS

This application claims the benefit of U.S. Provisional Application No. 60/020,975, filed Jun. 28, 1996.

BACKGROUND OF THE INVENTION

The invention relates generally to modulating cell adhesion and to inhibiting the binding of fibrinogen and other proteins to blood platelets, and inhibiting the aggregation of blood platelets specifically to the gp IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in *Science*, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in *Proc. Nat'l Acad. Sci. U.S.A.*, 84, 6471–6475, (1987), describes an Arg-Gly-Asp directed adhesion receptor expressed by human endothethial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. of Biol. Chem.*, 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the stereochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In *Proc. Nat'l Acad. Sci. U.S.A.*, 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., *Proc. Nat'l Acad. Sci. U.S.A.*, 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., *Biochem.* 23, 1767–1774 (1984); Ginsberg et al., *J. Biol. Chem.* 260(7), 3931–3936 (1985); and Haverstick et al., *Blood* 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa complex. For example, Huang et al., *J. Biol Chem.*, 262, 16157–16163 (1987); Huang et al., *Biochemistry*, 28, 661–666 (1989) describe the primary structure of the venom trigramin which is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., *J. Biol. Chem.*, 263, 19827–19832 (1988). See also, Dennis et al., *Proc. Nat'l Acad. Sci. USA*, 87, 2471–2475 (1989). However, these snake venom factors also have high affinity for other members of the adhesive protein receptor family including the vitronectin and fibronectin receptors so are not selective for the gp IIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No 5,023,233 discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IIIa receptor. U.S. Pat. No. 5,037,808 discloses guanidino peptide mimetic compounds that retain an Asp residue which inhibit platelet aggregation. WO9014103 describes the use of antibody-polypeptide conjugates wherein said polypeptides contain the Arg-Gly-Asp (RGD) sequence.

WO9111458 discloses the use of large cyclic peptides containing RGD flanked by proline residues which are platelet aggregation inhibitors. WO9101331 discloses small cyclic platelet aggregation inhibitors which are synthetic cyclic pentapeptides containing the tripeptide sequence Arg-Gly-Asp and a thioether linkage in the cycle. U.S. Pat. No. 5,051,405 also discloses the use of peptides and pseudopeptides such as N-amidino-piperidine-3-carboxylglycyl-L-aspartyl-L-valine that inhibit platelet aggregation and thrombus formation in mammalian blood. EP 445 796 discloses linear compounds which can include internal piperazinyl or piperidinyl derivatives. EP437 367 discloses linear polypeptide fibrinogen receptor antagonists. U.S. Pat. No. 5,256,812 discloses compounds of the formula $R^1-A-(W)_a-X-(CH_2)_b-(Y)_c-B-Z-COOR$ wherein $R^1$ is a guandidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

The invention includes compounds of the formula

X—Y—Z—A—B and pharmaceutically acceptable salts,
wherein
x is a 5, 6 or 7 membered aromatic or nonaromatic ring, having 1, 2 or 3 heteroatoms selected from N, O, and S, and either unsubstituted or monosubstituted on the carbon and nitrogen atoms with $R^1$, or disubstituted on the carbon and nitrogen atoms with $R^1$ and $R^2$, where $R^1$ and $R^2$ are independently selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino $C_{1-8}$ alkyl,
$C_{1-6}$ alkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl, or
a 9 or 10 membered fused aromatic or nonaromatic ring, having 1, 2 or 3 heteroatoms selected from N, O, and S, and either unsubstituted or monosubstituted on the carbon and nitrogen atoms with $R^1$, or disubstituted on the carbon and nitrogen atoms with $R^1$ and $R^2$, where $R^1$ and $R^2$ are independently selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino $C_{1-8}$ alkyl,
$C_{1-6}$ alkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl;

Y is a 5 or 6 membered aromatic or nonaromatic ring, having 0, 1, 2 or 3 heteroatoms selected from N, O, and S, and either unsubstituted or substituted on carbon and nitrogen atoms with $R^3$ selected from the group consisting of
hydrogen,
halogen,
$C_{1-10}$ alkyl,
$C_{3-9}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl; or X and Y combined together form the structures

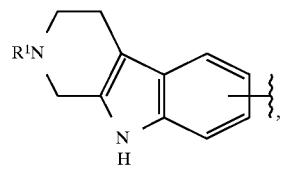

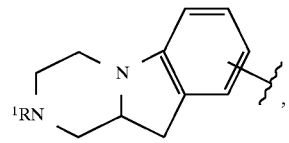

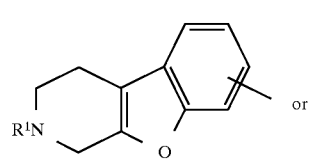

-continued

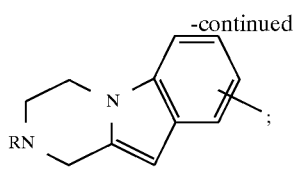

Z is

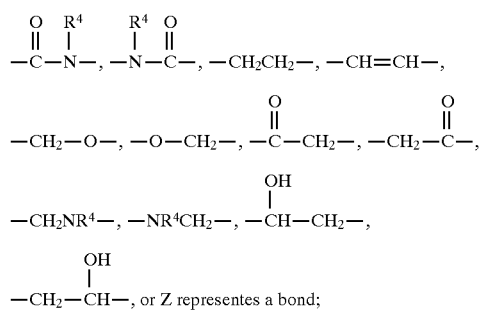

—CH₂—CH—, or Z representes a bond;
            |
            OH $R^4$ is hydrogen, $C_{1-4}$ alkyl, or $C_{3-6}$ cycloalkyl;

A is a 5 or 6 membered aromatic ring, having 0, 1, 2 or 3 heteroatoms selected from N, O, and S, and either unsubstituted or monosubstituted on carbon and nitrogen atoms with $R^5$, disubstituted on carbon and nitrogen atoms with $R^5$ and $R^6$, or trisubstituted on carbon and nitrogen atoms with $R^5$, $R^6$ and $R^7$, where $R^5$, $R^6$ and $R^7$ are each independently selected from the group consisting of
hydrogen,
halogen,
$C_{1-10}$ alkyl,
$C_{3-8}$ cycloalkyl,
aryl,
aryl $C_{1-8}$ alkyl,
arylsulfonylamino,
amino,
amino $C_{1-8}$ alkyl,
nitro,
$C_{1-3}$ acylamino,
$C_{1-3}$ acylamino $C_{1-8}$ alkyl,
$C_{1-6}$ alkylamino,
$C_{1-3}$ alkylsulfonylamino,
$C_{1-6}$ alkylamino $C_{1-8}$ alkyl,
$C_{1-6}$ dialkylamino,
$C_{1-6}$ dialkylamino $C_{1-9}$ alkyl,
$C_{1-6}$ alkoxy,
$C_{1-6}$ alkoxy $C_{1-6}$ alkyl,
trihaloalkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl, or A is a 9 or 10 membered fused aromatic ring, having 0, 1, 2 or 3 heteroatoms selected from N, O, and S, and either unsubstituted or monosubstituted on carbon and nitrogen atoms with $R^5$, disubstituted on carbon and nitrogen atoms with $R^5$ and $R^6$, or trisubstituted on carbon and nitrogen atoms with $R^5$, $R^6$ and $R^7$, where $R^5$, $R^6$ and $R^7$ are each independently selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl;

B is —O(CH₂)$_m$CO₂R⁹, —(CH₂)$_n$CO₂R⁹,

—CH(CH₂)$_p$CO₂R⁹, or
     |
     $R^8$

—OCH($R^8$)(CH₂)$_p$CO₂R⁹ wherein
m is 1, 2, or 3,
n is 0, 1, 2, or 3, and
p is 0, 1, 2, or 3;

$R^8$ is selected from the group consisting of
hydrogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy,
hydroxy $C_{1-6}$ alkyl; and $R^9$ is
hydrogen,
$C_{1-8}$ alkyl,
aryl,
aryl $C_{1-6}$ alkyl,
$C_{1-8}$ alkylcarbonyloxy $C_{1-6}$ alkyl
aryl carbonyloxy $C_{1-6}$ alkyl, aryl $C_{1-6}$ alkylcarbonyloxy $C_{1-6}$ alkyl,
$C_{1-8}$ alkylaminocarbonyl $C_{1-6}$ alkyl, or
$C_{1-8}$ dialkylamino carbonyl $C_{1-6}$ alkyl.

The invention also includes the use of a compound of the invention, or a pharmaceutically acceptable salt thereof, in the manufacture of a medicament for inhibiting the aggregation of blood platelets, preventing platelet thrombosis, preventing thromboembolism or preventing reocclusion, in a mammal.

DETAILED DESCRIPTION OF THE INVENTION

The invention includes compounds of the formula

X—Y—Z—A—B and pharmaceutically acceptable salts,
wherein
X is a 5, 6 or 7 membered aromatic or nonaromatic ring, having 1, 2 or 3 heteroatoms selected from N, O, and S, and either unsubstituted or monosubstituted on the carbon and nitrogen atoms with $R^1$, or disubstituted on the carbon and nitrogen atoms with $R^1$ and $R^2$, where $R^1$ and $R^2$ are independently selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino $C_{1-8}$ alkyl,
$C_{1-6}$ alkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl, or
a 9 or 10 membered fused aromatic or nonaromatic ring, having 1, 2 or 3 heteroatoms selected from N, O, and S, and either unsubstituted or monosubstituted on the carbon and nitrogen atoms with $R^1$, or disubstituted on the carbon and nitrogen atoms with $R^1$ and $R^2$, where $R^1$ and $R^2$ are independently selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino $C_{1-8}$ alkyl,
$C_{1-6}$ alkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl;

Y is a 5 or 6 membered aromatic ring or non-aromatic ring, having 0, 1, 2 or 3 heteroatoms selected from N, O, and S, and either unsubstituted or substituted on the carbons and nitrogens with $R^3$ selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl;

X and Y combined together form the structures

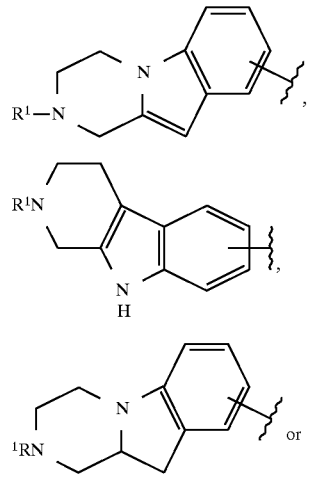

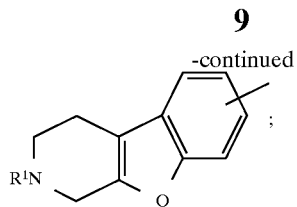

Z is

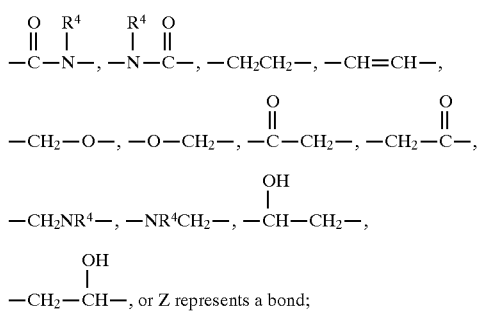

$-CH_2-\overset{OH}{\underset{|}{CH}}-$, or Z represents a bond;

$R^4$ is hydrogen, $C_{1-4}$ alkyl, or $C_{3-6}$ cycloalkyl;
A is a 5 or 6 membered aromatic ring, having 0, 1, 2 or 3 heteroatoms selected from N, O, and S, and either unsubstituted or monosubstituted on the carbons or nitrogen with $R^5$, disubstituted with $R^5$ and $R^6$, or trisubstituted with $R^5$, $R^6$ and $R^7$, where $R^5$, $R^6$ and $R^7$ are independently selected from the group consisting of
hydrogen,
halogen,
$C_{1-10}$ alkyl,
$C_{3-8}$ cycloalkyl,
aryl,
aryl $C_{1-8}$ alkyl,
arylsulfonylamino,
amino,
amino $C_{1-8}$ alkyl,
nitro,
$C_{1-3}$ acylamino,
$C_{1-3}$ acylamino $C_{1-8}$ alkyl,
$C_{1-6}$ alkylamino,
$C_{1-3}$ alkylsulfonylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
trihaloalkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl, or
a 9 or 10 membered fused aromatic ring, having 0, 1, 2 or 3 heteroatoms selected from N, O, and S, and either unsubstituted or monosubstituted on the carbons or nitrogen with $R^5$, disubstituted with $R^5$ and $R^6$, or trisubstituted with $R^5$, $R^6$ and $R^7$, where $R^5$, $R^6$ and $R^7$ are independently selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl;
B is $-O(CH_2)_mCO_2R^9$, $-(CH_2)_nCO_2R^9$, or

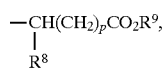

$OCH(R^8)(CH_2)_pCO_2R^9$ wherein
m is 1, 2, or 3,
n is 0, 1, 2, or 3, and
p is 0, 1, 2, or 3;
$R^8$ is selected from the group consisting of
hydrogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy,
hydroxy $C_{1-6}$ alkyl; and
$R^9$ is
hydrogen,
$C_{1-8}$ alkyl,
aryl,
aryl $C_{1-6}$ alkyl,
$C_{1-8}$ alkylcarbonyloxy $C_{1-6}$ alkyl
aryl carbonyloxy $C_{1-6}$ alkyl,
aryl $C_{1-6}$ alkylcarbonyloxy $C_{1-6}$ alkyl,
$C_{1-8}$ alkylaminocarbonyl $C_{1-6}$ alkyl, or $C_{1-8}$ dialkylamino carbonyl $C_{1-6}$ alkyl.

In one class, the compounds have the structure

X—Y—Z—A—B and pharmaceutically acceptable salts,
wherein
X is a 5, 6 or 7 membered aromatic or nonaromatic ring having 1, 2 or 3 nitrogen atoms and unsubstituted or substituted with $NH_2$;
Y is a 5 or 6 membered aromatic or nonaromatic ring having 0, 1, 2 or 3 nitrogen atoms and unsubstituted or substituted with $C_{1-3}$alkyl;
or X and Y together form the fused ring systems:

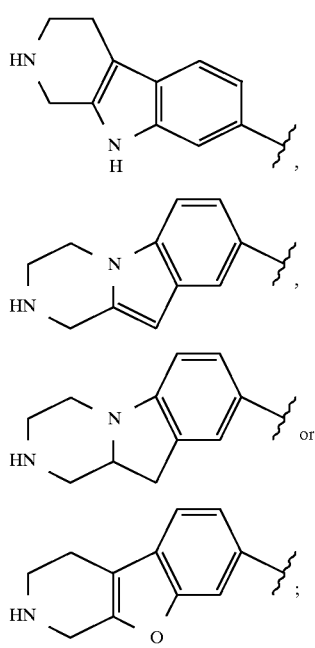

Z is

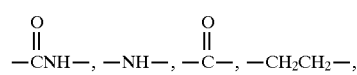
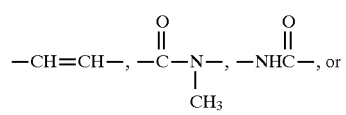

Z represents a bond;
A is a 5 or 6 membered aromatic ring, having 0, 1, 2, or 3 nitrogen atoms and unsubstituted or monosubstituted on the carbons or nitrogen with $R^5$, disubstituted with $R^5$ and $R^6$, same or different, or trisubstituted with $R^5$, $R^6$ and $R^7$, same or different, wherein $R^5$, $R^6$ and $R^7$ are selected from the group consisting of
arylsulfonylamino,
$C_{1-3}$ alkylsulfonylamino,
$C_{1-3}$ alkyl,
—$CF_3$,
$C_{1-3}$alkyloxy,
halogen,
nitro, or
A is a 9 membered fused aromatic ring system having 0, 1, 2 or 3 nitrogen atoms, or A is isoindolinone or indolinone;
B is —$OCH(R^8)(CH_2)_pCO_2R^9$, $(CH_2)_nCO_2R^9$,
n=0, 1, 2, 3,
p=0, 1, 2, 3,
wherein
$R^8$ is hydrogen or $C_{1-3}$alkyl and
$R^9$ is hydrogen or —$(CH_2)_{1-3}C(O)NH(CH_2)_{0-2}CH_3$ or —$(CH_2)_{1-3}$ $C(O)N((CH_2)_{0-2}CH_3)_2$.

In a subclass of the class, the compounds have the structure

X—Y—Z—A—B and pharmaceutically acceptable salts,
wherein
X is a 5 or 6 membered aromatic or nonaromatic ring having 1 or 2 nitrogen atoms and unsubstituted or substituted with $NH_2$;
Y is a 6 membered aromatic or nonaromatic ring having 0 or 1 nitrogen atoms and unsubstituted or substituted with $CH_3$;
or X and Y form the fused ring systems:

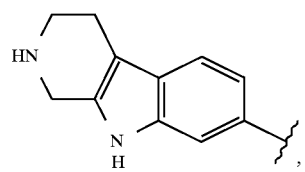
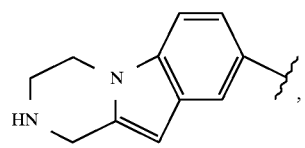
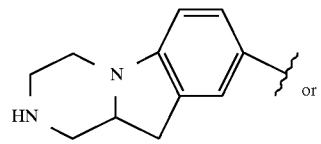
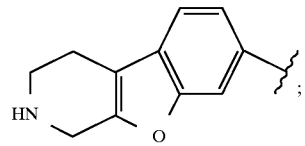

Z is

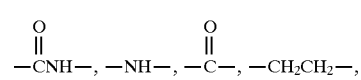
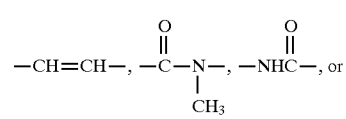

Z represents a bond;
A is phenyl unsubstituted, monosubstituted with $R^5$, disubstituted with $R^5$ and $R^6$, or trisubstituted with $R^5$, $R^6$, or $R^7$, where $R^5$, $R^6$, or $R^7$ are selected from
—$NHSO_2C_6H_5$,

—NHSO$_2$CH$_3$

—NHSO$_2$—[pyridyl group with N],

—CH$_3$,
—CF3,
—OCH$_3$,
—Cl,
—NO$_2$, and
—Br, or

A is a 9 membered fused aromatic ring system having 1 nitrogen atom, or

A is isoindolinone or indolinone;

B is —OCH(R$^8$)CO$_2$R$^9$, —(CH$_2$)$_n$CO$_2$R$^9$
wherein n=1 or 2
R$^8$ is hydrogen or C$_{1-3}$alkyl and
R$^9$ is hydrogen, —(CH$_2$)$_{1-3}$C(O)NH(CH$_2$)$_{0-2}$CH$_3$, or —(CH$_2$)$_{1-3}$ C(O)N((CH$_2$)$_{0-2}$CH$_3$)$_2$.

In a group of the subclass, the compounds have the structure

X—Y—Z—A—B and pharmaceutically acceptable salts,
wherein
X is

[structures: piperazine, piperidine, pyridyl, pyrrolidine with NH$_2$, aminopyrrolidine, diaminopyridyl]

Y is

[structures: phenylene, piperidine-piperidine linked, pyridyl, methylphenyl]

or X and Y form the fused ring systems:

[tetrahydro-β-carboline structure with HN and NH]

[indoline with piperazine structure], or

[dibenzofuran-like structure with HN]

Z is $$-\overset{O}{\underset{\|}{C}}NH-, \quad -NH-, \quad -\overset{O}{\underset{\|}{C}}-, \quad -CH_2CH_2-,$$

$$-CH=CH-, \quad -\overset{O}{\underset{\|}{C}}-\underset{CH_3}{\overset{|}{N}}-, \quad -NH\overset{O}{\underset{\|}{C}}-, \text{ or }$$

Z represents a bond;

A is

[various substituted biphenyl structures with substituents: NHSO$_2$C$_6$H$_5$, CH$_3$, OCH$_3$, CF$_3$, Cl]

[diphenylamine with CH$_3$]

[dimethylphenyl-isoindolinone structure]

[phenyl with NHSO$_2$CH$_3$],

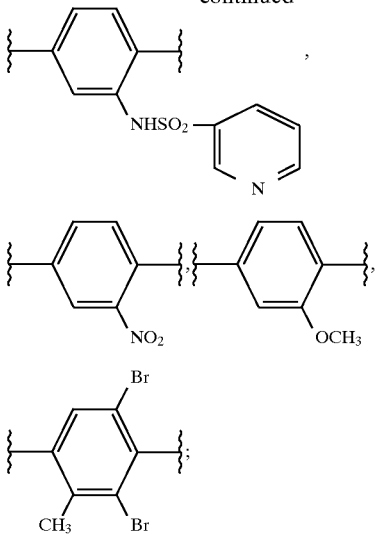

and

B is —OCH₂CO₂H, —OCH₂CO₂CH₂C(O)NHCH₃,
—OCH₂CO₂CH₂C(O)N(CH₂CH₃)₂,
—OCH₂CO₂CH₂CH₃, —CH₂CH₂CO₂H,
—CH₂COOH,
—OCH(CH₃)CO₂H, or
—OCH(CH₃)CO₂CH₂CH₃.

Exemplary compounds of the group include
3-(4-(4-piperazin-1-ylphenylcarbonylamino)phenyl) propanoic acid,
2-(4-(4-Piperazinyl-1-yl)phenylcarbonylamino)phenoxy) acetic acid,
Ethyl 2-(4-(4-(1-piperazinyl)phenylcarbonylamino) phenoxy)acetate, hydrochloride,
2-(5-(4-(1-Piperazinyl)phenylcarbonylamino)indol-1-yl) acetic acid,
3-(3-(4-Piperazin-1-ylphenyl)carbonylamino)phenyl) propanoic acid,
Ethyl 2-(4-(4-(piperazin-1-yl)phenylcarbonylamino) phenoxy)propanoate
2-(4-(4-(Piperazin-1-yl)phenylcarbonylamino)phenoxy) propionic acid,
2-(4-(((2-Piperazin-1-yl)pyridin-5-yl)carbonylamino) phenoxy)acetic acid,
3-Methyl-4-((1,2,3,4-tetrahydro-9H-pyrido[3,4-b]indol-7-yl)carbonylamino)phenoxyacetic acid,
2-(4-(5-(4-(1,1-Dimethylethoxycarbonyl)-piperazin-1-yl)-2-thienylcarbonylamino)-3-methylphenoxy)-acetic acid,
4-(2-(1,1-dimethylethoxycarbonyl)-1,2,3,4-tetrahydro-9H-pyrido[3,4-b]benzofuran-7-yl)carbonylamino)-3-methylphenoxy acetic acid,
4-((2,3,4,5-tetrahydropyrazino-[1,2-a]indole-8-yl) carbonylamino)-3-methylphenoxyacetic acid, and
(+/−)4-((3-(1,1-Dimethylethoxycarbonyl)-1,1a,2,3,4,5-hexahydropyrazino-[1,2-a]indole-8-yl)carbonylamino)-3-methylphenoxyacetic acid.

One test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2\times10^8$ per ml), fibrinogen (100 micrograms per ml (ug/ml)), $Ca^{2+}$ (1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

The following compounds were tested and found to have $IC_{50}$ values in the range between 10 nM and 50 mM:
3-(4-(4-piperazin-1-ylphenylcarbonylamino)phenyl) propanoic acid,
2-(4-(4-Piperazinyl-1-yl)phenylcarbonylamino)phenoxy) acetic acid,
Ethyl 2-(4-(4-(1-piperazinyl)phenylcarbonylamino) phenoxy)acetate, hydrochloride,
2-(5-(4-(1-Piperazinyl)phenylcarbonylamino)indol-1-yl) acetic acid,
3-(3-(4-Piperazin-1-ylphenyl)carbonylamino)phenyl) propanoic acid,
Ethyl 2-(4-(4-(piperazin-1-yl)phenylcarbonylamino) phenoxy)propanoate
2-(4-(4-(Piperazin-1-yl)phenylcarbonylamino)phenoxy) propionic acid,
2-(4-(((2-Piperazin-1-yl)pyridin-5-yl)carbonylamino) phenoxy)acetic acid,
3-Methyl-4-((1,2,3,4-tetrahydro-9H-pyrido[3,4-b]indol-7-yl)carbonylamino)phenoxyacetic acid,
2-(4-(5-(4-(1,1-Dimethylethoxycarbonyl)-piperazin-1-yl)-2-thienylcarbonylamino)-3-methylphenoxy)-acetic acid
4-(2-(1,1-dimethylethoxycarbonyl)-1,2,3,4-tetrahydro-9H-pyrido[3,4-b]benzofuran-7-yl)carbonylamino)-3-methylphenoxy acetic acid,
4-((2,3,4,5-tetrahydropyrazino-[1,2-a]indole-8-yl) carbonylamino)-3-methylphenoxyacetic acid, and
(+/−) 4-((3-(1,1-Dimethylethoxycarbonyl)-1,1a,2,3,4,5-hexahydropyrazino-[1,2-a]indole-8-yl)carbonylamino)-3-methylphenoxyacetic acid.

Additionally, these compounds are useful for treating mammals suffering from a bone condition caused or mediated by increased bone resorption, who are in need of such therapy. Pharmacologically effective amounts of the compounds, including pharamaceutically acceptable salts thereof, are administered to the mammal, to inhibit the activity of mammalian osteoclasts.

Additionally, these compounds are useful for treating angiogenesis (formation of new blood vessels). It has been postulated that the growth of tumors depends on an adequate blood supply, which in turn is dependent on the growth of new vessels into the tumor. Inhibition of angiogenesis can cause tumor regression in animal models. (See, *Harrison's Principles of Internal Medicine*, 12th ed., 1991). These compounds are therefore useful in the treatment of cancer by inhibiting tumor growth. (See e.g., Brooks et al., *Cell*, 79:1157–1164 (1994)).

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Compounds of the present invention may be chiral; included within the scope of the present invention are racemic mixtures and separated enantiomers of the general formula. Furthermore, all diastereomers, including E, Z isomers, of the general formula are included in the present scope. Furthermore, hydrates as well as anhydrous compositions and polymorphs of the general formula are within the present invention.

Prodrugs, such as ester derivatives of described compounds, are compound derivatives which, when absorbed into the bloodstream of a warm-blooded animal, cleave in such a manner as to release the drug form and permit the drug to afford improved therapeutic efficacy.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like; the term alkenyl means straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like; alkynyl means straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "aryl" means a 5- or 6-membered aromatic ring containing 0, 1, or 2 heteroatoms selected from O, N, and S, e.g. phenyl, pyridine, pyrimidine, imidazole, thiophene, oxazole, isoxazole, thiazole, and amino- and halogen- substituted derivatives thereof.

The terms "alkyloxy" or "alkoxy" include an alkyl portion where alkyl is as defined above, e.g., methyloxy, propyloxy, and butyloxy.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit. Examples of arylalkyl include benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include toluene, ethylbenzene, propylbenzene, methylpyridine, ethylpyridine, propylpyridine, butylpyridine, butenylpyridine, and pentenylpyridine.

The term "halogen" includes fluorine, chlorine, iodine and bromine.

The term "oxy" means an oxygen (O) atom. The term "thio" means a sulfur (S) atom. Under standard nonmenclature used throughout this disclosure, the terminal portion of the designated side chain is described first followed by the adjacent functionality toward the point of attachment. For example, a $C_{1-6}$ alkyl substituted with $C_{1-5}$ alkylcarbonylamino is equivalent to

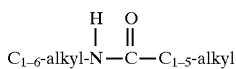

In the schemes and examples below, various reagent symbols have the following meanings:
BOC
(or Boc): t-butyloxycarbonyl
Pd—C: palladium on activated carbon catalyst
DMF: dimethylformamide
DMSO: dimethylsulfoxide
CBZ: carbobenzyloxy
$CH_2Cl_2$: methylene chloride
$CHCl_3$: chloroform
EtOH: ethanol
MeOH: methanol
EtOAc: ethyl acetate
HOAc: acetic acid
BOP: benzotriazol-1-yloxytris(dimethylamino) phosphonium, hexafluorophosphate
EDC: 1-(3-dimethylaminopropyl)-3-ethylcarbodiimide hydrochloride
Oxone: potassium peroxymonosulfate
LDA: lithium diisopropylamide
PYCLU: Chloro—N,N,N',N'-bis(pentamethylene) formamidinium hexafluorophosphate
NMM: N-methylmorpholine The compounds of the present invention can be administered in such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., *Amer. J. Physiol.*, 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.01–100 mg/kg/day and most preferably 0.01–20 mg/kg/day. For example, a typical 90 kg patient would receive oral dosages ranging between about 0.9 mg/day and about 9 g/day, most preferably between about 0.9 mg/day and 1.8 g/day. Suitable pharmaceutical oral compositions such as tablets or capsules may contain between 10–500 mg of active drug, for example, 10 mg, 100 mg, 200 mg and 500 mg. Intravenously, the most preferred doses will range from about 1 to about 10 mg/kg/minute during a constant rate infusion.

Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

SCHEME 1

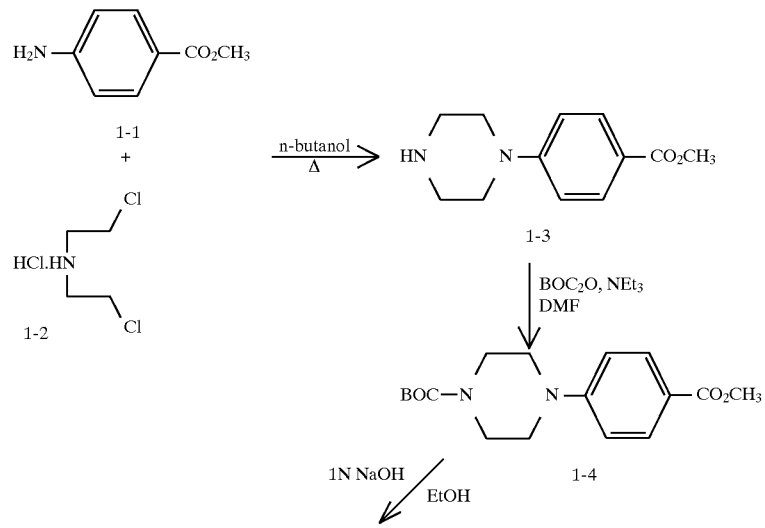

-continued
SCHEME 1
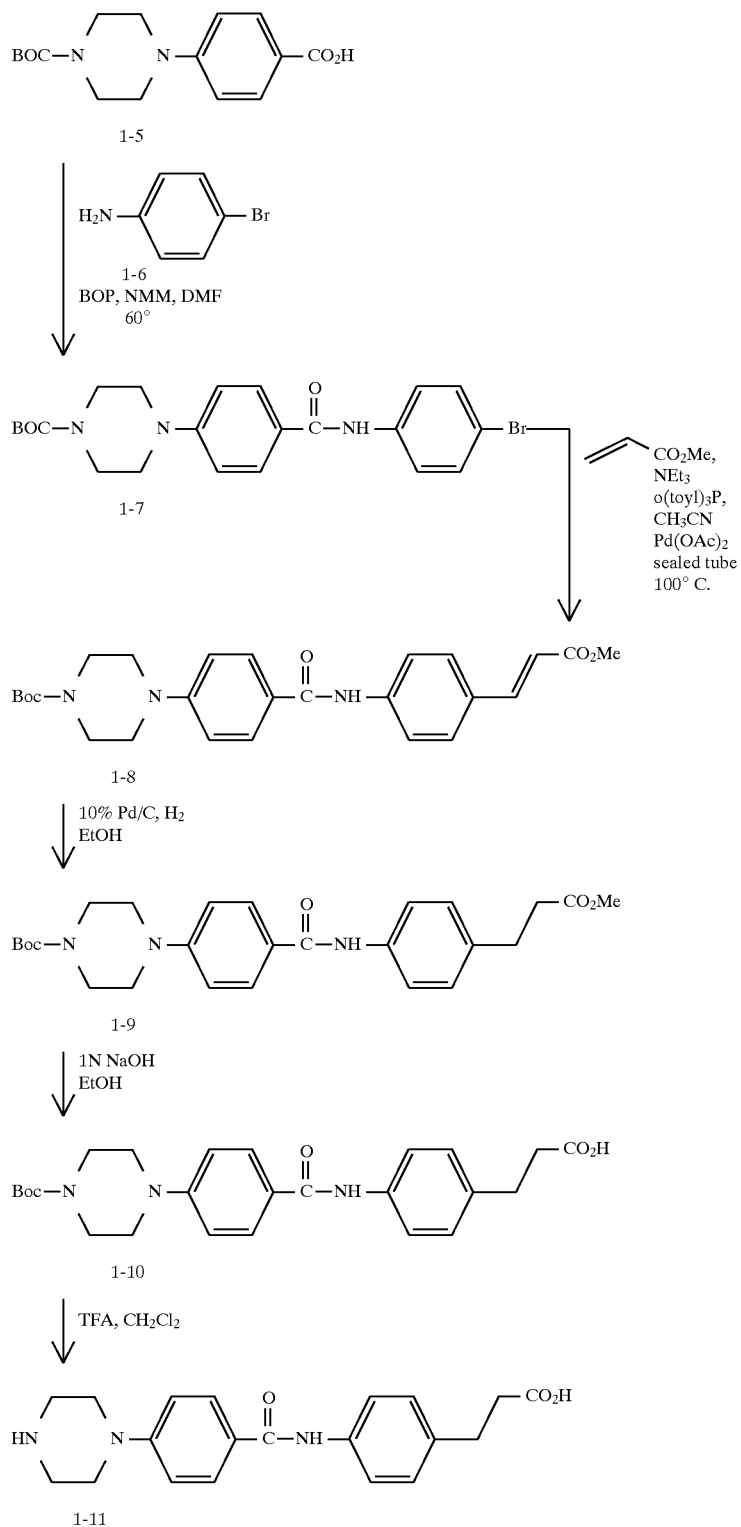

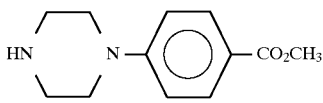

Methyl 4-(1-piperazinyl)benzoate (1-3)

A solution of amine 1—1 (20.0 g, 132 mmol), amine 1-2 (23.6 g, 132 mmol) and n-butanol (500 ml) was refluxed for 168 h. The solution was allowed to cool to ambient temperature. The crystals were collected, washed with $Et_2O$ and dried in vacuo to give ester 1-3 as a white solid.

$^1$H NMR ($CD_3OD$): δ 7.86 (d, J=9 Hz, 2H), 7.98 (d, J=9 Hz, 2H), 3.78 (s, 3H), 3.53 (m, 4H), 3.31 (m, 4H).

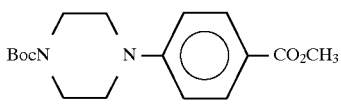

Methyl 4-(4-(1,1-dimethylethoxycarbonyl)piperazin-1-yl) benzoate (1-4)

To a stirred solution of amine 1-3 (15.0 g, 61.1 mmol), $NEt_3$ (7.42 g, 73.4 mmol) and DMF (150 ml) was added $Boc_2O$ (14.7 g, 67.2 mmol). After 1.0 h, the solution was diluted with EtOAc and then washed with $H_2O$, 10% $KHSO_4$, brine, dried ($MgSO_4$) and concentrated to furnish ester 1-4 as a yellow solid.

TLC $R_f$=0.63 (silica, 40% EtOAc/hexanes) $^1$H NMR ($CD_3OD$): δ 7.91 (d, J=9 Hz, 2H), 7.01 (d, J=9 Hz, 2H), 3.88 (s, 3H), 3.59 (m, 4H), 3.38 (m, 4H).

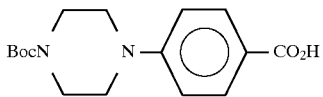

4-(4-(1,1-Dimethylethoxycarbonyl)piperazin-1-vl)benzoic acid (1-5)

A solution of ester 1-4 (21.1 g, 61.1 mmol) 1N NaOH (100 ml, 100 mmol) and EtOH (200 ml) was heated to 60° C. for 2.0 h. The solution was acidifed with 10% $KHSO_4$ and then extracted with EtOAc. The EtOAc phase was washed with brine, dried ($MgSO_4$) and concentrated to furnish acid 1-5 as a white solid.

$^1$H NMR ($CD_3OD$): δ 7.81 (d, J=9 Hz, 2H), 6.88 (d, J=9 Hz, 2H), 3.49 (m, 4H), 3.24 (m, 4H), 1.40 (s, 9H).

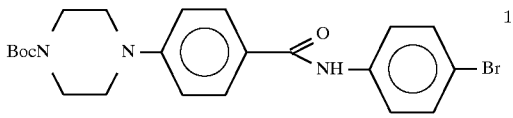

N-(4-bromophenyl)-4-(4-(1,1-dimethylethoxycarbonyl) piperazin-1-yl)benzamide (1-7)

A solution of acid 1-5 (400 mg, 1.31 mmol), amine 1-6 (248 mg, 1.44 mmol), BOP reagent (867 mg, 1.97 mmol), NMM (575 μl, 5.24 mmol) and DMF was heated at 60° C. for 72 h. The solution was diluted with EtOAc and then washed with $H_2O$, sat. $NaHCO_3$, 10% $KHSO_4$ brine, dried ($MgSO_4$) and concentrated. Flash chromatography (silica, 20% EtOAc/hexanes) furnished amide 1-7 as a yellow solid.

TLC $R_f$=0.36 (silica, 20% EtOAc/hexanes) $^1$H NMR ($CDCl_3$): δ 7.78 (d, J=9 Hz, 2H), 7.70 (s, 1H), 7.54 (d, J=9 Hz, 2H), 7.46 (d, J=9 Hz, 2H), 6.92 (d, J=9 Hz, 2H), 3.58 (m, 4H), 3.30 (m, 4H), 1.49 (s, 9H).

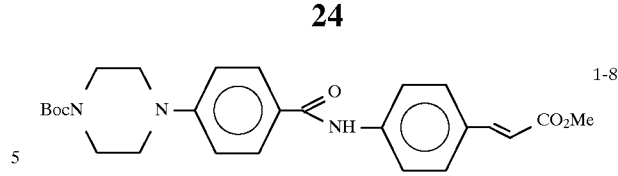

(E)-Methyl 3-(4-(4-(4-(1,1-dimethylethoxycarbonyl) piperazin-1-yl)phenylcarbonylaminophenyl)prop-3-enoate (1-9)

A solution of amide 1-7 (300 mg, 0.6519 mmol), methyl acrylate (587 μl, 6.52 mmol), $O(tolyl)_3P$ (120 mg, 0.311 mmol), $NEt_3$ (184 μl, 1.30 mmol), Pd $(OAc)_2$ (15 mg, 0.0512 mmol) and $CH_3CN$ (5 ml) was heated to 100° C. in a sealed tube for 18 h. The solution was diluted with EtOAc and then washed with $H_2O$, sat. $NaHCO_3$, 10% $KHSO_4$, brine, dried ($MgSO_4$) and concentrated. Flash chromatography (silica, 25%→40% EtOAc/hexanes) furnished olefin 1-8 as a yellow solid.

TLC $R_f$=0.36 (silica, 50% EtOAc/hexanes) $^1$H NMR ($CDCl_3$): δ 7.87 (s, 1H), 7.81 (d, J=9 Hz, 2H), 7.68 (m, 3H), 7.53 (d, J=9 Hz, 2H), 6.94 (d, J=9 Hz, 2H), 6.39 (d, J=16 Hz, 1H), 3.81 (s, 3H), 3.61 (m, 4H), 3.30 (m, 4H), 1.50 (s, 9H).

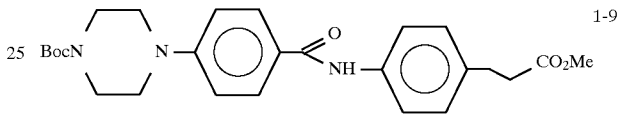

Methyl 3-(4-(4-(4-(1,1-dimethylethoxycarbonyl)piperazin-1-yl)phenylcarbonylaminophenyl)propanoate (1-9)

A mixture of ester 1-8 (260 mg, 0.56 mmol), 10% Pd/C (100 mg) and EtOH (10 ml) was stirred under 1 atm $H_2$ for 18 h. The reaction mixture was filtered through a celite pad and concentrated to furnish ester 1-9 as a brown solid.

$^1$H NMR ($CDCl_3$): δ 7.79 (d, J=9 Hz, 2H), 7.67 (s, 1H), 7.54 (d, J=8 Hz, 2H), 7.19 (d, J=8 Hz, 2H), 6.92 (d, J=9 Hz, 2H), 3.67 (s, 3H), 3.60 (m, 4H), 3.29 (m, 4H), 2.94 (t, J=8 Hz, 2H), 2.63 (t, J=8 Hz, 2H), 1.49 (s, 9H).

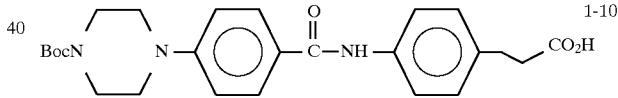

3-(4-(4-(4-(1,1-dimethylethoxycarbonyl)piperazin-1-yl) phenylcarbonylaminophenyl)propanoic acid (1-10)

A solution of ester 1-9 (250 mg, 0.53 mmol), 1N NaOH (1 ml, 1.00 mmol) and EtOH (3 ml) was stirred at ambient temperature for 1.5 h. The solution was acidified with 10% $KHSO_4$ and then extracted with EtOAc. The EtOAc phase was washed with brine, dried ($MgSO_4$) and concentrated to furnish acid 1-10 as a tan solid.

TLC $R_f$=0.11 (silica, 10:0.2:0.2 $CH_2Cl_2$/MeOH/AcOH) $^1$H NMR ($CD_3OD$): δ 7.86 (d, J=9 Hz, 2H), 7.55 (d, J=8 Hz, 2H), 7.20 (d, J=9 Hz, 2H), 7.08 (d, J=8 Hz, 2H), 3.60 (bs, 4H) 3.45 (m, 4H), 2.89 (t, J=8 Hz, 2H), 2.59 (t, J=8 Hz, 2H), 1.48 (s, 9H).

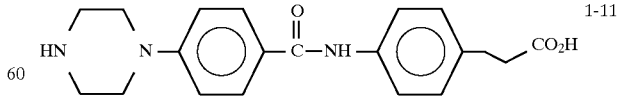

3-(4-(4-piperazin-1-ylphenylcarbonylamino)phenyl) propanoic acid (1-11)

To a solution of acid 1-10 (215 mg, 0.4743 mmol), TFA (3.0 ml) and $CH_2Cl_2$ (3.0 ml) was stirred at ambient temperature for 1.5 h. The solution was concentrated and then azeotroped with toluene. The residue was triturated with 10:0.2:0.2 EtOH/NH₄OH/H₂O, filtered, washed with Et₂O and dried in vacuo to furnish acid 1-11 as a tan solid.

TLC R_f=0.55 (silica, 10:1:1 EtOH/NH₄OH/H₂O) ¹H NMR (D₂O): δ 7.83 (d, J=9 Hz, 2H), 7.42 (d, J=8 Hz, 2H), 7.31 (d, J=8 Hz, 2H), 7.16 (d, J=9 Hz, 2H), 3.25 (m, 4H), 2.96 (m, 4H), 2.89 (t, J=8 Hz, 2H), 2.49 (t, J=8 Hz, 2H).

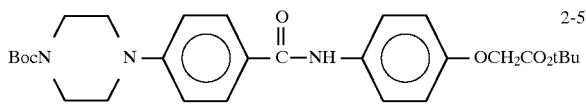

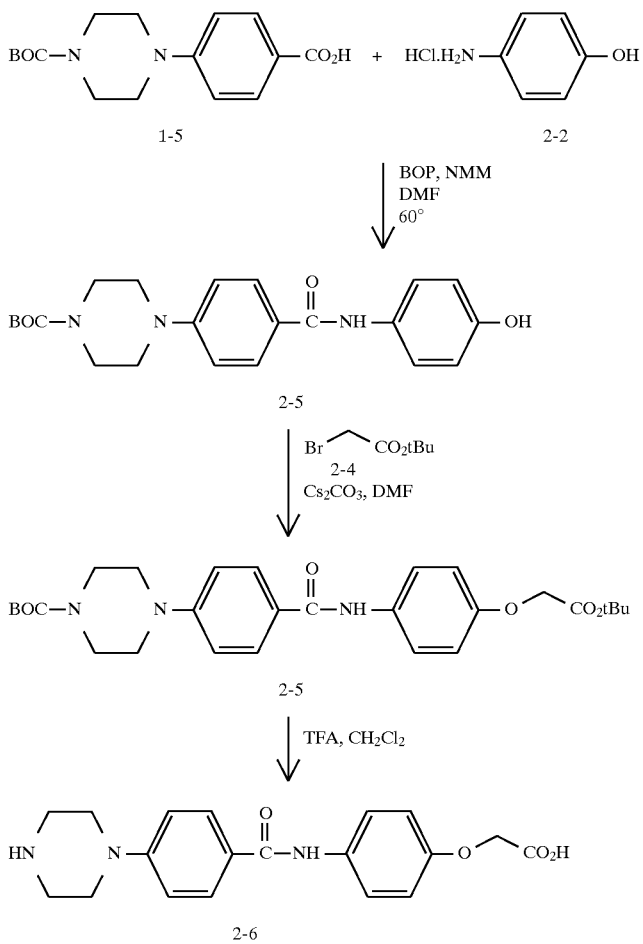

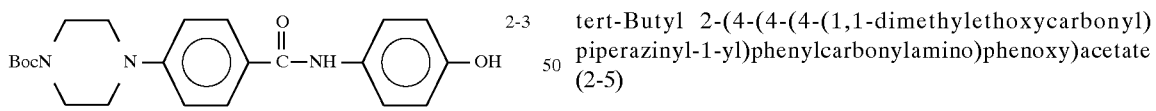

N-(4-Hydroxyphenyl)-4-(4-(1,1-dimethylethoxycarbonyl)piperazinyl-1-yl)benzamide (2-3)

A solution of carboxylic acid 2-1 (400 mg, 1.31 mmole), 4-aminophenyl 2—2 (210 mg, 1.44 mmol), BOP reagent (867 mg, 1.97 mmole), NMM (575 μl, 5.24 mmol) and DMF (10 ml) was heated to 60° C. for 72 h. The reaction mixture was diluted with EtOAc and then washed with H₂O, sat NaHCO₃, 10% KHSO₄, dried (MgSO₄) and then concentrated. Flash chromatography (silica, 50% EtOAc/hexanes) furnished the amide 2-3 as a white solid.

TLC R_f=0.25 (silica, 50% EtOAc/hexanes) ¹H NMR (CD₃OD): δ 7.82 (d, J=9 Hz, 2H), 7.40 (d, J=9 Hz, 2H), 7.0 (d, J=9 Hz, 2H), 6.75 (d, J=9 Hz, 2H), 3.57 (bs, 4H), 3.30 (bs, 4S), 1.47 (s, 9H).

tert-Butyl 2-(4-(4-(4-(1,1-dimethylethoxycarbonyl)piperazinyl-1-yl)phenylcarbonylamino)phenoxy)acetate (2-5)

To a stirred solution of amide 2-3 (400 mg, 1.01 mmol) and DMF (5 ml) was added cesium carbonate (820 mg, 2.53 mmole) followed by t-butyl bromoacetate (195 μl, 1.21 mmol). After 20 h, the reaction mixture was diluted with EtOAc and then washed with H₂O, 10% KHSO₄, brine, dried (MgSO₄) and concentrated. Flash chromatography (silica, 25% EtOAc/hexanes) furnished ester 2-5 as a white solid.

TLC R_f=0.40 (silica, 50% EtOAc/hexanes) ¹H NMR (CDCl₃): δ 7.79 (d, J=9 Hz, 2H), 7.63 (s, 1H), 7.54 (d, J=9 Hz, 2H), 6.92 (m, 4H), 4.51 (s, 2H), 3.60 (m, 4H), 3.30 (m, 4H), 1.50 (s, 18H).

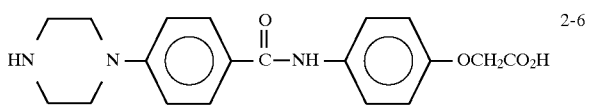

2-(4-(4-Piperazinyl-1-yl)phenylcarbonylamino)phenoxy) acetic acid (2-6)

A solution of ester 2-5 (275 mg, 0.5378 mmol), TFA (5 ml) and CH$_2$Cl$_2$ (5 ml) was stirred at ambient temperature for 2.0 h. The solution was concentrated and then azeotroped with toluene. The residue was trituated with 10:0.5:0.5 EtOH/NH$_4$OH/H$_2$O, filtered, washed with EtOH and then washed with EtOH to furnish acid 2-6 as a white solid.

TLC R$_f$=0.34 (silica, 10:0.5:0.5 EtOH/NH$_4$OH/H$_2$O) $^1$H NMR (CD$_3$OD): δ 7.83 (d, J=9 Hz, 2H), 7.50 (d, J=9 Hz, 2H), 7.00 (d, J=9 Hz, 2H), 6.92 (d, J=9 Hz, 2H), 4.36 (s, 2H), 3.30 (m, 4H), 2.96 (m, 4H).

followed by CH$_3$I (29 μl, 0.47 mmol). After heating at 60° for 2.0 h, the reaction mixture was diluted with EtOAc and then washed with H$_2$O, 10% KHSO$_4$, brine, dried (MgSO$_4$) and concentrated. Flash chromatography (silica, 40% EtOAc/hexanes) furnished ester 3-1 as a yellow solid.

TLC R$_f$=0.45 (silica, 50% EtOAc/hexanes) $^1$H NMR (CDCl$_3$): δ 7.21 (d, J=9 Hz, 2H), 6.97 (d, J=9 Hz, 2H), 6.75 (d, J=9 Hz, 2H), 6.63 (d, J=9 Hz, 2H), 4.45 (s, 2H), 3.52 (bt, 4H), 3.43 (s, 3H), 3.13 (bt, 4H), 1.47 (s, 18H).

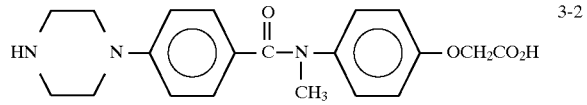

2-(4-(4-(1-Piperazinyl)phenylcarbonyl(N-methyl)amino) phenoxy)-acetic acid (3-2)

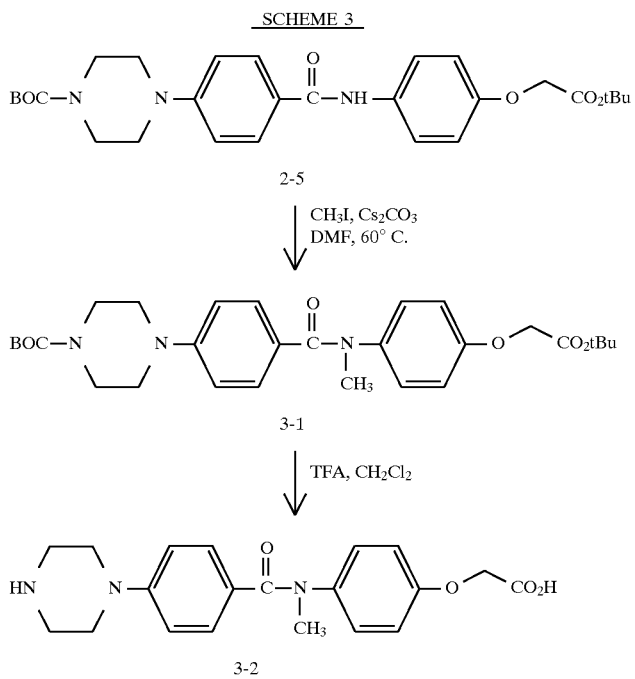

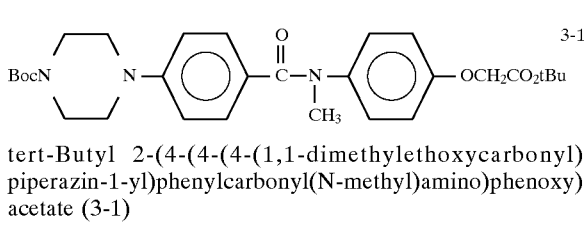

tert-Butyl 2-(4-(4-(4-(1,1-dimethylethoxycarbonyl) piperazin-1-yl)phenylcarbonyl(N-methyl)amino)phenoxy) acetate (3-1)

To a stirred solution of ester 2-5 (200 mg, 0.3911 mmol) was added cesium carbonate (318 mg, 0.9778 mmole)

A solution of ester 3-1 (190 mg, 0.3617 mmole), TFA (3 ml) and CH$_2$Cl$_2$ (3 ml) was stirred at ambient temperature for 30 minutes. The solution was concentrated and then azeotroped with toluene. Flash chromatography (silica, 10:0.2:0.2 EtOH/NH$_4$OH/H$_2$O) furnished acid 3-2 as a white solid.

TLC R$_f$=0.42 (silica, 10:0.2:0.2 EtOH/NH$_4$OH/H$_2$O) $^1$H NMR (CD$_3$OD): δ 7.25 (d, J=9 Hz, 2H), 7.06 (d, J=9 Hz, 2H), 6.91 (d, J=9 Hz, 2H), 6.82 (d, J=9 Hz, 2H), 4.66 (s, 2H), 3.50 (m, 4H), 3.41 (s, 3H), 3.35 (m, 4H).

SCHEME 4
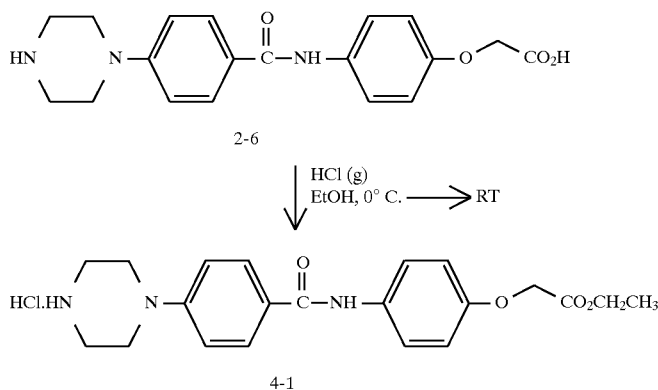
Ethyl 2-(4-(4-(1-piperazinyl)phenylcarbonylamino) phenoxy)acetate hydrochloride (4-1)
To a stirred solution of acid 2-6 (40 mg, 0.1125 mmol) and EtOH (2 ml) at 0° C. was bubbled HCl gas for 3 minutes. After 24 h at ambient temperature, the solution was concentrated to give ethyl ester 4-1 as a white solid.
$^1$H NMR (D$_2$O): δ 7.87 (d, J=9 Hz, 2H), 7.44 (d, J=9 Hz, 2H), 7.19 (d, J=9 Hz, 2H), 7.05 (d, J=9 Hz, 2H), 4.80 (s, 2H), 4.31 (q, J=7 Hz, 2H) 3.62 (m, 4H), 3.43 (m, 4H), 1.30 (t, J=7 Hz, 3H).
SCHEME 5
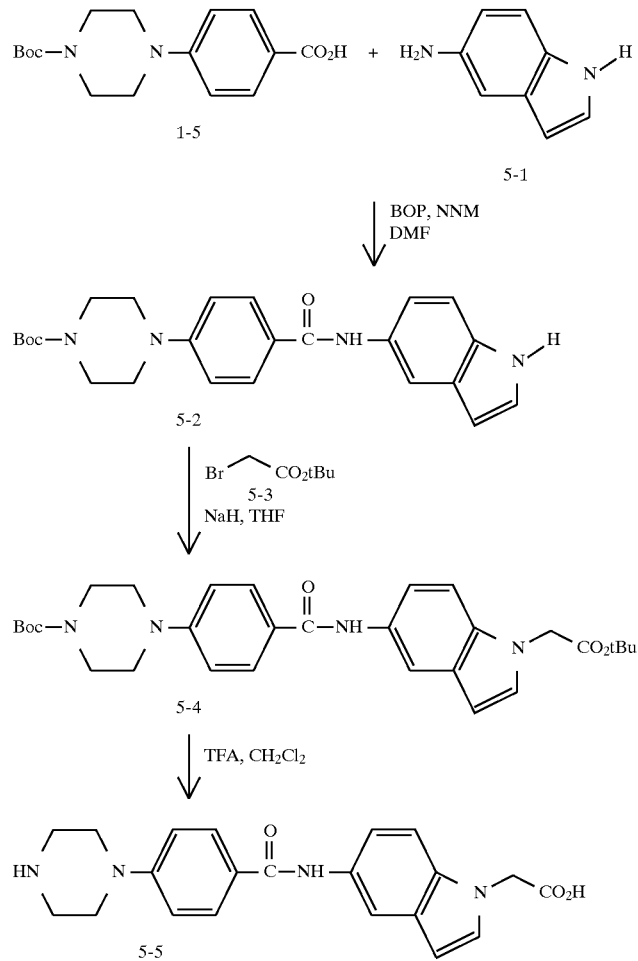

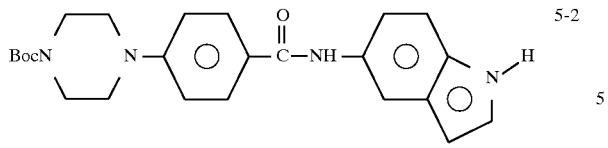

N-(5-Indolyl)-4-(4-(1,1-dimethylethoxycarbonyl)piperazin-1-yl)benzamide (5-2)

To a stirred solution of acid 2-1 (500 mg, 1.63 mmol), NMM (715 μl, 6.52 mmol) and DMF (5 ml) was added BOP reagent (1.08 g, 2.45 mmol). After 30 minutes, amine 5-1 (Aldrich 260 mg, 1.96 mmole) was added. After 18 h at 60° C., the solution was diluted with EtOAc and then washed with $H_2O$, brine, dried ($MgSO_4$) and concentrated. Flash chromatography (silica, 20% EtOAc/$CHCl_3$) afforded amide 5-2 as a yellow solid.

TLC $R_f$=0.13 (silica, 20% EtOAc/$CHCl_3$) $^1$H NMR (10% $CD_3OD/CDCl_3$): δ 7.90 (s, 1H), 7.83 (d, J=9 Hz, 2H), 7.63 (m, 2H), 7.22 (9s, 1H), 6.94 (d, J=9 Hz, 2H), 6.52 (d, J=3 Hz, 1H) 3.59 (m, 4H), 3.28 (m, 4H), 1.49 (s, 9H).

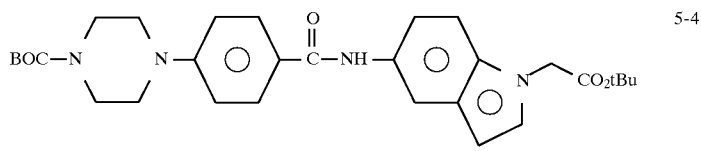

tert-Butyl 2-(5-(4-(4-(1,1-dimethylethoxycarbonyl)piperazin-1-yl)phenylcarbonylamino)indol-1-yl)acetate (5-4)

To a stirred solution of amide 5-2 (300 mg, 0.71 mmol) and THF (5 ml) was added NaH (60% dispersion in mineral oil; 29 mg, 0.7137 mmol). After 10 minutes, bromide 5-3 (115 μl, 0.71 mmol) was added. After 30 minutes, the solution was diluted with EtOAc and then washed with $H_2O$, brine, dried ($MgSO_4$) and concentrated. Flash chromatography (silica, 40% EtOAc/hexanes) afforded ester 5-4 as a yellow solid.

TLC $R_f$=0.18 (silica, 40% EtOAc/hexanes) $^1$H NMR: δ 7.92 (s, 1H), 7.83 (d, J=9 Hz, 2H), 7.77 (s, 1H), 7.39 (dd, J=9 Hz, 2 Hz, 1H), 6.93 (d, J=9 Hz, 2H), 6.52 (d, J=3 Hz, 1H), 4.72 (s, 2H), 3.60 (m, 4H), 3.28 (m, 4H), 1.49 (s, 9H), 1.43 (s, 9H).

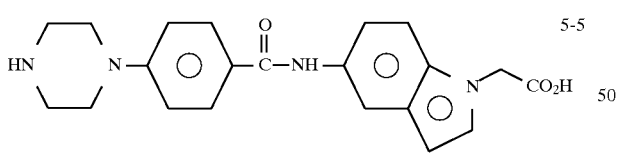

2-(5-(4-(1-Piperazinyl)phenylcarbonylamino)indol-1-yl)acetic acid (5—5)

To a stirred solution of ester 5-2 (250 mg, 0.4678 mmol), anisole (203 μl, 1.87 mmol) and $CH_2Cl_2$ (3 ml) at 0° C. was added TFA. After 30 min., the solution was concentrated and then azeotroped with toluene. Flash chromatography (silica, 10:0.1:0.1 EtOH/$NH_4O$/$H_2O$) afforded crude acid. The crude material was purified by prep HPLC to furnish acid 5—5.

TLC $R_f$=0.31 (silica, 10:0.5:0.5 EtOH/$NH_4OH/H_2O$) 1H NMR (50:50 $d_6$- DMSO/$D_2O$, 2 drops 1N NaOD): δ 7.87 (d, J=9 Hz, 2H), 7.71 (s, 1H), 7.24 (m, 3H), 7.07 (d, J=9 Hz, 2H), 6.47 (d, J=3 Hz, 1H), 4.63 (s, 2H), 3.25 (m, 4H), 2.89 (m, 4H).

SCHEME 6

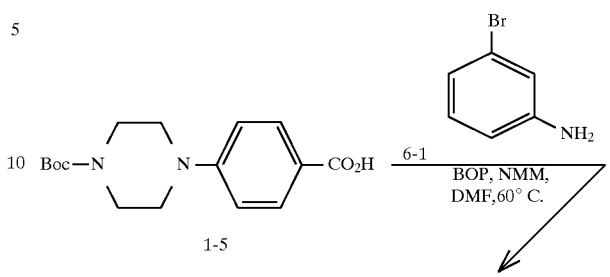

-continued
SCHEME 6

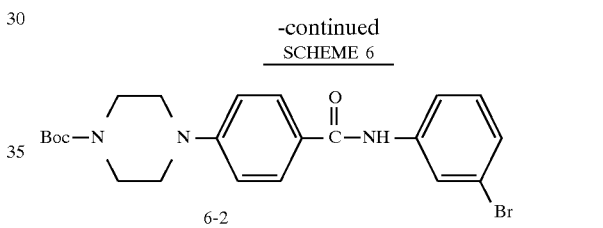

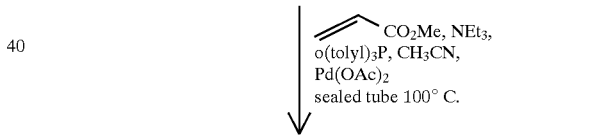

SCHEME 6 -continued

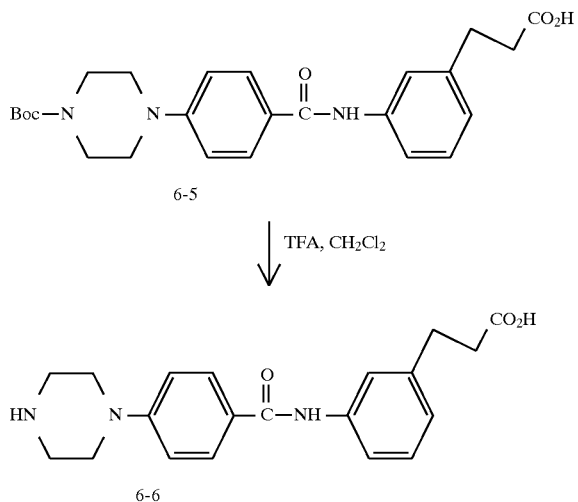

N-(3-bromophenyl)-4-(4-(1,1-dimethylethoxycarbonyl)piperazin-1-yl))benzamide (6-2)

A solution of acid 1-5 (400 mg, 1.31 mmol), amine 6-1 (248 mg, 1.44 mmol), BOP reagent (867 mg, 1.97 mmol), NMM (575 μl, 5.24 mmol) and DMF (10 ml) was heated to 60° C. for 72 h. The solution was diluted with EtOAc and then washed with $H_2O$, sat. $NaHCO_3$, 10% $KHSO_4$, brine, dried ($MgSO_4$) and concentrated. Flash chromatography (silica, 25% EtOAc/hexanes) furnished amide 6-2 as a yellow solid.

TLC $R_f$=0.31 (silica, 25% EtOAc/hexanes) $^1$H NMR ($CD_3OD$): δ 7.99 (s, 1H), 7.84 (d, J=9 Hz, 2H), 7.60 (m, 1H), 7.25 (m, 2H), 7.02 (d, J=9 Hz, 2H), 3.57 (m, 4H), 3.31 (m, 4H), 1.47 (s, 9H).

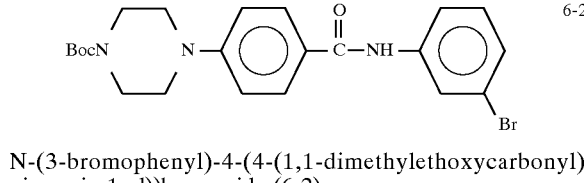

(E)-Methyl (3-(3-(4-(4-(1,1-dimethylethoxycarbonyl)piperazin-1-yl))phenyl)carbonylaminophenyl)prop-3-enoate (6-3)

A solution of amide 6-2 (400 mg, 0.86 mmol), methyl acrylate (783 μl, 8.69 mmole), O(tolyl)$_3$P (159 mg, 0.415 mmol), NEt$_3$ (245 μl, 1.74 mmole), Pd(OAc)$_2$ (20 mg, 0.069 mmole) and $CH_3CN$ (5 ml) was heated to 100° C. in a sealed tube for 18 h. The solution was diluted with EtOAc and then washed with $H_2O$, sat. $NaHCO_3$, 10% $KHSO_4$, brine, dried ($MgSO_4$) and concentrated. Flash chromatography (silica, 20%→30% EtOAc/hexanes) furnished olefin 6-3 as a yellow solid.

TLC $R_f$=0.47 (silica, 50% EtOAc/hexanes) $^1$H NMR ($CD_3OD$): δ 7.94 (s, 1H), 7.87 (dd, J=2 Hz, 9 Hz, 2H), 7.71 (m, 2H), 7.36 (m, 2H), 7.03 (dd, J=2 Hz, 9 Hz, 2H), 6.52 (d, J=16 Hz, 1H), 3.78 (s, 3H), 3.57 (m, 4H), 3.29 (m, 4H), 1.47 (s, 9H).

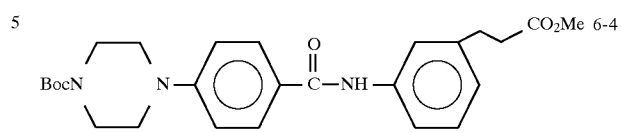

Methyl (3-(3-(4-(4-(1,1-dimethylethoxycarbonyl)piperazin-1-yl))phenyl)carbonylaminophenyl)propanoate (6-4)

A mixture of ester 6-3 (300 mg, 0.64 mmol), 10% Pd/C (100 mg) and EtOH (10 ml) was stirred under 1 atm $H_2$ for 18 h. The reaction mixture was filtered through a celite pad and concentrated to furnish ester 6-4 as a yellow oil.

$^1$H NMR ($CDCl_3$): δ 7.80 (m, 3H), 7.54 (s, 1H), 7.47 (d, J=8 Hz, 1H), 7.27 (m, 1H), 6.96 (d, 8 Hz, 1H), 6.92 (d, J=9 Hz, 2H), 3.68 (s, 3H), 3.60 (m, 4H), 3.29 (m, 4H), 2.96 (t, J=8 Hz, 2H), 2.66 (t, J=8 Hz, 2H), 1.50 (s, 9H).

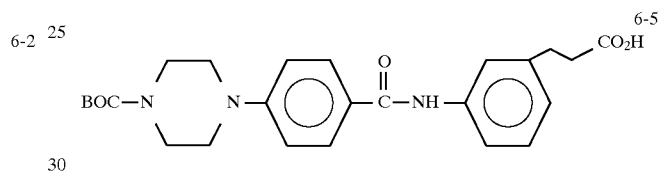

3-(3-(4-(4-(1,1-Dimethylethoxycarbonyl)piperazin-1-yl))phenyl)-carbonylaminophenyl)propanoic acid (6-5)

A solution of ester 6-4 (260 mg, 0.5563 mmol), 1N NaOH (1 ml, 1 mmol) and EtOH (3 ml) was stirred at ambient temperature for 1.0 h. The solution was acidified with 10% $KHSO_4$ and then extracted with EtOAc. The EtOAc phase was washed with brine, dried ($MgSO_4$) and concentrated to furnish acid 6-5 as a white solid.

TLC $R_f$=0.08 (silica, 10:0.2:0.2 $CH_2Cl_2$/MeOH/AcOH) $^1$H NMR ($CD_3OD$): δ 7.84 (d, J=9 Hz, 2H), 7.51 (m, 2H), 7.25 (t, J=8 Hz, 1H), 7.03 (m, 3H), 3.57 (m, 4H), 3.29 (m, 4H), 2.91 (t, J=8 Hz, 2H), 2.60 (t, J=8 Hz, 2H), 1.47 (s, 9H).

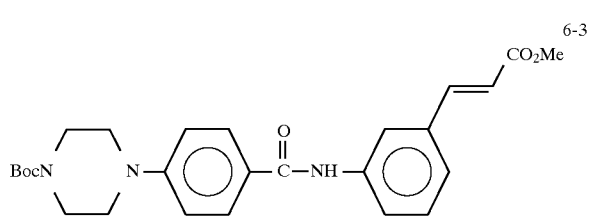

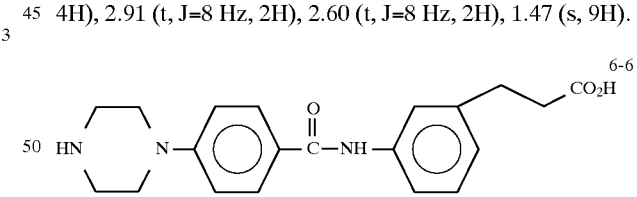

3-(3-(4-Piperazin-1-ylphenyl)carbonylamino)phenyl) propanoic acid (6-6)

A solution of acid 6—5 (210 mg, 0.4633 mmol), TFA (3 ml) and $CH_2Cl_2$ (3 ml) was stirred at ambient temperature for 1.0 h. The solution was concentrated and then azeotroped with toluene. Flash chromatography (silica, 10:0.1:0.1→10:0.5:0.5 EtOH/$NH_4OH$/$H_2O$) furnished acid 6—6 as a tan solid.

TLC $R_f$=0.59 (silica, 10:1:1 EtOH/$NH_4OH$/$H_2O$) $^1$H NMR ($D_2O$): δ 7.82 (d, J=9 Hz, 2H), 7.38 (m, 2H), 7.34 (s, 1H), 7.15 (d, J=9 Hz, 3H), 3.25 (m, 4H), 2.96 (m, 4H), 2.90 (t, J=8 Hz, 2H), 2.50 (t, J=8 Hz, 2H).

SCHEME 7

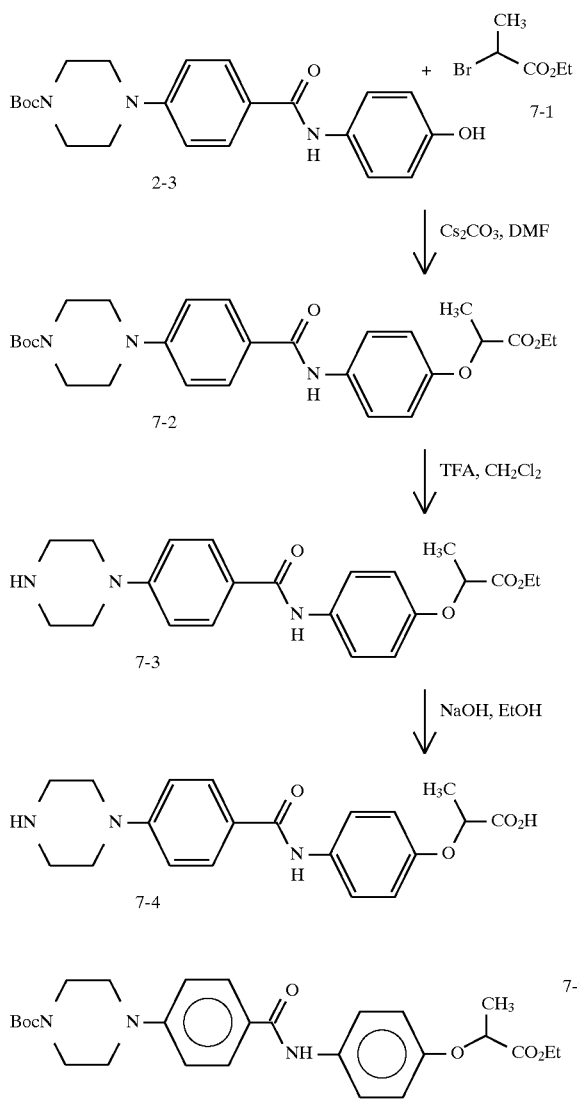

Ethyl 2-[4-(4-(4-(1,1-Dimethylethoxycarbonyl)piperazin-1-yl)phenylcarbonylamino)phenoxypropanoate (7-2)

Phenol 2-3 (381 mg, 0.993 mmol), ethyl 2-bromopropionate (7-1, 129 μl, 0.99 mmol), and $Cs_2CO_3$ (807 mg, 2.5 mmol) were combined in 5 mL DMF. After stirring overnight the reaction was diluted with EtOAc, washed with water (3×), 10% $KHSO_4$ (3×) and brine, dried ($MgSO_4$), filtered and concentrated. Flash chromatography (silica, 40% EtOAc/hexane) provided 7-2 as a white solid.

TLC $R_f$=0.41 (silica, 50% EtOAc/hexane) $^1$H NMR (400 MHz, $CDCl_3$): δ 7.78 (d, J=9 Hz, 2H), 7.60 (s, 1H), 7.52 (d, J=9 Hz, 2H), 6.92 (d, J=9 Hz, 2H), 6.89 (d, J=9 Hz, 2H), 4.72 (q, J=7 Hz, 1H), 4.22 (q, J=7 Hz, 2H), 3.59 (m, 4H), 3.28 (m, 4H), 1.61 (d, J=7 Hz, 3H), 1.49 (s, 9H), 1.26 (t, J=7 Hz, 3H).

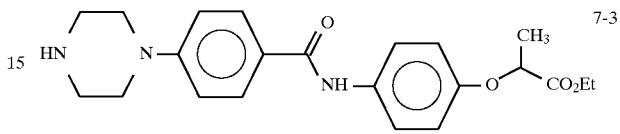

Ethyl 2-(4-(4-(piperazin-1-yl)phenylcarbonylamino)phenoxy)propanoate(7-3)

A solution of 7-2 (266 mg, 0.53 mmol) and anisole (200 μl, 1.8 mmol) in 5 mL 1:1 $CH_2Cl_2$/TFA was stirred for 20 min. After concentration and azeotroping with toluene, flash chromatography (silica, 33:1:1 EtOH/$H_2O$/$NH_4OH$) provided 7-3 as a white solid.

TLC $R_f$=0.37 (silica, 20:1:1 EtOH/$H_2O$/$NH_4OH$ $^1$H NMR (400 MHz, $CD_3OD$): δ 7.84 (d, J=9 Hz, 2H), 7.54 (d, J=9 Hz, 2H), 7.01 (d, J=9 Hz, 2H), 6.88 (d, J=9 Hz, 2H), 4.21 (q, J=7 Hz, 2H), 3.31 (m, 4H), 2.98 (m, 4H), 1.57 (d, J=7 Hz, 3H), 1.26 (t, J=Hz, 3H).

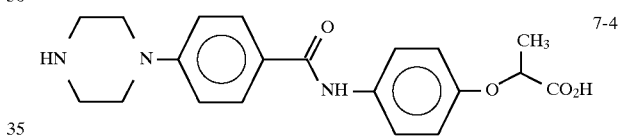

2-(4-(4-(Piperazin-1-yl)phenylcarbonylamino)phenoxy) propionic acid (7-4)

Ester 7-3 (44 mg, 0.11 nmmol) was dissolved in 1 mL EtOH, then 1M NaOH (122 μL, 0.12 mmol) was added. After 3 h the reaction was neutralized with 1N HCl, concentrated, then purified by flash chromatography (silica, 50:1:1 EtOH/$H_2O$/$NH_4OH$) providing 7-4 as a white solid.

TLC $R_f$=0.15 (silica, 50:1:1 EtOH/$H_2O$/$NH_4OH$) $^1$H NMR (400 MHz, $D_2O$): δ 7.69 (d, J=9 Hz, 2H), 7.22 (d, J=9H, 2H), 7.01 (d, J=9 Hz, 2H), 6.80 (d, J=9 Hz, 2H), 4.48 (q, J=7 Hz, 1H), 3.10 (m, 4H), 2.82 (m, 4H), 1.40 (d, J=7 Hz, 3H).

SCHEME 8

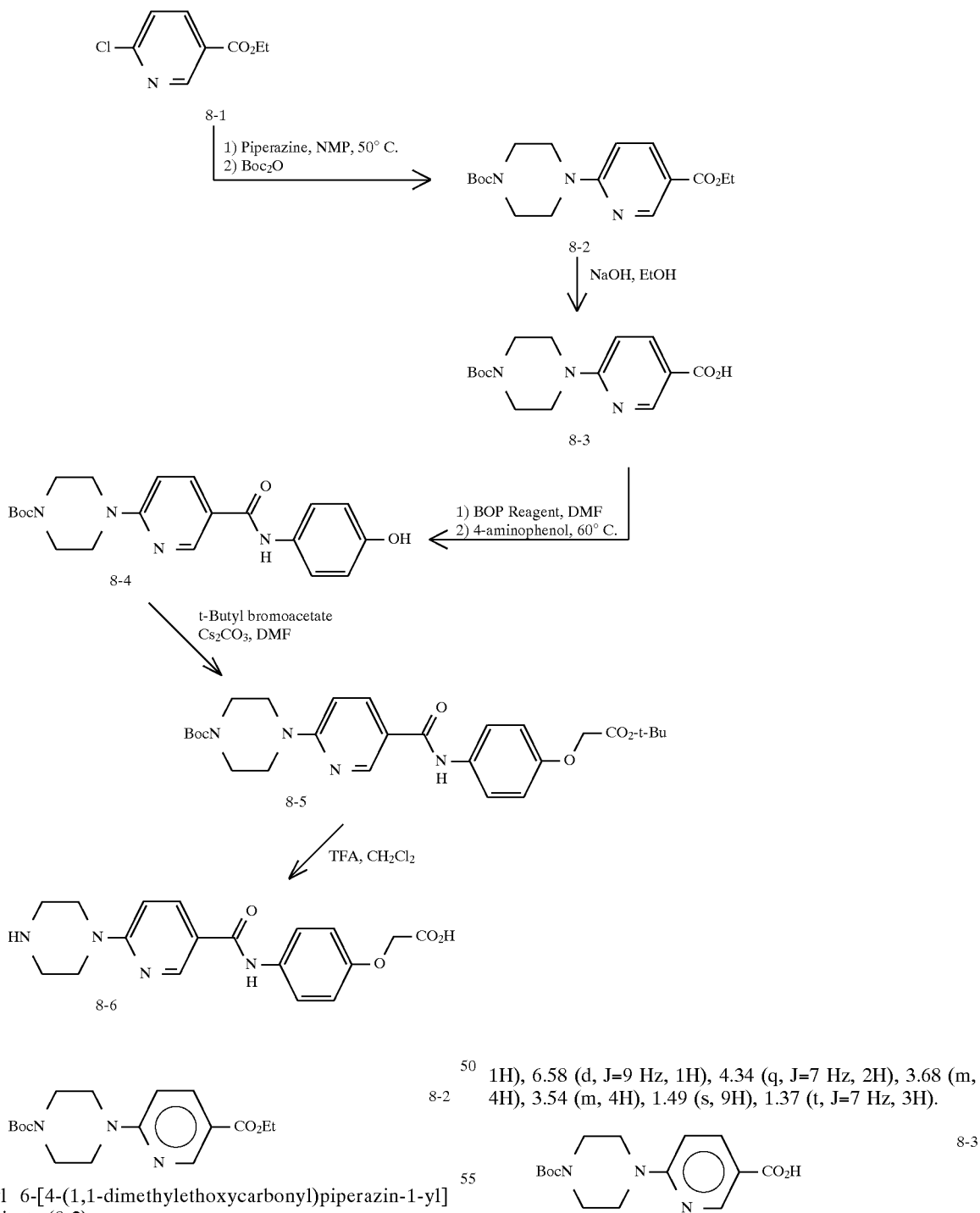

Ethyl 6-[4-(1,1-dimethylethoxycarbonyl)piperazin-1-yl]nicotinate (8-2)

Ethyl 6-chloronicotinate (8-1, Maybridge Chemical Co., 2.0 g, 10.9 mmol) and piperazine (1.4 g, 15 mmol) were combined in 54 mL NMP and heated at 50° C. overnight. After cooling, $Boc_2O$ (2.6 g, 11.9 mmol) was added. The reaction mixture was stirred overnight then diluted with EtOAc, washed with water, sat $NaHCO_3$ and brine, dried ($MgSO_4$), filtered and concentrated. Flash chromatography (silica, 25% EtOAc/hexane) provided 8-2 as a white solid.

TLC $R_f$=0.63 (silica, 40% EtOAc/hexane) $^1H$ NMR (400 MHz, $CDCl_3$): δ 8.80 (d, J=2 Hz, 1H), 8.04 (dd, J=9, 2 Hz, 1H), 6.58 (d, J=9 Hz, 1H), 4.34 (q, J=7 Hz, 2H), 3.68 (m, 4H), 3.54 (m, 4H), 1.49 (s, 9H), 1.37 (t, J=7 Hz, 3H).

6-[4-(1,1-Dimethylethoxycarbonyl)piperazin-1-yl]nicotinic acid (8-3)

Ester 8-2 (3.0 g, 9.3 mmol) was dissolved in 93 mL EtOH, 1M NaOH (23 mL, 23 mmol) was added, and the reaction mixture was stirred overnight. After concentrating, the residue was dissolved in water, washed with EtOAc, and the aqueous layer was acidified with 10% $KHSO_4$. After extracting with EtOAc, the organic layer was washed with brine, dried ($MgSO_4$), filtered and concentrated providing 8-3 as a white solid.

¹H NMR (400 MHz, CD₃OD): δ 8.71 (d, J=2 Hz, 1H), 8.08 (dd, J=9, 2 Hz, 1H), 6.77 (d, J=9 Hz, 1H), 3.61 (m, 4H), 3.53 (m, 4H), 1.49 (s, 9H).

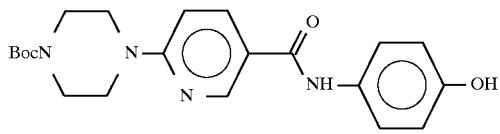

N-(4-Hydroxyphenyl)-6-(4-(1,1-dimethylethoxycarbonyl) piperazin-1-yl)nicotinamide (8-4)

Acid 8-3 (500 mg, 1.6 mmol), NMM (720 μL, 6.5 mmol) and BOP reagent (793 mg, 1.8 mmol) were combined in 8 mL DMF. After 1.5 h, 4-aminophenol (260 mg, 1.8 mmol) was added and the reaction was heated to 60° C. overnight. The reaction mixture was diluted with EtOAc, washed with water (5×), sat. NaHCO₃ and brine, dried (MgSO₄), filtered and concentrated. Flash chromatography (silica, 50–60% EtOAc/hexane) provided 8-4 as a brown solid.

TLC R$_f$=0.40 (silica, 70% EtOAc/hexane) ¹H NMR (400 MHz, CDCl₃): δ 8.66 (d, J=2 Hz, 1H), 7.98–7.95 (m, 2H), 7.33 (d, J=9 Hz, 2H), 6.75 (d, J=9 Hz, 2H), 6.58 (d, J=9 Hz, 1H), 3.61 (m, 4H), 3.52 (m, 4H), 1.48 (m, 9H).

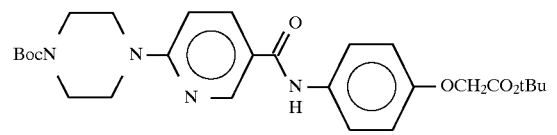

tert-Butyl 2-((4-(2-(4-(1,1-dimethylethoxycarbonyl) piperazin-1-yl)pyridin-5-yl)carbonylamino)phenoxy) acetate (8-5)

Phenol 8-4 (374 mg, 0.94 mmol), t-butyl bromoacetate (151 μL, 0.94 mmol) and Cs₂CO₃ (761 mg, 2.3 mmol) were combined in 5 mL DMF. After 90 min. the reaction mixture was diluted with EtOAc, washed with water (4×) and brine, dried (MgSO₄), filtered and concentrated. Flash chromatography (silica, 50% EtOAc/hexane) provided 8-5 as a brown solid.

TLC R$_f$=0.53 (silica, 70% EtOAc/hexane) ¹H NMR (400 MHz, CDCl₃): δ 8.66 (d, J=2 Hz, 1H), 7.99 (dd, J=9, 2 Hz, 1H), 7.56 (s, 1H), 7.52 (d, J=8 Hz, 2H), 6.90 (d, J=8 Hz, 2H), 6.65 (d, J=9 Hz, 1H), 4.51 (s, 2H), 3.68 (m, 4H), 3.56 (m, 4H), 1.49 (s, 18H).

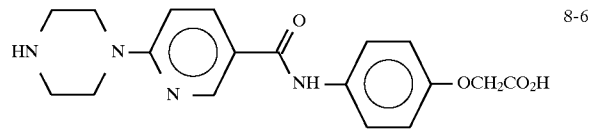

2-(4-(((2-Piperazin-1-yl)pyridin-5-yl)carbonylamino) phenoxy)acetic acid (8-6)

Ester 8-5 (290 mg, 0.57 mmol) was dissolved in 5 mL 1:1 TFA/CH₂Cl₂. After 1 h the reaction was concentrated and azeotroped with toluene. Flash chromatography (silica, 10:1:1 EtOH/H₂O/NH₄OH) and trituration with Et₂O provided 8-6 as a light brown solid. ¹H NMR (400 MHz, D₂O): δ 8.42 (d, J=2 Hz, 1H), 7.89 (dd, J=9, 2 Hz, 1H), 7.04 (d, J=8 Hz, 2H), 6.78 (d, J=9 Hz, 2H), 6.76 (d, J=10 Hz, 1H), 4.32 (s, 2H), 3.37 (m, 4H), 2.74 (m, 4H).

SCHEME 9

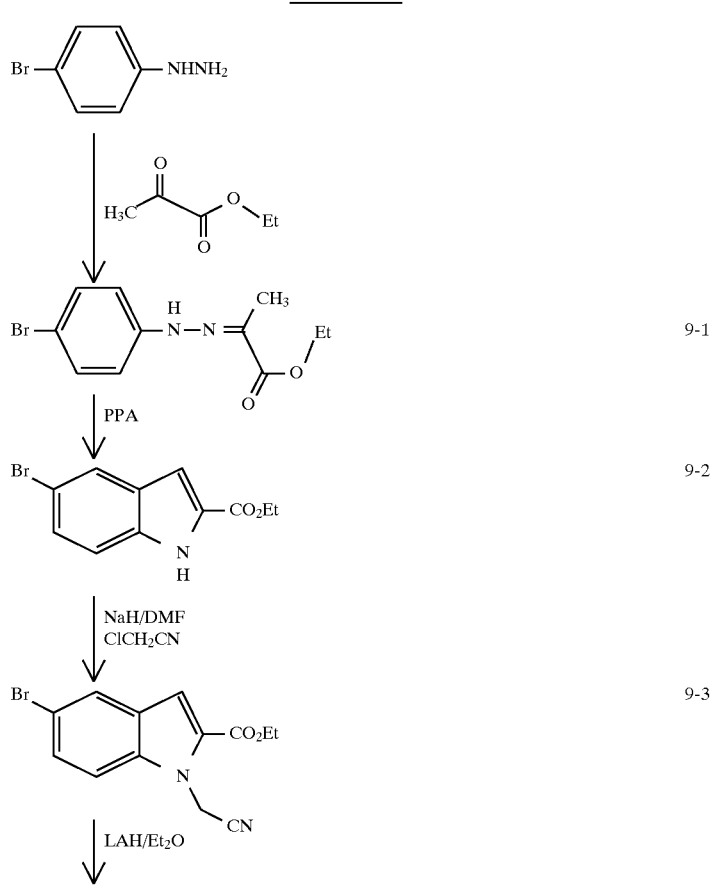

-continued
SCHEME 9
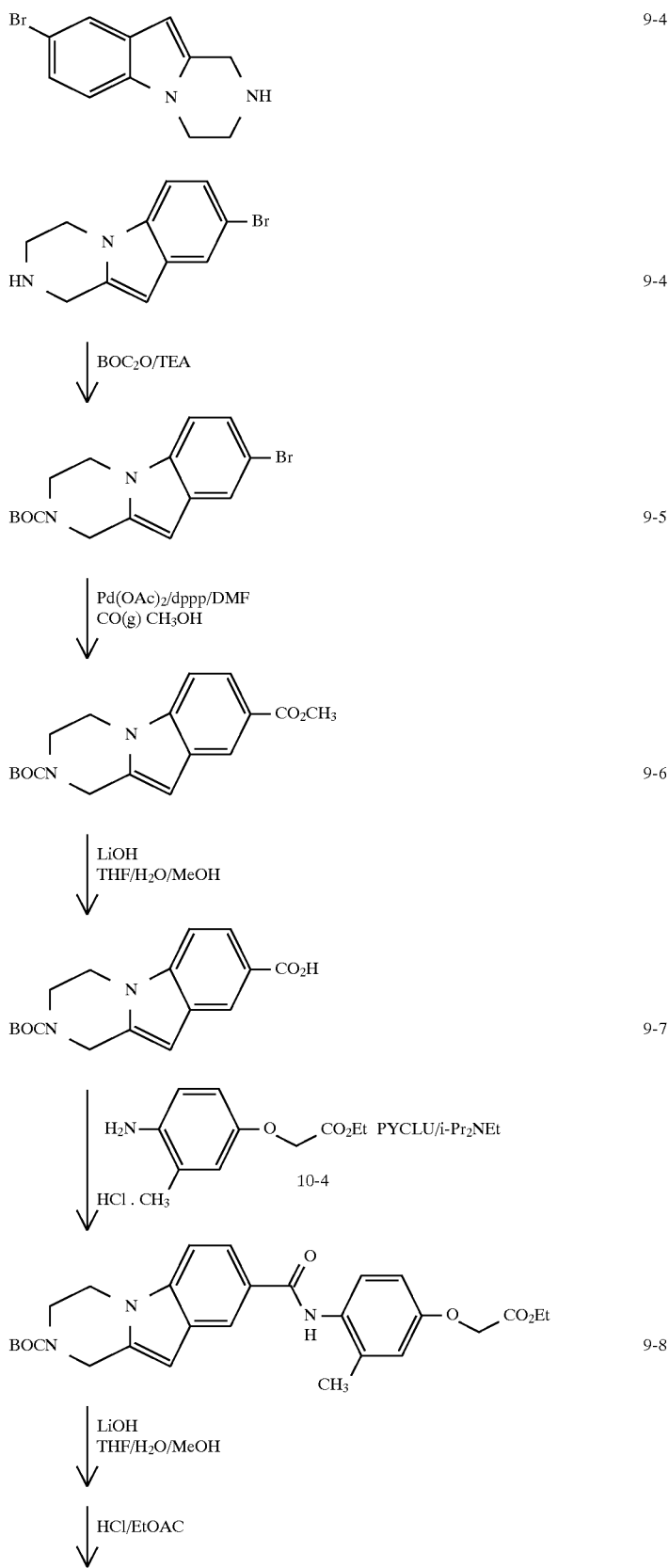

-continued
SCHEME 9
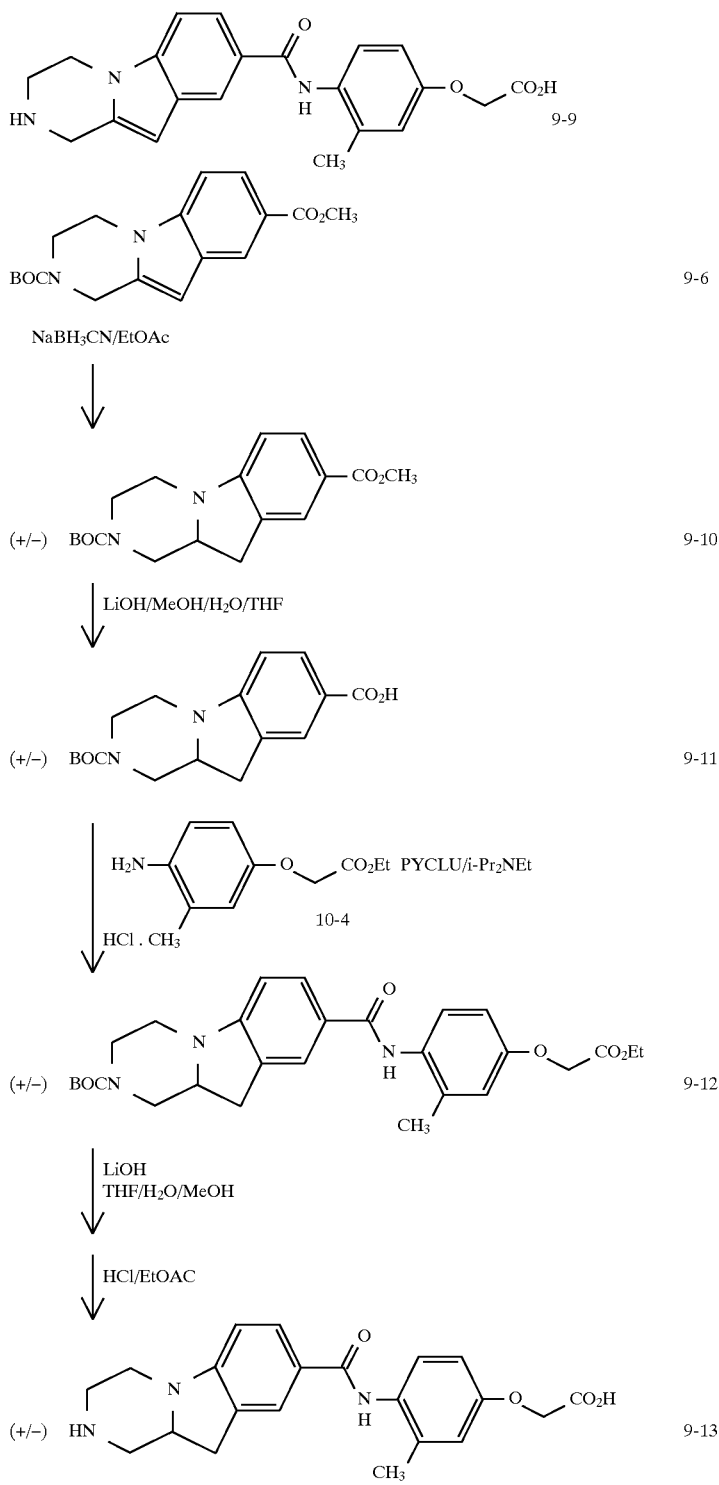

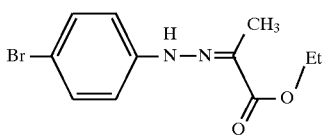

Ethyl 2-(4-bromo-1-hydrazinimine)propanoate 9-1

A mixture of 4-bromophenylhydrazine (Aldrich, 0.5 g, 2.2 mmol) and ethyl acetoacetate (Aldrich, 0.24 mL, 2.2 mmol) in pyridine (0.6 mL) was heated to reflux overnight. The reaction was cooled, diluted with water and the precipitate that resulted was collected and washed with water, dried under vacuum to give 9-1.

Rf(10% MeOH/CHCl$_3$ saturated with NH$_3$)=0.86 $^1$H NMR (400 MHz, CDCl$_3$) δ 7.64 (s, 1H), 7.41 (d, 2H), 7.39 (d, 2H), 4.30–4.34 (q, 2H), 2.10 (s, 3H), 1.36 (t, 3H).

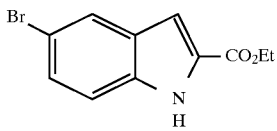

5-Bromo-2-ethoxycarbonyl indole 9-2

A mixture of 9-1 (0.54 g, 1.9 mmol) and polyphosphoric acid (1.6 mL) was heated to 115° C. for 10 minutes, then diluted with cold water and extracted with EtOAc. The layers were separated and the aqueous layer extracted with EtOAc. The organic layers were combined, washed with brine, dried with MgSO$_4$, filtered and concentrated to give 9-2 as a brown solid.

Rf(30% EtOAc/hexanes)=0.45 $^1$H NMR (400 MHz, CDCl$_3$) δ 8.95(bs, 1H), 7.82 (s, 1H), 7.41 (d, 1H), 7.30 (d, 1H), 7.15 (s, 1H), 4.44 (q, 2H), 1.40 (t, 3H).

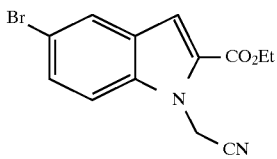

1-(Cyanomethyl)-2-ethoxycarbonyl-5-bromo-indole 9-3

A solution of 9-2 (11.2 g, 44.4 mmol) in DMF (400 mL) was treated with NaH (3.2 g of 60% dispersion in oil, 66.6 mmol) for 0.5 hour and then chloroacetonitrile (Aldrich, 5.6 mL, 88.8 mmol) was added and the reaction was stirred overnight. The solvent was removed in vacuo and the residue was partitioned between water and EtOAc. The water layer was extracted with EtOAc, the organic layers were combined, washed with water, brine, dried with MgSO$_4$, filtered and evaporated to give 9-3 as a brown solid.

Rf(30% EtOAc/hexanes)=0.46 $^1$H NMR (400 MHz, CDCl$_3$) δ 7.82–7.83 (bs, 1H), 7.51–7.54 (dd, 1H), 7.30–7.32 (bd, 2H), 5.60 (s, 2H), 4.41–4.43 (q, 2H), 1.41–1.43 (t, 3H).

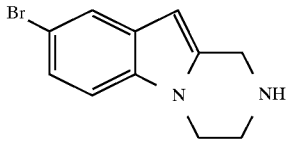

8-Bromo-2,3,4,5-tetrahydropyrazino-[1,2-a]indole 9-4

A slurry of 9-3 (12.2 g, 39.7 mmol) in diethyl ether (400 mL) was added via dropping funnel to a solution of LAH in ether (79.4 mL, 1M in ether, 79.4 mmol) and stirred at room temperature overnight. The slurry was diluted with saturated sodium potassium tartrate (Rochelle's salt) and stirred for 15 minutes, then transferred to a separatory funnel containing EtOAc and the layers separated. The aqueous layer was extracted with EtOAc, the organic layers were combined, washed with water, brine, dried with MgSO$_4$, filtered and evaporated to give 9-4 as a brown solid.

Rf(10% MeOH/CHCl$_3$ saturated with NH$_3$)=0.42 $^1$H NMR (400 MHz, CDCl$_3$) δ 8.38–8.41 (bs, 1H), 7.66 (s, 1H), 7.21–7.22 (dd, 2H), 7.14 (d, 2H), 6.14 (s, 1H), 4.22 (s, 2H), 3.99 (t, 2H), 3.36–3.37 (t, 2H).

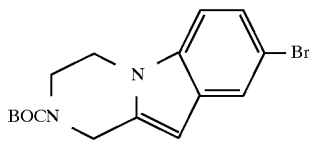

8-Bromo-3-(1,1-dimethylethoxycarbonyl)-2,3,4,5-tetrahydropyrazino-[1,2-a]indole 9-5

A solution of 9-4 (10 g, 40 mmol) in CH$_2$Cl$_2$ (200 mL) was cooled to 0° C. and treated with di-tertbutyldicarbonate (8.7 g, 40 mmol) and triethylamine (5.6 mL, 40 mmol). The solution was allowed to warm slowly and after 48 hours was concentrated and the residue dissolved in EtOAc, washed with water and brine, dried over Na$_2$SO$_4$, filtered and evaporated. The residue was chromatographed (30% EtOAc/hexanes) to give 9-5 as a solid.

Rf(30% EtOAc/hexanes)=0.22 $^1$H NMR (400 MHz, CDCl$_3$) δ 7.67 (d, 1H), 7.23 (d, 1H), 7.13 (d, 1H), 6.21 (s, 1H), 4.80 (s, 2H), 4.04 (t, 2H), 3.93 (t, 2H), 1.50 (s, 9H).

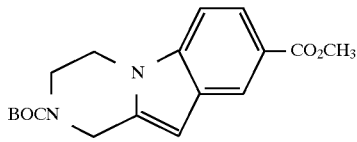

8-Methoxycarbonyl-3-(1,1-dimethylethoxycarbonyl)-2,3,4,5-tetrahydropyrazino-[1,2-a]indole 9-6

A solution of 9-5 (3.0 g, 8.5 mmol) in MeOH (60 mL) and DMSO (20 mL) was treated with triethylamine (3.55 mL, 25.5 mmol), 1,3-Bis(diphenylphosphino)propane (1.75 g, 4.25 mmol) and palladium (II) acetate (0.952 g, 4.25 mmol). Carbon monoxide was bubbled through the solution while it was heated to reflux for 2 hours. The reaction was heated at reflux overnight under a balloon atmosphere of carbon monoxide. Additional 1,3-Bis(diphenylphosphino)propane (0.8 g, 2.12 mmol) and palladium acetate (0.476 g, 2.12 mmol) were added and the reaction was heated at reflux for 48 hours under a balloon atmosphere of carbon monoxide. The reaction was cooled to room temperature, the residue was partitioned between water and EtOAc. The water layer was extracted with EtOAc, the organic layers were combined, washed with water, brine, dried with MgSO$_4$, filtered and evaporated. The residue was chromatographed (25% EtOAc/hexanes) to give 9-6 as a yellow solid.

Rf(30% EtOAc/hexanes)=0.21 $^1$H NMR (400 MHz, CDCl$_3$) δ 8.32 (s, 1H), 7.90 (d, 1H), 7.26 (d, 1H), 6.38 (s, 1H), 4.83 (s, 2H), 4.12 (t, 2H), 3.96–3.93 (m, 5H), 1.50 (s, 9H).

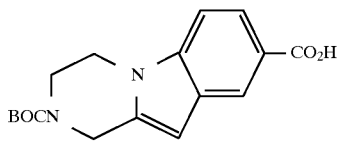

3-(1,1-dimethylethoxycarbonyl)-2,3,4,5-tetrahydropyrazino-[1,2-a]indole-8-carboxylic acid 9-7

A slurry of 9-6 (150 mg, 0.454 mmol) in THF/H$_2$O/MeOH was treated with LiOH (38.2 mg, 0.91 mmol) and stirred for 1 hour. TLC indicated no reaction. LiOH (38.2 mg.) was added and the reaction mixture (still a slurry) was stirred for an additional hour with no reaction. The reaction mixture was concentrated to dryness and dissolved in MeOH and H₂O. LiOH (114 mg) was added and the reaction mixture was stirred and heated to 75° for 3 hours and stirred at RT for 16 hours resulting in a complete reaction. The reaction mixture is diluted with EtOAc and 10% citric acid. The layers are separated and the organic layer is washed with water and brine, dried, filtered and concentrated to give 9-7 as a white solid. ¹H NMR (400 MHz; CDCl₃) δ 8.40 (s, 1H), 7.95(d, 1H), 7.32 (d, 1H), 6.41 (s, 1H), 4.84 (s, 2H), 4.14–4.11 (m, 2H), 3.96 (m, 2H), 1.50 (s, 9H).

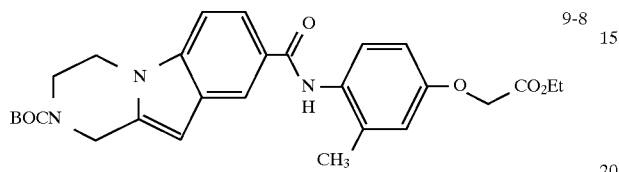

9-8

Ethyl 4-((3-(1,1-dimethylethoxycarbonyl)-2,3,4,5-tetrahydropyrazino-[1,2-a]indole-8-yl)carbonylamino)-3-methylphenoxyacetate 9-8

A solution of 9-7 (110 mg, 0.35 mmol) and 10-4 (85.7 mg, 0.35 mmol) in CH₂Cl₂ were treated with diisopropylethylamine and PYCLU as described for 23-5 to give 9-8 as a white solid after chromatography in 50% EtOAC/Hexane.

Rf (50% EtOAc/Hexane) 0.34 ¹H NMR (400 MHz, CDCl₃) δ 8.12 (s, 1H), 7.8–7.65 (m, 2H), 7.59 (s, 1H), 7.36 (d, 1H), 6.84 (m, 2H), 6.39 (s, 1H), 4.85 (s, 2H), 4.62 (s, 2H), 4.29–4.27 (q, 2H), 4.15–4.13 (t, 2H), 3.96 (t, 2H), 2.33 (s, 3H), 1.50 (s, 9H), 1.33–1.31 (t, 3H).

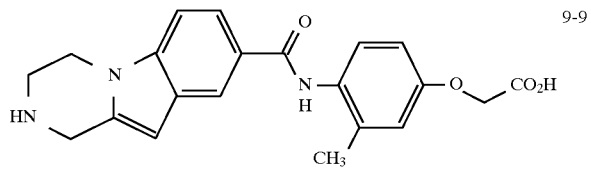

9-9

4-((2,3,4,5-tetrahydropyrazino-[1,2-a]indole-8-yl) carbonylamino)-3-methylphenoxyacetic acid 9—9

A slurry of 9-8 (0.15 mmol, 75 mg) and THF/H₂O/MeOH was treated with LiOH (13 mg, 0.30 mmol) and stirred for 1 hour. The reaction mixture was diluted with EtOAC and 10% citric acid. The layers were separated and the organic layer was washed with H₂O and brine. The organic layer was dried, filtered and concentrated to give desired acid as a white solid. This solid is slurried in EtOAc, cooled to –78° and saturated with HCl. The reaction mixture is warmed to 0° and stirred for 15 min. The reaction mixture was concentrated to yield a white solid which was taken up in a EtOAc/hexane/ether mixture and filtered. The solids were washed with ether to give 9—9 as a white solid.

Rf 10/1/1 EtOH/NH₄OH/H₂O) 0.16 ¹H NMR (400 MHz; D₂O) δ 8.09 (s, 1H), 7.62–7.60 (d, 1H), 7.45 (d, IH), 7.14–7.12 (d, 1H), 6.84 (d, 1H), 6.79–6.76 (dd, 1H), 6.35 (s, 1H), 4.40 (s, 2H), 4.07–4.02 (m, 4H), 3.23–3.22 (t, 2H), 2.15 (s, 3H).

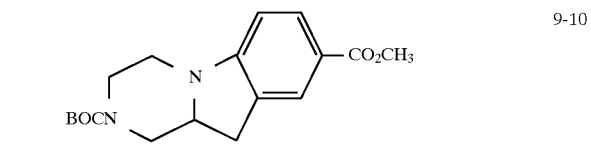

9-10

(+/−) 8-Methoxycarbonyl-3-(1,1-dimethylethoxycarbonyl)-1,1a,2, 3,4,5-hexahydropyrazino-[1,2-a]indole 9-10

9-6 (0.091 mmol, 30 mg) was dissolved in EtOAc and cooled to 0° C. NaBH₃CN (0.45 mmol, 28 mg) was added portion-wise and the reaction was warmed to room temperature for 15 min. The reaction mixture was basified with saturated NaHCO₃ and extracted into EtOAc. The organic layer was washed with brine, dried (MgSO₄), filtered and concentrated to yield 9-10 as a colorless oil.

Rf (2:1 hexane/ EtOAc)=0.4 ¹H NMR (400 MHz; CDCl₃) δ 7.83–7.82 (d, 1H), 7.73 (s, 1H), 6.40–6.38 (d, 1H), 4.15–4.0 (bs, 2H), 3.85 (s, 3H), 3.60–3.56 (m, 2H), 0.305–2.65 (m, 4H), 2.60–2.58 (dd, 1H), 1.50 (s, 9H).

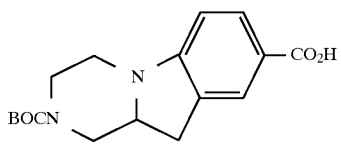

9-11

(+/−) 3-(1,1-Dimethylethoxycarbonyl)-1,1a,2,3,4,5-hexahydropyrazino-[1,2-a]indole-8-carboxylic acid 9-11

9-10 (0.90 mmol, 300 mg) was slurried in THF/H₂O/MeOH (2 mL/2/2). LiOH (1.8 mmol, 76 mg) was added and the reaction mixture was heated to 50° C. After 0.5 hours, the reaction mixture became homogeneous, and was then stirred at room temperature for an additional 2 hours. The reaction mixture was diluted with 10% citric acid and EtOAc. The layers were separated, and the organic layer was washed with H₂O and brine. Drying (MgSO₄), filtering and concentrating gave 9-11 as a yellow solid.

Rf (97/3/1 CHCl₃/MeOH/HOAC)=0.70 ¹H NMR (400 MHz; CDCl₃) δ 7.90 (d, 1H), 7.87 (s, 1H), 6.41–6.39 (d, 1H), 4.25–4.0 (bs, 2H), 3.65–3.57 (m, 2H), 3.10–3.0 (dd, 1H), 3.02–2.98 d, 1H), 2.98–2.91 (bs, 1H), 2.69–2.66 (bs, 1H), 2.62–2.60 (dd, 1H), 1.50 (s, 9H).

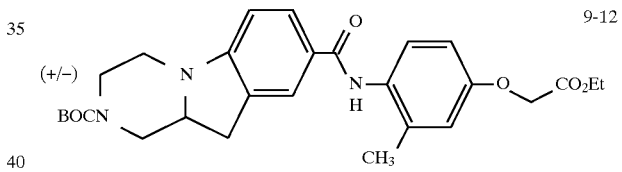

9-12

(+/−) Ethyl 4-((3-(1,1-Dimethylethoxycarbonyl)-1,1a,2,3,4,5-hexahydro-pyrazino-[1,2-a]indole-8-yl)carbonylamino)-3-methylphenoxyacetate 9-12

A solution of 9-11 (250 mg, 0.79 mmol) and 10-4 (193 mg, 0.79 mmol) in CH₂Cl₂ were treated with diisopropylethylamine and PYCLU as described for 23-5 to give 9-12 as a white solid after chromatography in 50% EtOAC/ Hexane.

Rf (50% EtOAc/Hexane) 0.35 ¹H NMR (400 MHz, CDCl₃) δ 7.70–7.63 (m, 3H), 7.36 (s, 1H), 6.82–6.76 (m, 2H), 6.45–6.43 (d, 1H), 4.60 (s, 2H), 4.30–4.25 (q, 2H), 4.21–4.09 (bs, 2H), 3.59–3.57 (m, 2H), 3.10–3.09 (m, 1H), 3.05–2.51 (m, 3H), 2.78–2.60 (m, 1H), 2.29 (s, 3H), 1.50 (s, 9H), 1.32–1.29 (t,3H).

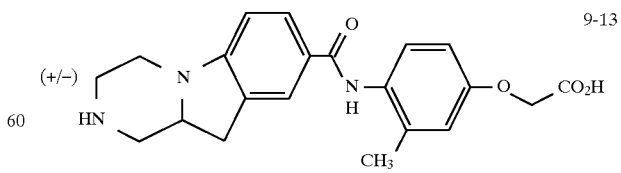

9-13

(+/−) 4-((3-(1,1-Dimethylethoxycarbonyl)-1,1a,2,3,4,5-hexahydropyrazino-[1,2-a]indole-8-yl)carbonylamino)-3-methylphenoxyacetic acid 9-13

A slurry of 9-12 (0.25 mmol, 125 mg) and THF/H₂O/MeOH was treated with LiOH (21 mg, 0.50 mmol) and heated to 80° for 1 hour. The reaction mixture was diluted with EtOAC and 10% citric acid. The layers were separated and the organic layer was washed with H₂O and brine. The organic layer was dried, filtered and concentrated to give desired acid as a white solid. This solid is slurried in EtOAc, cooled to −78° and saturated with HCl. The reaction mixture is warmed to 0° and stirred for 15 min. The reaction mixture was concentrated and the white solid triturated with ether to give 9-13 as a white solid.

Rf 10/1/1 EtOH/NH₄OH/H₂O) 0.3 ¹H NMR (400 MHz, D₂O) δ 7.70–7.67 (d, 1 H), 7.63 (s, 1 H), 7.11–7.09 (d, 1H), 6.86 (d, 1H), 6.78–6.76 (dd, 1H), 6.69–6.68 (d, 1H), 4.57 (s, 2H), 3.93–3.90 (bd, 2H), 3.39–3.31 (m, 3H), 3.19–3.07 (m, 3H), 2.74–2.68 (dd, 1H).

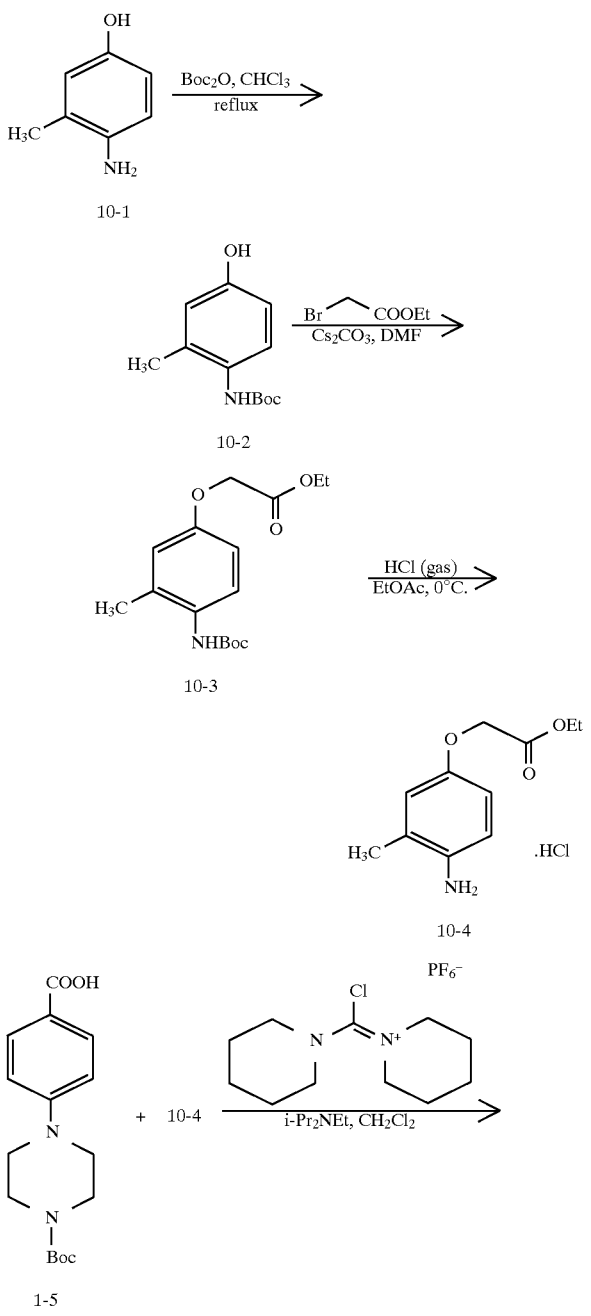

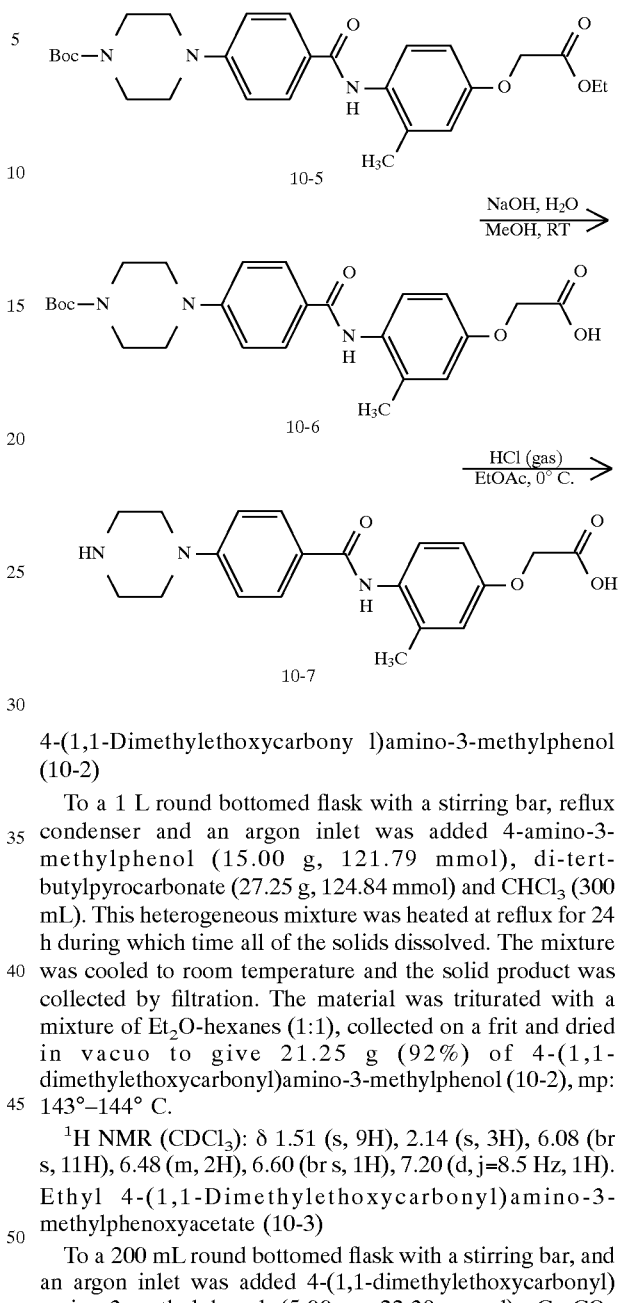

4-(1,1-Dimethylethoxycarbony l)amino-3-methylphenol (10-2)

To a 1 L round bottomed flask with a stirring bar, reflux condenser and an argon inlet was added 4-amino-3-methylphenol (15.00 g, 121.79 mmol), di-tert-butylpyrocarbonate (27.25 g, 124.84 mmol) and CHCl₃ (300 mL). This heterogeneous mixture was heated at reflux for 24 h during which time all of the solids dissolved. The mixture was cooled to room temperature and the solid product was collected by filtration. The material was triturated with a mixture of Et₂O-hexanes (1:1), collected on a frit and dried in vacuo to give 21.25 g (92%) of 4-(1,1-dimethylethoxycarbonyl)amino-3-methylphenol (10-2), mp: 143°–144° C.

¹H NMR (CDCl₃): δ 1.51 (s, 9H), 2.14 (s, 3H), 6.08 (br s, 11H), 6.48 (m, 2H), 6.60 (br s, 1H), 7.20 (d, j=8.5 Hz, 1H).

Ethyl 4-(1,1-Dimethylethoxycarbonyl)amino-3-methylphenoxyacetate (10-3)

To a 200 mL round bottomed flask with a stirring bar, and an argon inlet was added 4-(1,1-dimethylethoxycarbonyl) amino-3-methylphenol (5.00 g, 22.39 mmol), Cs₂CO₃ (14.59 g, 44.78 mmol), DMF (50 mL), and ethyl bromoacetate (2.61 mL, 23.51 mmol). This mixture was stirred vigorously at ambient temperature for 24 h. The mixture was filtered through a frit and the DMF was removed under high vacuum. The residue was dissolved in EtOAc (300 mL) and washed with H₂O (2×) and brine (1×). Drying (MgSO₄), filtration, and removal of the solvent in vacuo gave a solid. This material was triturated with 5% Et₂O-hexane, the solid was collected by filtration and dried in vacuo to give 5.40 g (78%) of ethyl 4-(1,1-dimethylethoxycarbonyl)amino-3-methylphenoxyacetate as a white, crystalline solid.

¹H NMR (CDCl₃): δ 1.29 (t, j=7.2 Hz, 3H), 1.51 (s, 9H), 2.22 (s, 3H), 4.26 (q, j=7.2 Hz, 2H), 4.57 (s, 2H), 6.08 (br s, 1H), 6.72 (m, 2H), 7.56 (s, 1H).

Ethyl 4-amino-3-methylphenoxyacetate, hydrochloride (10-4)

To a 500 mL round bottomed flask with a gas dispersion tube was added a solution of ethyl 4-(1,1-dimethylethoxycarbonyl)amino-3-methylphenoxyacetate (5.31 g, 17.13 mmol) in EtOAc (200 mL). This solution was cooled in an ice bath and dry HCl gas was sparged through the solution, vigorously, for 10 min. The resulting mixture was aged for 15 min. at 0° C. The excess HCl gas was removed with a stream of argon and the solvent was removed in vacuo. The product was triturated with 50 mL of EtOAc and collected on a frit. The crystals were washed with additional EtOAc and dried in vacuo to give 4.21 g (100%) of ethyl 4-amino-3-methylphenoxyacetate, hydrochloride as white crystals, mp: 198°–200° C.

$^1$H NMR (DMSO-d$_6$): δ 1.21 (t, j=7.1 Hz, 3H), 2.33 (s, 3H), 4.17 (q, j=7.1 Hz, 2H), 4.78 (s, 2H), 6.82 (dd, j=3,9 Hz, 1H), 6.92 (d, j=3 Hz, 1H), 7.39 (d, j=9 Hz, 1H), 10.21 (br s, 3H).

Ethyl 2-(4-(4-(4-(1,1-dimethylethoxycarbonyl)piperazin-1-yl)phenylcarbonylamino)-3-methylphenoxy)acetate (10-5)

To a 100 mL round bottomed flask with a stirring bar and an argon inlet was added 4-(4-(1,1-dimethylethoxycarbonyl)piperazinyl)benzoic acid (0.75 g, 2.45 mmol), ethyl 4-amino-3-methylphenoxyacetate hydrochloride (0.60 g, 2.45 mmol), chloro-N,N,N',N',-bis(pentamethylene)formamidinium hexafluorophosphate (0.97 g, 2.69 mmol), and CH$_2$Cl$_2$ (30 mL). This mixture was cooled in an ice bath and diisopropylethylamine (1.74 mL, 10.0 mmol) was added. The ice bath was allowed to expire and the solution was stirred at ambient temperature for 48 h. The solution was diluted with CHCl$_3$ and washed with 10% aqueous citric acid, saturated aqueous NaHCO$_3$, and brine. Drying (MgSO$_4$), filtration and removal of the solvent in vacuo gave an oil. This material was chromatographed on 75 g of silica gel using 50% EtOAc-hexane as eluant. There was obtained 1.22 g (100%) of ethyl 2-(4-(4-(4-(1,1-dimethylethoxycarbonyl)piperazin-1-yl)phenylcarbonylamino)-3-methylphenoxy)acetate as a crystalline solid.

$^1$H NMR (CDCl$_3$): δ 1.30 (t, j=7.1 Hz, 3H), 1.49 (s, 9H), 2.27 (s, 3H), 3.27 (m, 4H), 3.59 (m, 4H), 4.26 (q, j=7.1 Hz, 2H), 4.59 (s, 2H), 6.75 (m, 2H), 6.90 (d, j=8.8 Hz, 2H), 7.54 (br s, 1H), 7.65 (m, 1H), 7.79 (d, j=8.8 Hz, 2H).

2-(4-(4-(4-(1,1-Dimethylethoxycarbonyl)piperazin-1-yl)phenylcarbonylamino)-3-methylphenoxy)acetic acid (10-6)

To a 100 mL round bottomed flask with a stirring bar and an argon inlet was added ethyl 2-(4-(4-(4-(1,1-dimethylethoxycarbonyl)piperazin-1-yl)phenylcarbonylamino)-3-methylphenoxy)acetate (1.22 g, 2.45 mmol) and 20 mL of CH$_3$OH. To this solution was added aqueous NaOH (10 mL of a 1N solution). The mixture was stirred at ambient temperature for 18 h. The mixture was neutralized with 10 mL of 1N HCl and diluted with H$_2$O. The product was collected on a frit and washed with a little H$_2$O. This material was dried in vacuo to give 0.953 g (83%) of 2-(4-(4-(4-(1,1-dimethylethoxycarbonyl)piperazin-1-yl)phenylcarbonylamino)-3-methylphenoxy)acetic acid as a white solid.

$^1$H NMR (CDCl$_3$): δ 1.49 (s, 9H), 2.26 (s, 3H), 3.27 (m, 4H), 3.58 (m, 4H), 4.57 (s, 2H), 6.74 (m, 2H), 6.90 (d, j=8.5 Hz, 2H), 7.60 (m, 1H), 7.65 (m, 1H), 7.79 (d, j=8.5 Hz, 2H).

2-(4-(4-(1-Piperazinyl)phenylcarbonylamino)-3-methylphenoxy)acetic acid, dihydrochloride (10-7)

To a 200 mL round bottomed flask equipped with a stirring bar and a gas dispersion tube was added 2-(4-(4-(4-(1,1-dimethylethoxycarbonyl)piperazin-1-yl)phenylcarbonylamino)-3-methylphenoxy)acetic acid (0.95 g, 2.03 mmol) and 100 mL of dry EtOAc. This well stirred suspension was cooled in an ice bath and HCl gas was sparged through the solution for 15 min. This mixture was aged 30 min. at 0° C. then the excess HCl was removed with a stream of argon and the EtOAc was removed in vacuo. The product was triturated with EtOAc, collected on a frit and dried in vacuo to give 895 mg of 2-(4-(4-(1-piperazinyl)phenylcarbonylamino)-3-methylphenoxy)acetic acid, dihydrochloride, mp: >250° C.

$^1$H NMR (DMSO-d$_6$): δ 2.16 (s, 3H), 3.20 (m, 4H), 3.54 (m, 4H), 4.66 (s, 2H), 6.72 (d, j=3 Hz, 1H), 6.75 (s, 1H), 7.06 (d, j=9.0 Hz, 2H), 7.15 (d, j=3.0 Hz, 1H), 7.90 (d, j=9.0 Hz, 2H), 9.43 (br s, 1H), 9.56 (s, 1H).

SCHEME 11

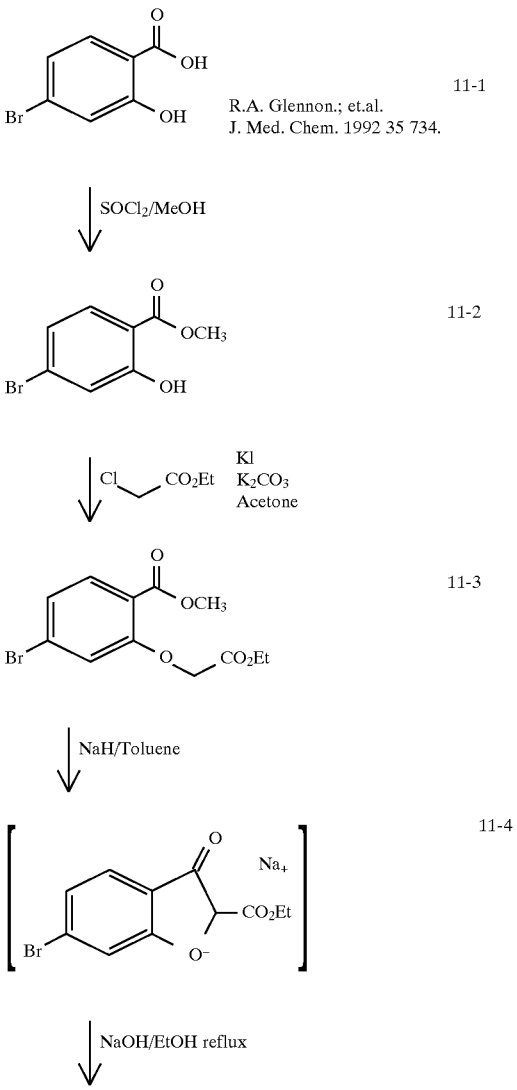

-continued
SCHEME 11
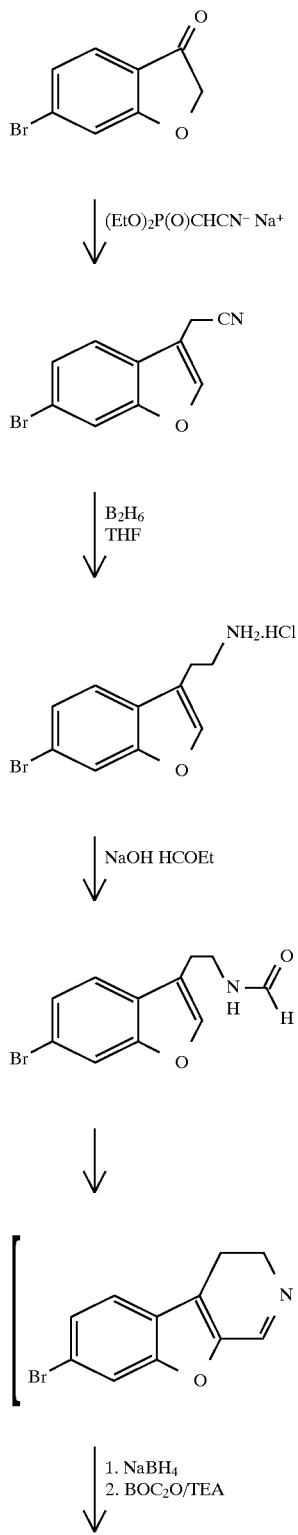
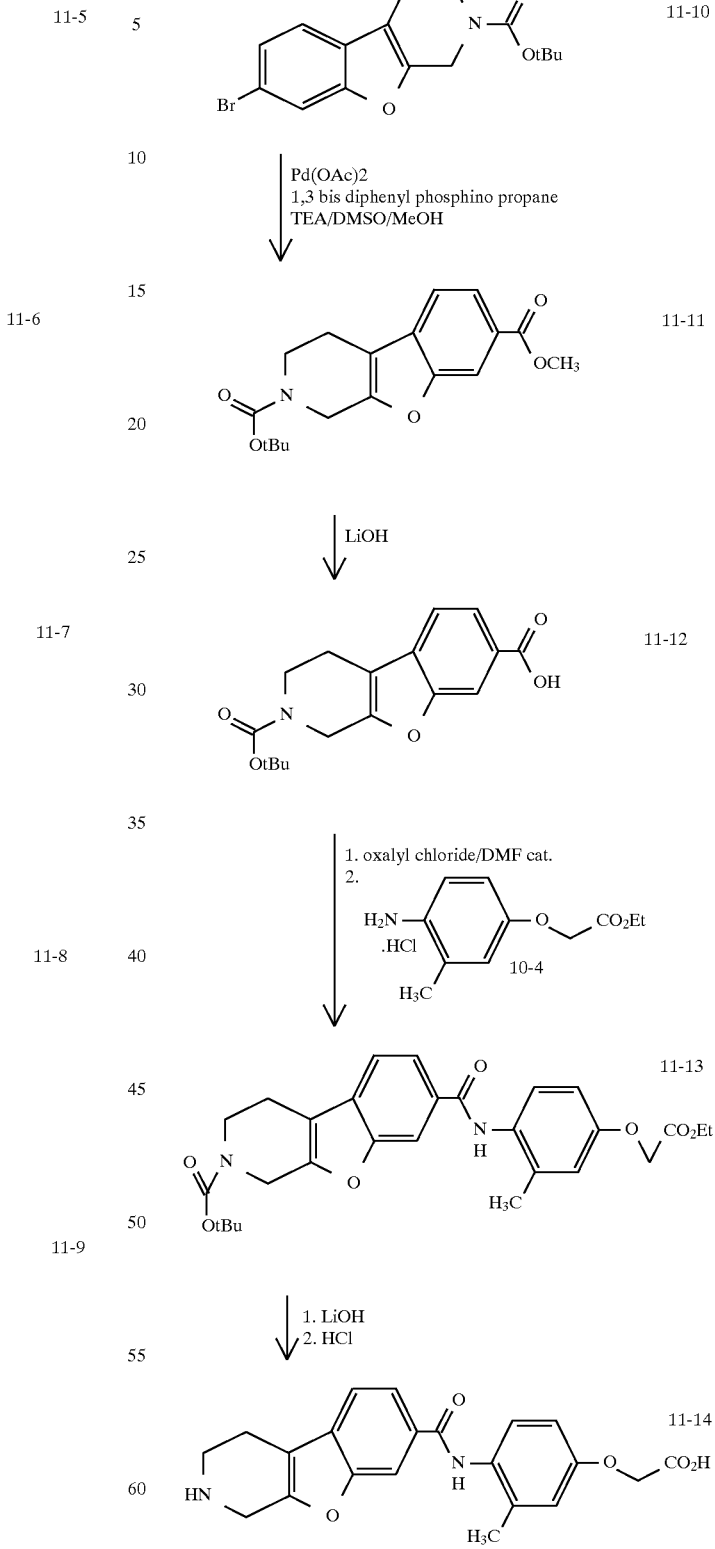

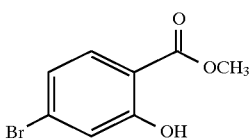

11-2

Methyl 4-bromo-2-hydroxy benzoate 11-2

200 mL of MeOH was cooled to 0° C. and treated dropwise with thionyl chloride (30 mL, 0.4 mole) so that the reaction temperature was kept below 15° C. throughout the addition. A solution of 11-1 (12.7 g, prepared by the method of R. Glannon et al., *J. Med. Chem.* 1992 35, 734, 0.0585 mol) in 50 mL MeOH was added to the reaction and the mixture was warmed to room temperature and stirred for 48 hours, then heated to 60° C. for 7 hours. The volatile components were removed under high vacuum and the residue chromatographed (silica, gradient straight hexanes to 10% EtOAc/Hexanes) to give 11-2 as a bright yellow oil that solidified on standing.

Rf (5% EtOAc/Hexanes) 0.6 $^1$H NMR (400 MHz, CDCl$_3$) δ 10.8 (s, 1H), 7.68 (d, 1H), 7.19 (s, 1H), 7.03 (d, 1H), 3.95 (s, 3H).

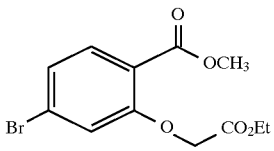

11-3

Methyl 4-Bromo-2-(ethyl acet-2-yloxy)-benzoate 11-3

A solution of 11-2 (26.6 g, 0.115 mole) in acetone (80 mL) was treated with chloroethylacetate (14 g, 0.115 mole), potassium iodide (3 g, 0.018 mole), and potassium carbonate (31.7 g, 0.23 mole) and heated to 50° C. with vigorous stirring for 2 hours. The suspension was filtered, evaporated to dryness, resuspended in ether, re-filtered and concentrated to give 11-3 as a golden-brown oil.

Rf (10% EtOAc/Hexanes) 0.11 $^1$H NMR (400 MHz, CDCl$_3$) δ 7.7 (d, 1H), 7.2 (d, 1H), 7.04 (s, 1H), 4.7 (s, 2H), 4.3 (q, 2H), 3.9 (s, 3H), 1.3 (t, 3H).

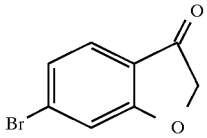

11-5

6-Bromo-benzofuran-3-one 11-5

Sodium hydride (5.52 g, 60% dispersion in oil, 0.138 mole) was placed in a 3 L vessel equipped with an overhead stirrer, argon line, reflux condenser and addition funnel. Toluene (215 mL) was added and the solution heated to reflux. A solution of 11-3 (36.3 g, 0.115 mole) in 100 mL toluene was added dropwise over 1.5 hours to give an orange suspension. The reaction was heated for an additional 3 hours, then cooled to room temperature and filtered through a glass-fiber filter. The cake was washed with 500 mL Et$_2$O and dried under vacuum to give 11-4 as a sandy orange solid (streaks from baseline in 30% EtOAc/Hexanes). A suspension of 11-4 (5 g, 0.016 mol) in EtOH (20 mL) was added to a solution of NaOH (4 g, 0.1 mole) in H$_2$O (35 mL). The reaction was heated to reflux for 1.25 hours, then cooled and the volatile components removed under vacuum. The residue was suspended in 200 mL 6N HCl and 200 mL CHCl$_3$ and stirred vigorously for 0.5 hours. The layers were separated and the aqueous layer was washed with CHCl$_3$. The organic layers were combined, dried with MgSO$_4$, filtered and evaporated to give 11-5 as a deep red solid.

Rf (20% EtOAc/Hexanes) 0.61 $^1$H NMR (400 MHz, CDCl$_3$) δ 7.53 (d, 1H), 7.35 (s, 1H), 7.24 (d, 1H), 4.64 (s, 2H).

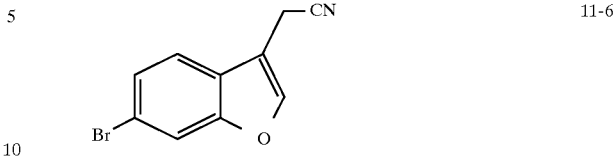

11-6

(6-Bromo-benzofuran-3-yl)-acetonitrile 11-6

Sodium hydride (0.7 g, 0.0173 mol) was washed with hexanes then suspended in THF (8 mL). Diethyl cyanomethylphosphonate (3.07 g, 0.0173 mol) was added dropwise and stirred 10 minutes to give clear yellow solution. A solution of 11-5 (3.38 g, 0.0158 mol) in THF (20 mL) was added dropwise, the solution stirred for 0.5 hour, then heated to reflux for 0.5 hour. A solution of 6N HCL (3.4 mL) was added and the THF was removed under vacuum. The concentrated solution was diluted with Et$_2$O and washed with 4×30 mL 6N HCl, the ether layer was dried (MgSO$_4$), filtered and evaporated. The residue was chromatographed (20% EtOAc/Hexanes) to give 11-6 as an orange solid.

Rf (20% EtOAc/Hexanes) 0.45 $^1$H NMR (400 MHz, CDCl$_3$) δ 7.7 (s, 1H), 7.65 (s, 1H), 7.45 (s, 2H), 3.75 (s, 2H).

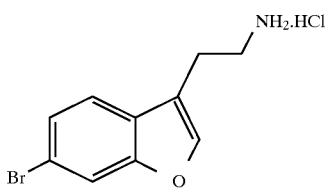

11-7

2-(6-Bromo-benzofuran-3-yl)-ethylamine 11-7

A solution of 11-6 (10.9 g, 0.0462 mol) in THF (100 mL) was cooled to 0° C. and treated dropwise with BH$_3$/THF solution (1Molar, 110.8 mL, 0.11 mol). The cold bath was removed and the reaction stirred overnight. MeOH was carefully added (20 mL) and the solvent removed under vacuum. The residue was dissolved in 50 mL MeOH and 400 mL MeOH saturated with HCl and heated to reflux for 3 hours. The volatile components were removed under vacuum and the residue was suspended in Et$_2$O. A bright yellow solid percipitated and was collected and washed five times with Et$_2$O, then dried under vacuum to give 11-7 as a tan solid.

Rf (5% MeOH/ CHCl$_3$ saturated with NH$_3$) 0.23 $^1$H NMR (400 MHz, CD$_3$OD) δ 7.72 (s, 2H), 7.6 (d, 1H), 7.45 (d, 1H), 3.25 (m, 2H), 3.06 (m, 2H).

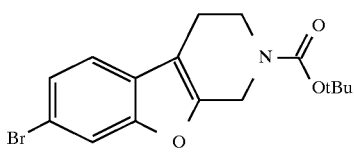

11-10

7-bromo-2-(1,1-dimethylethoxycarbonyl)-1,2,3,4-tetrahydro-9H-pyrido[3,4-b]benzofuran 1 1-10

A solution of 11-7 (11.8 g, 0.043 mol) in MeOH (150 mL) was diluted with CHCl$_3$ (400 mL) and washed with 75 mL 1N NaOH. The aqueous layer was backwashed with CHCl$_3$, the organic layers were combined, evaporated, and the residue azeotroped with toluene to remove residual water. The resulting brown oil was treated with 200 mL ethyl formate and brought to reflux for 1.5 hours until the solution was homogenous. The solvent was removed, the residue was dissolved in 200 mL CHCl$_3$, washed with 30 mL 1N HCl, brine, dried over MgSO$_4$, filtered and evaporated to give 11-8 as a solid that was used without further purification. Rf (5% MeOH/ CHCl$_3$ saturated with NH$_3$) 0.47

$^1$H NMR (400 MHz, CD$_3$OD) δ 8.04 (s, 1H), 7.67 (s, 1H), 7.63 (s, 1H), 7.55 (d, 1H), 7.4 (d, 1H), 3.53 (m, 2H), 2.4 (m, 2H). Solid 11-8 was crushed and placed in a flask equipped with an overhead stirrer. Polyphosphoric acid (20 mL) and CHCl$_3$ (5 mL) was added and the reaction heated to 80° C. for 1.5 hours. The reaction was removed from the oil bath and 250 mL H$_2$O, 30 mL NH$_4$OH, and 200 mL CHCl$_3$ was added and stirred vigorously. The resulting opaque mixture was transferred to a separatory funnel, the layers separated, and the aqueous layer was extracted repeatedly with CHCl$_3$. The organic layers were combined, filtered through a pad of SolkaFloc, dried over Na2SO$_4$, filtered and evaporated to give the intermediate cyclic imine (11-9) as a pale yellow foam. A 5 g sample of this material (0.02 mol) was dissolved in 200 mL MeOH and 20 mL 1N HCl. Sodium borohydride (1.5 g, 0.04 mol) was added in portions. After 0.5 hours the solvent was removed and the residue was partitioned between saturated NaHCO$_3$ and CHCl$_3$. The aqueous layer was extracted with CHCl$_3$, the organic layers were combined, dried (Na$_2$SO$_3$) and filtered to give a clear yellow solution. (Rf amine (5% MeOH/ CHCl$_3$ saturated with NH$_3$) 0.45). Di-tert-butyl dicarbonate (4.5 g, 0.02 mol) and TEA (2.8 mL, 0.02 mol) were added and the solution stirred overnight, then washed with 10% KHSO$_4$. The organic layer was evaporated and the residue was chromatographed in 10% EtOAc/Hexanes to give 11-10 as a white solid.

Rf (20% EtOAc/Hexanes) 0.60 $^1$H NMR (400 MHz, CDCl$_3$) δ 7.6 (s, 1H), 7.35 (d, 1H), 7.3 (d, 1H), 4.56 (bs, 2H), 3.75 (bs, 2H), 2.7 (bs, 2H), 1.5 (s, 9H).

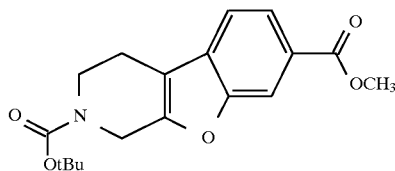

Methyl 2-(1,1-dimethylethoxycarbonyl)-1,2,3,4-tetrahydro-9H-pyrido[3,4-b]benzofuran-7-yl carboxylate 11-11

A solution of 11-10 (1 g, 2.84 mmol), 1,3 di-phenyl phosphino propane (0.35 g, 0.852 mmol) in DMSO/MeOH (1:1, 15 mL) was treated with TEA (1.5 mL, 10.7 mmol) and thouroughly purged with carbon monoxide, then treated with Pd(OAc)$_2$ (0.191 g, 0.852 mmol) and warmed to 80° C. After heating overnight, the reaction was cooled, treated with an additional amount of 1,3 di-phenyl phosphino propane (0.35 g, 0.852 mmol), re-purged with carbon monoxide and treated with an additional amount of Pd(OAc)$_2$ (0.191 g, 0.852 mmol). After heating for three days the reaction was evaporated, partitioned between water and CHCl$_3$, and the water layer washed with CHCl$_3$. The organic layers were combined, dried over MgSO$_4$, filtered through a sintered glass filter and concentrated. The residue was chromatographed (silica, gradient 5% EtOAc/Hexanes to 10% EtOAc/Hexanes) to give 11-11 as a yellow oil. Rf (20% EtOAc/Hexanes) 0.5 $^1$H NMR (400 MHz, CDCl$_3$) δ 8.13 (s, 1H), 7.96 (d, 1H), 7.48 (d, 1H), 4.6 (bs, 2H), 3.95 (s, 3H), 3.75 (bs, 2H), 2.75 (bs, 2H), 1.5 (s, 9H).

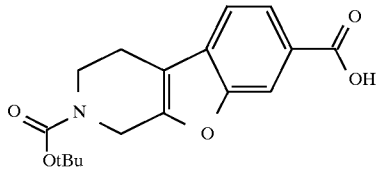

2-(1,1-dimethylethoxycarbonyl)-1,2,3,4-tetrahydro-9H-pyrido[3,4-b]benzofuran-7-yl carboxylic acid 11-12

A solution of 11-11 (0.79 g, 2.38 mmol) in 1:1 THF/MeOH (30 mL) was treated with LiOH (0.95 g, 23.8 mmol) in 10 mL of H$_2$O and heated to 30° C. overnight. The solvents were removed under vacuum and the residue was dissolved in H$_2$O and acidified with 10% KHSO$_4$ and extracted with EtOAc. The organic layer was dried over MgSO$_4$, filtered and evaporated to give 11-12 as an off-white solid.

Rf (97:3:1 CHCl$_3$/MeOH/HOAc) 0.27 $^1$H NMR (400 MHz, CDCl$_3$) δ 8.2 (s, 1H), 8.0 (d, 1H), 7.50 (d, 1H), 4.65 (bs, 2H), 3.8 (bs, 2H), 2.75 (bs, 2H), 1.52 (s, 9H).

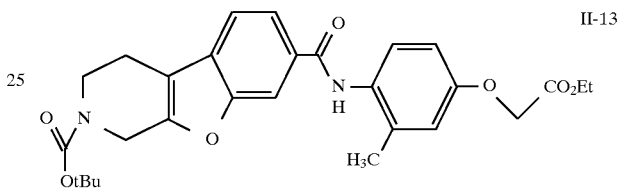

Ethyl 4-(2-(1,1-dimethylethoxycarbonyl)-1,2,3,4-tetrahydro-9H-pyrido[3,4-b]benzofuran-7-yl)carbonylamino)-3-methylphenoxyacetate 11-13

A solution of 11-12 (0.1 g, 0.321 mmol) in CH$_2$Cl$_2$ (10 mL) was treated with oxalyl chloride (0.06 mL, 0.7 mmol) and two drops of DMF. After stirring at room temperature for 0.5 hours, the reaction was diluted with benzene and evaporated. The resulting acid chloride was dissolved in CHCl$_3$ (5 mL) and treated with 10-4 (0.075 g, 0.26 mmol), then cooled to 0° C. and treated with diisopropylethylamine (0.167 mL, 0.3 nrnol). The reaction was warmed to room temperature and stirred overnight, then evaporated, partitioned between EtOAc and 10% KHSO$_4$, and the EtOAc layer was washed again with 10% KHSO$_4$. The EtOAc layer was washed with brine, dried over MgSO$_4$, filtered and evaporated to give 11-13.

Rf (60% EtOAc/Hexanes) 0.64 $^1$H NMR (400 MHz, CDCl$_3$) δ 8.0 (s, 1H), 7.73 (m, 2H), 7.62 (s, 1H), 7.53 (d, 1H), 6.85 (s, 1H), 6.8 (m, 1H), 4.62 (d, 2H), 4.61 (s, 2H), 4.29 (q, 2H), 3.68 (bs, 2H), 2.75 (bs, 2H), 2.30 (s, 3H), 1.5 (s, 9H), 1.3 (t, 3H).

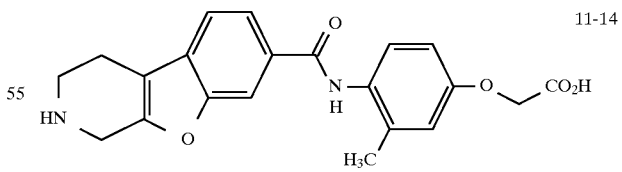

4-(2-(1,1-dimethylethoxycarbonyl)-1,2,3,4-tetrahydro-9H-pyrido[3,4-b]benzofuran-7-yl)carbonylamino)-3-methylphenoxy acetic acid 11-14

A solution of 11-13 (0.145 g, 0.285 mmol) in 1:1 THF/MeOH (6 mL) was treated with LiOH (0.114 g, 28.5 mmol) dissolved in 6 mL of H$_2$O. After stirring for 1 hour at room temperature the solvents were removed, the residue dissolved in H$_2$O/EtOAc/10% KHSO$_4$ and the layers separted. The water layer was washed with EtOAc, the organic layers were combined, dried, and filtered to give the intermediate acid as a yellow oil. This material was dissolved in EtOAc (10 mL), cooled to −78° C., the solution saturated with HCl gas and warmed to 0° C. for 0.5 hours, then concentrated and dried under vacuum to give 11-14 as fluffy solid.

Rf (9:1:1 EtOH/H$_2$O/NH$_4$OH) 0.78 $^1$H NMR (400 MHz, D$_2$O) δ 7.84 (s, 1H), 7.65 (d, 1H), 7.5 (d, 1H), 7.1 (d, 1H), 6.81 (s, 1H), 6.72 (d, 1H), 4.28 (s, 2H), 3.8 (bs, 2H), 2.96 (m, 2H), 2.6 (bs, 2H), 2.13 (s, 3H).

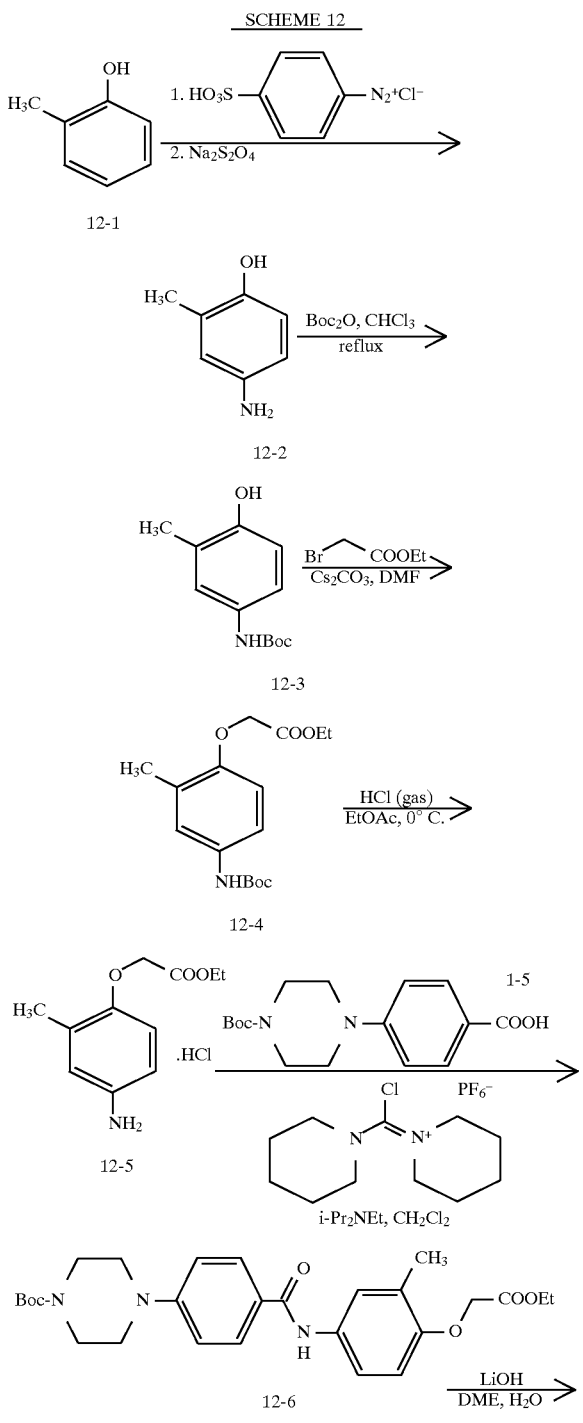

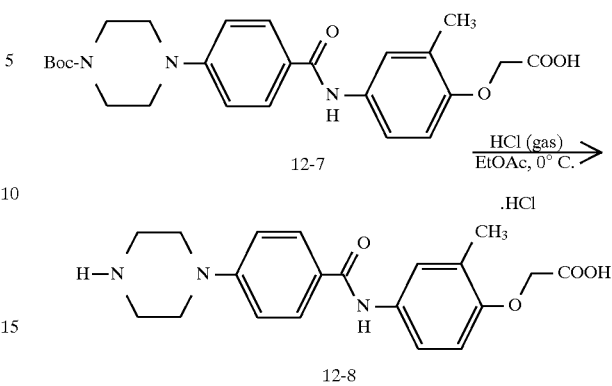

2-Methyl-3-aminophenol (12-2)

To a 500 mL erlenmeyer flask was added sulfanilic acid (14.38 g, 83 mmol), sodium carbonate (4.29 g, 40.5 mmol) and distilled H$_2$O (83 mL), when all of the sulfanilic acid dissolved, the solution was cooled in an ice bath to 0° C. and a solution of sodium nitrite (6.16 g, 89.3 mmol) in H$_2$O (15 mL) was added in one portion. The ice bath was allowed to warm to +15° C. and the mixture was stirred at this temperature 1 h. The reaction mixture was poured onto a mixture of ice (100 g) and 12N HCl (17.4 mL). The ice was allowed to melt and the solid diazonium salt was collected by suction filtration on a scintered glass frit. O-cresol (9.10 g, 84.1 mmol) was dissolved in a solution of NaOH (1.21 g, 30.25 mmol) in H$_2$O (100 mL). This solution was cooled to 0° C. and the solid diazonium salt was added in one portion. This well stirred mixture was maintained at +15° C. for 4 h. The temperature of the mixture was raised to +60° C. and sodium dithionite (35 g, 1.03 mol) was added portionwise. The reaction was allowed to proceed at +60° C. for 15 min. The mixture was cooled to room temperature, diluted with saturated aqueous NaHCO$_3$ and extracted with EtOAc. The EtOAc extract was dried (MgSO$_4$), filtered, concentrated in vacuo and chromatographed on 100 g of silica gel using 1:3 EtOAc-hexane as eluant. There was obtained 2-methyl-3-amino-phenol as a tan solid.

$^1$H NMR (CDCl$_3$) δ 2.18 (s, 3H), 3.35 (br s, 2H), 4.24 (br s, 1H), 6.42 (m, 1H), 6.50 (m, 1H), 6.61 (d, j=9 Hz, 1H).

4-(1,1-Dimethylethoxycarbonyl)amino-2-methylphenol (12-4)

Using a method similar to that described for compound 10-2, 4-(1,1-dimethylethoxycarbonyl)amino-2-methylphenol was prepared.

$^1$H NMR (CDCl$_3$): δ 1.51 (s, 9H), 2.21 (s, 3H), 4.62 (br s, 1H), 6.22 (br s, 1H), 6.62 (m, 1H), 6.98 (m, 1H), 7.08 (br s, 1H).

Ethyl 4-(1,1-dimethylethoxycarbonyl)amino-2-methylphenoxyacetate (12-4)

Using a method similar to that described for compound 10-3, ethyl 4-(1,1-dimethylethoxycarbonyl)amino-2-methylphenoxyacetate was prepared.

$^1$H NMR (CDCl$_3$): δ 1.29 (t, j=7.2 Hz, 3H), 1.52 (s, 9H), 2.28 (s, 3H), 4.25 (q, j=7.2 Hz, 2H), 4.58 (s, 2H), 6.25 (br s, 1H), 6.65 (d, j=8.5 Hz, 1H), 7.08 (br d, j=8.5 Hz, 1H), 7.17 (br s, 1H).

Ethyl 4-amino-2-methylphenoxyacetate. hydrochloride (12-5)

Using a method similar to that described for compound 10-4, ethyl 4-amino-2-methylphenoxyacetate, hydrochloride was prepared.

¹H NMR (CD₃OD): δ 1.21 (t, j=7.1 Hz, 3H), 2.35 (s, 3H), 4.25 (q, j=7.1 Hz, 2H), 4.81 (s, 2H), 6.95 (d, j=,9 Hz, 1H), 7.21 (m, 2H).

Ethyl 2-(4-(4-(4-(1,1-dimethylethoxycarbonyl)piperazin-1-yl)phenylcarbonylamino)-2-methylphenoxy)acetate (12-6)

Using a method similar to that described for compound 10-5, ethyl 2-(4-(4-(4-(1,1-dimethylethoxycarbonyl)piperazin-1-yl)phenylcarbonylamino)-2-methylphenoxy)acetate was prepared.

¹H NMR (DMSO-d₆): δ 1.41 (t, j=7 Hz, 3H), 1.42 (s, 9H), 2.20 (s, 3H), 2.50 (m, 4H), 3.29 (m, 4H), 4.29 (q, j=7 Hz, 2H), 4.78 (s, 2H), 6.80 (d, j=8.5 Hz, 1H), 7.01 (d, j=8.8 Hz, 2H), 7.50 (m, 2H), 7.86 (d, j=8.8 Hz, 2H), 9.68 (s, 1H).

2-(4-(4-(4-(1,1-dimethylethoxycarbonyl)piperazin-1-yl)phenylcarbonylamino)-2-methylphenoxy)acetic acid (12-7)

Using a method similar to that described for compound 10-6, 2-(4-(4-(4-(1,1-dimethylethoxycarbonyl)piperazin-1-yl)phenylcarbonylamino)-2-methylphenoxy)acetic acid was prepared and used in the next step without purification.

2-(4-(4-(1-Piperazinyl)phenylcarbonylamino)-2-methylphenoxy)acetic acid, dihydrochloride (12-9)

Using a method similar to that described for compound 10-7, 2-(4-(4-(1-piperazinyl)phenylcarbonylamino)-2-methylphenoxy)acetic acid, dihydrochloride was prepared, mp: >250° C.

¹H NMR (D₂O): δ 2.15 (s, 3H), 3.29 (m, 4H), 3.48 (m, 4H), 4.65 (s, 2H), 6.76 (d, j=8.5 Hz, 1H), 7.04 (d, j=8.6, 2H), 7.17 (m, 2H), 7.69 (d, j=8.6 Hz, 2H).

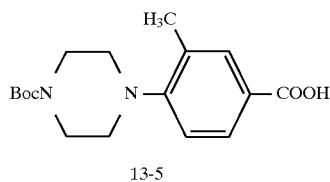

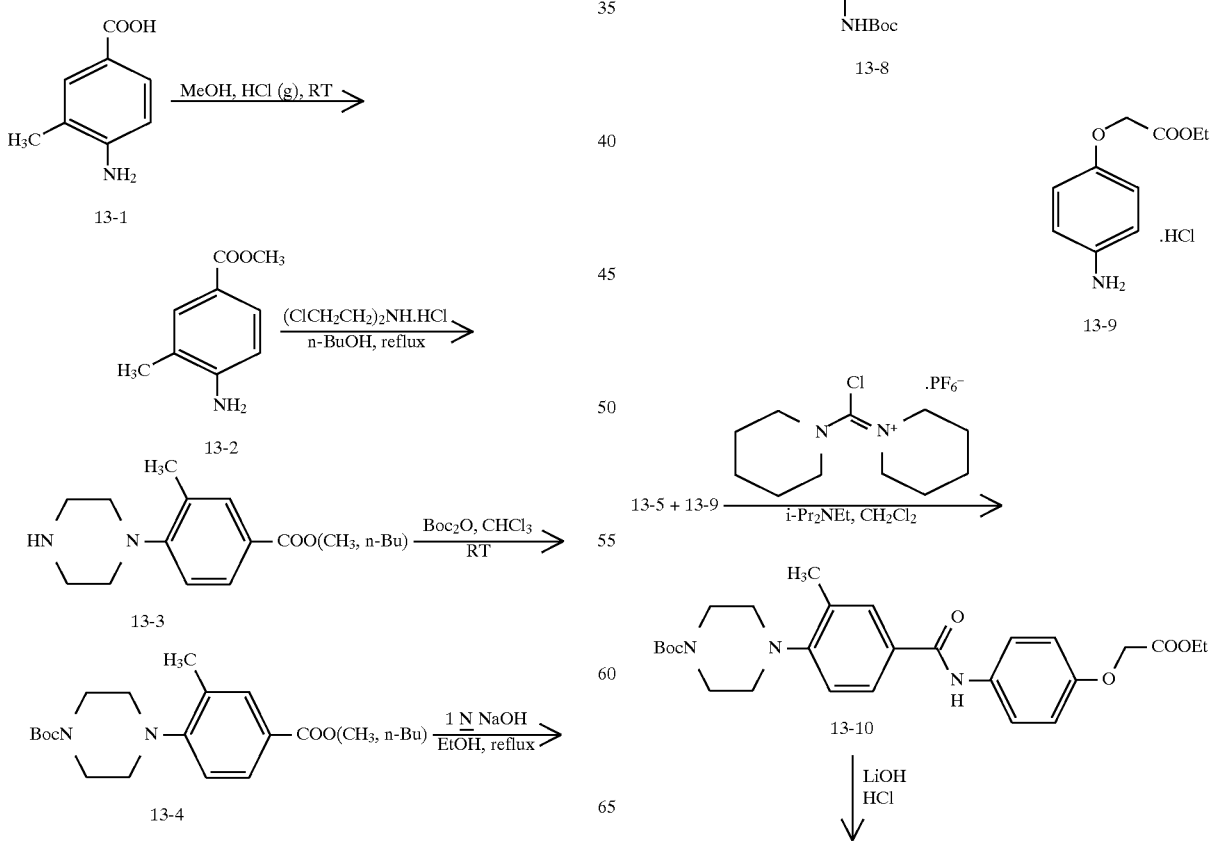

-continued
SCHEME 13

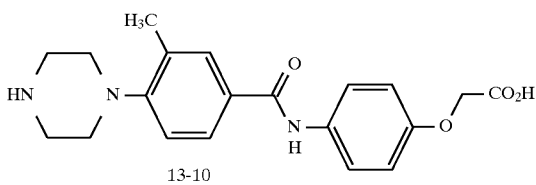

13-10

Methyl 3-methyl-4-aminobenzoate (13-2)

To a 500 mL round bottomed flask equipped with a stirring bar, reflux condenser and a drying tube was added 3-methyl-4-aminobenzoic acid (8.00 g, 52.92 mmol) and anhydrous methanol (300 mL). This solution was saturated with anhydrous HCl gas and the mixture was stirred at ambient temperature for 26 h. The methanol and HCl were removed in vacuo and the solid product was suspended in 400 mL of EtOAc. This mixture was made basic by careful addition of aqueous NaHCO$_3$ solution. The layers were separated and the organic phase was washed with brine, dried (MgSO$_4$), filtered and concentrated in vacuo to give methyl 3-methyl-4-aminobenzoate as a yellow solid.

$^1$H NMR (CDCl$_3$): δ 2.18 (s, 3H), 3.85 (s, 3H), 3.99 (br s, 2H), 6.63 (d, j=8.3 Hz, 1H), 7.75 (m, 3H).

Methyl and n-Butyl 3-methyl-4-(1-piperazinyl)benzoate (13-3)

To a 1L round bottomed flask with a stirring bar, reflux condenser, and an argon inlet was added methyl 3-methyl-4-aminobenzoate (8.74 g, 52.74 mmol), bis 2-chloroethylamine hydrochloride (9.81 g, 55.0 mmol) and n-BuOH (175 mL). This mixture was heated at reflux for 8 days. The n-BuOH was removed in vacuo and the residue was partitioned between EtOAc (200 mL) and 0.2N HCl (300 mL). The layers were separated and the organic phase was extracted with another 100 mL portion of 0.2N HCl. The aqueous phases were combined and made basic with solid NaHCO$_3$. This mixture was extracted with EtOAc (2×200 mL) and the combined EtOAc extracts were washed with brine, dried (Na$_2$SO$_4$), filtered and concentrated in vacuo to give 10.39 g of a mixture of ethyl and n-butyl 3-methyl-4-(1-piperazinyl)benzoates. This material was used in the next step without further purification.

Methyl and n-Butyl 3-methyl-4-(1-(4-(1,1-dimethylethoxy)carbonyl)piperazinyl)benzoates (13-4)

To a 1L round bottomed flask equipped with a stirring bar and an argon inlet was added a mixture of ethyl and n-butyl 3-methyl-4-(1-piperazinyl)benzoates (10.39 g, 44.35 mmol based on the mw of the methyl ester only; vide supra), di-tert-butyldicarbonate (14.67 g, 67.22 mmol) and dry CHCl$_3$ (100 mL). This solution was heated at reflux for 19 h. The cooled reaction mixture was concentrated in vacuo and the residue was chromatographed on silica gel (300 g) using 40% EtOAc-hexane as eluant to give 5.0 g of a mixture of methyl and n-butyl 3-methyl-4-(1-(4-(1,1-dimethylethoxy)carbonyl)piperazinyl)benzoates. This material was used in the next step without further purification.

3-Methyl-4-(1-(4-(1,1-dimethylethoxy)carbonyl)piperazinyl)benzoic acid (13-5)

The product from the preceding step, a mixture of methyl and n-butyl 3-methyl-4-(1-(4-(1,1-dimethylethoxy)carbonyl)piperazinyl)benzoates (5.00 g) was dissolved in 95% EtOH (100 mL) and NaOH (10 g, 250 mmol) was added. This solution was heated at reflux for 2 h. The mixture was cooled to room temperature and the EtOH was removed in vacuo. The residue was dissolved in 300 mL of H$_2$O. This solution was washed with Et$_2$O (200 mL) then acidified with 10% aqueous citric acid. This mixture was extracted with EtOAc (2×250 mL). The combined EtOAc extracts were washed with H$_2$O and brine. Drying (MgSO$_4$), filtration and removal of the solvent in vacuo gave an oil. This material was chromatographed on 75 g of silica gel using 40% EtOAc-hexane as eluant. The chromatographed product was recrystallized from 15 mL of 20% EtOAc-hexane to give 228 mg of 3-methyl-4-(1-(4-(1,1-dimethylethoxy)carbonyl)piperazinyl)benzoic acid as white crystals.

$^1$H NMR (CDCl$_3$): δ 1.49 (s, 9H), 2.35 (s, 3H), 2.94 (m, 4H), 3.59 (m, 4H), 6.99 (d, j=8 Hz, 1H), 7.92 (m, 2H), 11.65 (br s, 1H).

4-(1.1-Dimethylethoxycarbonylamino)phenol (13-7)

To a 500 mL round bottomed flask with a stirring bar, reflux condenser and an argon inlet was added 4-aminophenol (10.00 g, 91.63 mmol), di-tert-butyldicarbonate (20.00 g, 91.63 mmol) and dry CHCl$_3$ (250 mL). This solution was heated at reflux for 6 h. The mixture was cooled in an ice bath and the product was collected by filtration. The product was washed with a little cold CHCl$_3$ and dried in vacuo to give 16.43 (86%) of 4-(1,1-dimethylethoxycarbonylamino)phenol as white crystals, mp: 142°–143° C.

$^1$H NMR (CDCl$_3$): δ 1.51 (s, 9H), 5.27 (br s, 1H), 6.34 (br s, 1H), 6.72 (d, j=8 Hz, 2H), 7.16 (d, j=8 Hz, 2H).

Ethyl (4-(1,1-dimethylethoxycarbonylamino)phenoxy)acetate (13-8)

To a 500 mL round bottomed flask with a stirring bar and an argon inlet was added 4-(1,1-dimethylethoxycarbonylamino)phenol (8.20 g, 39.19 mmol), Cs$_2$CO$_3$ (25.54 g, 78.38 mmol), DMF (75 mL), and ethyl bromoacetate (4.78 mL, 43.11 mmol). This heterogeneous mixture was stirred at ambient temperature for 3.5 h. The mixture was diluted with a little CHCl$_3$ and filtered through a frit to remove the salts. The DMF was removed under high vacuum and the residue was suspended in 500 mL of EtOAc. This mixture was washed with H$_2$O (3×), and brine. Drying (MgSO$_4$), filtration and removal of the solvent in vacuo, gave an oil. This material was chromatographed on 400 g of silica gel using 20% EtOAc-hexane as eluant. There was obtained 11.9 g (100%) of ethyl (4-(1,1-dimethylethoxycarbonylamino)phenoxy)acetate as an oil.

$^1$H NMR (CDCl$_3$): δ 1.29 (t, j=6.4 Hz, 3H), 1.50 (s, 9H), 4.25 (q, j=6.4 Hz, 2H), 4.57 (s, 2H), 6.36 (br s, 1H), 6.84 (d, j=8 Hz, 2H), 7.26 (d, j=8 Hz, 2H).

Ethyl 4-aminophenoxyacetate, hydrochloride (13-9)

To a 500 mL round bottomed flask with a stirring bar and a gas dispersion tube was added ethyl (4-(1,1-dimethylethoxycarbonylamino)phenoxy)acetate (11.9 g, 40.29 mmol) and dry EtOAc. This solution was cooled in an ice bath and saturated with anhydrous HCl gas over 15 min. The resulting suspension was aged 30 min. at 0° C. The excess HCl was removed with a stream of argon and the EtOAc was removed in vacuo. The solid product was triturated with EtOAc, collected on a frit, and dried in vacuo at room temperature to give 7.33 g (78%) of ethyl 4-aminophenoxyacetate, hydrochloride as a white crystalline soild.

$^1$H NMR (DMSO-d$_6$): δ 1.211 (t, j=6.4 Hz, 3H), 4.16 (q, j=6.4 Hz, 2H), 4.82 (s, 2H), 7.05 (d, j=8 Hz, 2H), 7.34 (d, j=8 Hz, 2H), 10.27 (br s, 3H).

Ethyl 2-(4-(4-(3-methyl-4-(1,1-dimethylethoxycarbonyl)piperazin-1-yl)phenylcarbonylamino)phenoxy)acetate (13-10)

In a manner similar to that described for compound 10-5, using acid 13-5 and aniline 13-8, ethyl 2-(4-(4-(3-methyl-4-(1,1-dimethylethoxycarbonyl)piperazin-1-yl)phenylcarbonylamino)-phenoxy)acetate was prepared.

¹H NMR (CDCl₃): δ 1.29 (t, j=7.0 Hz, 3H), 1.48 (s, 9H), 2.37 (s, 3H), 2.95 (m, 4H), 3.59 (m, 4H), 4.25 (q, j=7.0 Hz, 2H), 4.61 (s, 2H), 6.95 (d, j=8.5 Hz, 2H), 7.03 (d, j=8.5 Hz, 1H), 7.55 (d, j=8.5 Hz, 2H), 7.62 (m, 2H).

2-(4-(4-(3-Methyl-4-(1-piperazinyl)phenylcarbonylamino)phenoxy)acetic acid (13-11)

To a 100 mL round bottomed flask with a stirring bar was added ethyl 2-(4-(4-(3-methyl-4-(1,1-dimethylethoxycarbonyl)piperazin-1-yl)phenylcarbonylamino)phenoxy)acetate (311 mg, 0.63 mmol), MeOH (5 mL), THF (20 mL), and 1N LiOH (20 mL). This solution was stirred at ambient temperature for 24 h. The solvents were removed in vacuo and the residue was acidified with 10% aqueous citric acid. This mixture was extracted with EtOAc. The EtOAc extract was dried (MgSO₄), filitered and cooled to 0° C. in an ice bath. This solution was saturated with dry HCl gas and aged 30 min. at 0° C. The excess HCl was removed with a stream of argon and the solvent was removed in vacuo. The product was purified by preparative reverse phase HPLC using a H₂O—CH₃CN gradient on a Waters C-18 column. Obtained 105 mg of 2-(4-(4-(3-methyl-4-(1-piperazinyl)phenylcarbonylamino)phenoxy)acetic acid as a white solid.

¹H NMR (D₂O): δ 2.28 (s, 3H), 3.17 (m, 4H), 3.35 (m, 4H), 4.55 (s, 2H), 6.94 (d, j=7.5 Hz, 2H), 7.12 (d, j=8.2 Hz, 1H), 7.33 (d, j=7.5 Hz, 2H), 7.63 (m, 2H).

SCHEME 14

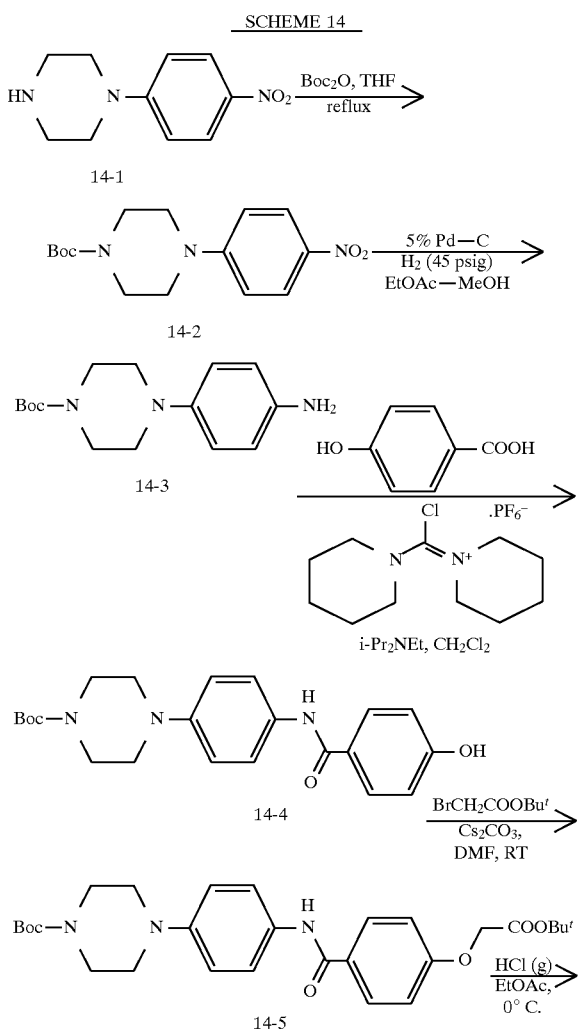

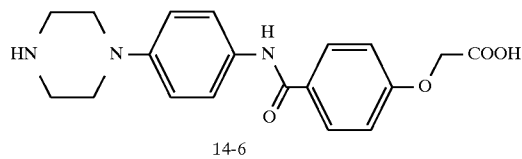

1-Nitrophenyl-4-(1,1-dimethylethoxvcarbonyl)piperazine (14-2)

To a 200 mL round bottomed flask was added 1-nitrophenylpiperazine (5.01 g, 24.2 mmol), di-tert-butyldicarbonate (5.85 g, 26.8 mmol), triethylamine (3.97 mL, 27.8 mmol), and dry THF (100 mL). This solution was heated at reflux for 18 h. The mixture was cooled to room temperature and the solvents were removed in vacuo. The residue was dissolved in EtOAc and washed with 10% aqueous citric acid, H₂O, and brine. Drying (MgSO₄), filtration, and removal of the solvent in vacuo gave 7.7 g of 1-nitrophenyl-4-(1,1-dimethylethoxycarbonyl)piperazine as a yellow solid.

¹H NMR (CDCl₃): δ 1.42 (s, 9H), 3.41 (m, 4H), 3.62 (m, 4H), 6.81 (d, j=8.5 Hz, 2H), 8.16 (d, j=8.5 Hz, 2H).

4-(4-(1,1-Dimethylethoxycarbonyl)piperazin-1-yl)aniline (14-3)

To a 250 mL Parr haydrogenation bottle was added 1-nitrophenyl-4-(1,1-dimethylethoxycarbonyl)piperazine (4.5 g, 16.34 mmol), EtOAc (81 mL), MeOH (27 mL), and 5% Pd-C (0.18 g). This mixture was hydrogenated under 45 psig H₂ at ambient temperature for 24 h. The mixture was filtered through a celite pad and the solvents were removed in vacuo. The residue was chromatographed on 250 g of silica gel using 70% EtOAc-hexane as eluant. There was obtained 3.43 g of 4-(4-(1,1-dimethylethoxycarbonyl)piperazin-1-yl)aniline as a yellow solid.

¹H NMR (CDCl₃): δ 1.49 (s, 9H), 2.98 (m, 4H), 3.49 (br s, 2H), 3.57 (m, 4H), 6.66 (d, j=9 Hz, 2H), 6.82 (d, j=9 Hz, 2H).

N-(4-(4-(1,1-dimethylethoxycarbonyl)piperazin-1-yl)phenyl)-4-hydroxybenzamide (14-4)

To a 100 mL round bottomed flask with a stirring bar and an argon inlet was added 4-(4-(1,1-dimethylethoxycarbonyl) piperazin-1-yl)aniline (0.868 g, 3.13 mmol), 4-hydroxybenzoic acid (0.525 g, 3.80 mmol), chloro-N,N,N',N',-bis(pentamethylene)formamidinium hexafluorophosphate (1.35 g, 3.74 mmol), and CH₂Cl₂ (45 mL). This mixture was cooled in an ice bath and diisopropylethylamine (0.96 mL, 5.52 mmol) was added. The ice bath was allowed to expire and the mixture was stirred at ambient temperature 18 h. The mixture was diluted with EtOAc and washed with 10% aqueous citric acid, water and brine. Drying (MgSO₄), filtration and removal of the solvent in vacuo gave an oil. This material was chromatographed on 100 g of silica gel using 70% EtOAc-hexane as eluant to give 0.57 g of N-(4-(4-(1,1-dimethylethoxycarbonyl)piperazin-1-yl)phenyl)-4-hydroxybenzamide as a grey solid.

¹H NMR (CDCl₃): δ 1.48 (s, 9H), 3.01 (m, 4H), 3.48 (m, 4H), 6.82 (d, J=9 Hz, 2H), 6.85 (d, j=9 Hz, 2H), 7.58 (d, j=8 Hz, 2H), 7.81 (d, j=8 Hz, 2H), 9.80 (br s, 1H), 10.01 (br s, 1H).

tert-Butyl 4-(4-(4-(1,1-dimethylethoxycarbonyl)piperazin-1-yl)phenylaminocarbonyl)phenoxyacetate (14-5)

To a 100 mL round bottomed flask with a stirring bar and an argon inlet was added N-(4-(4-(1,1-dimethylethoxycarbonyl)piperazin-1-yl)phenyl)-4- hydroxybenzamide (0.56 g, 1.41 mmol) DMF (35 mL), Cs₂CO₃ (0.49 g, 1.51 nmmol) and tert-butyl bromoacetate (0.28 mL, 1.75 mmol). This mixture was stirred at ambient temperature for 18 h. The mixture was diluted with EtOAc and washed with H₂O and brine. Drying (MgSO₄), filtration and removal of the solvent in vacuo gave 0.78 g of tert-butyl 4-(4-(4-(1,1-dimethylethoxycarbonyl)piperazin-1-yl)phenylaminocarbonyl)phenoxyacetate which was used in the next step without purification.

¹H NMR (DMSO-d₆): δ 1.48 (s, 9H), 1.49 (s, 9H), 3.02 (m, 4H), 3.39 (m, 4H), 4.78 (s, 2H), 6.88 (d, j=9 Hz, 2H), 7.02 (d, j=9 Hz, 2H), 7.62 (d, j=8 Hz, 2H), 7.82 (d, j=8 Hz, 2H), 9.82 (br s, 1H).

4-(4-(Piperazin-1-yl)phenylaminocarbonyl)phenoxyacetic acid (14-6)

To a 100 mL round bottomed flask with a stirring bar and a gas dispersion tube was added tert-butyl 4-(4-(4-(1,1-dimethylethoxycarbonyl)piperazin-1-yl)phenylaminocarbonyl)phenoxyacetate (0.78 g, 1.52 mmol) and EtOAc (40 mL). This solution was cooled in an ice bath and HCl gas was sparged through the solution for 15 min. The resulting mixture was aged 90 min. The excess HCl and EtOAc were removed in vacuo and the crude product was purified by preparative reverse phase HPLC. There was obtained 0.218 g of 4-(4-(piperazin-1-yl)phenylaminocarbonyl)phenoxyacetic acid as a crystalline solid.

¹H NMR (0.1N NaOD-D₂O): δ 2.99 (m, 4H), 3.15 (m, 4H), 4.59 (s, 2H), 7.03 (d, j=9 Hz, 2H), 7.16 (d, j=9 Hz, 2H), 7.7.37 (d, j=8 Hz, 2H), 7.88 (d, j=8 Hz, 2H).

SCHEME 15

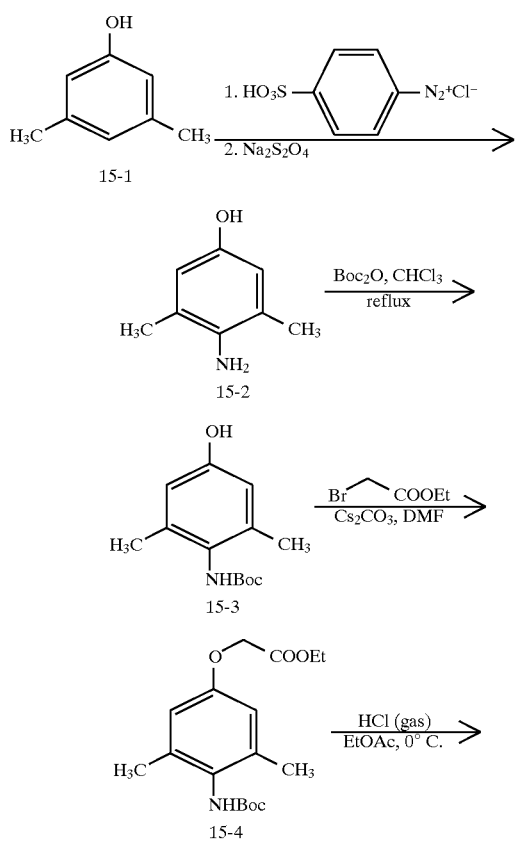

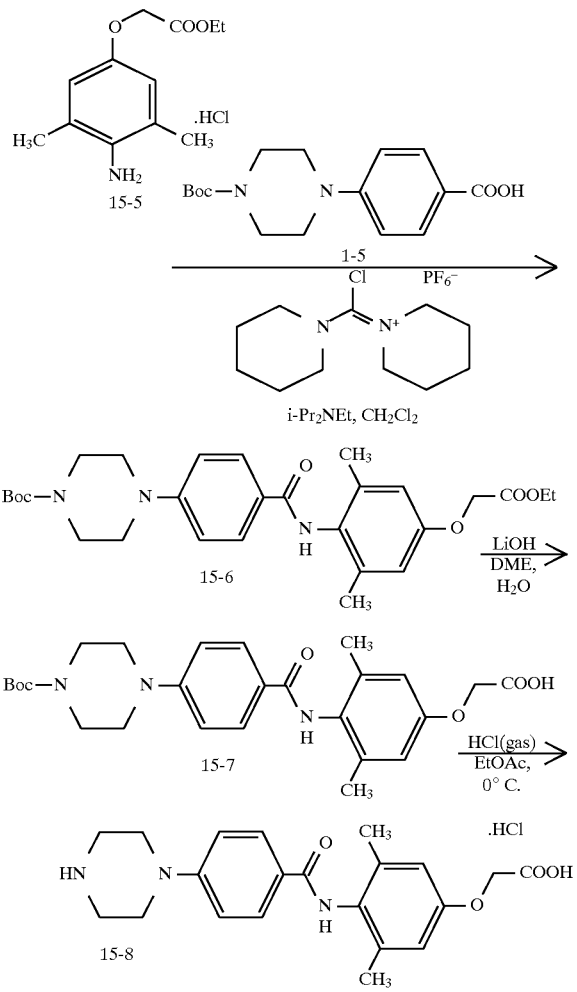

2-(4-(4-(1-Piperazinyl)phenylcarbonylamino)-3,5-dimethylphenoxy)acetic acid, dihydrochloride (15-8)

Using a sequence essentially the same as described for compound 12-9, but starting with 3,5-dimethylphenol (15-1), 2-(4-(4-(1-piperazinyl)phenylcarbonylamino)-3,5-dimethylphenoxy)acetic acid, dihydrochloride was prepared, mp: >250° C.

¹H NMR (D₂O): δ 2.15 (s, 6H), 3.32 (m, 4H), 3.54 (m, 4H), 4.64 (s, 2H), 6.72 (s, 2H), 7.12 (d, j=8.6, 2H), 7.17 (m, 2H), 7.83 (d, j=8.6 Hz, 2H).

SCHEME 16

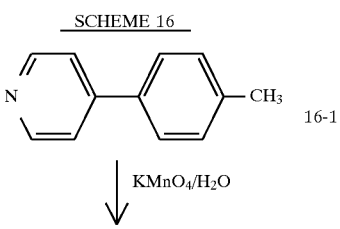

-continued
SCHEME 16

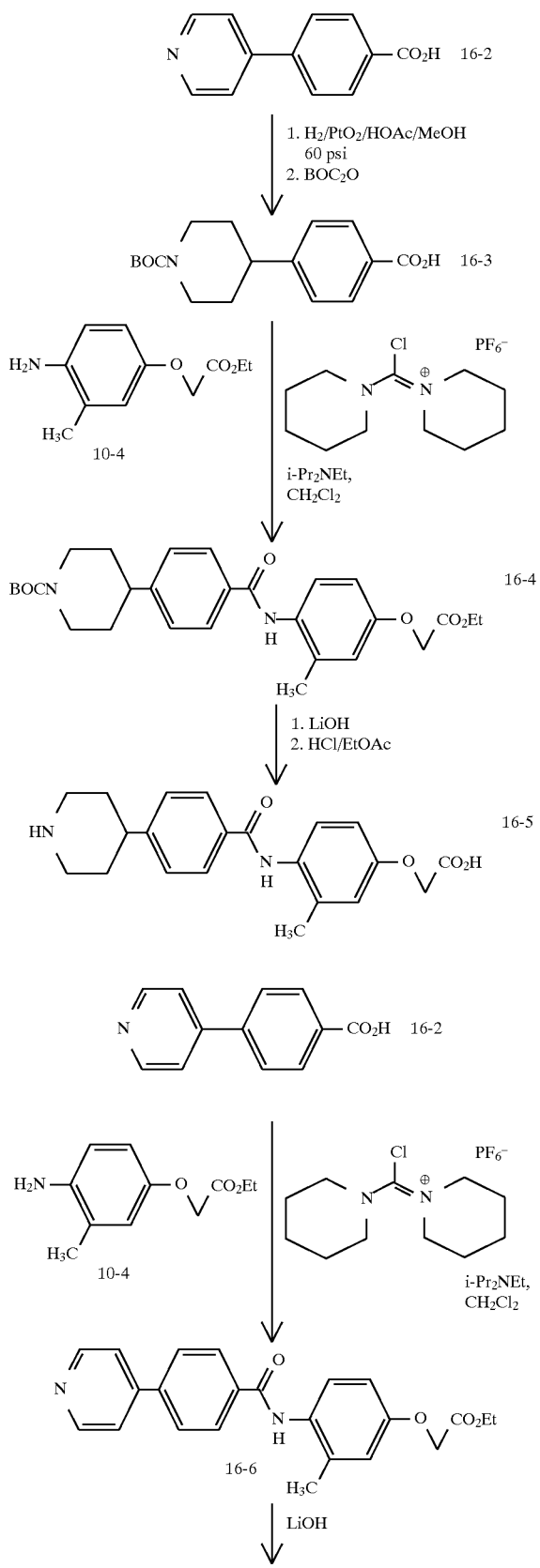

-continued
SCHEME 16

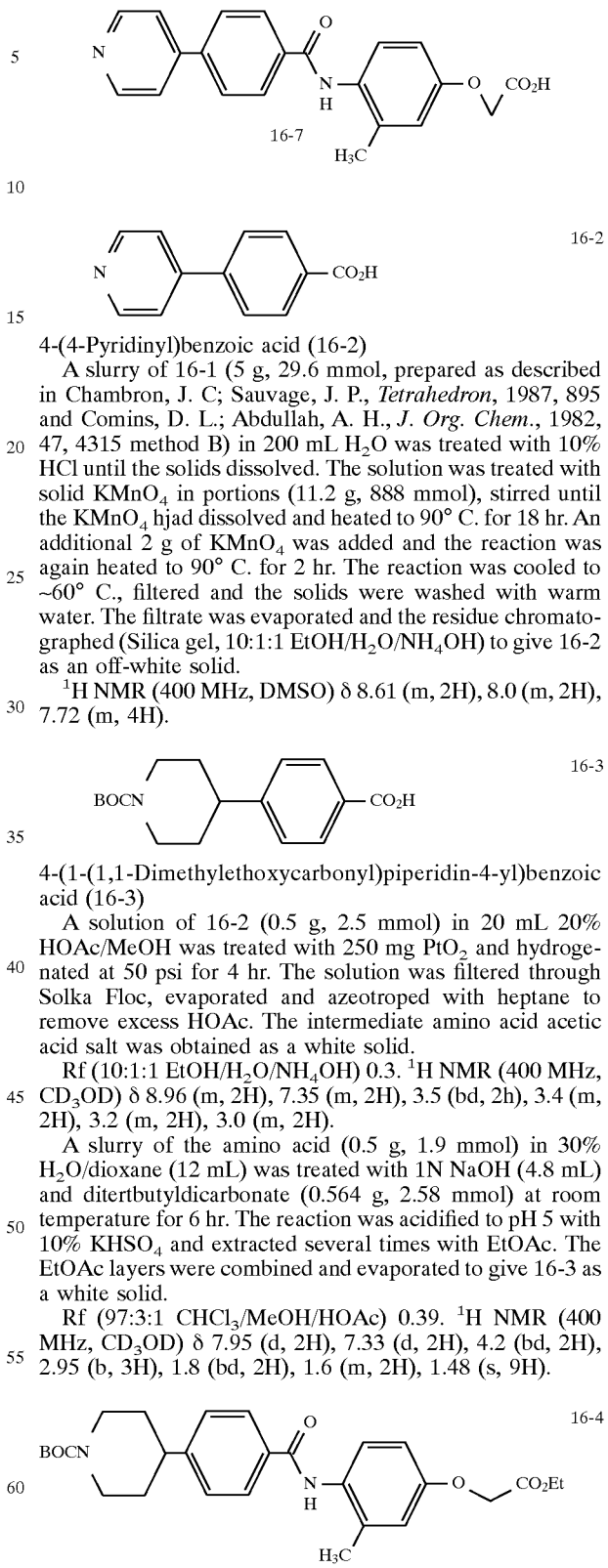

4-(4-Pyridinyl)benzoic acid (16-2)

A slurry of 16-1 (5 g, 29.6 mmol, prepared as described in Chambron, J. C; Sauvage, J. P., *Tetrahedron*, 1987, 895 and Comins, D. L.; Abdullah, A. H., *J. Org. Chem.*, 1982, 47, 4315 method B) in 200 mL $H_2O$ was treated with 10% HCl until the solids dissolved. The solution was treated with solid $KMnO_4$ in portions (11.2 g, 888 mmol), stirred until the $KMnO_4$ hjad dissolved and heated to 90° C. for 18 hr. An additional 2 g of $KMnO_4$ was added and the reaction was again heated to 90° C. for 2 hr. The reaction was cooled to ~60° C., filtered and the solids were washed with warm water. The filtrate was evaporated and the residue chromatographed (Silica gel, 10:1:1 $EtOH/H_2O/NH_4OH$) to give 16-2 as an off-white solid.

$^1$H NMR (400 MHz, DMSO) δ 8.61 (m, 2H), 8.0 (m, 2H), 7.72 (m, 4H).

4-(1-(1,1-Dimethylethoxycarbonyl)piperidin-4-yl)benzoic acid (16-3)

A solution of 16-2 (0.5 g, 2.5 mmol) in 20 mL 20% HOAc/MeOH was treated with 250 mg $PtO_2$ and hydrogenated at 50 psi for 4 hr. The solution was filtered through Solka Floc, evaporated and azeotroped with heptane to remove excess HOAc. The intermediate amino acid acetic acid salt was obtained as a white solid.

Rf (10:1:1 $EtOH/H_2O/NH_4OH$) 0.3. $^1$H NMR (400 MHz, $CD_3OD$) δ 8.96 (m, 2H), 7.35 (m, 2H), 3.5 (bd, 2h), 3.4 (m, 2H), 3.2 (m, 2H), 3.0 (m, 2H).

A slurry of the amino acid (0.5 g, 1.9 mmol) in 30% $H_2O$/dioxane (12 mL) was treated with 1N NaOH (4.8 mL) and ditertbutyldicarbonate (0.564 g, 2.58 mmol) at room temperature for 6 hr. The reaction was acidified to pH 5 with 10% $KHSO_4$ and extracted several times with EtOAc. The EtOAc layers were combined and evaporated to give 16-3 as a white solid.

Rf (97:3:1 $CHCl_3$/MeOH/HOAc) 0.39. $^1$H NMR (400 MHz, $CD_3OD$) δ 7.95 (d, 2H), 7.33 (d, 2H), 4.2 (bd, 2H), 2.95 (b, 3H), 1.8 (bd, 2H), 1.6 (m, 2H), 1.48 (s, 9H).

Ethyl 2-(4-(4-(1-(1,1-Dimethylethoxycarbonyl)piperidin-4-yl)phenylcarbonyl amino)-3-methylphenoxy)acetate (16-4)

A slurry of 16-3 (0.15 g, 0.49 mmol) and 10-4 (0.12 g, 0.49 mmol) in $CH_2Cl_2$ was treated with chloro-N,N,N',N',- bis(pentamethylene)formamidinium hexafluorophosphate (0.194 g, 0.54 mmol) and diisopropylethyl amine (0.34 mL, 1.96 mmol) and stirred at room temperature for 24 hours. The solution was diluted with EtOAc and washed with H₂, 10% citric acid, saturated NaHCO₃ and brine, dried over MgSO₄, filtered and evaporated. The residue was chromatographed (silica gel 50% EtOAc/Hexanes) then triturated with ether/hexanes to give 16-4.

Rf(50% EtOAc/Hexanes) 0.33. ¹H NMR (400 MHz, CDCl₃) δ 7.81 (2s,2H), 7.70(d,1H), 7.50 (s, 1H), 7.31 (2s, 2H), 6.8 (m, 2H), 4.6 (s, 2H), 4.28 (q, 2H), 2.8 (m, 2H), 2.72 (m, 1H), 2.30 (s, 3H), 1.85 (bd, 2H), 1.75 (m,2H), 1.48 (s, 9H) 1.3 (t, 3H).

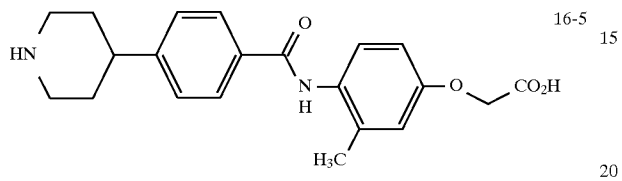

2-(4-(4-(Piperidin-4-yl)phenylcarbonylamino)-3-methylphenoxy) acetate (16-5)

A solution of 16-4 (0.1 g, 0.2 mmol) in 1:1:1 THF/MeOH/H₂O was treated with LiOH (0.094 g, 2 mmol) at room temperature. After 1 hour the reaction was diluted with EtOAc and 10% KHSO₄ and the layers were separated. The organic layer was washed with H₂O, brine, dried with MgSO₄, filtered and evaporated to give the acid as a clear oil.

Rf(9:1:1 CH₂Cl₂/MeOH/HOAc) 0.57. 1H NMR (400 MHz,CD₃OD) δ 7.94 (2s,2H), 7.44(2s,2H), 7.2 (d, 1H), 6.90 (m, 1H), 6.8 (m, 1H), 4.62 (s, 2H), 4.24 (bd, 2H), 2.9 (b, 2H), 2.83 (m, 1H), 2.28 (s, 3H), 1.86 (bd, 2H), 1.7–1.6 (m, 2H), 1.5 (s, 9H).

A slurry of the intermediate acid (0.9 g, 1.19 mmol) was cooled to −78° C. and saturated with HCl gas. The reaction was warmed to 0° C., then concentrated in vacuo to give 16-5 as the HCl salt.

Rf (10:1:1 EtOH/H₂O/NH₄OH) 0.81. ¹H NMR (400 MHz, CD₃OD) δ 7.94 (2s, 2H), 7.44 (2s, 2H), 7.2 (d, 1H), 6.90 (m, 1H), 6.8 (m, 1H), 4.65 (s, 2H), 3.52 (bd, 2h), 3.15 (bt, 2H), 3.05 (m, 1H), 2.12 (bd, 2H), 1.97 (m, 2H).

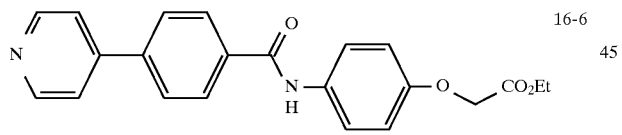

Ethyl 2-(4-(4-(Pyridin-4-yl)phenylcarbonylamino)-3-methylphenoxy)acetate (16-6)

16-2 (0.5 g, 2.5 mmol) and Ethyl 2-acetoxy-4-amino benzene hydrochloride (13-9) (0.579 g, 2.5 mmol) were coupled as described for 16-4 to give 16-6 after chromatography (silica gel, 5% MeOH/EtOAc) followed by reverse phase preparative HPLC.

¹H NMR (400 MHz, CD₃OD) δ 8.82 (d, 2H), 8.30 (d, 2H), 8.15 (d, 2H), 8.05 (d, 2H), 7.60 (d, 2H), 6.98 (d, 2H), 4.70 (s, 2H), 4.23 (q, 2H), 1.30 (t, 3H).

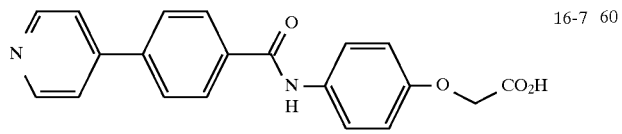

2-(4-(4-(Pyridin-4-yl)phenylcarbonylaminophenoxy)acetic acid (16-7)

16-6 was treated with LiOH as described for 16-5 to give 16-7 after chromatography (silica gel, 10:1:1 EtOH/H₂O/NH₄OH) followed by preparative reverse phase HPLC.

Rf (10:1:1 EtOH/H₂O/NH₄OH) 0.76. ¹H NMR (400 MHz, DMSO) δ 8.65 (d, 2H), 8.10 (d, 2H), 7.96 (d, 2H), 7.8 (d, 2H), 7.65 (d, 2H), 6.90 (d, 2H), 4.58 (bs, 2H).

SCHEME 17

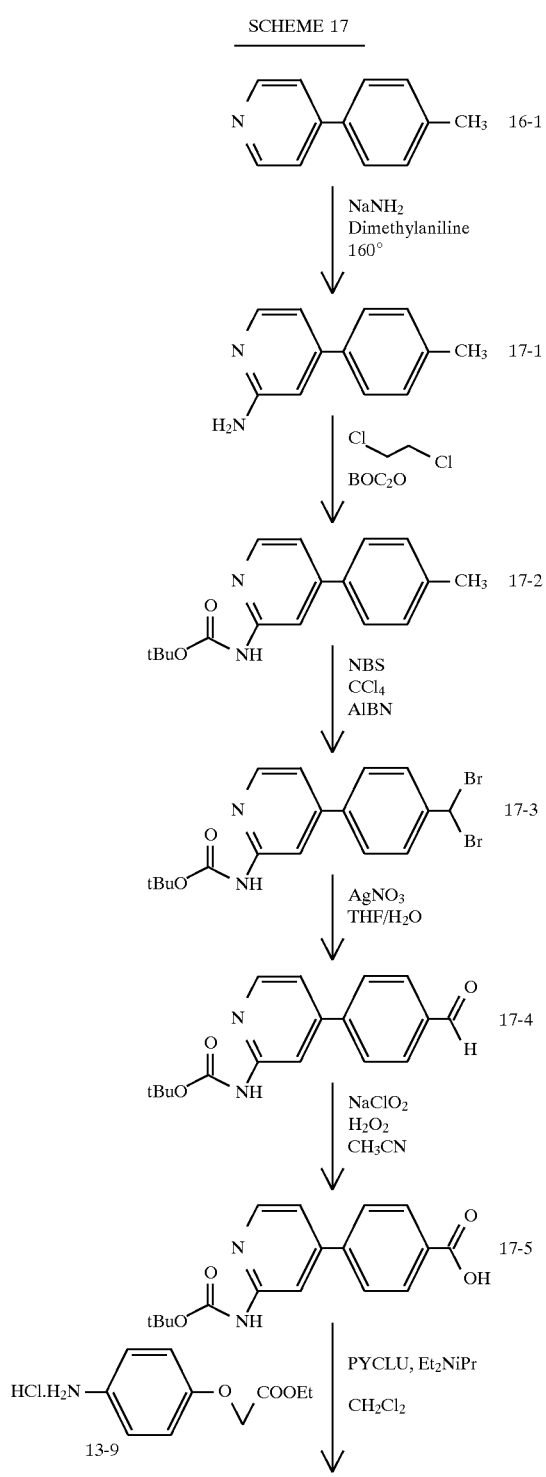

-continued
SCHEME 17

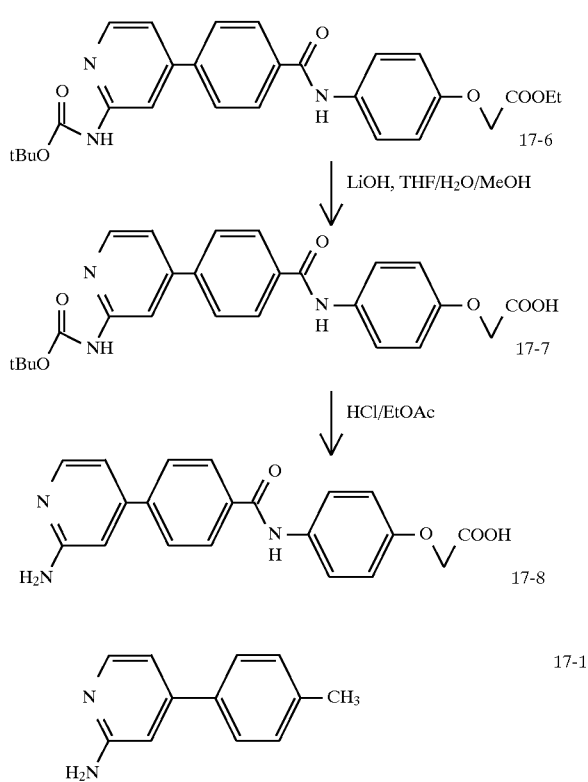

2-Amino-4-(4-methylphenyl)pyridine (17-1)

NaNH$_2$ (142 mmol) was prepared in situ as described in Leffler, M. T. *Organic Reactions* 1942 Vol. I. Dimethylaniline (20 ml) was added dropwise to the freshly prepared NaNH$_2$. 16-1 (8.0 g, 47.3 mmol) was dissolved in a small amount of dimethylaniline and added to the mixture. The slurry was heated to 160° for 2 hours. The reaction mixture is cooled and diluted with 10% KHSO$_4$ and water. The layers are separated, and the dimethylaniline layer is washed with 10% KHSO$_4$. The aqueous layers are combined, basified with saturated NaHCO$_3$, and extracted with EtOAC (3×). The combined organic layers are washed w/brine and concentrated to yield an oily solid. This oily solid was purified by flash chromatography (5% MeOH/EtOAc) to give 17-1 as a tan solid. R$_f$ (5% MeOH/EtOAc) 0.36. $^1$H NMR (400 MHz, DMSO-d$_6$) δ 7.9 (d, 1H), 7.5 (d, 2H), 7.3 (d, 2H), 6.7 (d, 1H), 6.6 (s, 1H), 5.9 (d, 1H), 2.3 (s, 3H).

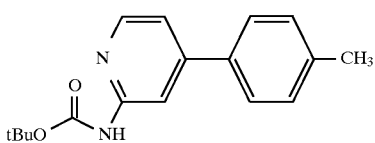

2-(1,1-Dimethylethoxycarbonylamino-4-(4-methylphenyl) pyridine (17-2)

17-1 is dissolved in dichloroethane (30 mL) and added dropwise, rapidly to a refluxing solution of Boc$_2$O in dichloroethane (10 mL). After the addition, the reaction is refluxed for 30 min, then stirred at RT overnight. The reaction mixture is cooled and concentrated to yield a yellow solid, which is purified by chromatography (silica, 30% EtOAc/Hexane) to give 17-2 as a white solid. R$_f$ (50% EtOAc/Hex) 0.73. $^1$H NMR (400 MHz, CDCl$_3$) δ 8.3 (d, 1H), 8.2 (s, 1H), 7.5–7.6 (m, 4H), 7.3 (bs, 1H), 7.1 (d, 2H), 2.3 (s, 3H), 1.5 (s, 9H)

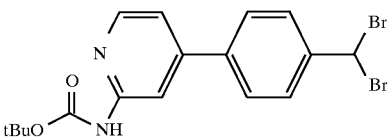

2-(1,1-Dimethylethoxycarbonylamino-4-(4-dibromomethylphenyl) pyridine (17-3)

17-2 (1.0 g, 3.5 mmol) is dissolved in CCl$_4$. NBS (1.3 g; 7.3 mmol) is added, followed by AIBN (28.7 mg, 0.18 mmol). The reaction is heated to reflux while shining a white light directly on the flask. After 2 hours, AIBN (28.7 mg) is added, the light is turned off, and the reacion is stirred overnight to effect completion to product. The reaction mixture is cooled and the succinimide is filtered off, washing the solids with CCl$_4$. The filtrate is concentrated to give 17-3 as a brown solid which is used in the next step without further purification. R$_f$ (50% EtOAc/Hex) 0.70. $^1$H NMR (400 MHZ, CDCl$_3$) δ 8.3 (d, 1H), 8.2 (S, 1H), 7.7 (m, 3H), 7.2 (bs, 1H), 7.1 (d, 1H), 6.7 (s, 1H), 1.5 (s,9H).

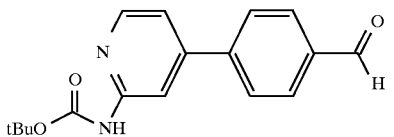

4-(2-(1,1-Dimethylethoxycarbonylamino)pyrid-4-yl) benzaldehyde (17-4)

17-3 (1.5 g, 34 mmol) is dissolved in water/THF (15 mL/45 mL). AgNO$_3$ (1.1 g, 6.8 mmol) is added and stirred for ½ hour. The reaction mixture is diluted w/EtOAc and water. The layers are separated and the organic layer is filtered to remove the solids. The filtrate is washed w/brine, dried (MgSO$_4$), filtered and concentrated to yield a brown solid. The solid is purified on a "plug" of silica, eluting first w/50% EtOAC/hexane, then 100% EtOAc to elute all of the product. The fractions are concentrated to give 17-4 as a brown solid. R$_f$ (50% EtOAc/Hexane) 0.62. $^1$H NMR (400 MHz, CDCl$_3$) δ 10.1 (s, 1H), 8.29 (d,1H), 8.26 (s,1H), 8.0 (d,2H), 7.8 (d, 2H), 7.5 (bs, 1H), 7.2 (d, 1H), 1.5 (s, 9H).

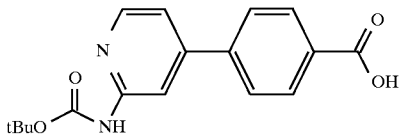

4-(2-(1,1-Dimethylethoxycarbonylamino)pyrid-4-yl) benzoic acid (17-5)

17-4 (1.0 g, 3.4 mmol) is slurried in CH$_3$CN (40 mL). 10% KHSO$_4$ (1.3 mL) and 30% H$_2$O$_2$ (0.957 mL) are added and the solution is cooled in an ice bath. NaClO$_2$ (8.5 mmol, 770 mg) is added dropwise in 50 mL water over 20 min. The reaction is stirred for 16 hrs. The reaction mixture is diluted w/EtOAc and washed with saturated NaHCO$_3$ (2×). The aqueous layers are combined, acidifed with 10% KHSO$_4$, and extracted w/CH$_2$Cl$_2$ (2×) and EtOAc (2×) to give 17-5 as a yellow solid. $^1$H NMR (400 MHz, DMSO-d$_6$) δ 12.6–12.8 (bs, 1H), 9.9 (s, 1H), 8.3 (d, 1H), 8.0–8.1 (m, 3H), 7.9 (d, 2H), 7.3 (d, 1H), 1.5 (s, 9H).

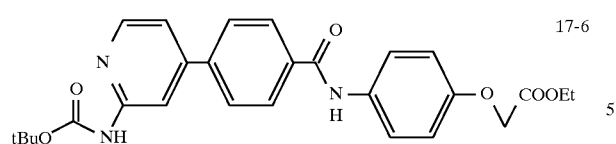

Ethyl 2-(4-(4-(2-(1,1-Dimethylethoxycarbonylamino)pyrid-4-yl)carbonylamino)phenoxy)acetate (17-6)

A mixture of 17-5 (300 mg, 0.956 mmol), 13-9 (0.956 mmol, 236 mg), diisopropylethylamine (3.8 mmol, 0.66 mL), PYCLU (1.05 mmol, 378 mg), and CH$_2$Cl$_2$ (10 ml) is stirred at RT for 16 hours. The reaction mixture is diluted with EtOAc and washed with saturated NaHCO$_3$ and Brine. The Organic layer is dried (MgSO$_4$), filtered and concentrated to yield a pink solid. Triturations with hexanes followed by flash chromatography (silica, 30% EtOAc/Hex) afforded 17-6 as a white solid. R$_f$ (30% EtOAc/Hexanes) 0.24. $^1$H NMR (400 MHz, CDCl$_3$) δ 8.3 (d, 1H), 8.2 (s, 1H), 7.9 (d, 2H), 7.8 (2d, 3H), 7.4 (bs, 1H), 7.6 (bs, 1H), 7.2 (d, 1H), 6.8 (s, 1H), 6.7 (d, 1H), 4.6 (s, 2H), 4.3 (q, 2H), 2.3 (s, 3H), 1.5 (s, 9H), 0.9 (t, 3H).

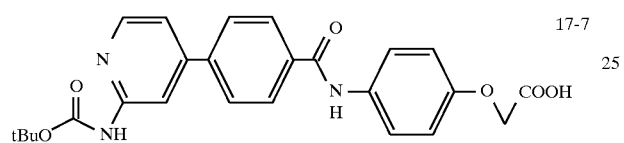

2-(4-(4-(2-(1,1-Dimethylethoxycarbonylamino)pyrid-4-yl)carbonylamino)phenoxy)acetic acid (17-7)

A mixture of 17-6 (0.17 mmol, 90 mg), LiOH (0.60 mmol, 25 mg), and THF/H$_2$O/MeOH/ (1 mL/1 mL/1 mL) is stirred for 2 hours. The reaction mixture is diluted with EtOAc and 10% KHSO$_4$. The aqueous layer is back-extracted with EtOAc. The organic layers are combined, washed with brine, dried (MgSO$_4$), filtered and concentrated to yield 17-7 as a white solid. $^1$H NMR (400 MHz, CD$_3$OD) δ 8.3 (d, 1H), 8.1 (bd, 3H), 7.9 (d, 2H), 7.5 (bs, 1H), 7.2 (s, 1H), 6.9 (s, 1H), 6.8 (d, 1H), 4.7 (s, 2H), 2.3 (s, 3H), 1.5 (s, 9H).

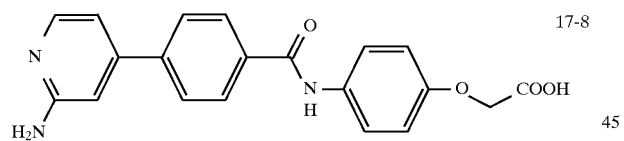

2-(4-(4-(2-Aminopyrid-4-yl)carbonylamino)phenoxy)acetic acid (17-8)

17-7 (0.14 mmol, 70 mg) is dissolved in EtOAC (3 mL) and cooled to −78°. HCl (g) is bubbled through until the solution is saturated. The reaction is stirred at 0° for 3 hours, then at 35° for 16 hours. The reaction mixture is concentrated to yield a tan solid, which is purified by flash chromatography (10/0.25/0.25 EtOH/NH$_4$OH/H$_2$O) to yield 17-8 as an off white solid. R$_f$ (10/0.5/0.5 EtOH/NH$_4$OH/ H$_2$O) 0.86. $^1$H NMR (400 MHz, DMSO-d$_6$) δ 9.8 (s, 1H), 8.0 (d, 2H), 7.9 (d, 1H), 7.7 (d, 2H), 7.2 (d, 1H), 6.9 (m, 2H), 6.8 (m, 2H), 6.0 (d, 1H), 2.2 (s, 3H).

SCHEME 18

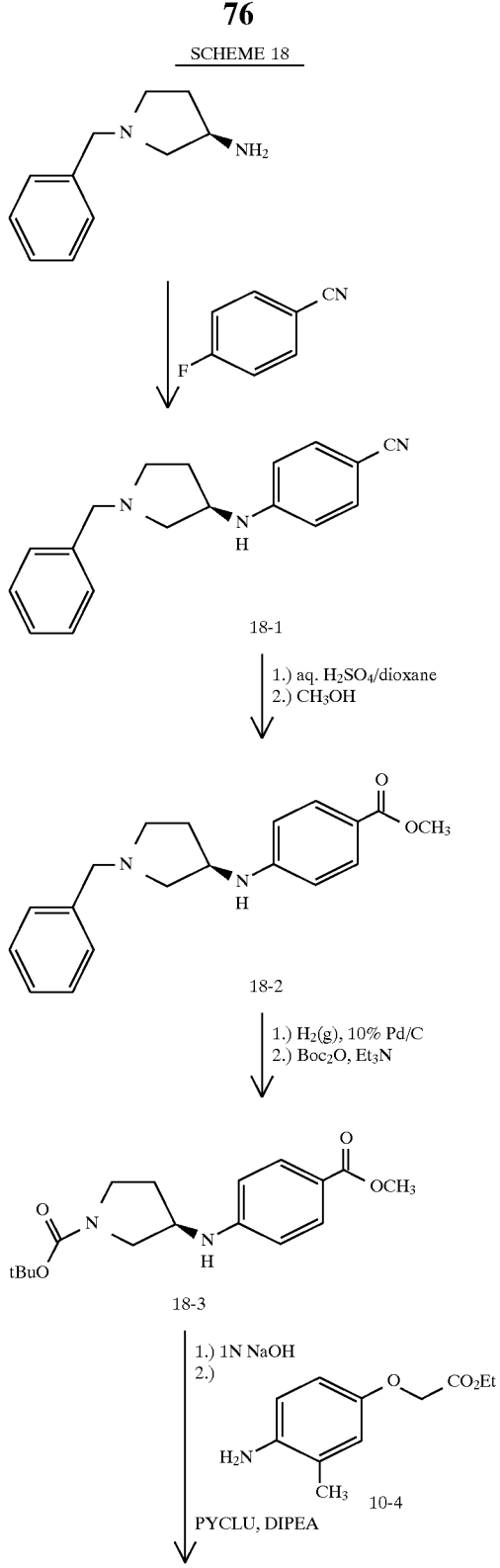

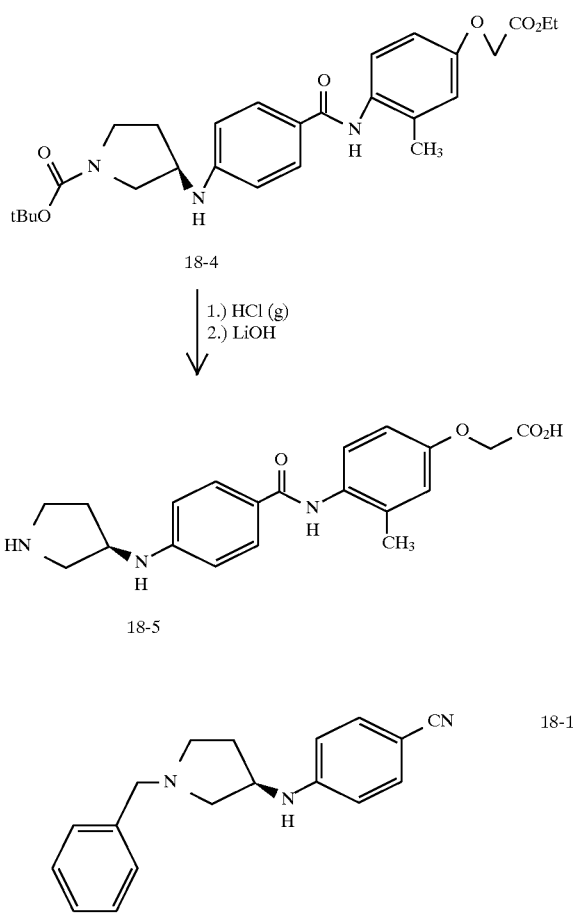

4-(3(R)-((N-benzyl)pyrrolidinyl)amino)phenylnitrile (18-1)

A solution of N-benzyl-3-(R)-aminopyrrolidine (TCI, 0.45 g, 2.27 mmol) in 1 mL acetonitrile was treated with 4-fluorophenylcyanide (Aldrich, 3 g, 25.5 mmol) and heated to 100° C. The acetonitrile was allowed to evaporate and the slurry was heated for 18 hours. Additional 4-fluorophenylcyanide (1 g) was added and the reaction heated for 18 hours. The oily mixture was absorbed onto silica gel and eluted first with 20% EtOAc/Hexanes, then with 5% MeOH/CHCl₃ saturated with NH₃ to give 18-1.

$R_f$ (5% MeOH/CHCl₃ saturated with NH₃) 0.55. ¹H NMR (400 MHz, CDCl₃) δ 7.4 (d, 2H), 7.3 (m, 5H), 6.5 (d, 2H), 4.45 (bd, 1H), 4.0 (m, 1H), 3.64 (s, 2H), 2.83 (m, 1H), 2.75 (dd, 1H), 2.6 (dd, 1H), 2.43(m, 1H), 2.34 (m, 1H), 1.6 (m, 1H).

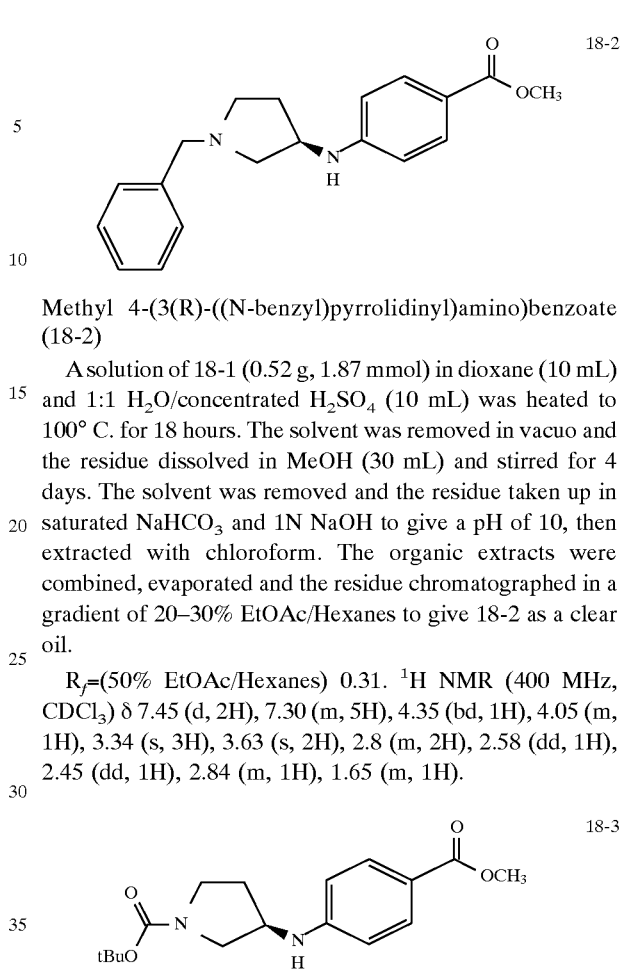

Methyl 4-(3(R)-((N-benzyl)pyrrolidinyl)amino)benzoate (18-2)

A solution of 18-1 (0.52 g, 1.87 mmol) in dioxane (10 mL) and 1:1 H₂O/concentrated H₂SO₄ (10 mL) was heated to 100° C. for 18 hours. The solvent was removed in vacuo and the residue dissolved in MeOH (30 mL) and stirred for 4 days. The solvent was removed and the residue taken up in saturated NaHCO₃ and 1N NaOH to give a pH of 10, then extracted with chloroform. The organic extracts were combined, evaporated and the residue chromatographed in a gradient of 20–30% EtOAc/Hexanes to give 18-2 as a clear oil.

$R_f$=(50% EtOAc/Hexanes) 0.31. ¹H NMR (400 MHz, CDCl₃) δ 7.45 (d, 2H), 7.30 (m, 5H), 4.35 (bd, 1H), 4.05 (m, 1H), 3.34 (s, 3H), 3.63 (s, 2H), 2.8 (m, 2H), 2.58 (dd, 1H), 2.45 (dd, 1H), 2.84 (m, 1H), 1.65 (m, 1H).

Methyl 4-(3-(R)-(1-(1,1-dimethylethoxycarbonyl) pyrrolidinyl) amino)benzoate (18-3)

A suspension of 18-2 (0.29 g, 0.93 mmol) and 10% Pd/C (0.068 g, 23% by weight) in CH₃OH (7 ml) was stirred under hydrogen atmosphere for 48 hours. The mixture was filtered through Solka Floc, and solvent removed. The residue was dissolved in CH₂Cl₂ (5 ml) and treated with Et₃N (0.65 ml, 4.7 mmol) and BOC₂O (0.45 g, 2.1 mmol). The reaction mixture was stirred 1 h at room temperature, then diluted with EtOAc and washed with 10% KHSO₄ and brine, dried (Na₂SO₄), and the solvent removed. The residue was purified by flash chromatography on silica gel, eluting with EtOAc (1)/hexane (1) to provide 18-3 as an oil.

$R_f$=0.3 (silica gel, EtOAc (3)/hexane (2)). ¹H NMR (400 MHz, CDCl₃) δ 1.47 (9H, s), 1.92 (1H, s), 2.20 (1H, q), 3.25 (3H, s), 4.11 (1H, m), 4.19 (1H, m), 6.55 (2H, d), 7.87 (2H, d).

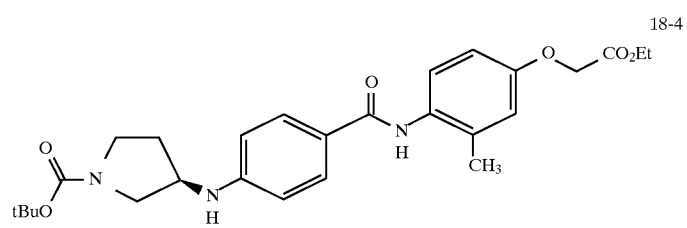

Ethyl 2-(3-methyl-4-(4-(3-(R)-((1,1-(1,1-dimethylethoxycarbonyl)pyrrolidinyl)amino)phenylcarbonylamino)phenyloxy)acetic acid (18-4)

A solution of 18-3 (0.245 g, 0.76 mmol) in dioxane (4 ml) was treated with 1N NaOH (3.0 ml, 3.0 mmol) at room temperature for 1 h. A second portion of 1N NaOH (3.0 ml, 3.0 mmol) was then added, and the reaction mixture was stirred for 15 h. The solution was then adjusted to pH 7 with 1N HCl and the solvent removed. The residue was suspended in $CH_2Cl_2$ (6 ml) and treated with 10-4 (0.19 g, 0.77 mmol), diisopropylethylamine (0.53 mmol, 3.0 mmol), and PYCLU (Fluka, 0.30 g, 0.83 mmol). The reaction mixture was stirred for 48 h at room temperature, then solvent was removed and the residue was purified by flash chromatography on silica gel, eluting with EtOAc (3)/hexane (2) to give 18-4 as an oil.

$R_f$=0.2 (silica gel, EtOAc (3)/hexane (2)). $^1$H NMR (400 MHz, $CDCl_3$) δ 1.30 (3H, t), 1.47 (9H, s), 1.93 (1H, s), 2.24 (1H, m), 2.28 (3H, s), 3.27 (1H, m), 3.49 (2H, m), 3.73 (1H, m), 4.11 (2H, m), 4.16 (1H, m), 4.29 (2H, q), 4.60 (2H, s), 6.62 (2H, d), 6.77 (1H, d), 6.81 (1H, s), 7.41 (1H, s), 7.68 (1H, d), 7.73 (2H, d).

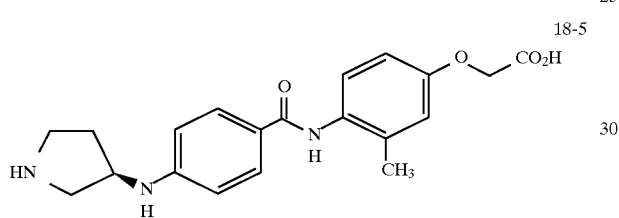

18-5

2-(3-Methyl-4-(4-(3(R)-(pyrrolidinyl)amino) phenylcarbonylamino) phenyloxy)acetic acid (18-5)

A solution of 18-4 (0.216 g, 0.434 mmol) in EtOAc (10 ml) was cooled to −78° C. and treated with HCl (g) for 1.5 min. The reaction mixture was stirred at 0° C. for 1 h and then solvent was removed. The residue taken up in THF (1)/$CH_3OH$ (1)/$H_2O$ (1) (6 ml) and treated with $LiOH·H_2O$ (0.11 g, 2.6 mmol) at room temperature for 2.5 h. The solvent was removed and the residue was purified by flash chromatography on silical gel eluting with EtOH (18)/$H_2O$ (1)/$NH_4OH$ (1) to afford 18-5 as a white solid.

$R_f$=0.2 (silica gel, EtOH (18)/$H_2O$ (1)/$NH_4OH$ (1)). $^1$H NMR (400 MHz, $D_2O$) δ 1.57 (1H, m), 2.06 (1H, m), 2.08 (3H, s), 2.60 (1H, m), 2.76 (1H, m), 2.86 (1H, m), 3.03 (1H, m), 3.93 (1H, m), 4.38 (2H, s), 6.71 (3H, m), 6.80 (1H, s), 7.05 (1H, d), 7.66 (2H, d).

SCHEME 19

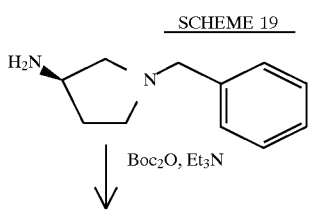

Boc$_2$O, Et$_3$N

SCHEME 19
-continued

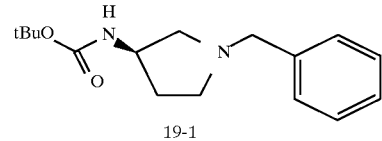

19-1

1.) H$_2$(g), 10% Pd/C
2.)

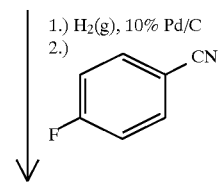

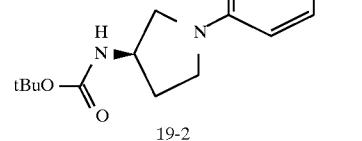

19-2

1.) aq. H$_2$SO$_4$, dioxane
2.) CH$_3$OH
3.) Boc$_2$O, Et$_3$N

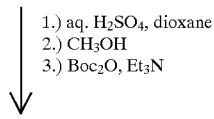

19-3

1.) 1N NaOH
2.)

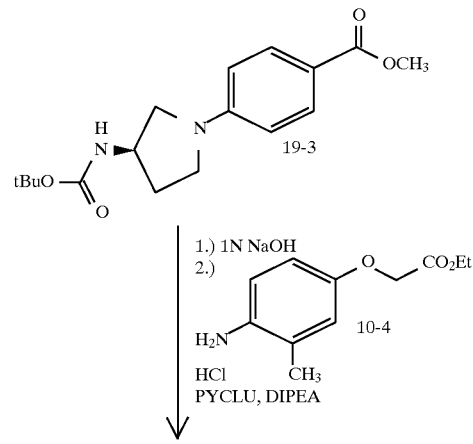

10-4

PYCLU, DIPEA

-continued
SCHEME 19

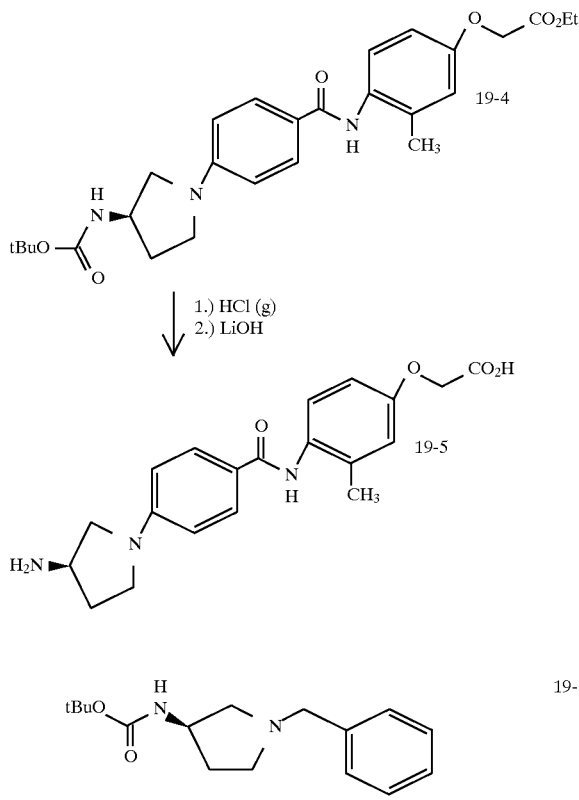

N-benzyl-3-(R)-((1,1-dimethylethoxycarbonyl)amino)pyrrolidine (19-1)

A solution of N-benzyl-3-(R)-aminopyrrolidine (TCI, 5.00 g, 28.4 mmol) in $CH_2Cl_2$ (100 ml) was treated with $Boc_2O$ (6.80 g, 31.2 mmol) and $Et_3N$ (7.9 ml, 57 mmol). The reaction was stirred at room temperature for 15 h, then solvent was removed. The residue was purified by flash chromatography on silica gel eluting with EtOAc (3)/hexane (2) to give 19-1 as an oil.

$R_f$=0.4 (silica gel, EtOAc (1)/hexane (1)). $^1$H NMR (400 MHz, $CDCl_3$) δ 1.43 (9H, s), 1.60 (1H, m), 2.27 (2H, m), 2.51 (1H, m), 2.62 (1H, m), 2.76 (1H, m), 3.58 (2H, s), 4.13 (1H, m), 4.89 (1H, m), 7.29 (5H, m).

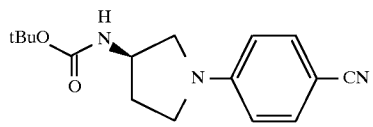

4-((3-(R)-(1,1-Dimethylethoxycarbonyl)amino)pyrrolidin-1-yl)phenylnitrile (19-2)

A suspension of 19-1 (7.43 g, 26.9 mmol) and 10% Pd/C (2.45 g, 33% by weight) in $CH_3OH$ (150 ml) was stirred under $H_2$ (g) atmosphere for 5 h. The reaction mixture was filtered through a pad of Solka Floc, and the solvent was removed. The residue was dissolved in $CH_3CN$ (20 ml) and treated with 4-fluorobenzonitrile (16.1 g, 133 mmol) at 70° C. for 18 h. The reaction mixture was then cooled to room temperature and the solvent was removed. The residue was purified by flash chromatography on silica gel eluting with EtOAc (1)/hexane (1) to afford 19-2 as a white solid.

$R_f$=0.4 (silica gel, EtOAc (2)/hexane (3)). $^1$H NMR (400 MHz, $CDCl_3$) δ 1.45 (9H, s), 1.99 (1H, m), 2.30 (1H, m), 3.18 (1H, m), 3.46 (2H, m), 3.62 (1H, m), 4.36 (1H, b), 4.67 (1H, b), 6.52 (2H, d), 7.47 (2H, d).

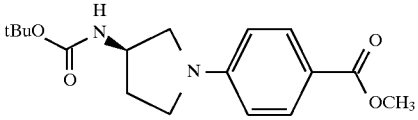

Methyl 4-((3-(R)-(1,1-dimethylethoxycarbonyl)amino)pyrrolidin-1-yl)-benzoate (19-3)

A solution of 19-2 (1.48 g) in dioxane (25 ml) and $H_2SO_4$ (1)/$H_2O$ (1) (25 ml) was heated at 70° C. for 15 h. The reaction mixture was then concentrated to remove the dioxane, diluted with $CH_3OH$ (100 ml), heated at 60° C. for 2 h, and stirred at room temperature for 48 h. The reaction mixture was concentrated to remove the $CH_3OH$, and the residue adjusted to pH 10 with 6N NaOH and sat. $NaHCO_3$. The aqueous mixture was then extracted with $CH_2Cl_2$, and the organic extracts concentrated to afford an oil. This residue was dissolved in $CH_2Cl_2$ (25 ml) and treated with $Boc_2O$ (2.96 g, 13.6 mmol) and $Et_3N$ (2.2 ml, 16 mmol). The reaction mixture was stirred at room temperature for 15 h. The solvent was then removed and the residue purified by flash chromatography on silica gel eluting with EtOAc (2)/hexane (3) to yield 19-3 as an oil.

$R_f$=0.5 (silica gel, EtOAc (2), hexane (3)). $^1$H NMR (400 MHz, $CDCl_3$) δ 1.27 (9H, s), 1.99 (1H, m), 2.30 (1H, m), 3.22 (1H, m), 3.42 (2H, m), 3.85 (3H, s), 4.37 (1H, b), 4.69 (1H, b), 6.51 (2H, d), 7.91 (2H, d).

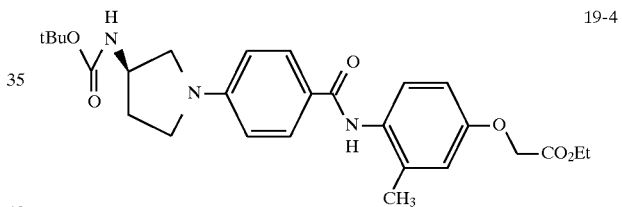

Ethyl 2-(4-((3-(R)-(1,1-dimethylethoxycarbonyl)amino)pyrrolidin-1-yl)phenylcarbonylamino)-3-methylphenoxy)acetic acid (19-4)

A solution of 19-3 (0.418 g, 1.30 mmol) in dioxane (10 ml) was treated with 1N NaOH (7.0 ml, 7.0 mmol), and the reaction mixture was stirred at room temperature for 15 h. A second portion of 1N NaOH (3.0 ml, 3.0 mmol) was then added and the reaction mixture was stirred an additional 15 h. Solvent was removed, and the residue was taken up in $H_2O$, adjusted to pH 6-7 with 10% $KHSO_4$ and extracted with EtOAc. The combined organic extracts were dried ($Na_2SO_4$) and the solvent was removed. The residue was taken up in $CH_2Cl_2$ (7 ml) and treated with 10-4 (0.33 g, 1.3 mmol), DIPEA (0.81 mmol, 4.6 mmol) and PYCLU (Fluka, 0.53 g, 1.5 mmol). The reaction mixture was stirred at room temperature for 48 h. The solvent was then removed and the residue was purified by flash chromatography on silica gel eluting with EtOAc (1)/hexane (1) to afford 19-4 as a white solid.

$R_f$=0.3 (silica gel, EtOAc (1)/hexane (1)). $^1$H NMR (400 MHz, $CDCl_3$) δ 1.30 (3H, t), 1.46 (9H, s), 2.04 (1H, m), 2.29 (3H, s), 2.31 (1H, m), 3.23 (1H, m), 3.45 (2H, m), 3.65 (1H, m), 4.27 (2H, q), 4.38 (1H, b), 4.60 (2H, s), 4.72 (1H, b), 6.57 (2H, d), 6.77 (1H, d), 7.67 (1H, s), 7.41 (1H, s), 7.72 (1H, d), 7.77 (2H, d).

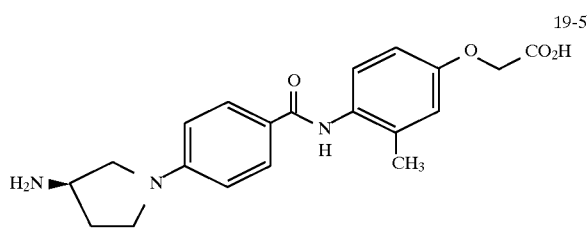

2-(4-((3(R)-amino)pyrrolidin-1-yl)phenylcarbonylamino)-3-methylphenoxy)acetic acid (19-5)

A solution of 19-4 (0.306 g, 0.615 mmol) in EtOAc (15 ml) at −78° C. was treated with HCl (g) for 1.5 min. The reaction mixture was then stirred at 0° C. for 1 h, and the solvent was removed. The residue was taken up in THF (1)/CH$_3$OH(1)/H$_2$O (1) (6 ml) and treated with LiOH.H$_2$O at room temperature for 1 h. The solvent was removed, and the residue was purified by flash chromatography on silica gel eluting with EtOH (18)/H$_2$O (1)/NH$_4$OH (1) to give 19-5 as a white solid.

$R_f$=0.4 (silica gel, EtOH (18)/H$_2$O (1)/NH$_4$OH. $^1$H NMR (400 MHz, D$_2$O) δ 1.74 (1H, m), 2.10 (3H, s), 2.12 (1H, m), 3.00 (1H, m), 3.28 (1H, m), 3.39 (1H, m), 3.47 (1H, m), 3.59 (1H, m), 4.39 (2H, s), 6.61 (2H, d), 6.71 (1H, d), 6.81 (1H, s), 7.07 (1H, d), 7.79 (2H, d).

SCHEME 20

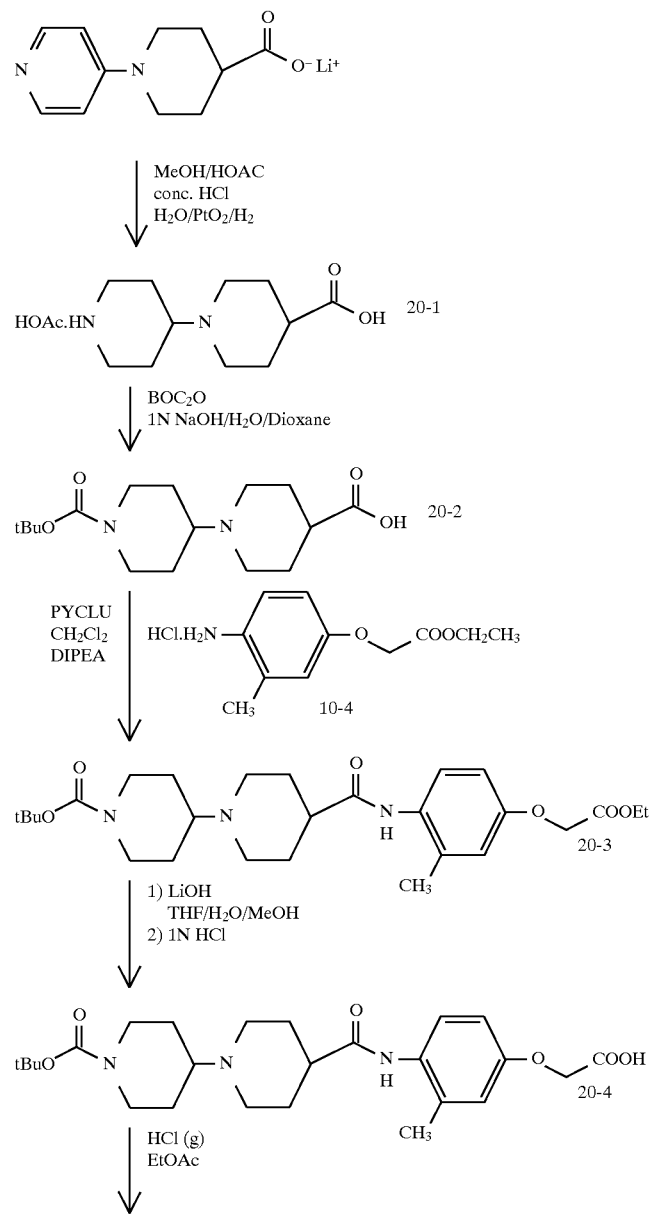

-continued
SCHEME 20

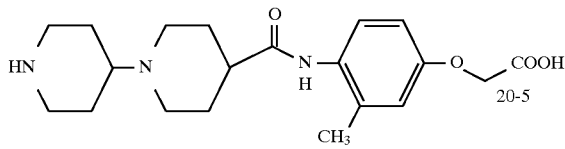

20-5

2H), 2.75 (bt, 2H), 2.9 (m, 1H), 2.15 (bd, 2H), 2.0 (bd, 2H), 1.7 (m, 2H), 1.55 (m, 2H), 1.35 (s, 9H).

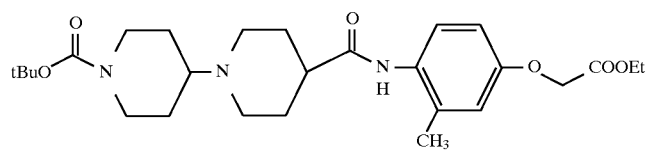

20-3

Ethyl 2-(4-(4-((1,1-dimethylethoxycarbonyl)piperidin-4-yl)piperidinylcarboxamido)3-methylphenoxy)acetic acid (20-3)

20-2 (486 mg; 1.6 mmol) and 10-4 (250 mg, 1.6 mmol) were dissolved in $CH_2Cl_2$. PYCLU (1.8 mmol, 634 mg) was added, followed by diisopropylethylamine (6.4 mmol, 1.1 mL). The reaction is stirred for 2 days. The reaction mixture is diluted with EtOAc and washed with $H_2O$, 10% $KHSO_4$, sat $NaHCO_3$ and brine. The organic layer is dried ($MgSO_4$), filtered and concentrated to yield a tan oil. Flash chromatography (10% $MeOH/CHCl_3$ sat $NH_3$) yielded desired product (20-3) plus bis piperidine urea by-product. This material is triturated with hexane to remove most of the by-product.

$R_f$ (10% MeOH/ $CHCl_3$ sat. $NH_3$)=0.20 $^1$H NMR (400 MHz, $CdCl_3$) δ 7.55–7.57 (d, 1H), 6.88 (s, 1H), 6.74 (s, 1H) 6.71–6.72 (d, 1H), 4.6 (s, 1H), 4.27–4.29 (q, 2H), 4.23–4.25 (bs, 2H), 2.9–3.0 (d, 2H), 2.6–2.7 (t, 2H), 2.35–2.45 (t, 2H).

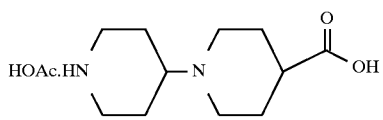

20-1

4-(Piperidin-4-yl)piperidinyl carboxylic acid, acetic acid salt (20-1)

A suspension of the lithium salt of N-(pyridin-4-yl)-4-piperidine carboxylic acid (prepared as described in Tetrahedron, 1988 44(23) 7095–7108, 1 g, 5.55 mmol) in 50 mL 20% HOAc/MeOH, 10 mL $H_2O$ and 10 mL concentrated HCl was treated with $PtO_2$ (1.7 g) and hydrogenated at 65 psi for 24 hrs. The solution was filtered, evaporated and the residue azeotroped with heptane to yield 20-1 as a white solid.

$R_f$(9:1:1 $EtOH/H_2O/NH_4OH$)=0.39. $^1$H NMR (400 MHz, $D_2O$) δ 3.6–3.5 (m, 4H), 3.9 (m, 1H), 3.1–3.0 (m, 4H), 2.65 (m, 1H), 2.32 (d, 2H), 2.25 (d, 2H), 2.0–1.7 (m, 4H).

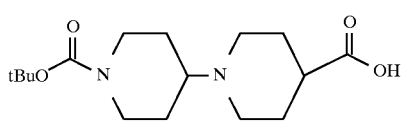

20-2

4-((1,1-Dimethylethoxycarbonyl)piperidin-4-yl)piperidinyl carboxylic acid (20-2)

A solution of 20-1 (1.7 g, 5.55 mmol) in $H_2O$ (10 mL) was treated with sufficient 1N NaOH to bring the solution to pH 11. Dioxane (20 mL) was added followed by BOC anhydride (1.33 g, 6.2 mmol) dissolved in 5 mL dioxane. After 1 hr the solvents were removed and the residue was triturated with acetonitrile and n-butanol, filtered and the filtrate concentrated. The residue was chromatographed (silica gel, 9:1:1 $EtOH/H_2O/NH_4OH$) to give 20-2 as a white solid.

$R_f$(9:1:1 $EtOH/H_2O/NH_4OH$)=0.70 $^1$H NMR (400 MHz, $D_2O$) δ 4.12 (bd, 2H), 3.5 (bd, 2H), 3.32 (m, 1H), 2.95 (bt,

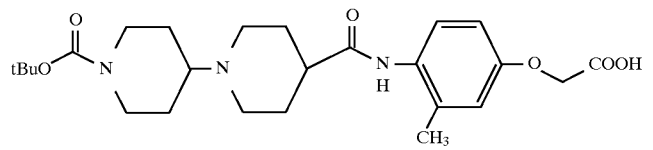

20-4

2-(-4-(4-((1,1-Dimethylethoxycarbonyl)piperidin-4-yl)piperidinylcarboxamido)3-methylphenoxy)acetic acid (20-4)

20-3 (300 mg) was dissolved in $THF/H_2O/MeOH$ (2 mL/2 mL/2 mL). LiOH (50 mg) was added and the reaction is stirred for 2 hours. 1N HCl was added (0.50 mL) and the reaction mixture was concentrated to yield 20-4 as a tan solid.

$R_f$(9/1/1 $CH_2Cl_2/MeOH/HOAc$)=0.16 $^1$H NMR (400 MHz, $CD_3OD$) δ 7.06–7.08 (d,1H), 6.81 (s, 1H), 6.75 (d, 1H), 4.88 (s, 2H), 4.12–4.15 (bd, 2H), 3.04–3.07 (bd, 2H), 2.6–2.8 (vbs, 2H), 2.25–2.45 (m, 4H), 2.17 (s, 3H), 1.46–1.56 (m, 6H), 1.45 (9H).

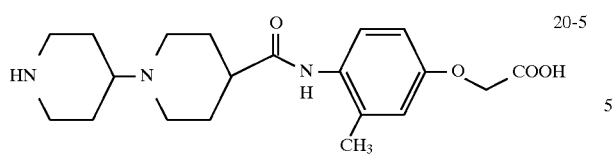

2-(4-(4-(Piperidin-4-yl)piperidinylcarboxamido)3-methylphenoxy) acetic acid (20-5)

20-4 (0.08 mmol) is dissolved in EtOAc and cooled to −78°. HCl (g) is bubbled through until the solution is saturated. The reaction is warmed to 0°, and stirred for five minutes. The reaction mixture is concentrated to yield a tan solid. The material was purified by flash chromatography using 10/1/1 EtOH/NH$_4$OH/H$_2$O as an eluent, resulting in pure 20-5 as a white solid.

$R_f$(10/1/1 EtOH/NH$_4$OH/H$_2$O)=0.15 $^1$H NMR (400 MHz, D$_2$O) 7.0 (d, 1H), 6.8 (s, 1H), 6.7 (dd, 1H), 4.7 (s, 1H), 3.4 (d, 2H), 3.1 (bd, 2H), 2.9 (t, 2H), 2.8 (bt, 1H), 2.5 (bs, 3H), 2.10–2.13 (d, 2H), 2.06 (s, 3H), 1.96–1.99 (d, 2H), 1.65–1.75 (m, 4H).

SCHEME 21

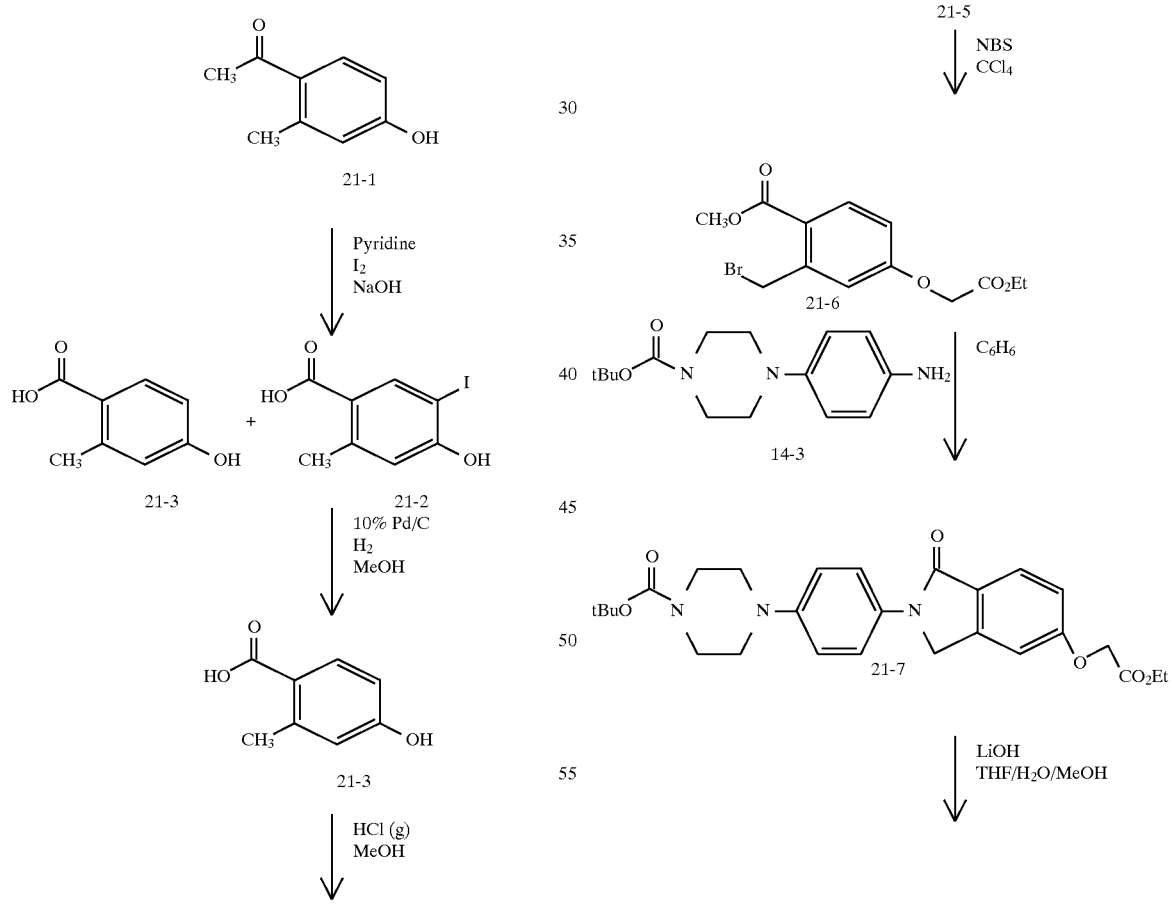

-continued
SCHEME 21

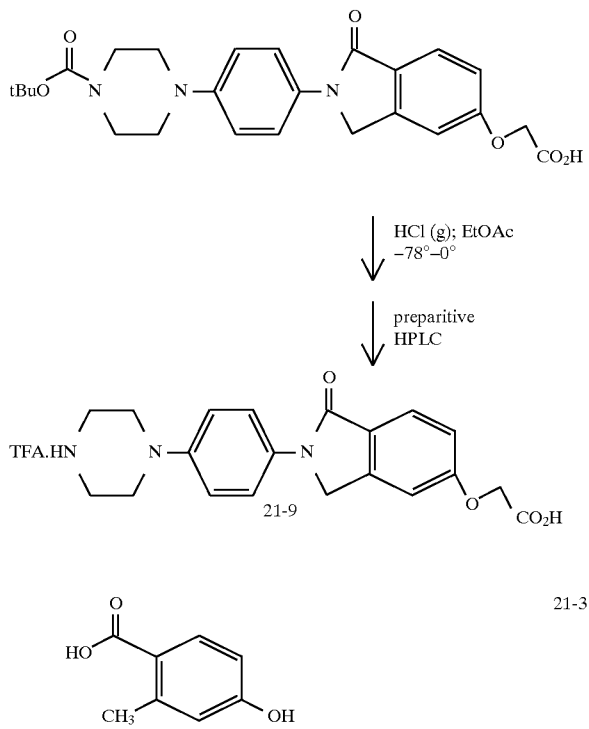

4-Hydroxy-2-methyl benzoic acid (21-3)

21-3 was prepared in two steps from 4'-hydroxy-2'methylacetophenone, 21-1, (Aldrich, 18.0 g, 0.120 mol).

The first step employed the procedure found in Merck Process Patent US 852870-92031, which resulted in a 70/30 mix of 21-3 and 3-iodo-4-hydroxy-6-methyl benzoic acid (21-2)

For the second step, the mixture (7.0 g) of 21-2 and 21-3 was reduced in MeOH (200 mL) using 10% Pd/C (700 mg) under a hydrogen balloon. After 16 hours of stirring, the reaction mixture was filtered through celite, the celite pad was washed with MeOH and the filtrate was concentrated to yield pure 21-3 as a tan solid.

$^1$H NMR (400 MHz, CDCl$_3$) δ 7.8 (d, 1H), 6.6 (m, 2H), 2.5 (s, 3H). $R_f$ (90 % Ethyl Acetate/Hexane)=0.34

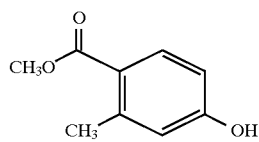

Methyl 4-hydroxy-2-methylbenzoate (21-4)

21-3 (5.0 g, 32.9 mmol) was redissolved in MeOH (150 mL) and cooled to 0°. HCl (g) was bubbled through for a few minutes, the cooling bath was removed and the reaction was stirred at RT for 16 hours. The reaction mixture was then concentrated to yield pure 21-4 as a tan solid.

$R_f$ (50% Ethyl Acetate/Hexane)=0.83 $^1$H NMR (400 MHz, CDCl$_3$) δ 7.9 (d, 1H), 6.7 (m, 2H), 3.85 (s, 3H), 2.57 (s, 3H).

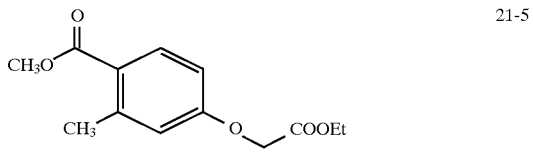

Ethyl 2-(3-methyl-4-methoxycarbonylphenoxy)acetate (21-5)

21-4 (1.5 g; 9.0 mmol) was dissolved in DMF (150 mL). Ethyl bromoacetate (9.0 mmol, 1.0 mL) was added followed by Cs$_2$CO$_3$ (9.0 mmol, 2.9 g). The slurry was stirred vigorously for 16 hours. The reaction mixture was diluted with EtOAc and washed twice with water, 10% KHSO$_4$ and brine. The organic layer was dried (MgSO$_4$), filtered and concentrated to yield 21-5 which will be used in the next step without any further purification.

$R_f$ (30 % Ethyl Acetate/Hexane)=0.40 $^1$H NMR (400 MHz, CDCl$_3$) δ 7.9 (d, 1H), 6.7–6.8 (m, 2H), 4.6 (s, 2H), 4.3–4.3 (q, 2H), 3.9 (s, 3H), 2.6 (s, 3H), 1.3 (t, 3H).

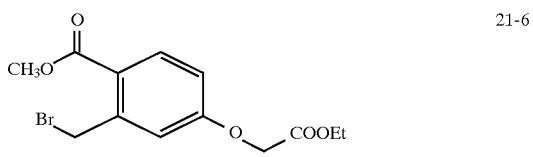

Ethyl 2-(3-bromomethyl-4-methoxycarbonylphenoxy)acetate (21-6)

21-5 (2.1 g; 8.3 mmol) was dissoved in CCl$_4$ (40 mL). NBS (10.3 mmol, 1.9 g) was added followed by dibenzoyl peroxide (1.66 mmol, 400 mg). The reaction mixture was heated to reflux for 16 hours. The reaction mixture was cooled and filtered through a celite pad to remove excess succinimide. The filtrate was concentrated to yield 21-6 as a tan oil, which was used in the next step without any further purification.

$R_f$ (30% Ethyl Acetate/Hexane)=0.52

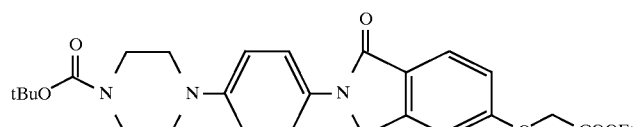

Ethyl 1-(4-(1,1-Dimethylethoxycarbonylpiperazin-1-yl)
phenyl)-2-oxo-isoindolin-5-oxy)acetate (21-7)

21-6 (8.3 mmol) was dissolved in benzene (100 mL),
followed by 14-3. The mixture was heated to reflux for 32
hours. Triethylamine (8.3 mmol) was added and the reaction
was refluxed for 2 more days. The reaction mixture was then
concentrated to yield a brown solid which was absorbed on
silica and purified by flash chromatography. A small amount
of the product was eluted with 50% EtOAC/Hex. Most of
the material was then flushed off the column with 10%
MeOH/CHCl$_3$ saturated with NH$_3$. These flushings yielded
a brown solid which was repurified on a column of silica
using 10% MeOH/CHCl$_3$ as a eluent to yield 21-7 as a
brown solid.

R$_f$ (50% EtOAc/Hex)=0.48 $^1$H NMR (400 MHz, CDCl$_3$)
δ 7.8 (d, 1H), 7.7 (d, 2H), 7.0 (m, 4H), 4.77 (s, 2H), 4.72 (s, 2H), 4.3 (q, 2H), 3.6 (m, 4H), 3.1 (m, 4H), 1.5 (s, 9H), 1.3 (t, 3H).

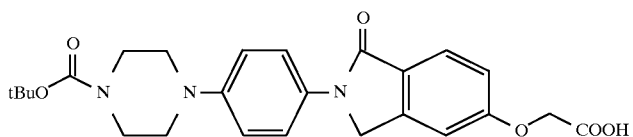

21-8

1-(4-(1,1-Dimethylethoxycarbonylpiperazin-1-yl)phenyl)-
2-oxo-isoindolin-5-oxy)acetic acid (21-8)

21-7 (1.3 g; 2.6 mmol) was dissolved in THF/H$_2$O/MeOH
(5 mL/5/5). LiOH (5.2 mmol, 218 mg) was added and the
reaction mixture was stirred for 2 hours. 1N HCl was added
(2.6 mL), and the reaction mixture was concentrated to yield
21-8 and excess LiCl as a brown solid.

R$_f$(9/1/1 CH$_2$CH$_2$/MeOH/HOAc)=0.80 $^1$H NMR (400
MHz, CD$_3$OD) δ 7.7 (m, 3H), 7.0–7.1 (m, 4H), 3.3 (bm, 4H), 3.1 (bm, 4H), 1.5 (s, 9H).

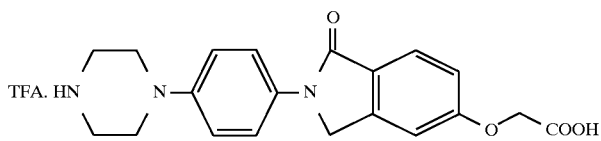

21-9

1-(((4-Piperazin-1-yl)phenyl)-2-oxo-isoindolin-5-oxy)
acetic acid (21-9)

21-8 (2.6 mmol) was dissolved in EtOAc and cooled to
−78°. HCl was bubbled through until the solution was
saturated. The reaction mixture was then stirred at 0° for 10
min and concentrated to yield a brown solid. Flash chromatography (10/0.8/0.8 EtOH/NH$_4$OH/H$_2$O) yielded 21-9 as a
brown solid. This material was further purified by preparative HPLC to yield pure 21-9 (TFA salt) as an off-white
solid.

R$_f$(10/1/1 EtOH/NH$_4$OH/H$_2$O)=0.72 $^1$H NMR (400 MHz,
DMSO- d$_6$) δ 7.8 (d, 2H), 7.7 (d, 1H), 7.2 (s, 1H), 7.1 (d, 3H), 4.9 (s, 2H), 4.8 (s, 2H), 3.2–3.3 (bd, 8H).

SCHEME 22

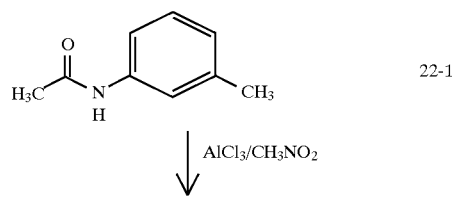

22-1

AlCl$_3$/CH$_3$NO$_2$

-continued
SCHEME 22
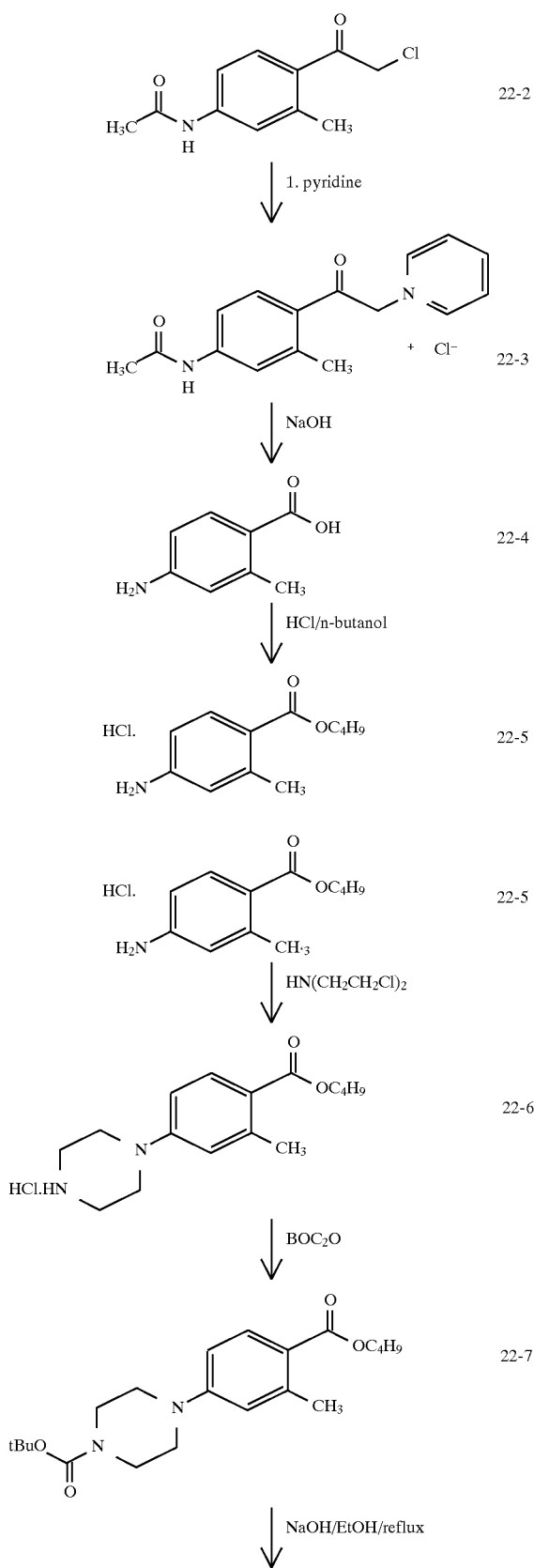

-continued
SCHEME 22
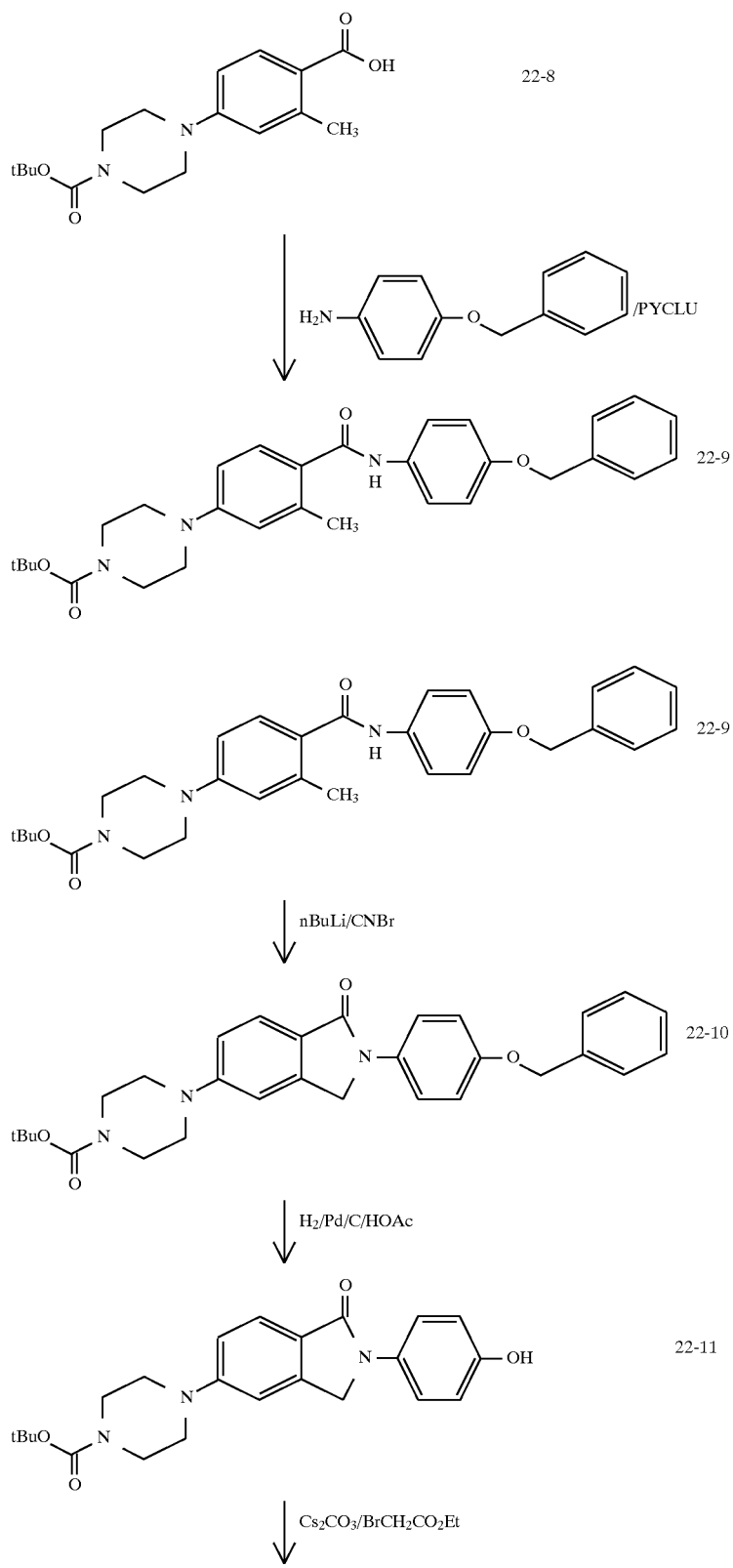

-continued
SCHEME 22

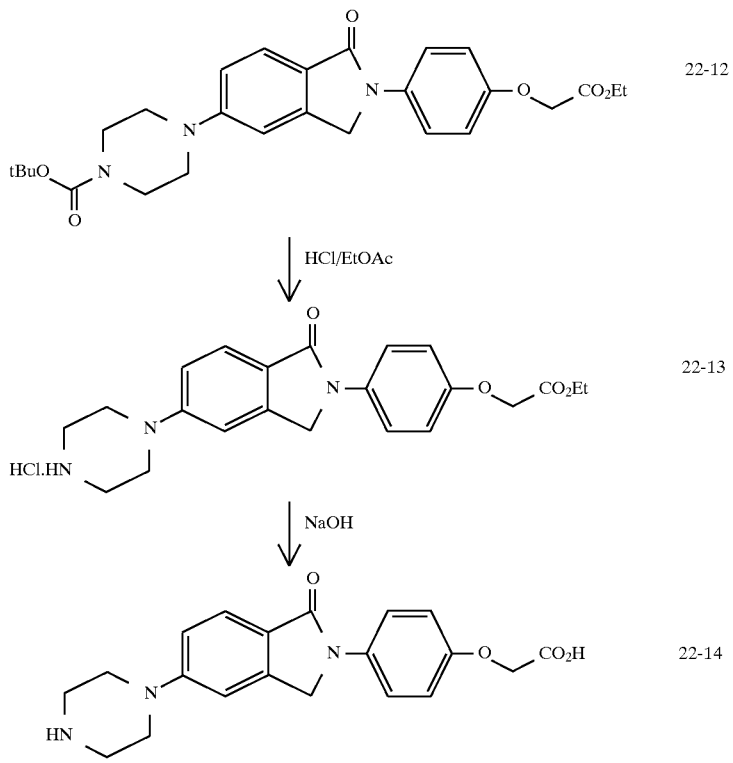

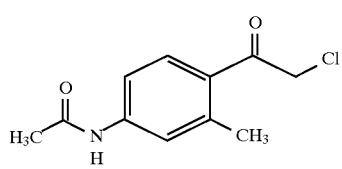

1-Chloro-2-(2-methyl-4-acetamidophenyl)ethanone (22-2)

A suspension of 3-acetamido toluene (Aldrich) (33.45 g, 0.224 mole) in nitromethane (100 mL) was treated with chloracetylchloride (69.3 mL, 0.739 mole). The solution became homogenous. Aluminum trichloride (92.3 g, 0.694 mol) was added in 10 g portions over 40 minutes. The temperature rose to 50° C. and the solution became dark brown. The reaction was heated to 80° C. for 2 hours, then cooled to room temperature and concentrated to give a thick green oil that was added to crushed ice and stirred with a overhead stirrer. The resulting tan solid was collected in a sintered glass funnel and washed with water and dried to give 22-2 as a tan solid.

$R_f$ (40% EtOAc/Hexanes)=0.14. $^1$H NMR (300 MHz, CDCl$_3$) δ 7.66 (d, 1H), 7.58 (m, 1H), 7.43 (s, 1H), 7.28 (s, 1H), 4.62 (s, 2H), 2.55 (s, 3H), 2.2 (s, 3H).

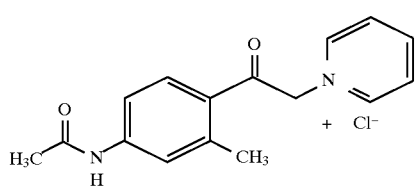

1-(1-Pyridinium)-2-(2-methyl-4-acetamidophenyl) ethanone. chloride (22-3)

A solution of 22-2 (21.8 g, 0.098 mol) in refluxing ethanol (110 mL) was treated with pyridine (28 mL). A salmon-pink percipitate formed and after 2 hours of reflux the mixture was cooled to room temperature, filtered and rinsed with cold (−20° C.) EtOH and dried to give 22-3 as an off-white solid.

$R_f$ (9:1:1 EtOH/H$_2$O/NH$_4$OH) 0.12 $^1$H NMR (400 MHz, D$_2$O) δ 8.66 (d, 2H), 8.5 (m, 1H), 8.08 (d, 2H), 7.92 (d, 1H), 7.5 (d, 1H), 7.33 (s, 1H), 2.4 (s, 3H), 2.1 (s, 3H).

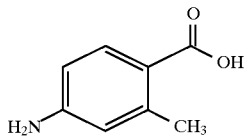

2-Methyl-4-amino-benzoic acid 22-4

To a 60° C. solution of 22-3 (23.5 g, 0.077 mol) in H$_2$O (155 mL) was added 2.5M NaOH solution (160 mL). An orange percipitate formed. The reaction was heated to reflux for 2.5 hours, then the homogenous solution was cooled to room temperature and treated with 2.5M HCl(160 mL) and stirred overnight. The pH of the solution was adjusted to pH 4–5 with NaOH solution and the yellow percipitate that formed was washed with water and dried to give 22-4 as a gummy yellow solid.

$R_f$(9:1:1 EtOH/H$_2$O/NH$_4$OH)=0.76. $^1$H NMR (300 MHz, CD$_3$OD) δ 7.75 (d, 1H), 6.43 (m, 2H), 2.42 (s, 3H).

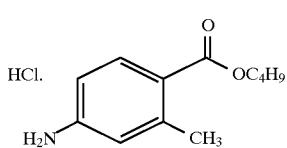

n-Butyl 2-methyl-4-amino-benzoate, hydrochloride (22-5)

A suspension of 22-4 (8.8 g, 58 mmol) in n-butanol (200 mL) was cooled to 0° C. under argon and saturated with HCl gas. A salmon-pink percipitate formed. The solution was heated to reflux for 18 hours then evaporated. The residue was dissolved in EtOAc and saturated NaHCO₃ and the layers were separated. The aqueous layer was washed repeatedly with EtOAc, the EtOAc layers were combined, dried with brine and MgSO₄, filtered and evaporated. The oily residue was dissolved in CHCl₃ and evaporated to give 22-5 as a brown solid.

R$_f$ (20% EtOAc/Hexanes) 0.5 ¹H NMR (300 MHz, CDCl₃) δ 7.83 (d, 1H), 6.48 (m, 2H), 4.23 (t, 2H), 3.9 (bs, 2H), 2.53 (s, 3H), 1.7 (m, 2H), 1.48 (m, 3H), 0.95 (t, 3H).

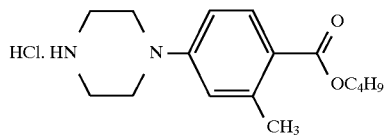

n-Butyl 2-methyl-4-piperizin-1-yl-benzoate, hydrochloride (22-6)

A solution of 22-5 (10.7 g, 52 mmol) in n-butanol (285 mL) was treated with bis chloroethylamine hydrochloride (9.22 g, 52 nmmol) and refluxed for one week. The ethanol was removed in vacuo and the residue was diluted with EtOAc. A percipitate formed and was collected and washed with EtOAc and dried to give 22-6 as tan solid.

R$_f$ (2.5% MeOH/CHCl₃ saturated with NH₃)=0.31 ¹H NMR (400 MHz, CD₃OD) δ 7.88 (d, 1H), 6.88 (m, 2H), 4.24 (t, 2H), 3.55 (m, 4H), 3.36 (m, 4H), 2.56 (s, 3H), 1.73 (m, 2H), 1.5 (m, 2H), 1.0 (t, 3H).

R$_f$ (5% EtOAc/Hexanes)=0.4 ¹H NMR (300 MHz, CDCl₃) δ 7.9 (d, 2H), 6.68 (m, 2H), 4.23 (t, 2H), 3.55 (m, 4H), 3.38 (m, 4H), 2.6 (s, 3H), 1.75 (m, 2H), 1.5 (m, 11H), 0.95 (t, 3H).

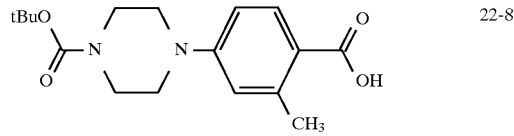

2-Methyl-4-(4-(1,1-dimethylethoxycarbonylpiperizin-1-yl) benzoic acid (22-8)

A solution of 22-6 (2.55 g, 6.78 mmol) in 4:1 EtOH/H₂O (125 mL) was treated with NaOH (2.7 g, 67.8 mmol) and refluxed overnight. The solvents were removed and the residue was partitioned between EtOAc and 10% KHSO₄. The layers were separated and the aqeous layer was washed with EtOAc several times. The organic layers were combined, washed with brine, dried over MgSO₄, filtered and evaporated to give 22-8 as a white solid.

¹H NMR (400 MHz, CDCl₃) δ 8.0 (d, 1H), 6.7 (m, 2H), 3.6 (m, 4H), 3.34 (m, 4H), 2.6 (s, 3H), 1.5 (s, 9H).

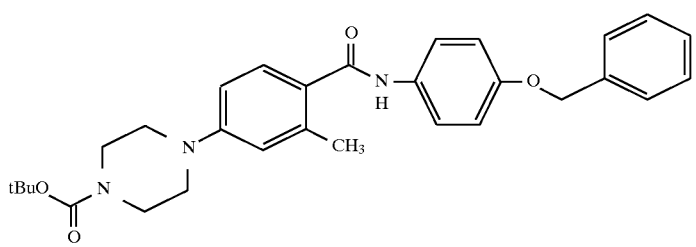

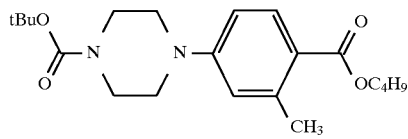

n-Butyl 2-methyl-4-(4-(1,1-dimethylethoxycarbonylpiperizin-1-yl)benzoate acid (22-7)

A solution of 22-6 (10.5 g, 33.3 mmol) in CH₂Cl₂ (100 mL) was cooled to 0° C. and treated with triethylamine (18.8 mL, 0.133 mol) and di-tert-butyldicarbonate (14.75 g, 66 mmol). The solution was allowed to warm to room temperature and after 1 hour was washed with 10% KHSO₄, brine, dried over MgSO₄, filtered and evaporated to give 22-7 as brown oil.

N-(4-Benzyloxyphenyl)-2-methyl-4-(4-(1,1-dimethylethoxycarbonyl) piperizin-1-yl)benzamide (22-9)

A solution of 22-8 (2.06 g, 6.43 mmol) in CH₂Cl₂ (50 mL) was treated with p-benzyloxy analine hydrochloride (Aldrich, 1.66 g, 7.08 mmol), diisopropyl amine (5.6 mL, 32 mmol) and PYCLU 93.47 g, 9.6 mmol). After stirring for 24 hours the volatile components were removed in vacuo and the residue was dissolved in EtOAc and washed with 10% KHSO₄, water, saturated NaHCO₃, water and brine, dried over MgSO₄, filtered and evaporated. The residue was chromatographed in a gradient of 20 to 50% EtOAc/ Hexanes to give 22-9 as an oil.

R$_f$ (50% EtOAc/Hexanes)=0.57 ¹H NMR (400 MHz, CDCl₃) δ 7.4 (m, 8H), 7.0 (d, 2H), 6.76 (m, 2H), 4.08 (s, 2H), 3.6 (s, 4H), 3.22 (bs, 4H), 2.53 (s, 3H), 1.5 (s, 9H).

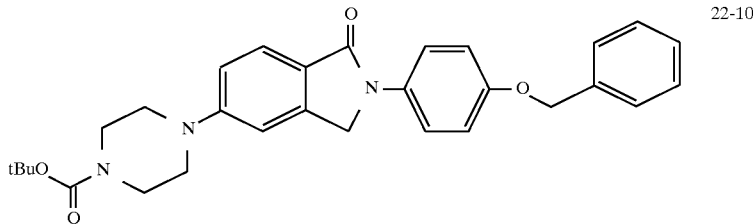

1-(4-Benzyloxyphenyl)-5-(4-(1,1-dimethylethoxycarbonyl) piperizin-1-yl)isoindolin-2-one (22-10)

A solution of 22-9 (0.66 g, 1.31 mmol) in THF (65 mL) was cooled to −78° C. under argon. n-Butyllithium (2.2M in hexanes, 2.4 mL) was added dropwise to give a deep red solution. The reaction was stirred for 20 minutes, then rapidly transferred via wide bore canulla to a −78° C. THF solution of cyanogen bromide (2.77 g, 26.2 mmol in 65 mL). The resulting colorless solution was stirred for 25 minutes, then quenched with methanol. The solution was diluted with water, the volatile solvents were removed in vacuo and the remaining water layer was extracted with EtOAc. The EtOAc layer was washed with brine, dried over MgSO₄, filtered and evaporated. The residue was chromatographed in a gradient of 20 to 30% EtOAc/Hexanes to give 22-10 as an oil.

$R_f$ (40% EtOAc/Hexanes)=0.25 $^1$H NMR (400 MHz, CDCl₃) δ 7.77 (s, 1H), 7.7 (d, 2H), 7.44 (m, 2H), 7.4 (m, 2H), 7.34 (m, 1H), 7.0 (m, 3H), 6.9 (s, 1H), 5.1 (s, 2H), 4.73 (s, 2H), 3.6 (m, 4H), 3.3 (m, 4H), 1.5 (s, 9H).

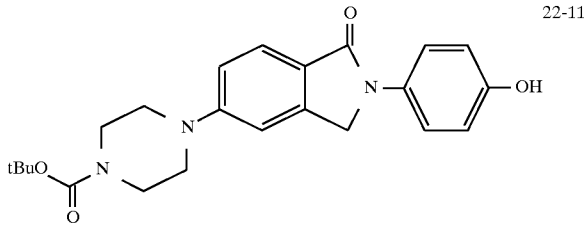

1-(4-Hydroxyphenyl)-5-(4-(1,1-dimethylethoxycarbonyl) piperizin-1-yl)isoindolin-2-one (22-11)

A solution of 22-10 (0.155 g, 0.31 mmol) in 10 mL glacial acetic acid was treated with 10% Pd/C (0.3 g) and hydrogenated at 60 psi for 5 hours. The solution was decanted from the catalyst, concentrated and the residue chromatographed using a gradient of 60 to 90% EtOAc/Hexanes to give 22-11 as an oil.

$R_f$(50% EtOAc/Hexanes)=0.19 $^1$H NMR (300 MHz, CDCl₃) δ 7.79 (d, 1H), 7.55 (d, 2H), 7.0 (m, 1H), 6.92 (bs, 1H), 6.86 (m, 2H), 4.72 (s, 2H), 3.6 (m, 4H), 3.3 (m, 4H), 1.5 (s, 9H).

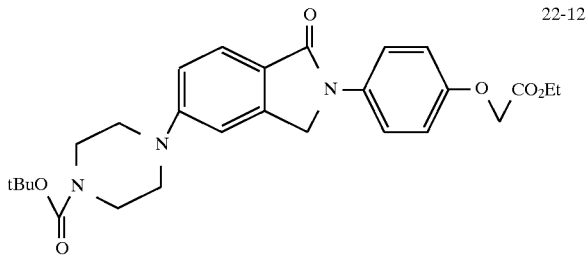

Ethyl 4-(2-oxo-5-(4-(1,1-dimethylethoxycarbonyl) piperizin-1-yl)iso-indolin-1-yl)phenoxyacetate (22-12)

A solution of 22-11 (0.045 g, 0.11 mmol) in DMF (5 mL) was treated with cesium carbonate (23 mg, 0.07 mmol) and ethyl bromoacetate (15 uL, 0.011 mmol). After 3 hours the solvents were removed in vacuo and the residue was dissolved in EtOAc and washed with water, brine, dried over MgSO₄, filtered and evaporated. The residue was chromatographed in a gradient of 30 to 50% EtOAc/Hexanes to give 22-12 as an oil.

$R_f$(40% EtOAc/Hexanes)=0.36 $^1$H NMR (400 MHz, CDCl₃) δ 7.74 (m, 3H), 7.0 (m, 2H), 6.95 (m, 2H), 4.73 (s, 2H), 4.62 (s, 2H), 4.28 (q, 2H), 3.6 (m, 4H), 3.3 (m, 4H), 1.5 (s, 9H).

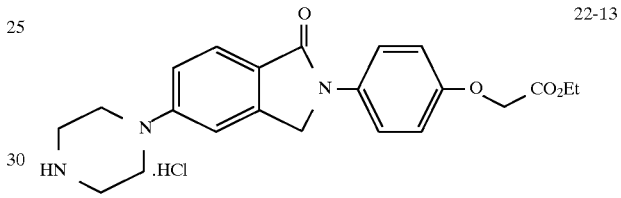

Ethyl 4-(2-oxo-5-piperizin-1-yl)isoindolin-1-yl) phenoxyacetate, hydrochloride (22-13)

A solution of 22-12 (0.04 g, 0.08 mmol) in EtOAc (10 mL) was cooled to −78° C., saturated with HCl gas, warmed to 0° C. and evaporated at ambient temperature to give 22-13 as a white solid.

$^1$H NMR (300 MHz, D₂O) δ 7.54 (d, 1H), 7.4 (d, 2H), 7.03 (m, 3H), 6.89 (d, 2H), 4.6 (s, 2H), 4.15 (q, 2H), 3.43 (m, 4H), 3.23 (m, 4H), 1.15 (t, 3H).

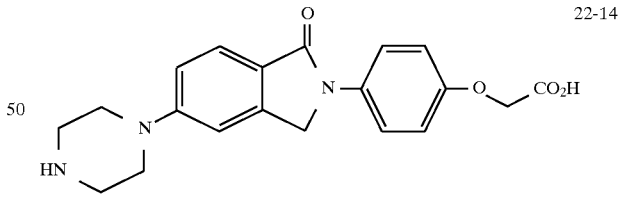

4-(2-Oxo-5-piperizin-1-yl)isoindolin-1-yl)phenoxyacetic acid (22-14)

A solution of 22-13 (0.04 g, 0.08 mmol) in 1:1 THF/H₂O (6 mL) was treated with 1N NaOH solution (0.4 mL). The reaction was concentrated and the residue chromatographed in 9:1:1 EtOH/H₂O/NH₄OH to give 22-14 as a white solid.

$R_f$(9:1:1 EtOH/H₂O/NH₄OH)=0.62 $^1$H NMR (400 MHz, D₂O+deutero trifluoroacetic acid) δ 7.49 (d, 1H), 7.44 (d, 2H), 6.95 (m, 3H), 6.74 (d, 2H), 4.33 (bs, 4H), 3.42 (bs, 4H), 3.25 (bs, 4H)

SCHEME 23
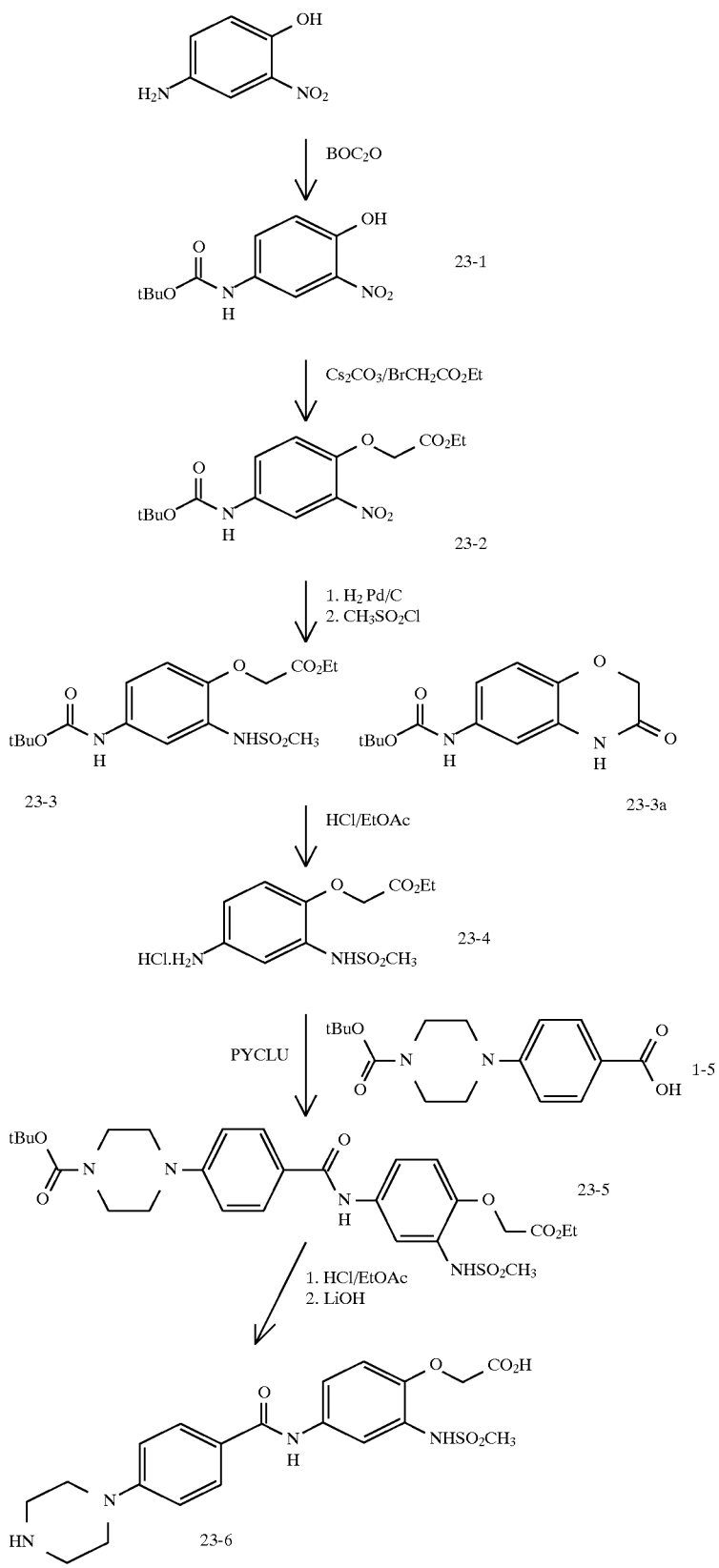

SCHEME 23
-continued
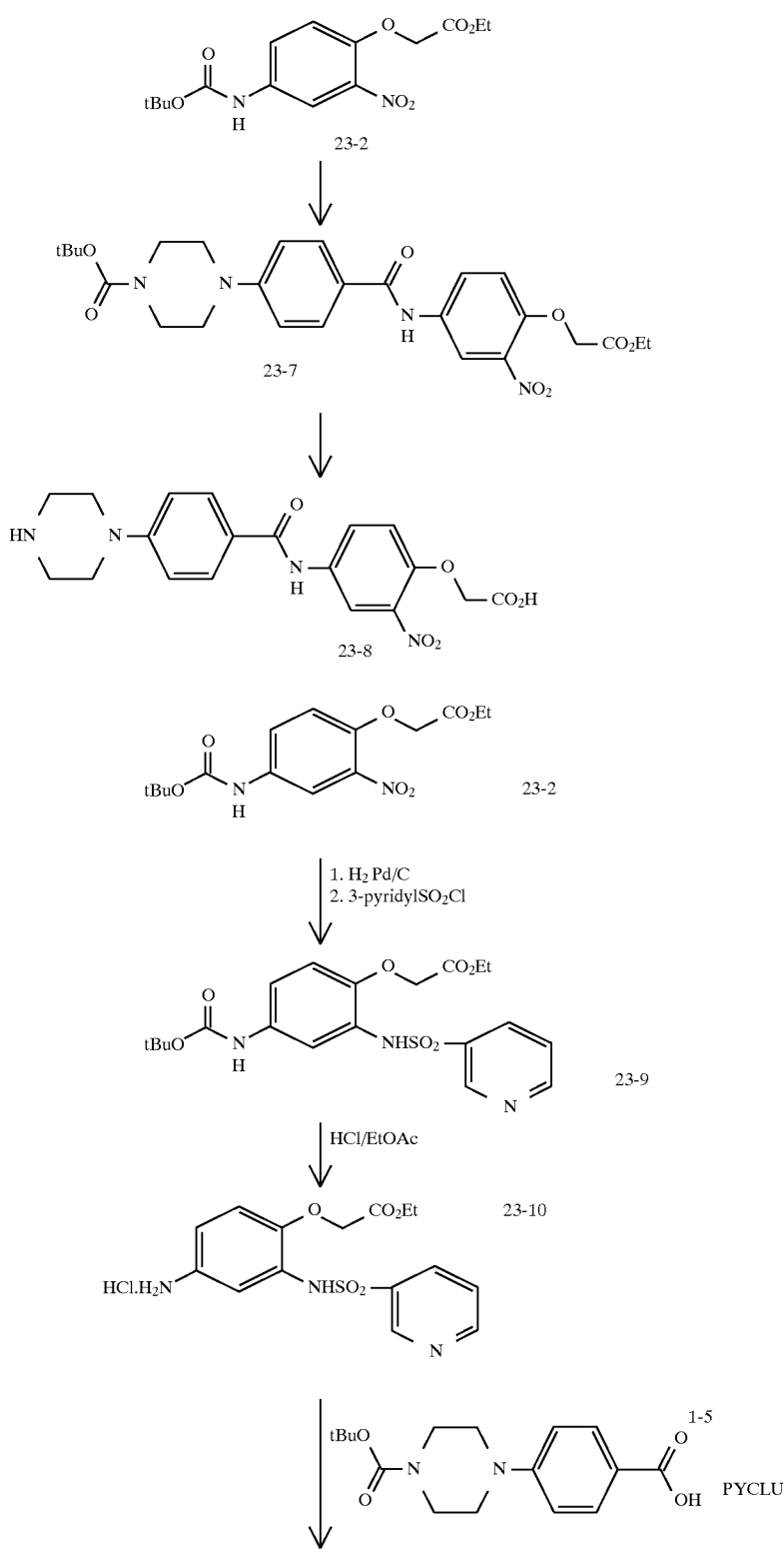

-continued
SCHEME 23

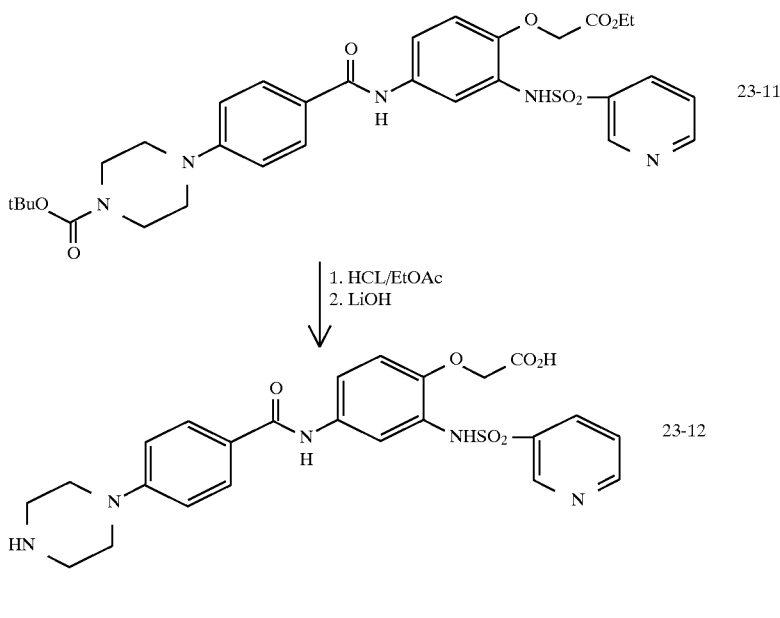

2-Nitro-4-(1,1-dimethylethoxycarbonylamino)phenol (23-1)

A solution of 2-nitro-4-amino phenol (Aldrich) (20 g, 130 mmol) in THF (500 mL) was cooled to 0° C. and treated with ditertbutyldicarbonate (64 g, 293 mmol) and triethylamine (37 mL, 265 mmol). After 24 hours the solution was concentrated and the residue dissolved in EtOAc, washed with 10% $KHSO_4$, saturated $NaHCO_3$, and brine, dried over $Na_2SO_4$, filtered and evaporated. The crude bisprotedted material ($R_f$ (40% EtOAc/Hexanes) 0.69) was then dissolved in 400 mL 1:1 THF/$H_2O$ and treated with $LiOH.H_2O$ (38 g, 1.3 mol). After stirring at room temperature overnight the solvent was removed and the residue was dissolved in EtOAc and washed with brine, dried with $Na_2SO_4$, filtered and concentrated to give 23-1 as a reddish oily solid.

$R_f$(20% EtOAc/Hexanes)=0.41 $^1$H NMR (400 MHz, $CDCl_3$) δ 10.35 (s, 1H), 8.18 (s, 1H), 7.58 (d, 1H), 7.13 (d, 1H), 6.45 (bs, 1H), 1.55 (s, 9H).

Ethyl 2-(2-nitro-4-(1,1-dimethylethoxycarbonylamino)phenoxy)acetic acid (23-2)

A solution of 23-1 (5 g, 19.7 mmol) in DMF (125 mL) was treated with cesium carbonate (3.17 g, 9.73 mmol), stirred for 10 minutes and treated with ethyl bromoacetate (2.2 mL, 19.8 mmol) at room temperature. After 1.5 hours the solution was concentrated under high vacuum and the residue was absorbed to silica gel and chromatographed in a gradient of 20 to 30% EtOAc/Hexanes to give 23-2 as a bright yellow solid.

$R_f$(30% EtOAc/Hexanes)=0.26 $^1$H NMR (400 MHz, $CDCl_3$) δ 7.95 (s, 1H), 7.5 (d, 1H), 6.97 (d, 1H), 6.62 (bs, 1H), 4.72 (s, 2H), 4.25 (q, 2H), 1.5 (s, 9H), 1.28 (t, 3H).

Ethyl 2-(2-methanesulfonamido-4-aminophenoxy)acetic acid hydrochloride (23-4)

A solution of 23-2 (2 g, 5.88 mmol) in EtOAc (25 mL) was treated with 10% Pd/C (0.67 g), and hydrogenated under balloon pressure for 1.5 hours. The solution was filtered through SolkaFloc, and the cake rinsed with EtOAc. The filtrate was not concentrated but was treated directly with methanesulfonyl chloride (3.0 mL, 39 mmol) and pyridine (5.0 mL, 62 mmol) and stirred overnight. The solution was concentrated and the residue was dissolved in EtOAc and washed with 10% $KHSO_4$, saturated $Na_2CO_3$, and brine, dried with $Na_2SO_4$, filtered and concentrated to give a yellow oil that was chromatographed (40% EtOAc/Hexanes) to give 23-3 ($R_f$ 30% EtOAc/Hexanes) 0.19) contaminated with 23-3a. The mixture (1.7 g) was dissolved in EtOAc (75 mL), cooled to −78° C. and saturated with HCl gas, warmed to 0° C. for 1 hour and concentrated. The residue was partitioned between $CH_2Cl_2$ and saturated $NaCO_3$, the layers separated and the aqueous layer extracted with $CH_2Cl_2$. The organic layer was dried over $Na_2SO_4$, filtered and evaporated and the residue chromatographed (60% EtOAc/Hexanes) to give 23-4 as an off-white solid.

$R_f$(60% EtOAc/Hexanes) 0.3 $^1$H NMR (400 MHz, $CDCl_3$) δ 7.7 (bs, 1H), 6.95 (s, 1H), 6.74 (d, 1H), 6.4 (d, 1H), 4.6 (s, 2H), 4.33 (q, 2H), 2.98 (s, 3H), 1.3 (t, 3H).

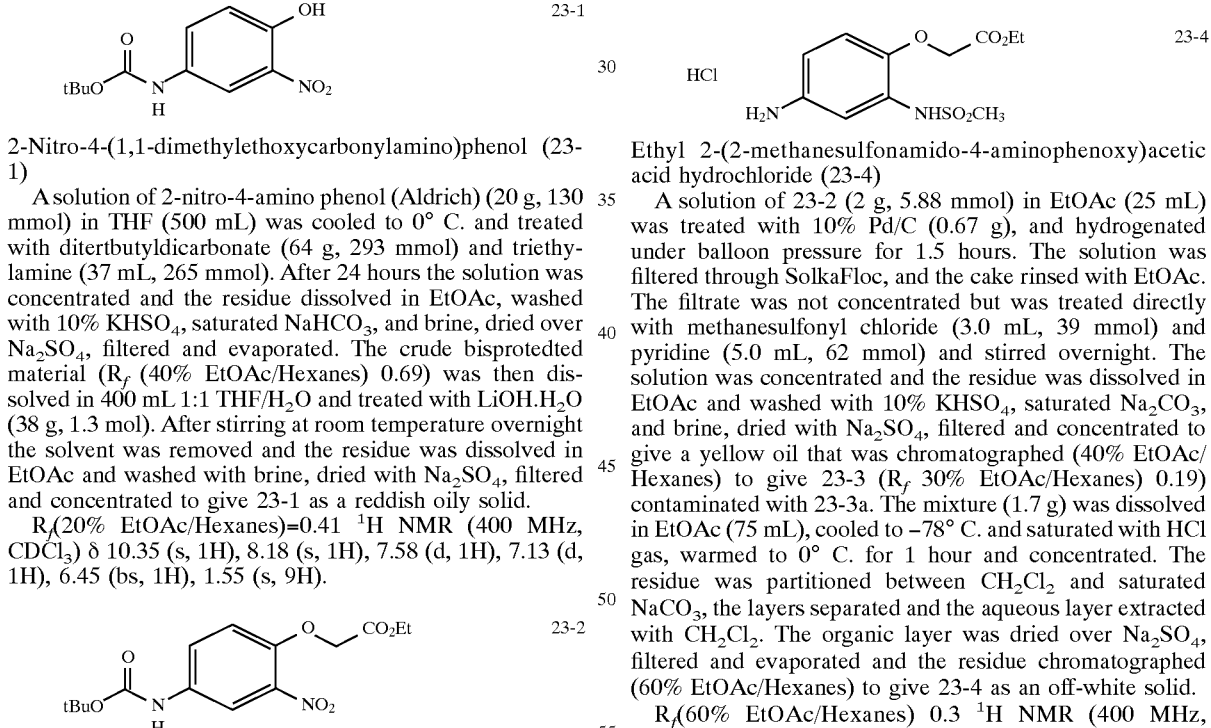

Ethyl 2-(4-(4-(4-(1,1-dimethylethoxycarbonyl)piperazin-1-yl)phenylcarbonylamino)-2-methanesulfonamidophenoxy)acetate (23-5)

A suspension of 23-4 (0.125 g, 0.433 mmol) and 1-5 (0.136 g, 0.444 mmol) in CH$_2$Cl$_2$ (4 mL) was treated with diisopropylamine (0.3 mL, 1.7 mmol) and PYCLU (0.173 g, 0.48 mmol) and stirred at room temperature for three days. The solution was concentrated and the residue was absorbed to silica gel and chromatographed in a gradient of 20 to 60% EtOAc/Hexanes to give 23-5 as a pale yellow oil.

R$_f$ (60% EtOAc/Hexanes)=0.27 $^1$H NMR (400 MHz, CDCl$_3$) δ 7.82 (dd, 1H), 7.79 (s, 1H), 7.77 (s, 1H), 7.54 (bs, 1H), 7.48 (s, 1H), 6.90 (m, 3H), 4.7 (s, 2H), 4.25 (q, 2H), 3.6 (m, 4H), 3.3 (m, 4H), 3.03 (s, 3H), 1.5 (s, 9H), 1.3 (t, 3H).

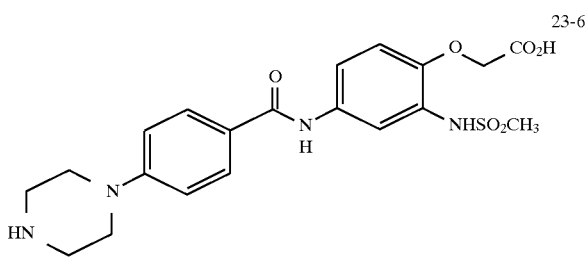

2-(4-(4-(Piperazin-1-yl)phenylcarbonylamino)-2-methanesulfonamidophenoxy)acetic acid (23-6)

A solution of 23-5 (0.093 g, 0.16 mmol) was dissolved in EtOAc (10 mL), cooled to −78° C. and saturated with HCl gas, warmed to 0° C. for 1 hour and concentrated. The resulting white solid was dissolved in 1:1:1H$_2$O/THF/MeOH, treated with LiOH.H$_2$O (0.038 g, 0.9 mmol) and stirred at room temperature for 1 hour. The reaction was concentrated and chromatographed (18:1:1 EtOH/H$_2$O/NH$_4$OH) to give a yellow oil that was diluted with CH$_2$Cl$_2$ and evaporated to give 23-6 as white solid.

R$_f$(9:1:1 EtOH/H$_2$O/NH$_4$OH)=0.48 $^1$H NMR (400 MHz, D$_2$O+NaOD) δ 7.74 (s, 1H), 7.72 (s, 1H), 7.21 (s, 1H), 7.07 (s, 1H), 7.05 (s, 1H), 6.9 (d, 1H), 6.74 (d, 1H), 4.38 (s, 2H), 3.15 (m, 4H), 2.85 (m, 7H).

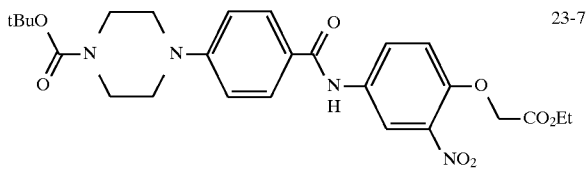

Ethyl 2-(4-(4-(4-(1,1-dimethylethoxycarbonyl)piperazin-1-yl )phenylcarbonylamino)-2-nitrophenoxy)acetate (23-7)

A solution of 23-2 (0.3 g, 0.88 mmol) was dissolved in EtOAc (10 mL), cooled to −78° C. and saturated with HCl gas, warmed to 0° C. for 1 hour and concentrated to give Ethyl 2-(2-nitro-4-aminophenoxy)acetic acid as a white solid that was coupled immediately (0.26 g, 0.88 mmol) to 1-5 (0.29 g, 0.95 mmol) as described for 23-5 to give 23-7 as a yellow solid after chromatography in a gradient of 40 to 100% EtOAc/Hexanes.

R$_f$(50% EtOAc/Hexanes)=0.22

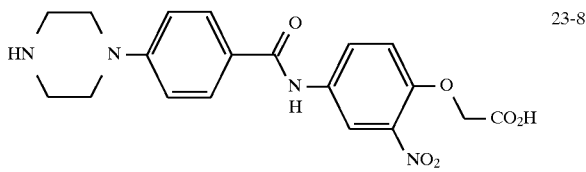

2-(4-(4-(Piperazin-1-yl)phenylcarbonylamino)-2-nitrophenoxy)-acetic acid (23-8)

A solution of 23-7 (0.186 g, 0.352 mmol) in EtOAc was treated first with HCl gas then with LiOH.H$_2$O as described for 23-6 to give 23-8 as a yellow solid after chromatography in 18:1:1 EtOH/H$_2$O/NH$_4$OH).

R$_f$(18:1:1 EtOH/H$_2$O/NH$_4$OH)=0.47 $^1$H NMR (400 MHz, D$_2$O) δ 8.0 (s, 1H), 7.68 (2s, 2H), 7.52 (d, 1H), 7.0 (m, 2H), 3.12 (bs, 4H), 2.85 (bs, 4H).

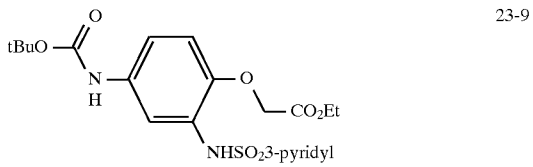

Ethyl 2-(2-(3-pyridyl)sulfonamido-4-(1,1-dimethylethoxycarbonyl)aminophenoxy)acetate (23-9)

A solution of 23-2 (2 g, 5.88 mmol) in EtOAc (25 mL) was treated with 10% Pd/C and 3-pyridylsulfonyl chloride (JOC, 1989, 54, 389–393) as described for 23-3 to give 23-9 after chromatography in a gradient of 30 to 50% EtOAc/Hexanes as a white solid.

R$_f$(40% EtOAc/Hexanes)=0.11 $^1$H NMR (400 MHz, CDCl$_3$) δ 9.02 (s, 1H), 8.71 (d, 1H), 8.1 (m, 2H), 7.4 (s, 1H), 7.33 (m, 2H), 6.69 (d, 1H), 6.58 (s, 1H), 4.4 (s, 2H), 4.23 (q, 2H), 1.5 (s, 9H), 1.25 (t, 3H).

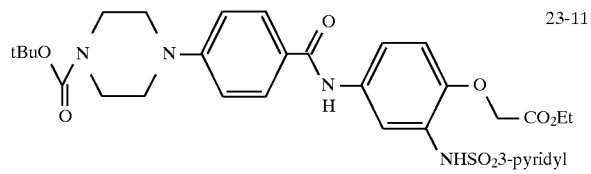

Ethyl 2-(4-(4-(4-(1,1-dimethylethoxycarbonyl)piperazin-1-yl)phenylcarbonylamino)-2-(3-pyridylsulfonamido)phenoxy)acetate (23-11)

A solution of 23-9 (0.318 g, 0.704 mmol) in EtOAc (10 mL) was treated with HCl gas as described for 23-4 to give 23-10 as a white solid that was coupled directly with 1-5 as described for 23-5 to give 23-11 as a oily yellow solid after chromatography in a gradient of 20 to 40% acetone/Hexanes.

R$_f$(50% EtOAc/Hexanes)=0.41 $^1$H NMR (400 MHz, CDCl$_3$) δ

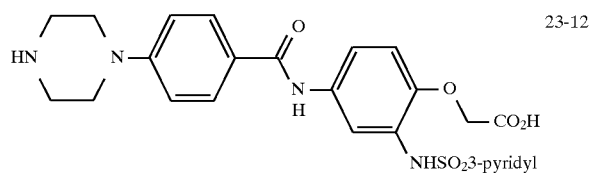

2-(4-(4-(Piperazin-1-yl)phenylcarbonylamino)-2-(2-(3-pyridylsulfonamido)phenoxy)acetic acid (23-12)

A solution of 23-11 (0.047 g, 0.087 mmol) in EtOAc was treated first with HCl gas then with LiOH.H$_2$O as described for 23-6 to give 23-12 as a yellow solid after chromatography in 18:1:1 EtOH/H$_2$O/NH$_4$OH).

R$_f$(18:1:1 EtOH/H$_2$O/NH$_4$OH)=0.38 $^1$H NMR (400 MHz, D$_2$O+NaOD) δ 8.76 (s, 1H), 8.5 (m, 1H), 8.13 (m, 1H), 7.7 (m, 2H), 7.45 (m, 1H), 7.12 (s, 1H), 7.08 (m, 2H), 6.84 (m, 1H), 6.67 (d, 1H), 4.13 (s, 2H), 3.25 (m, 4H), 2.87 (m, 4H).

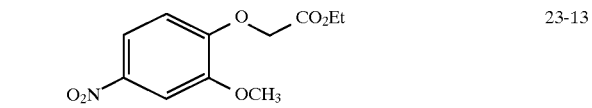

Ethyl 2-(2-methoxy-4-nitrophenoxy)acetic acid (23-13)

2-methoxy-4-nitro phenol (Aldrich) (1.0 g, 5.9 mmol) was treated with cesium carbonate and ethylbromoacetate as described for 23-2 to give crude 23-13 after removal of DMF. The crude material was partitioned between water and EtOAc, the organic layer was dried with brine and MgSO$_4$, filtered and evaporated to give 23-13 as a yellow solid.

R$_f$(50% EtOAc/Hexanes)=0.54 $^1$H NMR (400 MHz, CDCl$_3$) δ 7.8 (d, 1H), 7.76 (s, 1H), 6.75 (d, 1H), 4.71 (s, 2H), 4.2 (q, 2H), 3.9 (s, 3H), 1.21 (t, 3H).

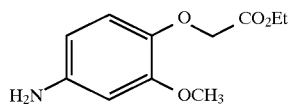

23-14

Ethyl 2-(2-methoxy-4-aminophenoxy)acetic acid (23-14)

A solution of 23-13 (0.7 g, 2.7 mmol) in EtOH (10 mL) was treated with 10% Pd/C (0.14 g) and hydrogenated at balloon pressure. The solution was filtered through Solka-Floc and evaporated to give 23-14 as a tan oil.

$^1$H NMR (400 MHz, CDCl$_3$) δ 6.78 (d, 1H), 6.33 (s, 1H), 6.21 (d, 1H), 4.59 (s, 2H), 4.21 (q, 2H), 3.8 (s, 3H), 3.45 (bs, 2H), 1.28 (t, 3H).

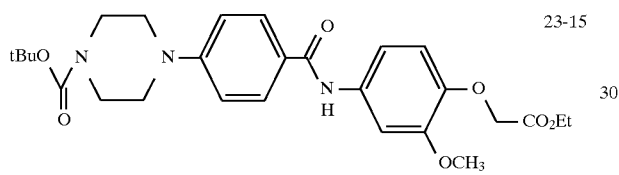

23-15

Ethyl 2-(4-(4-(4-(1,1-dimethylethoxycarbonyl)piperazin-1-yl)phenylcarbonylamino)-2-methoxyphenoxy)acetate (23-15)

Acid 1-5 and amine 23-14 were coupled as described for 23-5 to give 23-15 as brown solid after chromatography in 50% EtOAc/Hexanes.

R$_f$(50% EtOAc/Hexanes)=0.13 $^1$H NMR (400 MHz, CDCl$_3$) δ 7.8 (d, 2H), 7.6 (d, 1H), 6.92 (d, 2H), 6.86 (m, 2H), 4.64 (s, 2H), 4.24 (q, 2H), 3.9 (s, 3H), 3.6 (m, 4H), 3.3 (m, 4H), 1.5 (s, 9H), 1.25 (t, 3H).

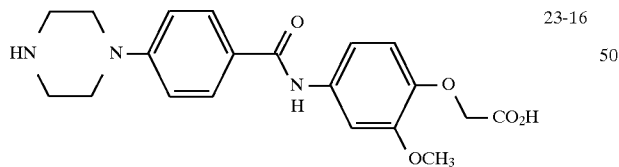

23-16

2-(4-(4-(4-Piperazin-1-yl)phenylcarbonylamino)-2-methoxyphenoxy)acetic acid (23-16)

Compound 23-15 was treated with LiOH and HCl gas as described for 23-6 to give 23-16 as a white solid after chromatography in 10:1:1 EtOH/H$_2$O/NH$_4$OH.

R$_f$ (10:1:1 EtOH/H$_2$O/NH$_4$OH)=0.15 $^1$H NMR (400 MHz, D$_2$O) δ 7.78 (d, 2H), 7.15 (s, 1H), 7.08 (d, 2H), 6.9 (m, 1H), 6.78 (d, 1H), 4.4 (s, 2H), 3.8 (s, 3H), 3.18 (bs, 4H), 2.88 (bs, 4H).

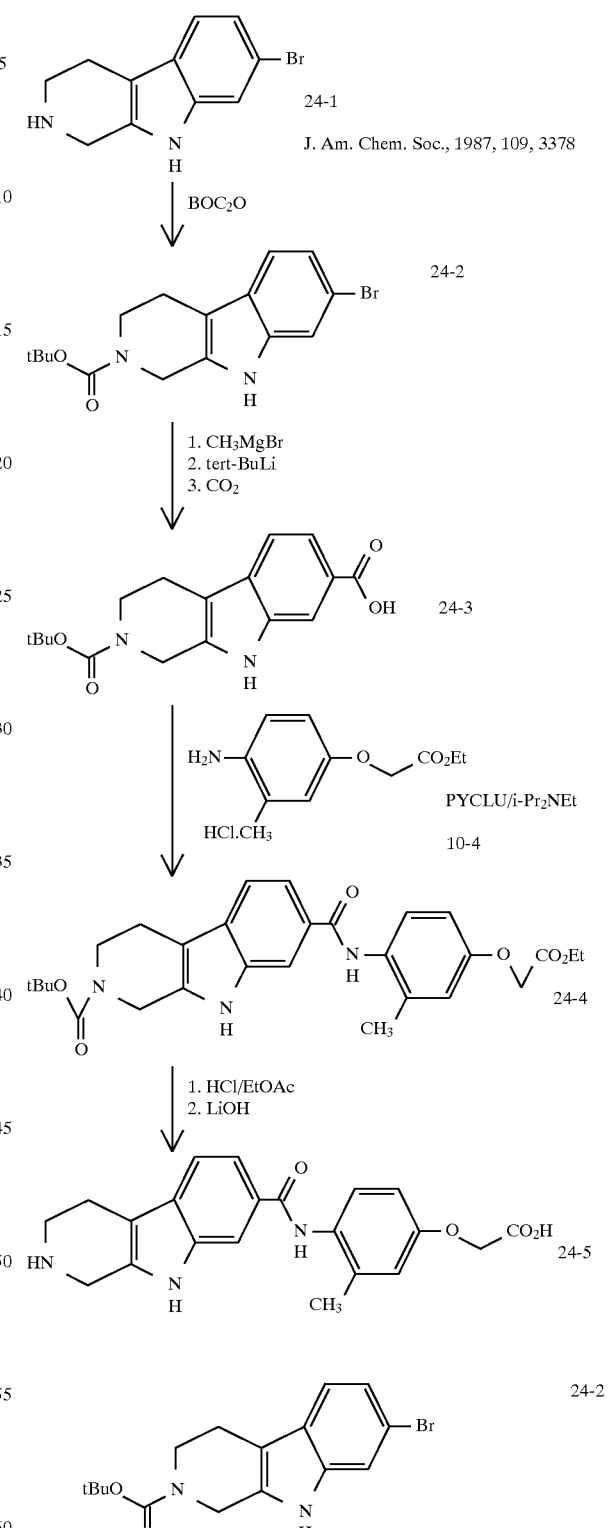

SCHEME 24

2-(1,1-Dimethylethoxycarbonyl)-7-bromo-1,2,3,4-tetrahydro-9H-pyrido[3,4-b]indole (24-2)

A suspension of 24-1, prepared by the method of Rinehard et al. (*J. Am. Chem. Soc.*, 1987, 109, p 3378–3387) (0.366 g, 1.46 mmol) in CH$_2$Cl$_2$ (8 mL) was treated with triethylamine (0.61 mL, 4.4 mmol) followed by di-tertbutyldicarbonate (0.38 g 1.7 mmol) for 1 hour at room temperature. The solution was concentrated and the residue chromatographed (20% EtOAc/Hexanes) to give 24-2 as a white solid.

$R_f$ (20% EtOAc/Hexanes)=0.28. $^1$H NMR (400 MHz, CDCl$_3$) δ 8.0–7.6 (m, 1H), 7.46 (s, 1H), 7.33 (d, 1H), 7.2 (d, 1H), 4.6 (bs, 2H), 3.78 (bs, 2H), 2.76 (bs, 2H), 1.5 (s, 9H).

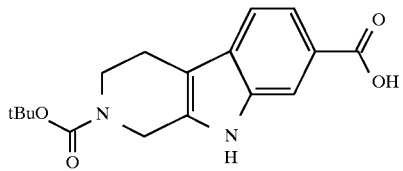

2-(1,1-Dimethylethoxycarbonyl)-1,2,3,4-tetrahydro-9H-pyrido[3,4-b]indol-7-yl carboxylic acid (24-3)

A solution of 24-2 (0.26 g, 0.734 mmol) in THF (10 mL) was cooled to 0° C. and treated with methylmagnesium chloride (3.0M in THF, 0.29 mL, 0.87 mmol) to give a pale yellow solution. After 15 minutes the solution was cooled to −78° C. and treated with tBuLi (1.7M in pentane, 4.35 mL, 7.39 mmol) to give a bright yellow solution. After 10 minutes CO$_2$ gas was bubbled vigorously through the solution for 10 minutes. Saturated NH$_4$Cl, water and enough 6N NaOH to reach pH$_{12}$ were added and the solution extracted with EtOAc. The EtOAc layer was back extracted with 0.5 NaOH and the aqueous layers combined, acidified to pH 7 and extracted with EtOAc, the EtOAc layer was dried (Na$_2$SO$_4$) filtered and concentrated to give 24-3 as an off-white solid.

$R_f$(75:25:1 CHCl$_3$/MeOH/HOAc)=0.48. $^1$H NMR (400 MHz, DMSO-d$_6$) δ 12.0 bs, 1H), 11.2 (s, 1H), 7.93 (s, 1H), 7.6 (d, 1H), 7.45 (d, 1H), 4.6 (s, 2H), 3.68 (m, 2H), 2.7 (m, 2H), 1.4 (s, 9H).

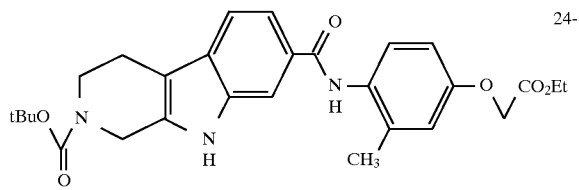

Ethyl 4-(2-(1,1-dimethylethoxycarbonyl)-1,2,3,4-tetrahydro-9H-pyrido[3,4-b]indol-7-yl)carbonylamino)-3-methylphenoxyacetate (24-4)

A solution of 24-3 (0.078 g, 0.25 mmol) and 10-4 (0.303 g, 1.23 mmol) in CH$_2$Cl$_2$ were treated with diisopropylamine and PYCLU as described for 23-5 to give 24-4 as a white solid after chromatography in a gradient of 40 to 60% EtOAc/Hexanes.

$R_f$ (40% EtOAc/Hexanes)=0.11 $^1$H NMR (400 MHz, CDCl$_3$) δ 8.5–8.2 (m, 1H), 8.0 (s, 1H), 7.75 (d, 1H), 7.63 (s, 1H), 7.52 (s, 2H), 6.83 (s, 1H), 6.80 (d, 1H), 4.7 (bs, 2H), 4.6 (s, 2H), 4.28 (q, 2H), 3.8 (bs, 2H), 2.83 (bs, 2H), 2.82 (s, 3H), 1.5 (s, 9H), 1.3 (t, 3H).

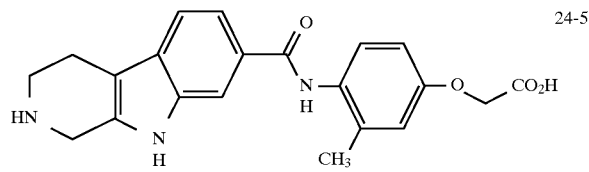

3-Methyl-4-((1,2,3,4-tetrahydro-9H-pyrido[3,4-b]indol-7-yl)carbonylamino)phenoxyacetic acid (24-5)

A solution of 24-4 (0.082 g, 0.16 mmol) in EtOAc (10 mL) was treated first with HCl gas, then with LiOH.H$_2$O as described for 23-6 to give 24-5 as a white solid after chromatography in 18:1:1 EtOH/H$_2$O/NH$_4$OH.

$R_f$ (18:1:1 EtOH/H$_2$O/NH$_4$OH)=0.48 $^1$H NMR (400 MHz, D$_2$O) δ 7.9 (s, 1H), 7.54 (m, 2H), 7.13 (d, 1H), 6.84 (s, 1H), 6.75 (d, 1H), 4.40 (s, 2H), 3.8 (s, 2H), 3.0 (m, 2H), 2.7 (m, 2H), 2.15 (s, 3H).

SCHEME 25

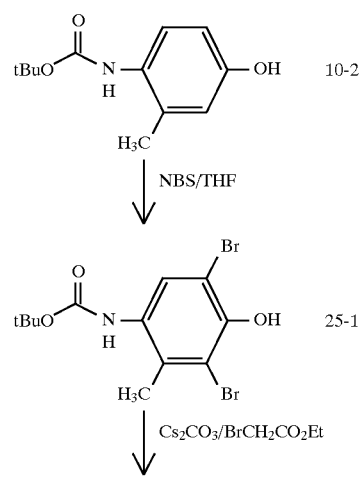

-continued
SCHEME 25
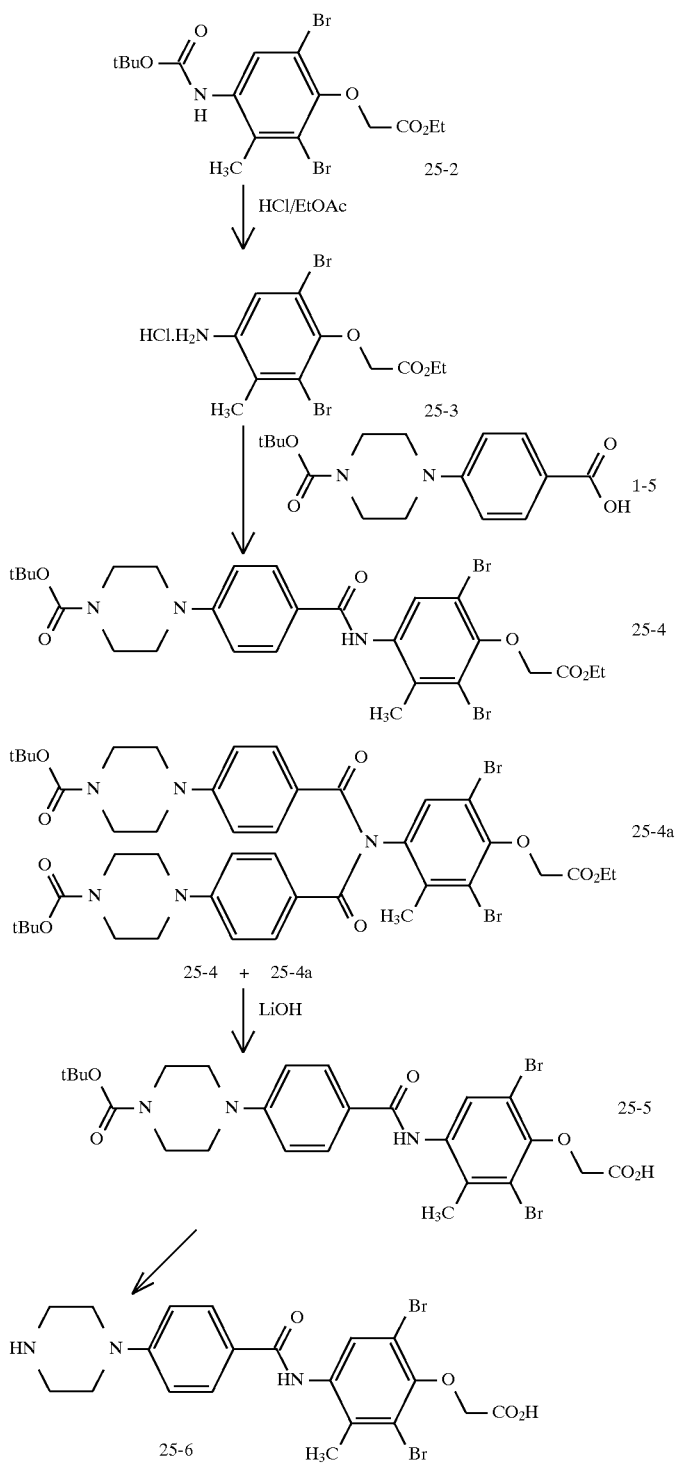

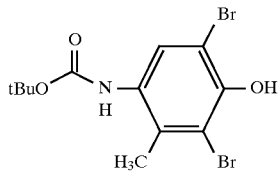

2,6-Dibromo-3-methyl-4-(1,1-dimethylethoxycarbonyl) aminophenol (25-1)

A solution of 10-2 (1.0 g, 450 mmol) in 20 mL THF under argon was treated with N—Bromosuccinimide (1.6 g, 9 mmol) for 2 hr. The solution was concentrated and the residue was resuspended in carbontetrachloride and filtered. The filtrate was concentrated and chromatographed (15% EtOAc/Hexanes) to give 25-1 as a white solid.

$R_f$(20% EtOAc/Hexanes)=0.56 $^1$H NMR (400 MHz, CDCl$_3$) δ 7.79 (bs, 1H), 6.08 (bs, 1H), 5.8 (s, 1H), 2.33 (s, 3H), 1.43 (s, 9H).

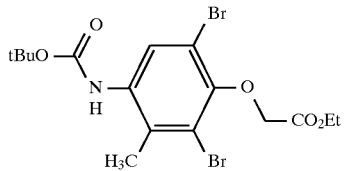

Ethyl 2-(2,6-dibromo-3-methyl-4-(1,1-dimethylethoxycarbonyl)aminophenoxy)acetate (25-2)

A solution of 25-1 (0.6 g, 1.57 mmol) in DMF was treated with cesium carbonate and ethyl bromo acetate as described for 10-3 to give 25-2 as a tan solid $R_f$(20% EtOAc/Hexanes)=0.56 $^1$H NMR (400 MHz, CDCl$_3$) δ 8.0 (bs, 1H), 6.21(bs, 1H), 4.56 (s, 2H), 4.3 (q, 2H), 2.35 (s, 3H), 1.5 (s, 9H), 1.33 (t, 3H).

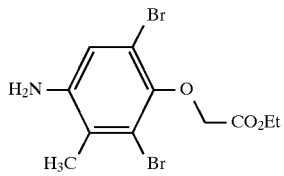

Ethyl 2-(2,6-dibromo-3-methyl-4-aminophenoxy)acetate (25-3)

A solution of 25-2 (0.6 g, 1.29 mmol) in EtOAc (10 mL) was treated with HCl gas as described for 16-10 to give 25-3 as a tan solid.

$^1$H NMR (400 MHz, DMSO) δ 7.0 (s, 1H), 4.8–4.4 (b, 2H), 4.41 (s, 2H), 4.2 (q, 2H), 2.18 (s, 3H), 1.2 (t, 3H).

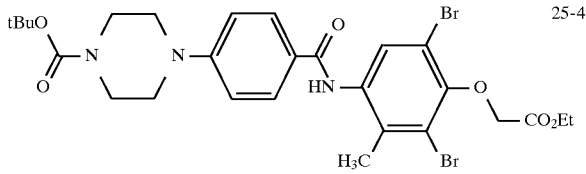

Ethyl 2-(2,6-dibromo-3-methyl-4-(4-(N-(1,1-dimethylethoxycarbonyl)piperizin-4-yl)phenylcarboxamide)phenoxy) acetate (25-4)

A solution of 25-3 (0.520 g, 1.29 mmol) and 1-5 (0.395 g, 1.29 mmol) in CH$_2$Cl$_2$ was treated with chloro-N,N,N'N',-bis(pentamethylene)formamidinium hexafluorophosphate (0.504 g, 0.1.4 mmol) and diisopropylethyl amine (0.9 mL, 5.16 mmol) and stirred at room temperature for 24 hours. The solution was diluted with EtOAc and washed with H$_2$O, 10% KHSO$_4$, saturated NaHCO$_3$ and brine, dried over MgSO$_4$, filtered and evaporated. The residue was chromatographed (silica gel 30% EtOAc/Hexanes) to give a mixture of 25-4 and 25-4a.

$R_f$25-4a(50% EtOAc/Hexanes)=0.45. $^1$H NMR (400 MHz, CDCl$_3$) δ 8.0 (m, 2H), 7.8 (d, 2H), 7.5 (s, 1H), 6.93 (d, 2H), 6.85 (d, 1H), 4.6 (s, 2H), 4.3 (q, 2H), 3.6 (bs, 8H), 3.35 (m, 8H), 2.4 (s, 3H), 1.45 (s, 9H), 1.35 (t, 3H).

$R_f$25-4(50% EtOAc/Hexanes)=0.37. $^1$H NMR (400 MHz, CDCl$_3$) δ 7.6 (d, 2H), 6.7 (d, 2H), 4.6 (s, 2H), 4.3 (q, 2H), 3.55 (bs, 4H), 3.3 (bs, 4H), 2.38 (s, 3H), 1.45 (s, 9H), 1.33 (t, 3H).

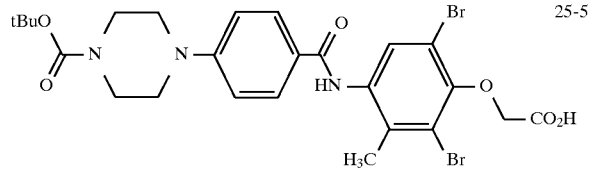

2-(2,6-Dibromo-3-methyl-4-(4-(1,1-dimethylethoxycarbonyl)piperizin-4-yl)phenylcarbonylamino)phenoxy) acetic acid (25-5)

A solution of 25-4 and 25-4a (0.3 g) in 1:1:1 THF/MeOH/H$_2$O was treated with LiOH (0.084 g, 2 mmol) at 60° C. After 1 hour the reaction was diluted with EtOAc and 10% KHSO$_4$ and the layers were separated. The organic layer was washed with H$_2$O, brine, dried with MgSO$_4$, filtered and evaporated to give 25-5 as a clear oil after chromatography in 9:0.5:0.5 CH$_2$Cl$_2$/MeOH/HOAc.

$R_f$(9:0.5:0.5 CHCl$_3$/MeOH/HOAc)=0.6. $^1$H NMR (400 MHz, CD$_3$OD) δ 7.90 (d, 2H), 7.6 (s, 2H), 7.05 (d, 2H), 4.55 (s, 2H), 3.6 (bs, 4H), 3.3 (bs, 4H), 2.35 (s, 3H), 1.5 (s, 9H).

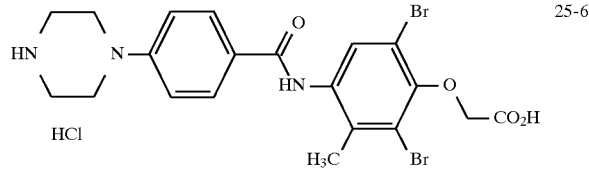

2-(2,6-Dibromo-3-methyl-4-(4-piperizin-4-yl)phenylcarbonylamino) phenoxy) acetic acid, hydrochloride (25-6)

A slurry of the intermediate acid (0.4 g, 0.6 mmol) in EtOAc was cooled to −78° C. and saturated with HCl gas. The reaction was warmed to 0° C., then concentrated in vacuo to give 25-6 as the HCl salt.

$R_f$(10:0.5:0.5 EtOH/H$_2$O/NH$_4$OH) 0.18. $^1$H NMR (400 MHz, D$_2$O) δ 7.73 (d, 2H), 7.23 (s, 1H), 7.02 (d, 2H), 4.3 (s, 2H), 3.1 (bs, 4H), 2.82 (bs, 4H), 2.1 (s, 3H).

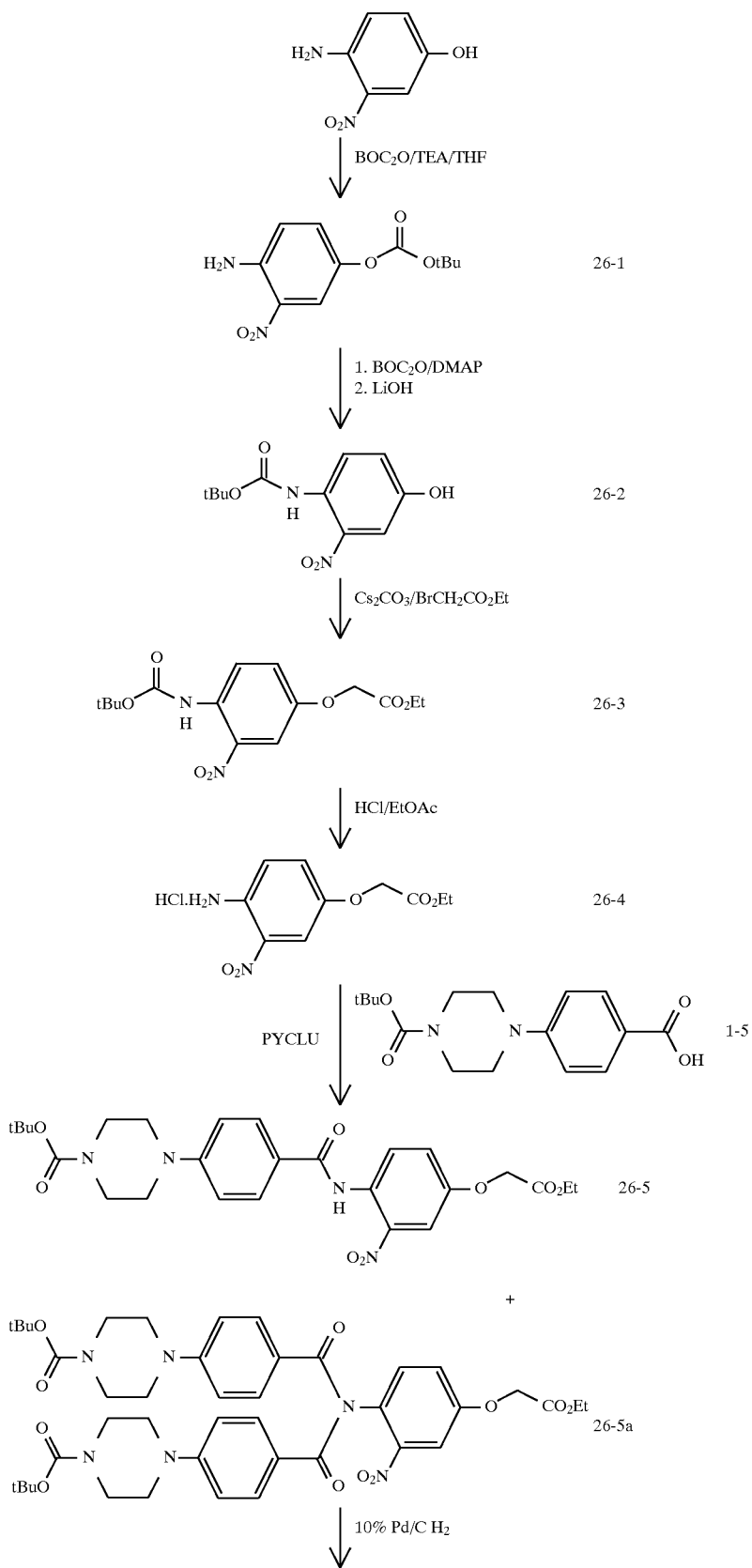

-continued
SCHEME 26

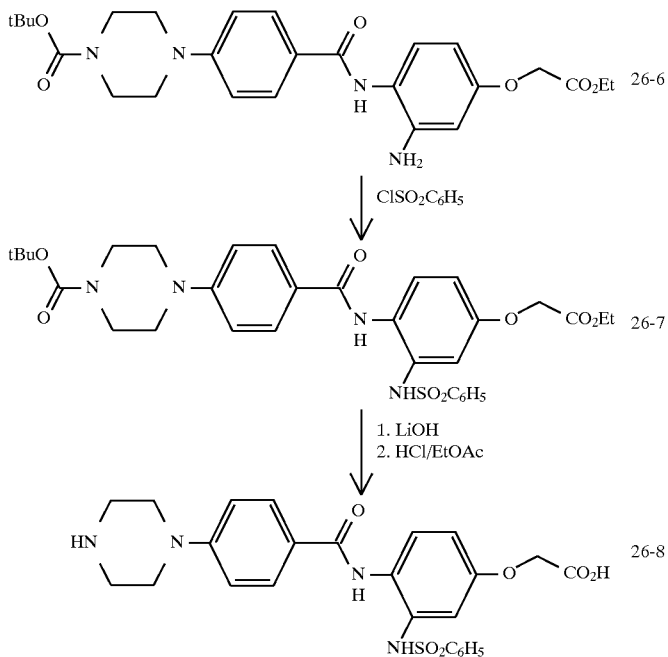

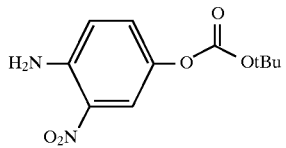

1-(1,1-dimethylethoxycarbonyloxy)-3-nitro-4-aminophenol (26-1)

A solution of 3-nitro-4-amino phenol (Aldrich) (8 g, 52.6 mmol) in THF (250 mL) was cooled to 0° C. and treated with ditertbutyldicarbonate (24 g, 110 mmol) and triethylamine (14 mL, 105 mmol). The solution was allowed to warm slowly and after 24 hours was concentrated and the residue dissolved in EtOAc, washed with 10% KHSO$_4$, saturated NaHCO$_3$, and brine, dried over Na$_2$SO$_4$, filtered and evaporated to give 26-1 as a brown oil.

$^1$H NMR (400 MHz, CDCl$_3$) δ 7.94 (s, 1H), 7.21 (dd, 1H), 6.8 (d, 1H), 6.04 (bs, 2H), 1.5 (s, 9H).

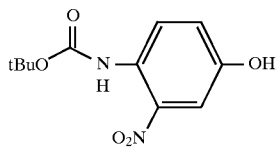

3-Nitro-4-(1,1-dimethylethoxycarbonylamino)phenol (26-2)

A solution of 26-1 (52.6 mmol) in dichloroethane (150 mL) was added at a rapid drip to a refluxing solution of di-tertbutyldicarbonate (12 g, 52.6 mmol) in dicloroethane (100 mL) and the resulting mixture was refluxed for 20 minutes, then cooled to room temperature and stirred overnight. Triethylamine (52.6 mmol) and 2,6-dimethylaminopyridine (1.3 g, 10.5 mmol) were added and the solution refluxed for 2 hours and stirred at room temperature overnight. The solvents were removed and the residue was dissolved in 240 mL 1:1:1 THF/MeOH/H$_2$O and treated with LiOH.H$_2$O (22 g, 526 mmol) for 48 hours. The solution was diluted with water, 10% KHSO$_4$ and EtOAc and the layers separated. The organic layer was washed with water and brine, dried over MgSO$_4$, filtered and evaporated. The residue was chromatographed (20% EtOAc/Hexanes) to give 26-2 as a yellow solid.

R$_f$ (20% EtOAc/Hexanes)=0.26 $^1$H NMR (400 MHz, CDCl$_3$) δ 9.5 (bs, 1H), 9.35 (d, 1H), 7.61 (s, 1H), 7.13 (d, 1H), 5.33 (s, 1H), 1.55 (s, 9H).

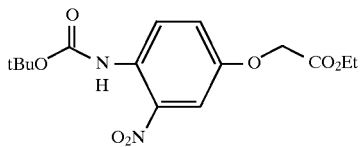

Ethyl 2-(3-nitro-4-(1,1-dimethylethoxycarbonylamino) phenoxy) acetate (26-3)

A solution of 26-2 (2 g, 7.87 mmol) in DMF (75 mL) treated with cesium carbonate (1.28 g, 3.93 mmol), stirred for 10 minutes and treated with ethyl bromoacetate (0.8 mL, 7.92 mmol) at room temperature. After 1.5 hours the solution was concentrated under high vacuum and the residue was absorbed to silica gel and chromatographed in 10% EtOAc/Hexanes to give 26-3 as a yellow solid.

R$_f$ (30% EtOAc/Hexanes) 0.18 $^1$H NMR (400 MHz, CDCl$_3$) δ 9.4 (bs, 1H), 8.44 (d, 1H), 7.65 (s, 1H), 7.26 (m, 1H), 4.63 (s, 2H), 4.24 (q, 2H), 1.55 (s, 9H), 1.3 (t, 3H).

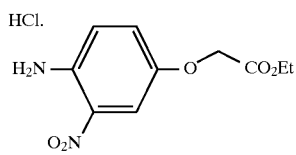

26-4

Ethyl 2-(3-nitro-4-aminophenoxy)acetate, hydrochloride (26-4)

A solution of 26-3 (0.5 g, 0.2.5 mmol) was dissolved in EtOAc (15 mL), cooled to −78° C. and saturated with HCl gas, warmed to 0° C. for 1 hour and concentrated to give 26-4 as an orange solid.

$R_f$ (10% MeOH/CHCl$_3$ saturated with NH$_3$)=0.13 $^1$H NMR (400 MHz, CD$_3$OD) δ 7.51 (d, 1H), 7.18 (dd, 1H), 7.0 (d, 1H), 4.68 (s, 2H), 4.24 (q, 2H), 1.15 (t, 3H).

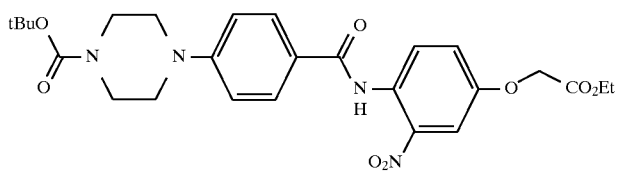

26-5

Ethyl 2-(3-nitro-4-(4-(4-(1,1-dimethylethoxycarbonyl)piperazin-1-yl)phenylcarbonylamino)phenoxy)acetate (26-5)

A solution of 26-4 (0.65 g, 2.46 mmol) and 1-5 (1.5 g, 4.9 mmol) were treated with PYCLU and diisopropylamine as described for 23-5 to give 26-5 and 26-5a after chromatography in 30% EtOAc/Hexanes.

$R_f$(30% EtOAc/Hexanes)=0.16 $^1$H NMR 26-5 (400 MHz, CDCl$_3$) δ 8.95 (d, 1H), 7.9 (d, 2H), 7.75 (s, 1H), 6.95 (d, 2H), 4.65 (s, 2H), 4.28 (q, 2H), 3.6 (m, 4H), 3.35 (m, 4H), 1.5 (s, 9H), 1.3 (t, 3H).

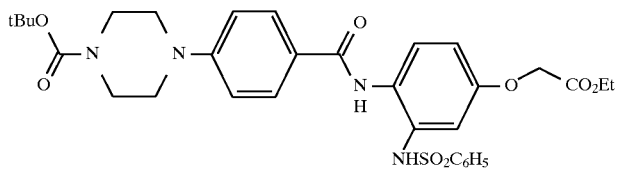

26-7

Ethyl 2-(3-phenylsulfonamido-4-(4-(4-(1,1-dimethylethoxycarbonyl)piperazin-1-yl)phenylcarbonylamino)phenoxy)acetate (26-7)

A solution of 26-5 (0.4 g, 0.76 mmol) in EtOH (10 mL) was treated with 10% Pd/C (0.070 g), and hydrogenated under balloon pressure for 1.5 hours. The solution was filtered through SolkaFloc, and the cake rinsed with EtOAc. The filtrate was concentrated to give 26-6.

$R_f$ (10% MeOH/CHCl$_3$ saturated with NH$_3$)=0.72.

The crude amine was dissolved in pyridine (3 mL) and treated with phenylsulfonyl chloride (0.10 mL, 0.83 mmol) and stirred for four hours. The solution was diluted with EtOAc and washed with water and brine, dried with MgSO$_4$, filtered and concentrated to give a yellow oil that was chromatographed (gradient 30% EtOAc/Hexanes to 100% EtOAc) to give 26-7 as an oil.

($R_f$ 30% EtOAc/Hexanes) 0.85) $^1$H NMR 26-5 (400 MHz, CDCl$_3$) δ 8.04 (s, 1H), 7.7 (d, 2H), 7.65 (d, 2H), 7.5 (s, 2H), 7.42 (d, 1H), 7.38 (m, 2H), 6.9 (m, 2H), 6.8 (d, 1H), 6.6 (s, 1H), 4.46 (s, 2H), 4.25 (q, 2H), 3.6 (m, 4H), 3.3 (m, 4H), 1.5 (s, 9H), 1.28 (t, 3H).

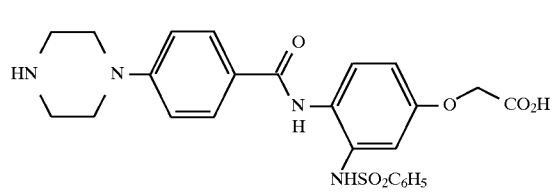

26-8

2-(3-Phenylsulfonamido-4-(4-(4-piperazin-1-yl)phenylcarbonylamino)phenoxy)acetic acid (26-8)

A solution of 26-7 (0.18 g, 0.28 mmol) was treated with LiOH and HCl gas as described for 23-6 to give 26-8 as a white solid after chromatography (10:0.5:0.5 EtOH/NH$_4$OH/H$_2$O) and further purification via reverse phase HPLC.

$^1$H NMR (400 MHz, D$_2$O) δ 7.6 (m, 3H), 7.48 (d, 2H), 7.23 (m, 1H), 7.18 (m, 2H), 7.1 (d, 2H), 6.59 (s, 1H), 6.5 (d, 1H), 4.23 (s, 2H), 3.2 (m, 4H), 2.9 (m, 4H).

SCHEME 27

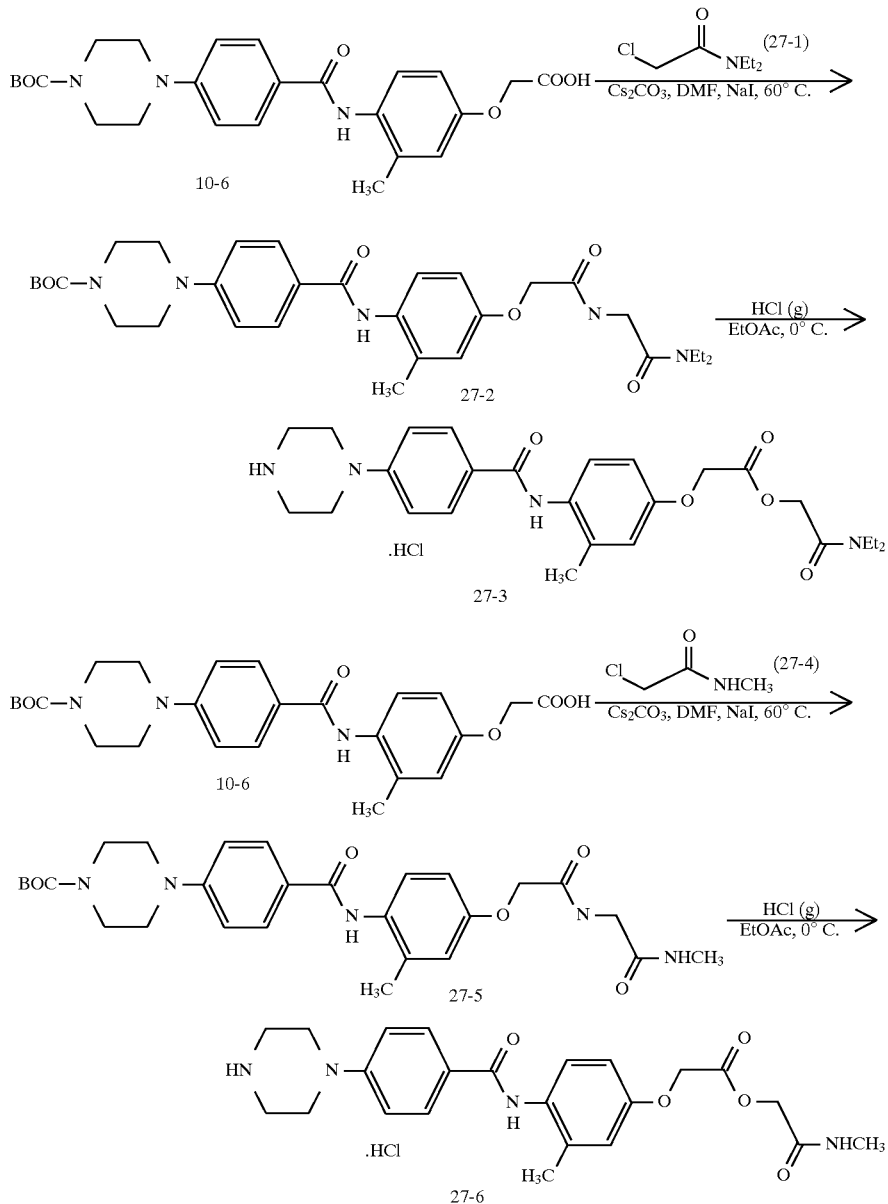

4-[4-(4-(1,1-dimethylethoxycarbonyl)piperazin-1-yl) phenylcarbonylamino]-3-methylphenoxyacetic acid; N,N-diethylglycolamide ester (27-2)

A solution of carboxylic acid 10-6 (500 mg, 1.07 mmol), N,N-diethyl chloroacetamide 27-1 (0.154 mL, 1.12 mmol), NaI (5 mg, 0.03 mmol), Cs$_2$CO$_3$, (173 mg, 0.535 mmol) and DMF (5 mL) was heated at 60° C. for 20 h. The reaction mixture was diluted with EtOAc and washed with water, 10% aqueous KHSO$_4$ and brine. Drying (MgSO$_4$), filtration, removal of the solvent in vacuo, and chromatography on silica gel using a gradient of 50 to 90% EtOAc in hexane as eluant gave 4-[4-(4-(1,1-dimethylethoxycarbonyl)piperazin-1-yl)phenylcarbonylamino]-3-methylphenoxyacetic acid N,N-diethylglycolamide ester (27-2) as a white solid. $^1$H NMR (CD$_3$OD): δ 1.23 (t, J=7 Hz, 6H), 1.48 (s, 9H), 2.25 (s, 3H), 3.32 (m, 8H), 3.58 (m, 2H), 4.83 (s, 2H), 4.92 (s, 2H), 6.83 (dd, J=3 Hz, 9 Hz, 1H), 6.90 (s, 1H), 7.03 (d, J=9 Hz, 2H), 7.19 (d, J=(Hz, 1H), 7.78 (d, J=9 Hz, 2H).

4-[4-(Piperazin-1-yl)phenylcarbonylamino]-3-methylphenoxyacetic acid; N,N-diethylglycolamide ester, hydrochloride (27-3)

To a stirred solution of EtOAc (7 mL) saturated with HCl gas was added ester 27-2 (500 mg, 0.86 mmol), suspended in EtOAc (3 mL). The mixture was stirred for 1 h at ambient temperature, purged with dry argon for 30 min and concentrated in vacuo to give 4-[4-(piperazin-1-yl) phenylcarbonylamino]-3-methylphenoxyacetic acid N,N-diethylglycolamide ester, hydrochloride (27-3) as a white solid. $^1$H NMR (D$_2$O): δ 1.11 (t, J=7 Hz, 3H), 1.21 (t, J=7 Hz, 3H), 2.23 (s, 3H), 3.37 (t, J=7 Hz, 4H), 3.44 (m, 4H), 3.62 (m, 4H), 4.96 (s, 2H), 5.01 (s, 2H), 6.92 (d, J=9 Hz, 1H), 7.00 (s, 1H), 7.21 (m, 3H), 7.90 (d, J=9 Hz, 2H).

4-[4-(4-(1,1-Dimethylethoxycarbonyl)piperazin-1-yl) phenylcarbonylamino]-3-methylphenoxyacetic acid; N-methylglycolamide ester (27-5)

A solution of carboxylic acid 10-6 (500 mg, 1.07 mmol), N-methyl chloroacetamide 27-4 (0.121 mg, 1.12 mmol), NaI (5 mg, 0.03 mmol), Cs$_2$CO$_3$, (173 mg, 0.535 mmol) and DMF (5 mL) was heated at 60° C. for 20 h. The reaction mixture was diluted with EtOAc and washed with water, 10% aqueous KHSO$_4$ and brine. Drying (MgSO$_4$), filtration, removal of the solvent in vacuo, and chromatography on silica gel using EtOAc as eluant gave 4-[4-(4-(1,1-dimethylethoxycarbonyl)piperazin-1-yl)phenylcarbonylamino]-3-methylphenoxyacetic acid N-methylglycolamide ester (27-5) as a white solid. $^1$H NMR (CD$_3$OD): δ 1.49 (s, 9H), 2.31 (s, 3H), 2.77 (d, J=5 Hz, 3H), 3.29 (m, 4H), 3.61 (m, 4H), 4.67 (s, 2H), 4.75 (s, 2H), 5.85 (br s, 1H), 6.87 (m, 2H), 6.95 (d, J=(Hz, 2H), 7.47 (s, 1H), 7.78 (m, 1H), 7.79 (d, J=9 Hz, 2H).

4-[4-(Piperazin-1-yl)phenylcarbonylamino]-3-methylphenoxyacetic acid; N-methylglycolamide ester, hydrochloride (27-6)

HCl gas was rapidly bubbled through a solution of 4-[4-(4-(1,1-dimethylethoxycarbonyl)piperazin-1-yl)phenylcarbonylamino]-3-methylphenoxyacetic acid N-methylglycolamide ester (27-5) (325 mg, 0.60 mmol) in EtOAc (30 mL) at 0° C. for 20 min. The mixture was aged 40 min., purged wityh argon and concentrated in vacuo. The solid was triturated with EtOAc and Et$_2$O to give 4-[4-(piperazin-1-yl)phenylcarbonylamino]-3-methylphenoxyacetic acid N-methylglycolamide ester, hydrochloride (27-6) as a white solid. $^1$H NMR (D$_2$O): δ 2.23 (s, 3H), 2.79 (s, 3H), 3.43 (m, 4H), 3.62 (m, 4H), 4.75 (s, 2H), 4.95 (s, 2H), 6.90 (d, J=8 Hz, 1H), 6.99 (s, 1H), 7.21 (m, 3H), 7.90 (d, J=9 Hz, 2H).

SCHEME 28

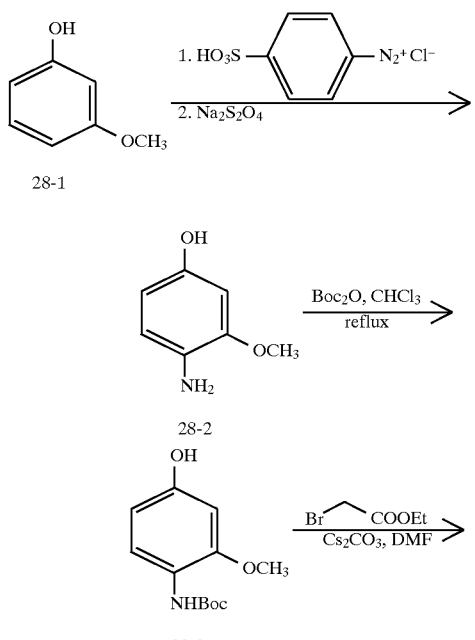

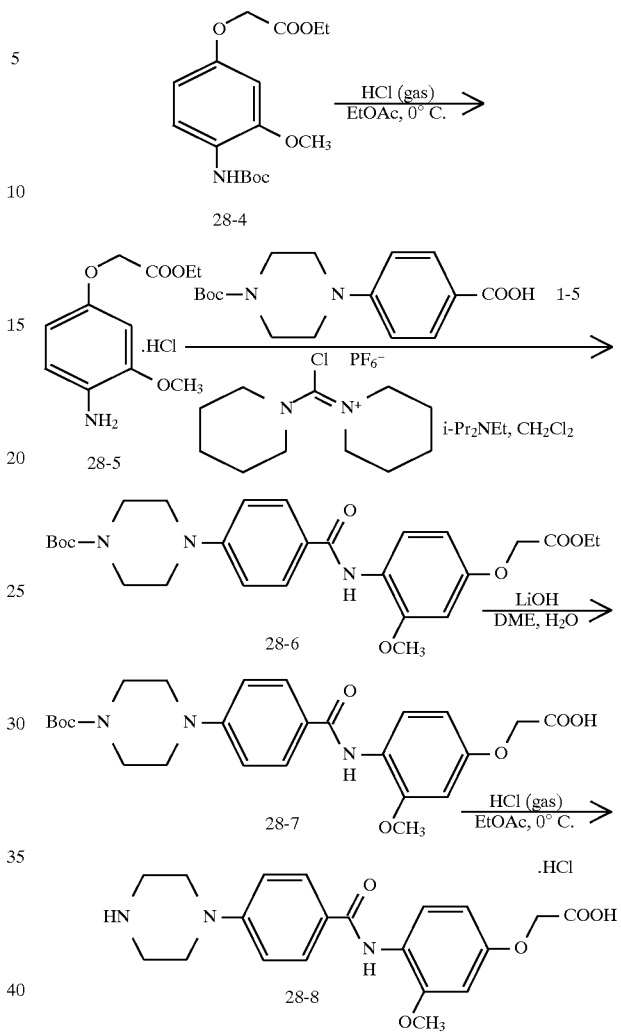

4-[4-(1-Piperazinyl)phenylcarbonylamino]-3-methoxyphenoxyacetic acid, hydrochloride (28-8)

Using a sequence essentially the same as described for compound 15-8, but starting with 3-methoxyphenol (28-1), 4-[4-(1-piperazinyl)phenylcarbonylamino]-3-methoxyphenoxyacetic acid, hydrochloride (28-8) as prepared. $^1$H NMR (D$_2$O): δ 3.33 (d, J=3.9 Hz, 4H), 3.51 (t, J=3.9 Hz, 4H), 3.75 (s, 3H), 4.62 (s, 2H), 6.51 (d, J=8.6 Hz, 1H), 6.64 (s, 1H), 7.05 (d, J=7.4 Hz, 2H), 7.32 (d, J=8.6 Hz, 1H), 7.75 (d, J=7.4 Hz, 2H).

SCHEME 29

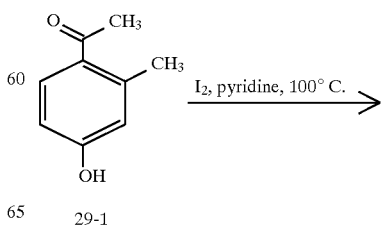

SCHEME 29 -continued

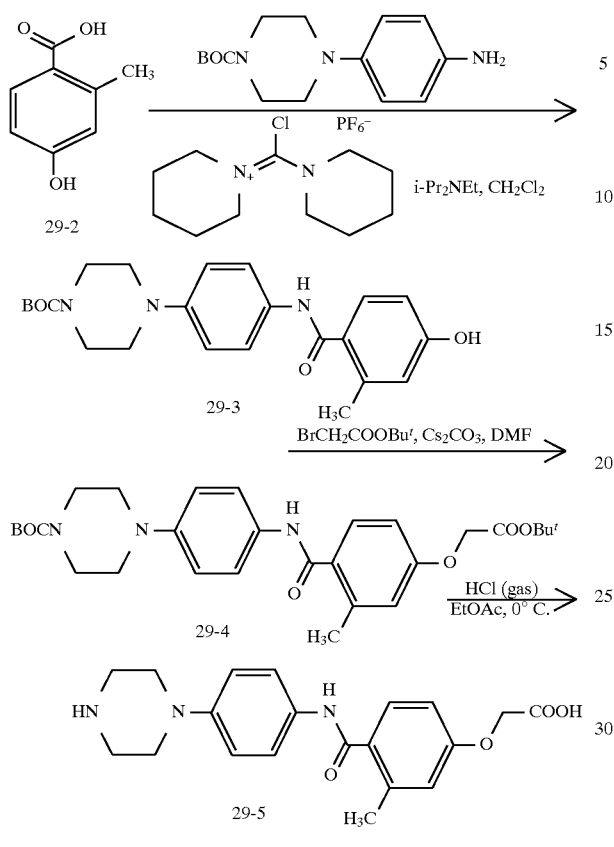

4-Hydroxy-2-methylbenzoic acid (29-2)

Following the procedure described in US 92-852870 920317, 4-hydroxy-2-methylbenzoic acid was prepared from 4-hydroxy-2-methylacetophenone 29-1. $^1$H NMR (CD$_3$OD): δ 2.52 (s, 3H), 6.64 (m, 2H), 7.84 (d, J=8.4 Hz, 1H).

4-[4-(1-Piperazinyl)phenylaminocarbonyl]-3-methylphenoxyacetic acid, hydrochloride (29-5)

Using a sequence essentially the same as described for compound 14-6, but starting with 4-hydroxy-3-methylbenzoic acid (29-2), 4-[4-(1-piperazinyl) phenylaminocarbonyl]-3-methylphenoxyacetic acid, hydrochloride (29-5) was prepared. $^1$H NMR (DMSO-D$_6$): δ 2.36 (s, 3H), 3,26 (d, J=7.3 Hz, SH), 3.80 (br s, 4H), 4.73, (s, 2H), 6.81 (dd, J=2.4, 8.4 Hz, 2H), 6.84 (d, J=2.4 Hz, 1H), 6.97 (d, J=8.7 Hz, 2H), 7.39 (d, J=8.4 Hz, 1H), 7.62 (d, J=8.7 Hz, 2H), 8.72 (br s, 1H), 9.99 (s, 1H).

SCHEME 30

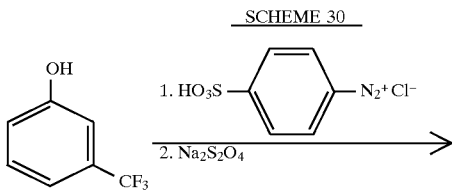

SCHEME 30 -continued

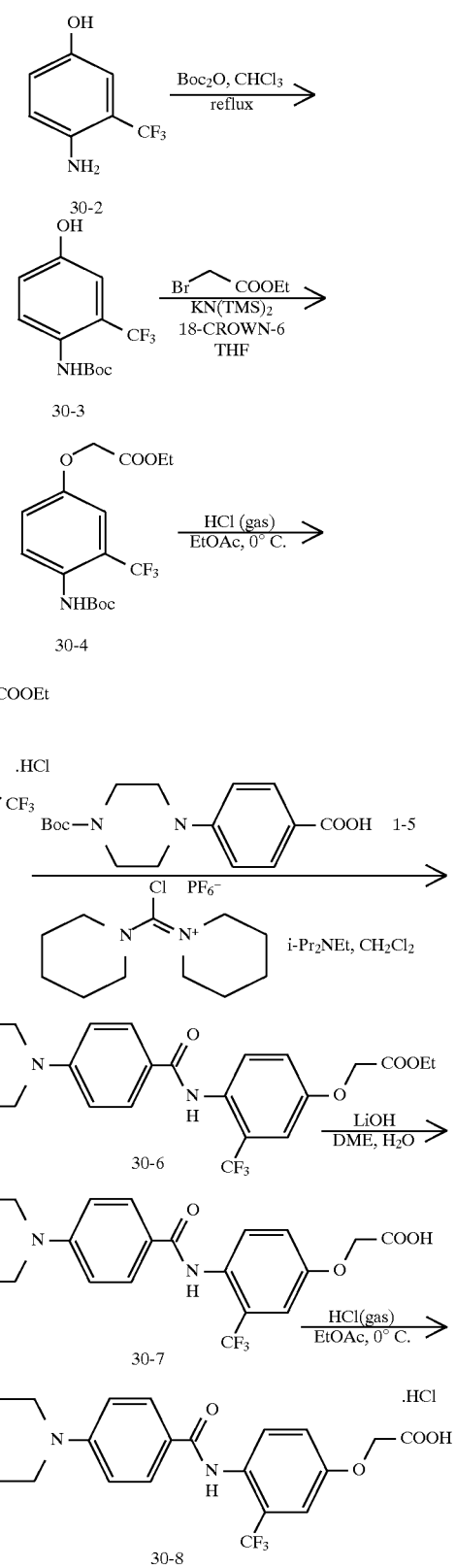

4-(1,1-Dimethylethoxycarbonyl)amino-3-trifluoromethylphenol (30-3)

Using a method similar to that described for compound 15-3, starting with 3-trifluorophenol, 4-(1,1-dimethylethoxycarbonyl)amino-3-trifluoromethylphenol (30-3) was prepared. $^1$H NMR (CDCl$_3$): δ 1.55 (s, 9H), 4.12 (m, 2H), 6.72 (d, 1H), 7.12 (m, 1H), 7.26 (m, 1H).

Ethyl 4-(1,1-dimethylethoxycarbonyl amino-3-trifluoromethylphenoxyacetate (30-5)

To a 200 mL round bottomed flask with a stirring bar and an argon inlet was added 4-(1,1-dimethylethoxycarbonyl) amino-3-trifluorophenol (4.80 g, 17.3 mmol), 18-crown-6 (4.63 g, 17.5 mmol), and THF (69 mL). This mixture was cooled to 0° C. in an ice-water bath, then a solution of potassium hexamethyl disilylazide in toluene (34.7 mL, 17.4 mmol) was added followed by ethyl bromoacetate (1.93 mL, 17.4 mmol). This mixture was stirred under argon for 16 h, allowing the cooling bath to expire. This mixture was transferred to a separatory funnel, acidified with 10% aqueous citric acid and extracted with EtOAc. The organic layer was washed with water and brine, dried (MgSO$_4$), filyered and concentrated in vacuo. The BOC group was removed as described for 29-9. This material was chromatographed on silica gel to give ethyl 4-(1,1-dimethylethoxy-carbonyl amino-3-trifluoromethylphenoxyacetate (30-5) as an oil. $^1$H NMR (CDCl$_3$): δ 1.58 (t, 3H), 3.93 (br s, 2H), 4.27 (q, 2H), 4.56 (s, 2H), 6.69 (d, 1H), 6.95 (dd, 1H), 7.00 (d, 1H).

4-[4-(1-Piperazinyl)phenylcarbonylamino]-3-trifluoromethylphenoxyacetic acid (30-8)

Using a sequence similar to that described for compound 12-8 but starting with ethyl 4-(1,1-dimethylethoxycarbonyl amino-3-trifluoromethylphenoxyacetate (30-5), 4-[4-(1-piperazinyl)phenylcarbonylamino]-3-trifluoromethylphenoxyacetic acid (30-8) was prepared. $^1$H NMR (DMSO-d$_6$): δ 3.25 (s, 4H), 3.50 (s, 4H), 4.84 (s, 2H), 7.09 (d, J=8.0 Hz, 2H), 7.25 (m, 2H), 7.39 (d, J=8.4 Hz, 2H), 7.88 (d, J=8.0 Hz, 2H), 8.82 (br s, 1H), 9.72 (s, 1H).

SCHEME 31

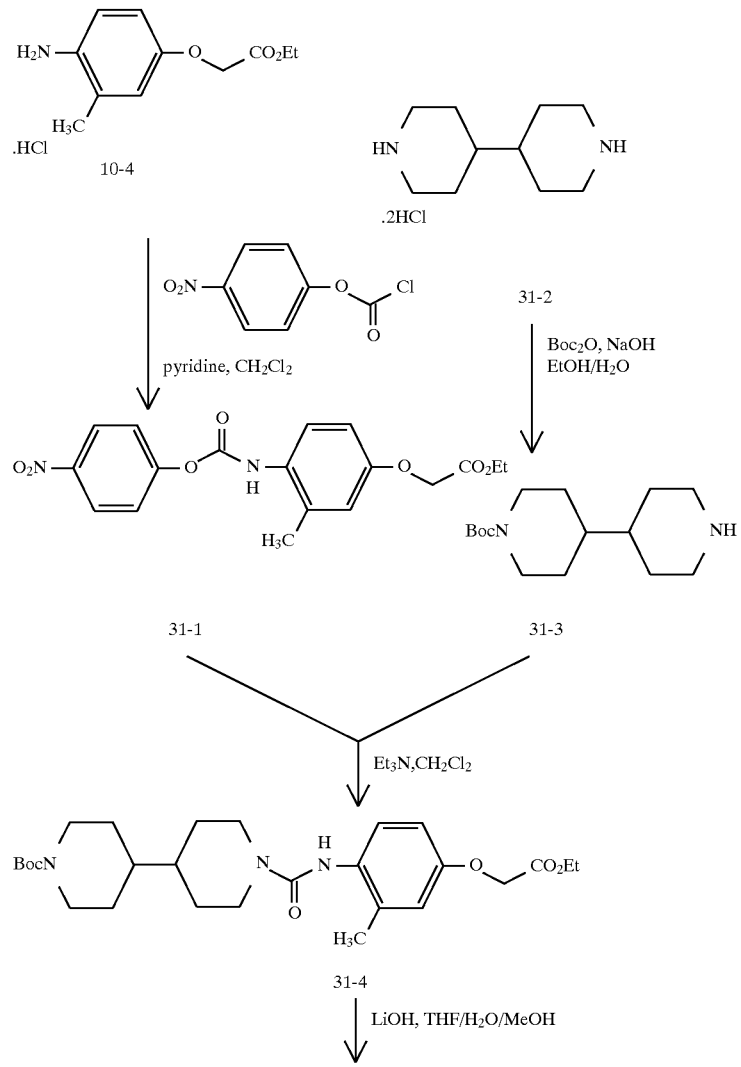

-continued
SCHEME 31

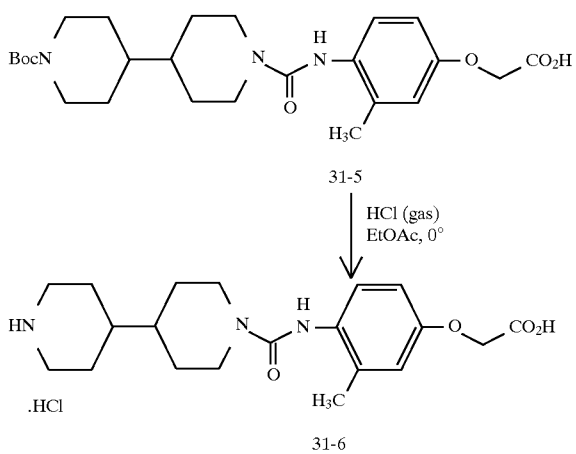

Ethyl 4-(4-nitrophenylcarbamate)-3-methylphenoxyacetate (31-1)

A solution of ethyl 4-amino-3-methylphenoxyacetate hydrochloride (10-4) (300 mg, 1.22 mmol) in $CH_2Cl_2$ (30 mL) was placed in a 50 mL flask. To this solution 4-nitrophenyl chloroformate (246 mg, 1.22 mmol) and pyridine (0.22 mL) were added at room temperature. The reaction was stirred at ambient temperature 18 h, then concentrated in vacuo to yield ethyl 4-(4-nitrophenylcarbamate)-3-methylphenoxyacetate (32-1). $^1H$ NMR ($CDCl_3$): δ 1.30 (t, j=7.0 Hz, 3H), 2.34 (s, 3H), 4.28 (q, j=7.0 Hz, 2H), 4.59 (s, 2H), 6.70 (dd, j=8.3, 2.0 Hz, 1H), 6.7 (d, j=2.0 Hz, 1H), 7.40 (d, j=8.3 Hz, 1H), 8.05 (d, j=7.0 Hz, 1H), 8.28 (d, j=7.0 Hz, 2H).

4-(1,1-Dimethylethoxycarbonyl)-4,4'-bipiperidine (31-3)

A solution of bipiperidine dihydrochloride (Aldrich 31-2) (25 g, 0.1 mol) in $H_2O$ (100 mL) was placed in a 2 L round bottomed flask. A solution of 6N NaOH was added dropwise to adjust the pH to 8–9. The solution was diluted with EtOH (1200 mL) and stirred vigorously at ambient temperature. The resulting mixture was treated with a solution of di-t-butyl dicarbonate (24 g, 0.11 mol) in EtOH (800 mL). Periodically, 6N NaOH was added to maintain pH 8–9. After stirring at ambient temperature 18 h. the reaction was concentrated in vacuo. The residue was dissolved in 1:1 ether: $H_2O$ (1000 mL) and the pH adjusted to 12 with 6N NaOH. The aqueous phase was separated and extracted again with ether. The ether phases were combined and washed with brine, 10% citric acid, and $H_2O$. The citric acid and $H_2O$ washes were combined and the pH adjusted to 12–13 with 6N NaOH, then extracted in 3 portions with ether (600 mL). The ether extract was washed (brine), dried ($Na_2SO_4$) and concentrated in vacuo to a clear oil which solidified on standing to yield 4-(1,1-dimethylethoxycarbonyl)-4,4'-bipiperidine (31-3). $^1H$ NMR ($CDCl_3$): δ 1.25 (br m, 7H), 1.45 (s, 9H), 1.66 (br d, 4H), 2.60 (dd, 4H), 3.1 (d, j=12 Hz, 2H), 4.21 (br s, 2H).

Ethyl-4-[(4-(1,1-dimethylethoxycarbonyl)-4,4'-bipiperidinyl-1-carbonyl)amino]-3-methylphenoxyacetate (31-4)

A solution of ethyl 4-(4-nitrophenylcarbamate)-3-methylphenoxyacetate (31-1), (457 mg, 1.22 mmol), 4-(1,1-dimethylethoxycarbonyl)-4,4'-bipiperidine (31-3) 327 mg, 1.22 mmol), and triethylamine (0.34 mL, 2.44 mmol) in $CH_2Cl_2$ (20 mL). The solution was refluxed 4 h, cooled and diluted with $CH_2Cl_2$ (10 mL). The reaction was extracted with $H_2O$ (15 mL). The $CH_2Cl_2$ extract was washed (1% NaOH, $H_2O$, 10% $KHSO_4$, brine), dried ($Na_2SO_4$), filtered, then concentrated in vacuo to an oil. The oil was chromatographed on silica using 50% EtOAc/hexane to obtain ethyl-4-[(4-(1,1-dimethylethoxycarbonyl)-4,4'-bipiperidinyl-1-carbonyl)amino]-3-methylphenoxyacetate (31-4) 1H NMR ($CDCl_3$): δ 1.27 (br m, 7H), 1.30 (t, j=7.0 Hz, 3H), 1.46 (s, 9H), 1.68 (d, j=12 Hz, 2H), 1.75 (d, j=10 Hz, 2H), 2.22 (s, 3H), 2.65 (t, j=12 Hz, 2H), 2.83 (t, j=12 Hz, 2H), 4.08 (d, j=12 Hz, 1H), 4.25 (br s, 2H), 4.27 (q, j=7 Hz, 2H), 4.58 (s, 2H), 5.97 (s, 1H), 6.70 (dd, j=8.3, 2 Hz, 1H), 6.73 (d, j=2 Hz, 1H), 7.40 (d,j=8.3 Hz, 1H), 4-[(4-(1,1-Dimethylethoxycarbonyl)-4,4'-bipiperidinyl-1-carbonyl)amino]-3-methylphenoxyacetic acid (31-5)

In a 25 mL round bottomed flask a solution of ethyl-4-[(4-(1,1-dimethylethoxycarbonyl)-4,4'-bipiperidinyl-1-carbonyl)amino]-3-methylphenoxyacetate (31-4) (100 mg, 0.2 mmol), 1M LiOH, (0.6 mL, 0.6 mmol), $H_2O$ (5 mL), THF (5 mL), and MeOH (5 mL) was stirred at ambient temperature 3 h. The reaction was concentrated in vacuo, then dissolved in $CHCl_3$ (20 mL). The $CHCl_3$ extract was washed (1N HCl, $H_2O$, and brine), dried ($NaSO_4$), filtered, and concentrated to yield 4-[(4-(1,1-dimethylethoxycarbonyl)-4,4'-bipiperidinyl-1-carbonyl) amino]-3-methylphenoxyacetic acid (31-5). $^1H$ NMR ($CDCl_3$): δ 1.22 (br m, 6H), 1.46 (s, 9H), 1.6 (br m, 4H), 2.2 (s, 3H), 2.6 (br t, 2H), 2.79 (t, j=11 Hz, 2H), 4.0 (br m, 5H), 4.58 (s, 2H), 6.1 (dd, j=9, 2 Hz, 1H), 6.75 (d, j=2 Hz, 1H), 7.21 (d, j=9 Hz, 1H), 8.1 (s, 1H).

4-[(4-[4,4']-Bipiperidinyl-1-carbonyl)amino]-3-methylphenoxyacetic acid hydrochloride (31-6)

In a 35 mL round bottomed flask 4-[(4-(1,1-dimethylethoxycarbonyl)-4,4'-bipiperidinyl-1-carbonyl) amino]-3-methylphenoxyacetic acid (31-5) (83 mg, 0.17 mmol) was dissolved in $CH_2Cl_2$ (10 mL) and cooled to 0°. Anhydrous HCl was bubbled through the solution for 5 min. The reaction was stirred at 0° 4 h, then concentrated in vacuo to yield 4-[(4-[4,4']-bipiperidinyl-1-carbonyl)amino]-3-methylphenoxyacetic acid, hydrochloride (31-6). $^1H$ NMR (DMSO-$d_6$): δ 1.04 (br d, j=11 Hz, 3H), 1.3 (br s, 3H), 1.62 (d, j=12 Hz, 2H), 1.79 (d, j=11 Hz, 2H), 2.07 (s, 3H), 2.67 (t, j=12 Hz, 2H), 2.74 (br m, 2H), 4.07 (d, j=12 Hz, 2H), 4.59 (s, 2H), 6.62 (dd, j=9, 2 Hz, 1H), 6.70 (d, j=2 Hz, 1H), 6.95 (d, j=9 Hz, 1H), 7.87 (s, 1H), 8.2 (br s, 1H), 8.5 (br s, 1H).

SCHEME 32

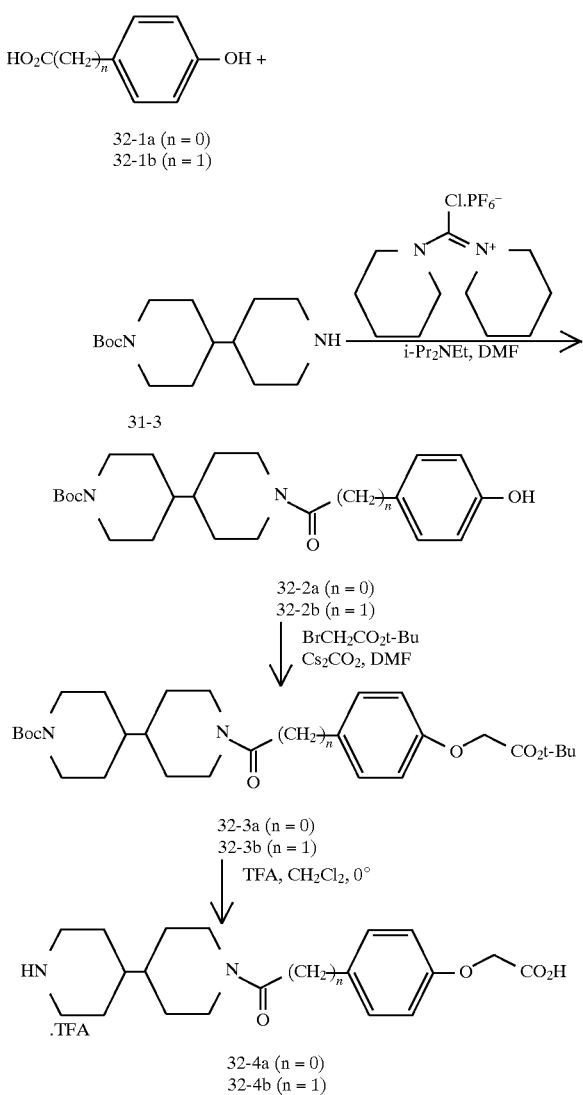

4-(2-(4-Dimethoxyethoxycarbonyl)-(4,4')-bipiperidinyl-1-carbonyl)phenol (32-2a)

In a 50 mL round bottomed flask a solution of 4-(1,1-dimethylethoxcarbonyl)-4,4'-bipiperidine (31-3) (400 mg, 1.49 mm), 4-hydroxybenzoic acid (206 mg, 1.49 mm), (32-1a), chloro-N,N,N',N'-bis(pentamethyl)formamidinium hexafluorophosphate (537 mg, 1.49 mm) and diisopropylethylamine (0.52 mL, 2.98 mm) in 25 mL DMF was stirred at ambient temperature 48 h. The reaction was concentrated in vacuo, then partitioned between EtOAc and H$_2$O. The EtOAc extract was washed (H$_2$O, sat'd NaHCO$_3$, H$_2$O, 10% KHSO$_4$ and brine), dried (Na$_2$SO$_4$), filtered and concentrated in vacuo. The resulting oil was chromatographed on silica using 5% MeOH/CHCl$_3$ as eluent to yield 4-(2-(4-dimethoxyethoxycarbonyl)-(4,4')-bipiperidinyl)-1-carbonyl)phenol (32-2a). $^1$H NMR (CDCl$_3$): δ 1.2 (br m, 6H), 1.4 (s, 9H), 1.58 (br m, 4H), 4.1 (m, 2H), 4.3 (m, 1H), 6.83 (d, j=8.5 Hz, 2H), 7.31 (d, j=8.5 Hz, 2H).

4-(2-(4-Dimethoxyethoxycarbonyl)-(4,4')-bipiperidinyl-1-yl-2-oxo-ethyl)phenol (32-2b)

In a manner similar to the preparation of compound 32-2a, 4-(2-(4-dimethoxyethoxycarbonyl)-(4,4')-bipiperidinyl-1-yl-2-oxo-ethyl)-phenol (32-2b) was prepared. $^1$H NMR (CDCl$_3$): δ 0.89 (m, 1H), 1.1 (m, 3H), 1.45 (s, 9H), 1.5 (br m, 6H) 2.49 (t, j=12 Hz, 1H), 2.62 (m, 2H), 2.91 (t, j=12 Hz, 1H), 3.64 (s, 2H). 3.90 (d, j=12 Hz, 1H), 4.1 (m, 2H), 4.68 (d, j=12 Hz, 1H), 6.12 (br m, 1H), 6.77 (d, j=8 Hz, 2H), 7.07 (d, j=8 Hz, 2H).

t-Butyl-4-(2-(4-Dimethoxyethoxycarbonyl)-(4,4')-bipiperidinyl-1-carbonyl)phenoxyacetate (32-3a)

In a 50 mL round bottomed flask a mixture of 4-(2-(4-dimethoxyethoxycarbonyl)-(4,4')-bipiperidinyl-1-carbonyl)-phenol (32-2a) (378 mg, 0.97 mm), t-butyl bromoacetate (0.16 mL, 1.067 mm) and cesium carbonate (348 mg, 1.067 mm) in 50 mL DMF was stirred at ambient temperature 18 h. The reaction was concentrated in vacuo, then partitioned between CHCl$_3$ and H$_2$O. The CHCl$_3$ extract was washed (10% KHSO$_4$, H$_2$O, NaHCO$_3$ and brine), dried (Na$_2$SO$_4$), filtered and concentrated in vacuo to yield t-butyl-4-(2-(4-dimethoxyethoxycarbonyl)-(4,4')-bipiperidinyl-1-carbonyl)-phenoxyacetate (32-3a). $^1$H NMR (CDCl$_3$): δ 1.2 (m, 6H), 1.42 (s, 9H), 1.45 (s, 9H), 2.68 (m, 4H), 2.61 (t, 2H), 2.8 (m, 2H), 4.18 (m, 4H), 4.5 (s, 2H), 6.9 (d, j=8 Hz, 2H), 7.35 (d, j=S Hz, 2H).

t-Butyl-4-(2-(4-dimethoxyethoxycarbonyl)-(4,4')-bipiperidinyl-1-yl-2-oxo-ethyl)phenoxyacetate (32-3b)

In a manner similar to the preparation of 32-3a, t-butyl-4-(2-(4-dimethoxyethoxycarbonyl)-(4,4')-bipiperidinyl-1-yl-2-oxo-ethyl)phenoxyacetate (32-3b) was prepared. $^1$H NMR (CDCl$_3$): δ 0.88 (m, 1H), 1.11 (m, 5H), 1.45 (s, 9H) 1.48 (s, 9H), 1.61 (m, 4H), 2.48 (t, j=12 Hz, 1H), 2.61 (br t, 2H), 2.88 (t, j=13 Hz, 1H), 3.66 (s, 2H), 3.88 (d, j=13 Hz, 1H) 4.1 (m, 2H), 4.49 (s, 2H), 4.68 (d, j=13 Hz, 1H), 6.84 (d, j=8.8 Hz, 2H), 7.15 (d, j=8.8 Hz, 2H).

[4-([4,4'-1-Bipiperidinyl-1-carbonyl)phenoxylacetic acid (32-4a)

In a round bottomed flask, t-butyl-4-(2-(4-dimethoxyethoxycarbonyl)-(4,4')-bipiperidinyl-1-carbonyl)-phenoxyacetate (32-3a) (56 mg, 0.11 mm) was stirred with trifluoracetic acid (2.5 mL) and CH$_2$Cl$_2$ (5 mL) at 0° 18 h. The reaction was concentrated in vacuo to yield [4-([4,4'-]-bipiperidinyl-1-carbonyl)phenoxy]-acetic acid (35-4a). $^1$H NMR (DMSO-d$_6$) δ 1.11 (m, 2H), 1.32 (m, 4H), 1.78 (m, 2H), 1.80 (d, j=12 Hz, 2H), 2.81 (dd, j=1 1 Hz, 4H), 3.28 (d, j=11 Hz, 2H), 4.73 (s, 2H), 6.94 (d, j=8.5 Hz, 2H), 7.32, J=8.5, 2H), 8.16 (br s, 1H), 8.47 (br s, 1H).

[4-(2-[4,4']-Bipiperidinyl-1-yl-2-oxo-ethyl)phenoxy]acetic acid (32-4b)

In a manner similar to the preparation of (32-4a), 4-(2-[4,4']-bipiperidinyl-1-yl-2-oxo-ethyl)-phenoxyl-acetic acid (32-4b) was prepared. $^1$H NMR (CDCl$_3$): δ 0.81 (m, 1H), 1.07 (m, 1H), 1.36 (br s, 2H), 1.62 (d, j=13 Hz, 1H), 1.74 (d, j=12 Hz, 1H), 1.87 (br s, 2H), 2.56 (t, j=11 Hz, 1H), 2.94 (m, 3H), 3.36 (d, j=12 Hz, 2H), 3.70 (m, 3H), 4.0 (d, j=13 Hz, 1H), 4.57 (d, j=13 Hz, 1H), 4.64 (s, 2H), 6.89 (d, j=8.5 Hz, 2H), 7.17 (d, j=8.5 Hz, 2H).

SCHEME 33

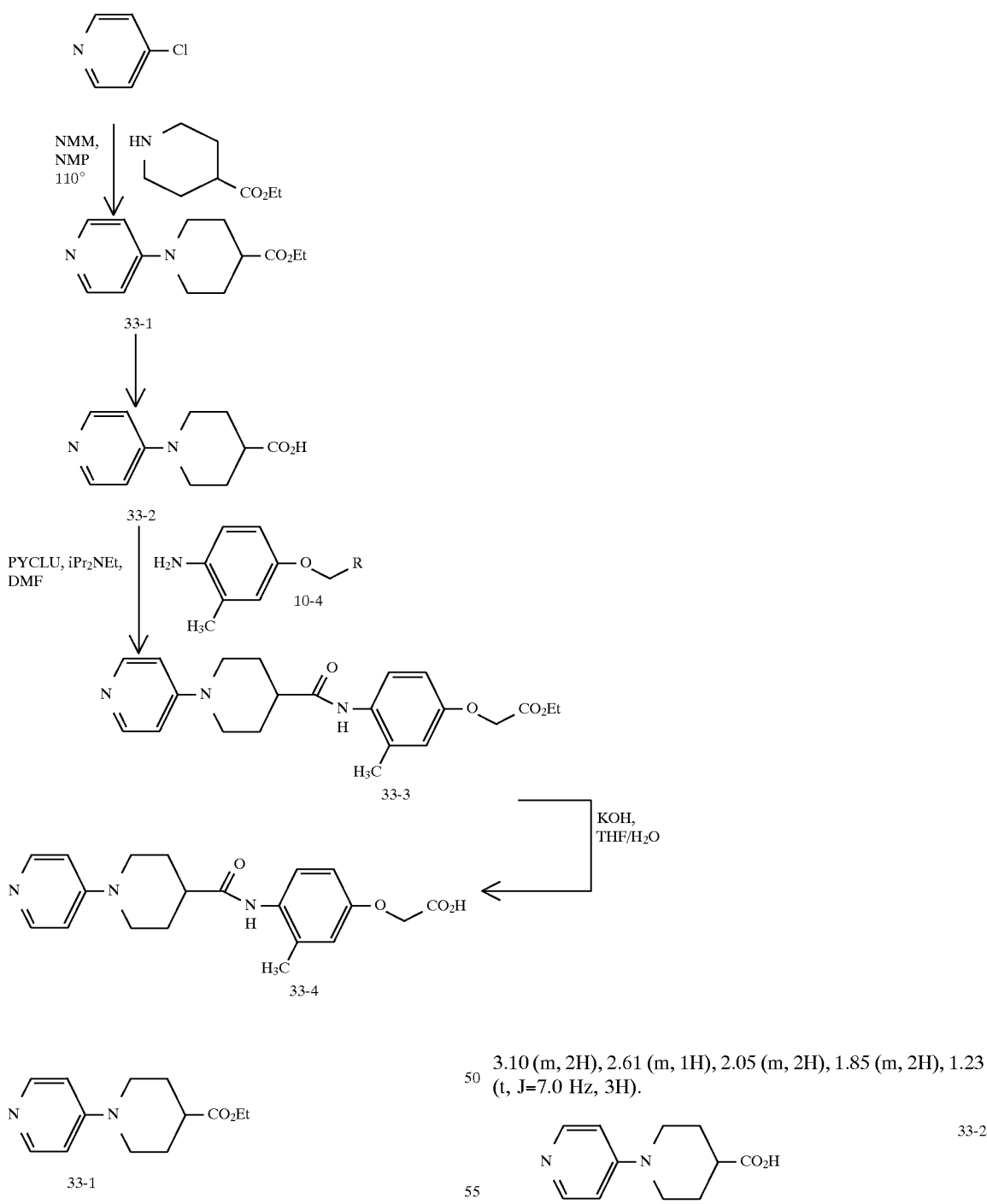

Ethyl 4-pyridylpiperidin-4-ylcarboxylate (33-1)

Ethyl isonipecotate (6.0 g 38.66 mmol), 4-chloropyridine hydrochloride (5.9 g, 38.66 mmol) and N-methylmorpholine (9.3 g mL, 85.00 mmol), were dissolved in N-methylpyrrolidine (50 mL) and the resulting solution was heated at 100° C. for 48 h. The solution was concentrated in vacuo and the residue was dissolved in EtOAc and washed with water and brine (2×100 mL), then dried ($Na_2SO_4$) and evaporated. The resulting residue was purified by flash chromatography (5% MeOH/$CHCl_3$) to afford 33-1 as a crystalline solid. $^1$H NMR ($CDCl_3$) δ 8.21 (d, J=6.8 Hz, 2H), 6.78 (d, J=6.8 Hz, 2H), 4.18 (q, J=7.0 Hz, 2H), 3.85 (m, 2H), 3.10 (m, 2H), 2.61 (m, 1H), 2.05 (m, 2H), 1.85 (m, 2H), 1.23 (t, J=7.0 Hz, 3H).

4-Pyridylpiperidin-4-ylcarboxylic acid (33-2)

A solution of 33-1 (10 g, 42.7 mmol) in THF (50 mL) was treated with 1N LiOH (47 mL, 47.0 mmol) and water (50 mL). The resulting solution was stirred at ambient temperature for 12 h. The solution was concentrated and the aqueous residue was cooled to 0° C., then adjusted to pH=6 with 1N HCl. The resulting solid was collected by filtration and dried in vacuo to afford 33-2 as a white solid. $^1$H NMR ($D_2O$) δ 7.95 (d, J=6.8 Hz, 2HO, 6.73 (d, J=6.8 Hz, 2h), 3.76 (d, J=12.8 Hz, 2HO, 2.81 (m, 2H), 2.20 (m, 1H), 1.85 (d, J=12.9 Hz, 2H), 1.55 (m, 2H).

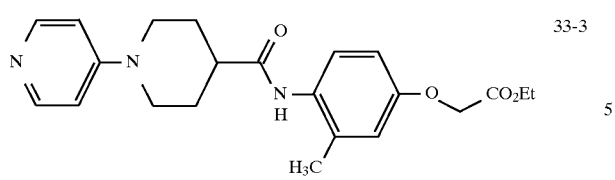

Ethyl 4-(Pyridyl)(piperidin-4-yl)-carbonylamino-3-methylphenoxyacetate (33-3)

Ethyl 4-amino-3-methylphenoxyacetate hydrochloride (10-4) (0.35 g, 1.41 mmol), 4-(Pyridyl)(piperidin-4-yl)-carboxylic acid (0.30 g, 1.41 mmol), chloro-N,N,N',N'-bis(pentamethylene)formamidinium hexafluorophosphate (0.50 g, 1.41 mmol), and diisopropylethylamine (0.25 mL, 1.41 mmol) were dissolved in dimethylformamide (15 mL). The solution was stirred at ambient temperature for 48 h and the solvent removed in vacuo to give an oil. This material was chromatographed on silica gel using 5:95 methanola-mmonia saturated chloroform as eluant to afford 33-3 as a beige solid. $^1$H NMR (CDCl$_3$): δ 8.27 (d, j=5.6 Hz, 2H), 7.53 (d, j=8.8 Hz, 1H), 7.03 (s, 1H), 6.78 (s, 1H), 6.73 (d, j=8.8 Hz, 1H) k, 6.68 (d, j=6.1 Hz, 2H), 4.59 (s, 2H), 4.27 (q, j=7.1 Hz, 2H), 3.97 (d, j=13.2 Hz, 2H), 2.95 (t, j=11.7 Hz, 2H), 2.53 (m, 1H), 2.06 (d, j=10.7 Hz, 2H), 1.92 (m, 2H), 1.73 (s, 3H), 1.30 (t, j=7.1 Hz, 3H).

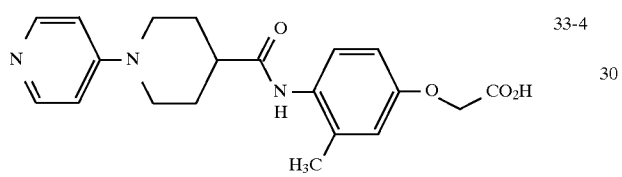

4-(Pyridyl)(piperidin-4-yl)-carbonylamino-3-methylphenoxyacetate (33-4)

A solution of Ethyl 4-(Pyridyl)(piperidin-4-yl)-carbonylamino-3-methylphenoxyacetate (33-3) (0.05 g, 0.126 mmol) in tetrahydrofuran (10 mL) was treated with 1N lithium hydroxide (0.13 mL, 0.132 mmol) and H$_2$O (10 mL). The resulting solution was stirred at ambient temperature and the solvent removed in vacuo to give 33-4 as a colorless glass. $^1$H NMR (CD$_3$OD) δ 8.09 (d, j=6.6 Hz, 2H), 7.09 (d, j=8.6 Hz, 2H), 6.87 (d, 6.8 Hz, 1H), 6.81 (s, 1H), 6.75 (d, j=8.6 Hz, 1H), 4.34 (s, 2H), 4.10 (d, j=13.2 Hz, 2H), 3.02 (t, 10.0 Hz, 2H), 2.82 (m, 1H), 2.18 (s, 3H), 1.98 (d, J=10.3 Hz, 2H), 1.83 (m, 2H).

SCHEME 34

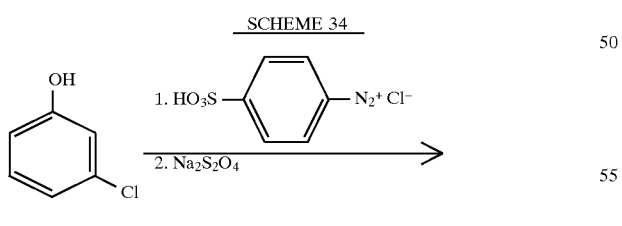

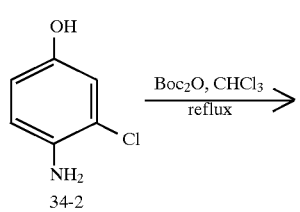

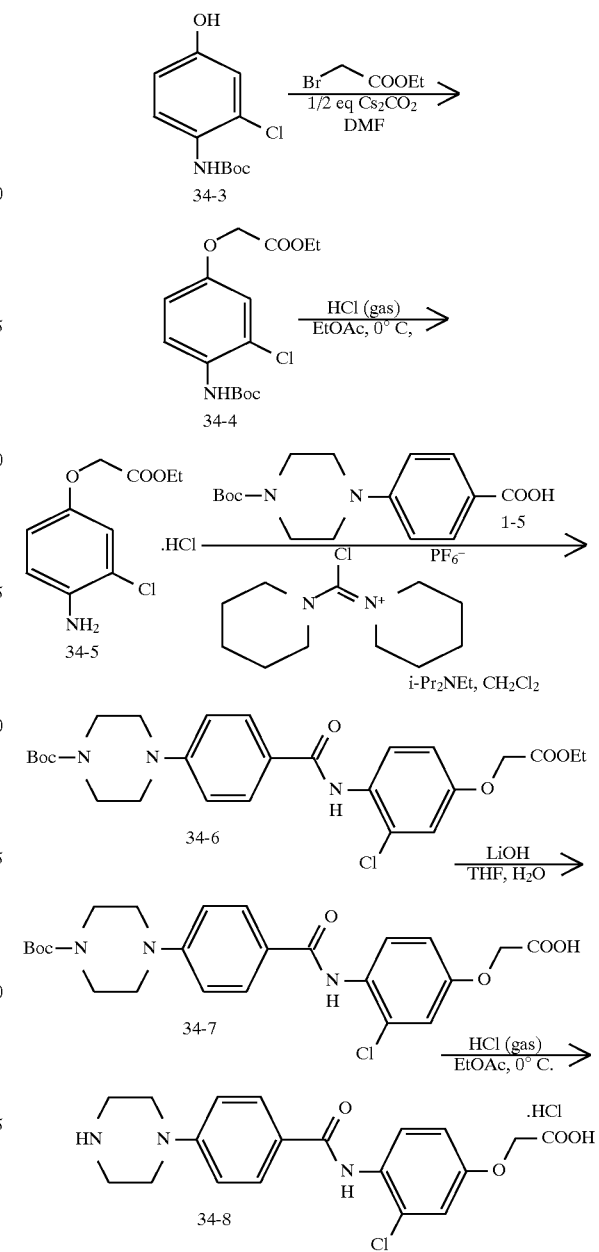

3-Chloro-4-aminophenol (34-2)

Using a procedure similar to that described for compound 12-2 but starting with 3-chlorophenol (34-1), 3-chloro-4-aminophenol (34-2) was prepared. $^1$H NMR (CDCl$_3$): δ 6.57 (dd, J=2.8, 8.6 Hz, 1H), 6.73 (m, 2H).

4-(1,1-Dimethylethoxycarbonyl)amino-3-chlorophenol (34-3)

To a 100 mL round bottomed flask with a stirring bar and an argon inlet was added 4-(1,1-dimethylethoxycarbonyl)amino-3-chlorophenol (1.91 g, 13.3 mmol), di-tert-butyldicarbonate (3.14 g, 14.4 mmol) and THF (50 mL). To this mixture was added triethylamine (2.23 mL, 16.0 mmol) and the mixture was stirred at room temperature for 98 h. The solvent was removed in vacuo. The residue was acidified with 10% aqueous citric acid and extracted with EtOAc. The EtOAc extract was washed with water and brine. Drying (MgSO$_4$), filtration, removal of the solvent in vacuo and chromatography on silica gel using EtOAc-hexane as eluant gave an oil. This material was dissolved in THF (25 mL) and MeOH (8 mL) and 1N LiOH (25 mL) were added. This solution was stirred at ambient temperature 4 h. This mixture was acidified with 10% citric acid and extracted with EtOAc. The organic layer was dried (MgSO$_4$), filtered and concentrated in vacuo to give 34-3 as an oil. $^1$H NMR (CDCl$_3$): δ 1.53 (s, 9H), 6.69 (dd, J=2.8, 8.9 Hz, 2H), 6.85 (d, J=2.8 Hz, 1H), 7.80 (d, J=8.9 Hz, 1H).

Ethyl 4-(1,1-dimethylethoxycarbonyl)amino-3-chlorophenoxyacetate (34-4)

To a 50 mL round bottomed flask with a stirring bar and an argon inlet was added 4-(1,1-dimethylethoxycarbonyl)amino-3-chlorophenol (0.831 g, 3.41 mmol) and DMF (16 mL). This mixture was cooled in an ice bath then Cs$_2$CO$_3$ (0.552 g, 1.69 mmol) and ethyl bromoacetate (0.37 mL, 3.34 mmol) were added. The resulting mixture was stirred for 6 h, during which time the cooling bath was allowed to expire. The mixture was filtered through a frit and the DMF was removed in vacuo. The residue was dissolved in EtOAc and washed with water (12×) and brine. Drying (MgSO$_4$), filtration and removal of the solvent in vacuo gave an oil which was purified by silica gel chromatography (EtOAc-hexane) to give ethyl 4-(1,1-dimethylethoxycarbonyl)amino-3-chlorophenoxyacetate (34-4) as an oil. $^1$H NMR (CDCl$_3$): δ 1.30 (m, 3H), 1.53 (s, 9H), 4.27 (m, 2H), 4.57 (s, 2H), 6.78 (br s, 1H), 6.83 (dd, J=2.8, 8.8 Hz, 1H), 6.96 (d, J=2.8 Hz, 1H), 8.02 (br d, J=8.8 Hz, 1H).

4-[4-(1-Piperazinyl)phenylcarbonylamino]-3-chlorophenoxyacetic acid (34-8)

Using a sequence similar to that described for compound 12-8, but starting with ethyl 4-(1,1-dimethylethoxycarbonyl)amino-3-chlorophenoxyacetate (34-4), 4-[4-(1-piperazinyl)phenylcarbonyl-amino]-3-chlorophenoxyacetic acid was prepared. $^1$H NMR (DMSO-d$_6$, HCl salt): δ 3.22 (t, J=5.0 Hz, 4H), 3.53 (t, J=5.0 Hz, 4H), 4.75 (s, 2H), 6.94 (dd, J=2.9, 8.8 Hz, 1H), 7.08 (d, J=8.9 Hz, 2H), 7.11 (d, J=2.9 Hz, 1H), 7.40 (d, J=8.8 Hz, 1H), 7.91 (d, J=8.9 Hz, 2H), 9.12 (br s, 1H), 9.69 (s, 1H).

SCHEME 35

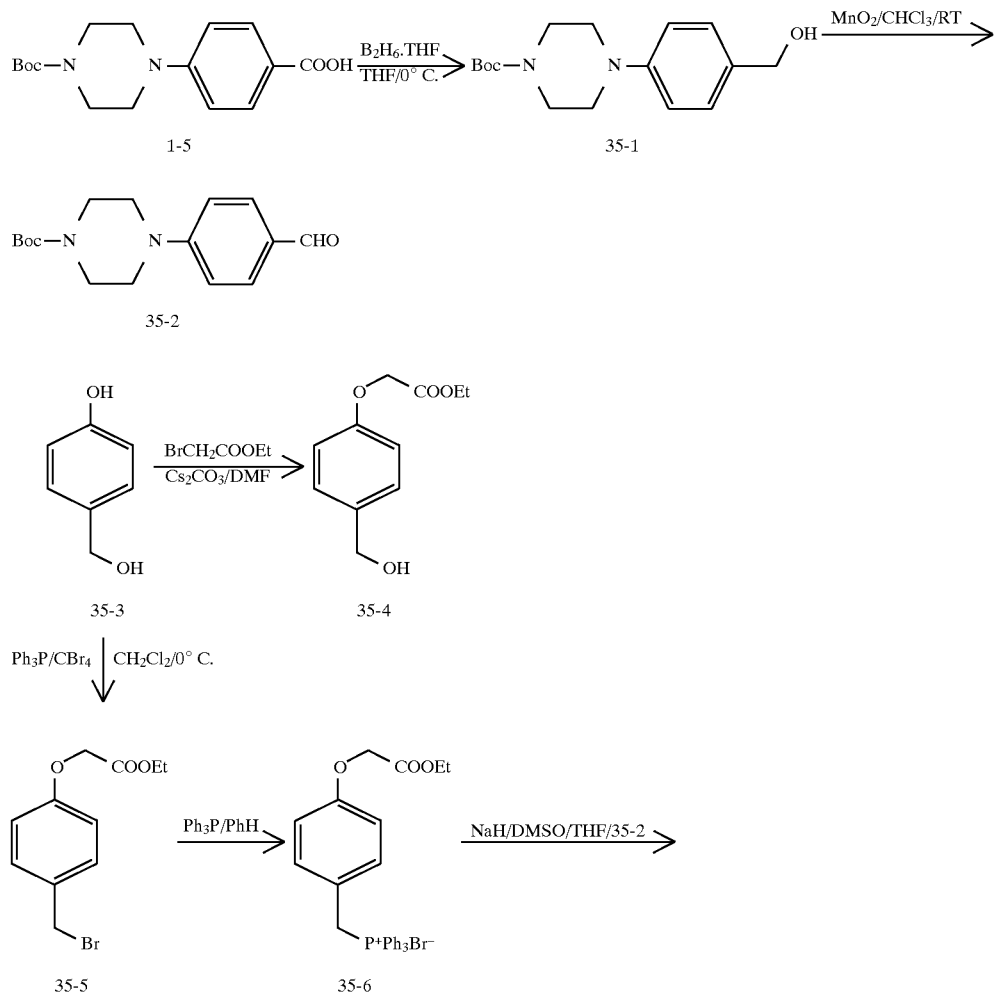

-continued
SCHEME 35

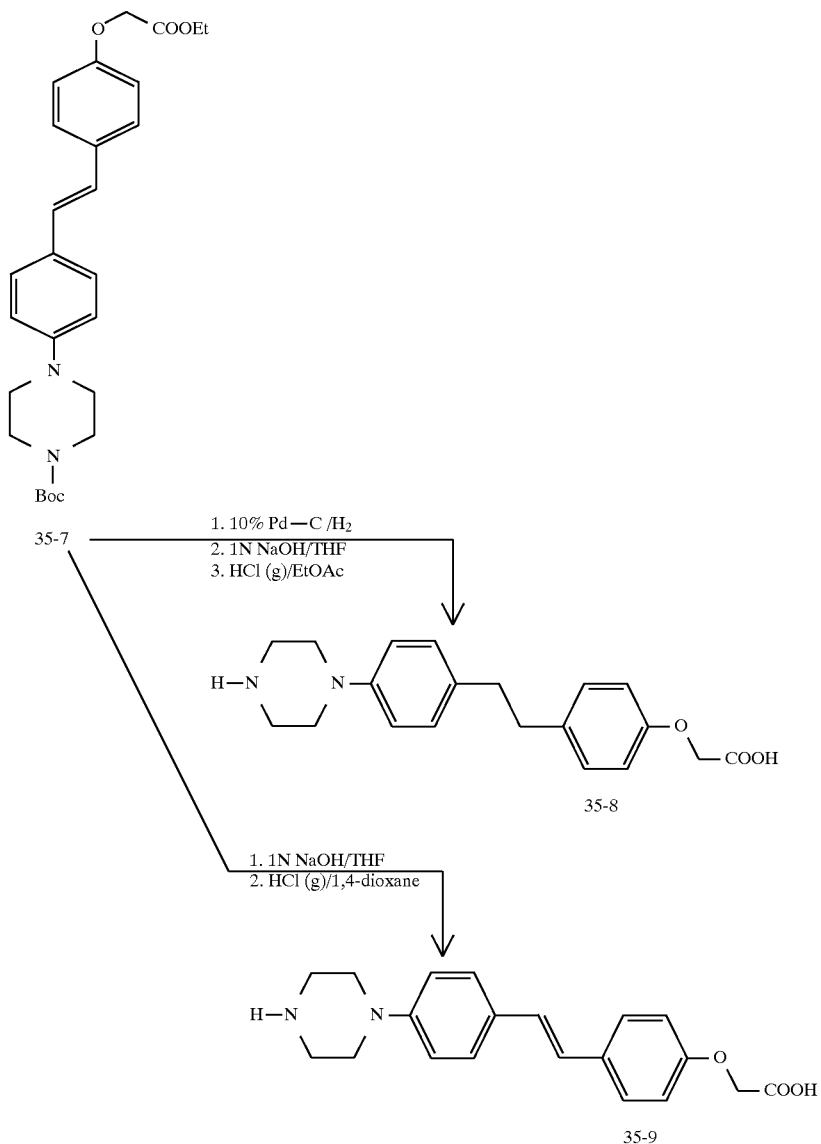

1-Hydroxymethyl-4-(4-(1,1-dimethylethoxycarbonyl)piperazinyl)benzene (35-1)

To an oven dried 500 mL round bottomed flask with a stirring bar and an argon inlet was added acid 1-5 (5.00 g, 16.32 mmol) and distilled, dry, THF (80 mL). This solution was cooled in an ice bath and borane.THF complex (125 mL of a 1M solution in THF, 125 mmol) was added with a syringe. The resulting solution was maintained at 0° C. for 3.5 h. The reaction was quenched by addition of MeOH (50 mL), slowly, with a syringe over 5 min. This mixture was stirred at ambient temperature for 18 h. The solvents were removed in vacuo and the residue was dissolved in EtOAc (300 mL). This solution was washed with saturated aqueous $NaHCO_3$ and brine. Drying ($MgSO_4$), filtration and removal of the solvent in vacuo gave 4.86 g of 1-hydroxymethyl-4-(4-(1,1-dimethylethoxycarbonyl)piperazinyl)benzene, 35-1, as a white solid. $^1$H NMR ($CDCl_3$): δ 1.48 (s, 9H), 3.11 (m, 4H), 3.59 (m, 4H), 4.61 (s, 2H), 6.91 (d, J=7 Hz, 2H), 7.27 (d, J=7 Hz, 2H).

4-(4-(1,1-Dimethylethoxycarbonyl)piperazinyl)benzaldehyde (35-2)

To a 50 mL round bottomed flask with a stirring bar and an argon inlet was added 1-hydroxymethyl-4-(4-(1,1-dimethylethoxycarbonyl)piperazinyl)benzene, 35-1 (2.15 g, 7.35 mmol), $CHCl_3$ (100 mL), and $MnO_2$ (12.0 g, 138 mmol). This mixture was stirred at ambient temperature for 24 h. The salts were removed by filtration and the solvent was removed in vacuo. The residue was chromatographed on 90 g of silica gel using 30/70 EtOAc-hexane as eluant. There was obtained 4-(4-(1,1-dimethylethoxycarbonyl)piperazinyl)benzaldehyde 35-2 (2.10 g, 99%) as a crystalline solid. $^1$H NMR ($CDCl_3$): δ 1.49 (s, 9H), 3.39 (m, 4H), 3.59 (m, 4H), 6.89 (d, J=9 Hz, 2H), 7.75 (d, J=9 Hz, 2H), 9.79 (s, 1H).

Ethyl 2-(4-hydroxymethylphenoxy)acetate (35-4)

To a 500 mL round bottomed flask with a stirring bar and an argon inlet was added 4-hydroxybenzyl alcohol (7.50 g, 60.42 mmol), $Cs_2CO_3$ (29.53 g, 90.63 mmol), DMF (100 mL), and ethyl bromoacetate (11.09 g, 66.46 mmol). This mixture was stirred at ambient temperature for 2 h. The mixture was filtered and the filtrate was concentrated in vacuo. The residue was partitioned between EtOAc and water. The layers were separated and the organic phase was washed with two additional portions of water. Drying (MgSO$_4$), filtration and removal of the solvent in vacuo, gave an oil. This material was chromatographed on 250 g of silica gel using 1:1 EtOAc-hexane as eluant. There was obtained ethyl 2-(4-hydroxymethyl-phenoxy)acetate 35-4 (7.47 g, 59%) as an oil. $^1$H NMR (CDCl$_3$): δ 1.29 (t, J=7 Hz, 3H), 2.07 (br s, 1H), 4.26 (q, J=7 Hz, 2H), 4.58 (s, 2H), 4.60 (s, 2H), 6.88 (d, J=9 Hz, 2H), 7.27 (d, J=9 Hz, 2H).

Ethyl 2-(4-bromomethylphenoxy)acetate (35-5)

To a 1 L round bottomed flask with a stirring bar, addition funnel and an argon inlet was added ethyl 2-(4-hydroxymethylphenoxy)acetate 35-4 (7.47 g, 35.53 mmol), CBr$_4$ (13.26 g, 39.97 mmol) and dry CH$_2$Cl$_2$ (300 mL). This solution was cooled in an ice bath and and a solution of triphenyl phosphine (10.48 g, 39.97 mmol) in CH$_2$Cl$_2$ (100 mL) was added dropwise over 1 h. The ice bath was allowed to expire and and the mixture was stirred at ambient temperature 18 h. The solvent was removed in vacuo and the residue was chromatographed directly on 200 g of silica gel useing 15% EtOAc-hexane as eluant. There was obtained ethyl 2-(4-bromomethylphenoxy)acetate 35-5 (7.2 g, 74%) as a low melting solid, mp.: 44°–45° C. $^1$H NMR (CDCl$_3$): δ 1.29 (t, J=7 Hz, 3H), 4.26 (q, J=7 Hz, 2H), 4.48 (s, 2H), 4.61 (s, 2H), 6.86 (d, J=9 Hz, 2H), 7.32 (d, J=9HZ, 2H).

4-(Ethoxycarbonylmethoxy)benzyltriphenylphosphonium bromide (35-6)

To a 100 mL round bottomed flask with a stirring bar and a reflux condenser topped with an argon inlet was added ethyl 2-(4-bromomethylphenoxy)acetate 35-5 (2.73 g, 10 mmol), triphenylphosphine (2.62 g, 10 mmol) and dry benzene (50 mL). This solution was warmed to 50° C. for 20 h. The mixture was cooled to room temperature and the product was collected by filtration. The white solid was washed with a little benzene and dried in vacuo to give 4-(ethoxycarbonylmethoxy)benzyltriphenyl-phosphonium bromide 35-6 as a white, crystalline solid (4.79 g, 89%). $^1$H NMR (CDCl$_3$): δ 1.28 (t, J=7 Hz, 3H), 4.27 (q, J=7 Hz, 2H), 4.53 (s, 2H), 5.38 (d, J=14 Hz, 2H), 6.66 (d, J=9 Hz, 2H), 7.06 (d, J=9 Hz, 2H), 7.62 (m, 6H), 7.76 (m, 9H).

(E) Ethyl 4-(2-(4-(4-(1,1-dimethylethoxycarbonyl)piperazinyl)phenyl)ethenyl)phenoxyacetate (35-7)

To an oven dried 100 mL round bottomed flask with a stirring bar and an argon inlet was added 4-(ethoxycarbonylmethoxy)benzyltriphenyl-phosphonium bromide (1.106 g, 2.07 mmol) and dry THF (50 mL). To this well stirred mixture was added a solution of lithium hexamethyldisilylazide (2.20 mL of a 1M solution in THF). The deep red solution was stirred 1 h at ambient temperature then cooled in an ice bath to 0° C. To this mixture was added a solution of 4-(4-(1,1-dimethylethoxycarbonyl)piperazinyl)benzaldehyde (0.60 g, 2.07 mmol) in 10 mL of THF. The ice bath was removed and the solution was stirred at ambient temperature for 3 h. The reaction mixture was diluted with EtOAc and washed with water and brine. Drying (MgSO$_4$), filtration and removal of the solvent in vacuo gave 1 g of an oil. This material was chromatographed on 80 g of silica gel using 25% EtOAc-hexane as eluant. There was obtained (E)-ethyl 4-(2-(4-(4-(1,1-dimethylethoxycarbonyl)piperazinyl)phenyl)ethenyl)phenoxyacetate 35-7 as an oil. $^1$H NMR (CDCl$_3$): δ 1.26 (t, j=7 Hz, 3H), 1.49 (s, 9H), 3.16 (m, 4H), 3.57 (m, 4H), 4.27 (q, j=7 Hz, 2H), 4.60 (s, 2H), 6.90 (m, 6H), 7.40 (m, 4H), and 175 mg of a mixture of E,Z isomers.

4-(2-(4-(1-Piperazinyl)phenyl)ethyl)phenoxyacetic acid (35-8)

To a 25 mL round bottomed flask with a stirring bar and a balloon hydrogenation adaptor was added (E,Z) ethyl 4-(2-(4-(4-(1,1-dimethylethoxycarbonyl)piperazinyl)phenyl)ethenyl)phenoxyacetate (175 mg, 0.36 mmol), absolute EtOH (10 mL) and 10% Pd—C. This mixture was hydrogenated at 1 atmosphere at ambient temperature for 18 h. The cataylst was removed by filtration and the filtrate was concentrated in vacuo. The residue was chromatographed on 40 g of silica gel using 20% EtOAc-hexane as eluant. The purified hydrogenation product was hydrolyzed in THF (2 mL) with 1N NaOH (1 mL) for 3 h at ambient temperature. The reaction mixture was diluted with EtOAc and washed with 10% aqueous citric acid, water, and brine. Drying (MgSO$_4$), filtration and removel of the solvent in vacuo gave the corresponding acid as a white solid. This material was dissolved in EtOAc (20 mL) and cooled to 0° C. in an ice bath. The solution was saturated with dry HCl gas for 15 min. The resulting suspension was aged 30 min at 0° C., then the solvent and excess HCl were removed in vacuo. The solid product was triturated with fresh EtOAC and collected on a frit, After drying at 60° C./0.05 torr there was obtained 103 mg of 4-(2-(4-(1-piperazinyl)phenyl)ethyl)phenoxyacetic acid 35-8 as the hydrochloride salt. mp >250° C. $^1$H NMR (DMSO-D$_6$): δ 2.76 (s, 4H), 3.20 (m, 4H), 3.33 (m, 4H), 4.61 (s, 2H), 6.80 (d, J=8 Hz, 2H), 6.90 (d, J=8 Hz, 2H), 7.12 (m, 4H), 9.21 (br s, 2H).

(E) 4-(2-(4-(1-Piperazinyl)phenyl)ethenyl )phenoxyacetic acid (35-9)

To a 25 mL round bottomed flask with a stirring bar and an argon inlet was added (E) ethyl 4-(2-(4-(4-(1,1-dimethylethoxycarbonyl)piperazinyl)phenyl)ethenyl)phenoxyacetate (57 mg, 0.12 mmol), THF (2.0 mL) and 1N NaOH (1.00 mL). This mixture was stirred at ambient temperature 18 h. The reaction was neutralized with 1N HCl (1.00 mL) and extracted with several portions of EtOAc. The combined EtOAc extracts were washed with water and brine. Drying (MgSO$_4$), filtration and removal of the solvent in vacuo gave 45 mg of a solid. This solid was dissolved in 4N HCl-1,4-dioxane. The mixture was stirred 18 h at ambient temperature. The milky suspension was concentrated in vacuo. The crude product was triturated with a little EtOAc and collected on a frit. This material was dried in vacuo to provide 24 mg of (E) 4-(2-(4-(1-piperazinyl)phenyl)ethenyl)phenoxyacetic acid 35-9 as the hydrochloride salt, mp >250° C. $^1$H NMR (DMSO-D$_6$): δ 3.2 (m, 4H), 3.45 (m, 4H), 4.69 (s, 2H), 6.89 (d, J=9 Hz, 2H), 6.98 (d, J=9 Hz, 2H), 7.02 (s, 2H), 7.48 (m, 4H), 9.15 (br s, 2H), 13.02 (br s, 1H).

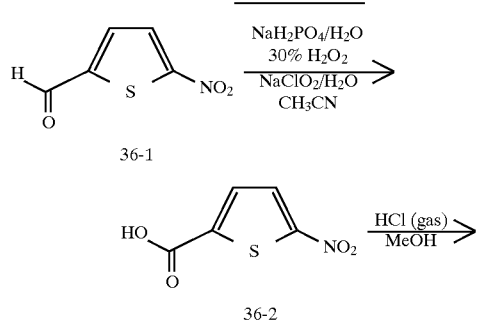

147

-continued
SCHEME 36

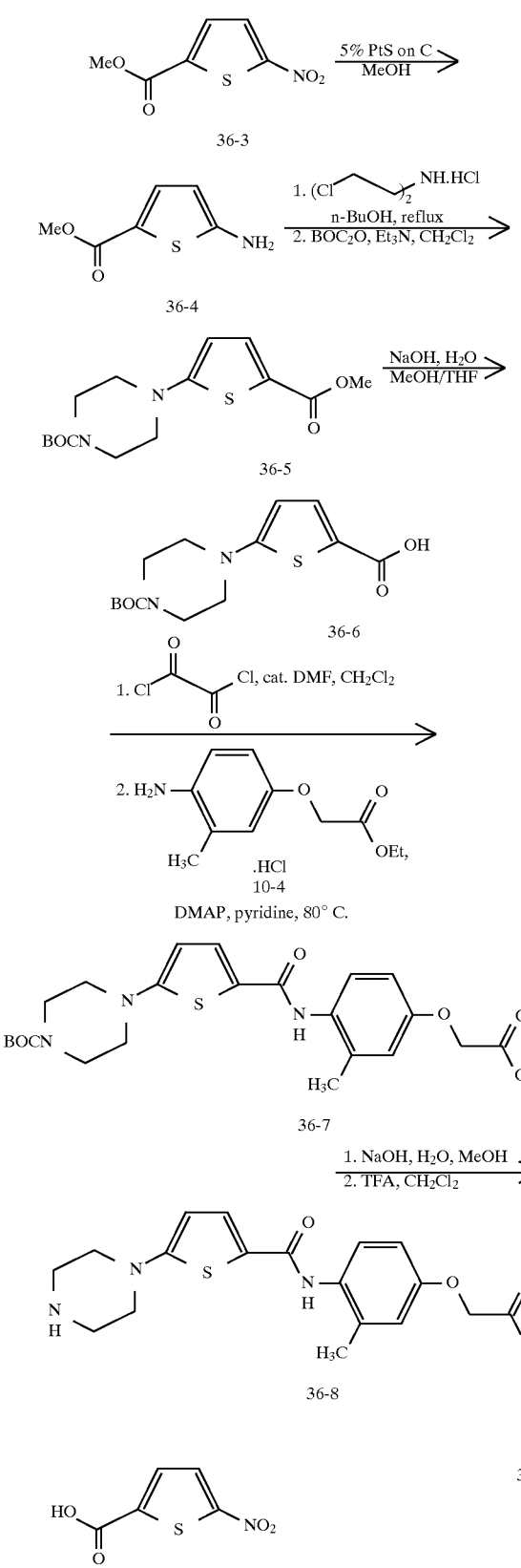

5-Nitrothiophene-2-carboxylic acid (36-2)

To a 500 mL round bottomed flask with a stirring bar, was added 5-nitrothiophene-2-carboxaldehyde (7.86 g, 50.00 mmol) in CH$_{13}$CN (50 mL), NaH$_2$PO$_4$ (1.86 g, 13.50 mmol) in water (20 mL), and 30% H$_2$O$_2$ (aq) (6 mL). To this mixture, cooled in an ice bath, was added NaClO$_2$ (8 g, 70.80 mmol) in water (70 mL) dropwise over a period of an hour. The reaction was stirred at room temperature for 5 hours. It was worked up by addition of Na$_2$SO$_3$ (500 mg), acidified with 1M HCl, and then extracted with ethyl acetate (3×). The combined organic layers were washed with water (1×), and brine (1×). Drying (MgSO$_4$), filtration and removal of the solvents in vacuo yielded 5-Nitrothiophene-2-carboxylic acid as a yellow powder.

$^1$H NMR (300 MHz, CDCl$_3$) δ 7.91(d, J=4.4 Hz, 1H), 7.80(d, J=4.4 Hz, 1H).

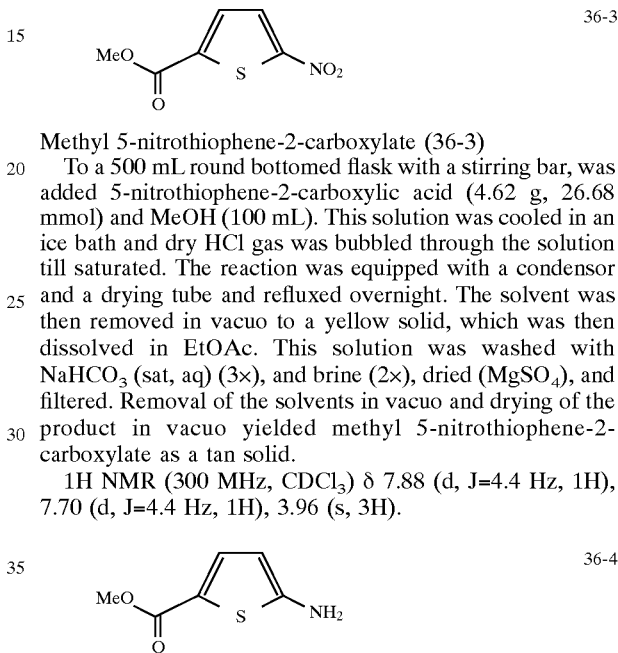

Methyl 5-nitrothiophene-2-carboxylate (36-3)

To a 500 mL round bottomed flask with a stirring bar, was added 5-nitrothiophene-2-carboxylic acid (4.62 g, 26.68 mmol) and MeOH (100 mL). This solution was cooled in an ice bath and dry HCl gas was bubbled through the solution till saturated. The reaction was equipped with a condensor and a drying tube and refluxed overnight. The solvent was then removed in vacuo to a yellow solid, which was then dissolved in EtOAc. This solution was washed with NaHCO$_3$ (sat, aq) (3×), and brine (2×), dried (MgSO$_4$), and filtered. Removal of the solvents in vacuo and drying of the product in vacuo yielded methyl 5-nitrothiophene-2-carboxylate as a tan solid.

1H NMR (300 MHz, CDCl$_3$) δ 7.88 (d, J=4.4 Hz, 1H), 7.70 (d, J=4.4 Hz, 1H), 3.96 (s, 3H).

Methyl 5-aminothiophene-2-carboxylate (36-4)

To a Parr flask was added methyl 5-nitrothiophene-2-carboxylate (5.00 g, 26.71 mmol) and MeOH (100 mL). The solution was purged with a stream of Ar, and 5% platinum on sulfide carbon (2.00 g) was added. The mixture was hydrogenated on a Parr apparatus set at 50 psi for 6.5 hours. The reaction was then filtered through celite and the solvents removed in vacuo to yield methyl 5-aminothiophene-2-carboxylate as an olive green oil.

$^1$H NMR (300 MHz, CDCl$_3$) δ 7.45(d, J=4.0 Hz, 1H), 6.09(d, J=4.0 Hz, 1H), 4.31 (br s, 2H), 3.81 (s, 3H)

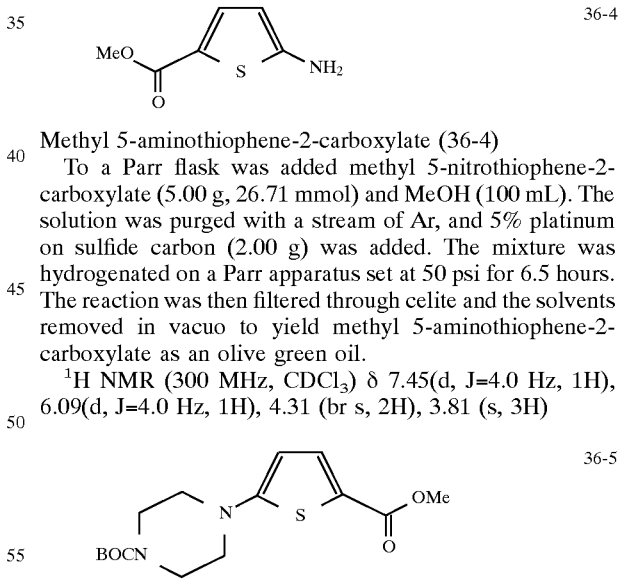

5-(4-(1,1-Dimethylethoxycarbonyl)-piperazin-1-yl)-thiophene-2-carboxylate, (36-5)

To a 500 mL round bottomed flask equipped with a condenser, stirring bar, and argon inlet was added methyl 5-aminothiophene-2-carboxylate (4.27 g, 27.16 mmol), bis (2-chloroethyl)amine, hydrochloride (5.82 g, 32.59 mmol) and n-BuOH (90 mL, previously purged with Ar). This solution was reluxed for 7 days under Ar, and the reaction was followed by HPLC. The solvents were then removed in vacuo, and the residue partitioned between EtOAc and NaHCO$_3$ (aq). Extracted aqueous with EtOAc (3×), and then washed the combined organics with brine (1×), dried (Na₂SO₄), filtered, and concentrated in vacuo. The residue was azeotroped with toluene (3×), and dried in vacuo overnight.

The dried product was dissolved in CH₂Cl₂ (80 mL), and triethylamine (4.2 mL, 30.13 mmol), di-tert-butylpyrocarbonate (6.53 g, 29.90 mmol), and CH₂Cl₂ (20 mL) were added and the reaction was stirred at room temperature for 2 hours. The reaction was then concentrated in vacuo. This yielded 490 mg of n-butyl 5-(4-(1,1-dimethylethoxycarbonyl)-piperazin-1-yl)-thiophene-2-carboxylate and 700 mg of 5-(4-(1,1-dimethylethoxycarbonyl)-piperazin-1-yl)-thiophene-2-carboxylate as a mixture of the methyl and n-butyl esters.

¹H NMR of n-butyl ester (300 MHz, CDCl₃) δ 7.55 (d, J=4.4 Hz, 1H), 6.06 (d, J=4.4 Hz, 1H), 4.24 (t, 2H), 3.58 (t, 4H), 3.22(t, 4H), 1.69 (m, 2H), 1.48 (s, 9H), 1.42 (m, 2H), 0.95 (t, 3H).

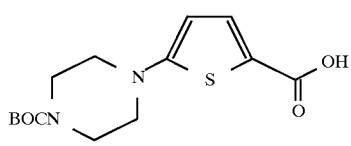

36-6

5-(4-(1,1-Dimethylethoxycarbonyl)-piperazin-1-yl)-thiophene-2-carboxylic acid, (36-6)

To a 50 ml round bottomed flask with a stirring bar was added n-butyl 5-(4-(1,1-dimethylethoxycarbonyl)-piperazin-1-yl)-thiophene-2-carboxylate (490 mg, 1.33 mmol) and 4.2 mL of a 2.5M NaOH solution in 3:1 MeOH/H₂O. THF (2 mL) was added to keep the reaction homogeneous. The reaction was stirred at room temperature and followed by HPLC. After 2 days, the reaction was concentrated in vacuo, acidified with 10% citric acid and extracted with EtOAc (3×). The combined organics were washed with water (1×), brine (1×), dried (Na₂SO₄), filtered, and the solvents removed in vacuo. The product was azeotroped with benzene (3×) and dried in vacuo over 2 days to yield 5-(4-(1,1-dimethylethoxycarbonyl)-piperazin-1-yl)-thiophene-2-carboxylic acid as a dark green solid.

¹H NMR (300 MHz, CD₃OD) δ 7.51 (d, J=4.4 Hz, 1H), 6.19 (d, J=4.4 Hz, 1H), 3.57 (t, 4H), 3.24 (t, 4H), 1.47 (s, 9H).

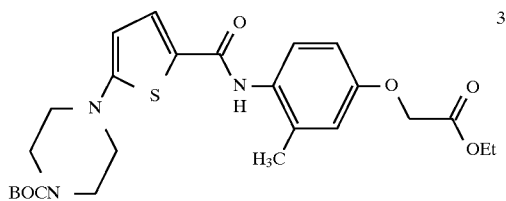

36-7

Ethyl 2-(4-(5-(4-(1,1-dimethylethoxycarbonyl)-piperazin-1-yl)-2-thienylcarbonylamino)-3-methylphenoxy)-acetate (36-7)

To a 100 ml round bottomed flask with a stirring bar and an argon inlet was added 5-(4-(1,1-dimethylethoxycarbonyl)-piperazin-1-yl)-thiophene-2-carboxylic acid (428 mg, 1.370 mmol), anhydrous CH₂Cl₂ (10 mL), DMF (0.05 mL), and distilled oxalyl chloride (0.180 mL, 2.06 mmol). It was stirred 1.5 hours at room temperature. The acid chloride was concentrated in vacuo, azeotroped with benzene (3×), and stored under a blanket of Ar.

To another 100 mL round bottomed flask with a stirring bar and an argon inlet was added ethyl 4-amino-3-methylphenoxyacetate hydrochloride, anhydrous pyridine (7 mL), and dimethylaminopyridine (34 mg, 0.278 mmol).

Cooled in an ice bath. A solution of the acid chloride in pyridine (3 mL) was added. The ice bath was removed and the reaction was stirred at 80° C. overnight.

The reaction was concentrated in vacuo, dissolved in EtOAc, washed with aq. KHSO₄ (3×), aq. NaHCO₃ (2×), brine (1×), dried (Na₂SO₄), filtered, and the solvents removed in vacuo. This material was chromatographed on silica gel in 18% EtOAc-hexane as eluant yielding ethyl 2-(4-(5-(4-(1,1-dimethylethoxycarbonyl)-piperazin-1-yl)-2-thienylcarbonylamino)-3-methylphenoxy)-acetate.

¹H NMR (300 MHz, DMSO-d₆) δ 9.42 (s, 1H), 7.67 (d, J=4.3 Hz, 1H), 7.13 (d, J=8.8 Hz, 1H), 6.83(d, J=2.7 Hz, 1H), 6.74 (dd, J=8.8, 2.7 Hz, 1H), 6.24 (d, J=4.3 Hz, 1H), 4.76 (s, 2H), 4.17 (q, J=7.1, 2H), 3.47 (t, 4H), 3.16 (t, 4H), 2.15 (s, 3H), 1.42(s, 9H), 1.22 (t, J=7.1 Hz, 3H).

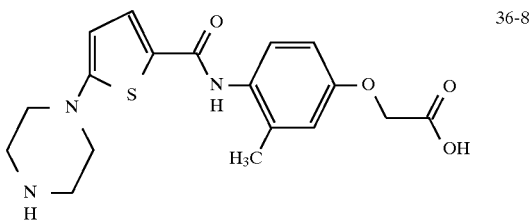

36-8

2-(4-(5-(4-(1,1-Dimethylethoxycarbonyl)-piperazin-1-yl)-2-thienylcarbonylamino)-3-methylphenoxy)-acetic acid (36-8)

To a 100 mL round bottomed flask with a stirring bar was added ethyl 2-(4-(5-(4-(1,1-dimethylethoxycarbonyl)-piperazin-1-yl)-2-thienylcarbonylamino)-3-methylphenoxy)-acetate (250 mg, 0.496 mmol), MeOH (8 mL), and 1M NaOH (1 mL). The reaction was stirred overnight at room temperature.

The reaction was concentrated in vacuo, acidified with aq. KHSO₄ and extracted with EtOAc (2×). The organic extracts were washed with brine (1×), dried (Na₂SO₄), filtered, and the solvents removed in vacuo.

This product was dissolved in CH₂Cl₂ (8 mL), and trifluoroacetic acid (2 mL) was added. The reaction was stirred for 2 hours at room temperature and then concentrated in vacuo. The residue was subjected to HPLC on a C-18 reverse-phase column eluting with 100% H₂O −50% H₂O/CH₃CN (with 0.1% TFA) over 40 minutes. Collection and lyophilization of the appropriate fractions yielded 2-(4-(5-(4-(1,1-Dimethylethoxycarbonyl)-piperazin-1-yl)-2-thienylcarbonylamino)-3-methylphenoxy)-acetic acid as a white fluffy solid.

¹H NMR (300 MHz, CD₃OD) δ 7.62(d, J=4.1 Hz, 1H), 7.16 (d, J=8.5 Hz, 1H), 6.86 (d, J=2.7 Hz, 1H), 6.79 (dd, J=8.5, 2.7 Hz, 1H), 6.34 (d, J=4.1 Hz, 1H), 4.65 (s, 2H), 3.50 (m, 4H), 3.40 (m, 4H), 2.24 (s, 3H).

EXAMPLE 37

Tablet Preparation

Tablets containing 25.0, 50.0, and 100.0 mg., respectively, of the active compound 3-(4-(4-piperazin-1-ylphenylcarbonylamino)phenyl)-propanoic acid are prepared as illustrated below:

TABLE FOR DOSES CONTAINING
FROM 25–100 MG OF THE ACTIVE COMPOUND

|  | Amount-mg | | |
|---|---|---|---|
| Active Compound | 25.0 | 50.0 | 100.0 |
| Microcrystalline cellulose | 37.25 | 100.0 | 200.0 |
| Modified food cornstarch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 38

Intravenous Formulations

An intravenous dosage form of the above-indicated active compound is prepared as follows:

| Active Compound | 0.5–10.0 mg |
|---|---|
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Phannacopeia/National Formulary for 1995, published by United States Pharmacopeial Convention, Inc., Rockville, Md., copyright 1994.

EXAMPLE 39

Intravenous Formulation

A pharmaceutical composition was prepared at room temperature using 3-(4-(4-piperazin-1-ylphenylcarbonylamino)phenyl) propanoic acid, a citrate buffer, and sodium chloride, to obtain a concentration of of 0.25 mg/ml.

800 grams of water was introduced into a standard pharmaceutical mixing vessel. 0.25 grams of 4-(N-piperazine)benzoyl-N-(aminophen-4-yl)propionic acid was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount |
|---|---|
| 3-(4-(4-piperazin-1-ylphenylcarbonylamino)phenyl)propanoic acid | 0.25 mg/ml |
| citrate buffer | 10 mM |
| sodium chloride | 8 mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transfered to an infusion bag.

Therapeutic Treatment

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

What is claimed is:

1. A compound having the formula $$X-Y-Z-A-B$$

or a pharmaceutically acceptable salt, wherein

X and Y form the fused ring systems:

[structure: tricyclic indole with HN and NH groups]

[structure: tetrahydroquinoline-type with HN], or

[structure: benzofuran-type with HN and O];

z is $$-\overset{O}{\underset{\|}{C}}NH-,\ -NH-,\ -\overset{O}{\underset{\|}{C}}-,\ -CH_2CH_2-,$$

$$-CH=CH-,\ -\overset{O}{\underset{\|}{C}}-\underset{\underset{CH_3}{|}}{N}-,\ -NH\overset{O}{\underset{\|}{C}}-,\ \text{or}$$

Z represents a bond;

A is

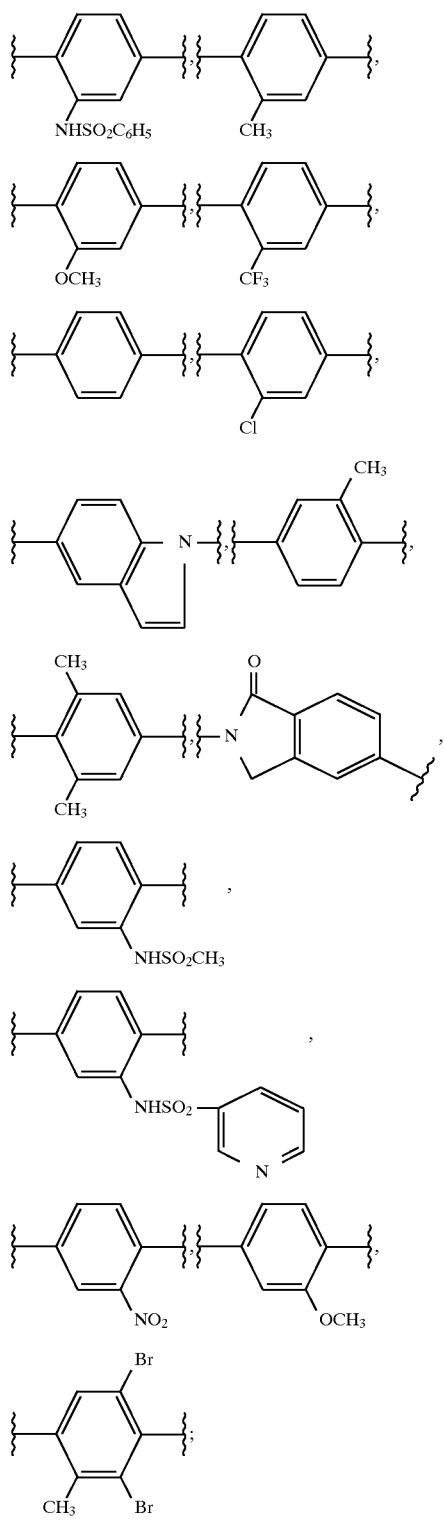

and
B is —OCH$_2$CO$_2$H, —OCH$_2$CO$_2$CH$_2$C(O)NHCH$_3$, —OCH$_2$CO$_2$CH$_2$C(O)N(CH$_2$CH$_3$)$_2$, —OCH$_2$CO$_2$CH$_2$CH$_3$, —CH$_2$CH$_2$CO$_2$H, —CH$_2$COOH, —OCH(CH$_3$)CO$_2$H, or —OCH(CH$_3$)CO$_2$CH$_2$CH$_3$.

2. A compound selected from the group consisting of
3-(4-(4-piperazin-1-ylphenylcarbonylamino)phenyl) propanoic acid,
2-(4-(4-Piperazinyl-1-yl)phenylcarbonylamino)phenoxy) acetic acid,
Ethyl 2-(4-(4-(1-piperazinyl)phenylcarbonylamino)phenoxy)acetate, hydrochloride,
2-(5-(4-(1-Piperazinyl)phenylcarbonylamino)indol-1-yl) acetic acid,
3-(3-(4-Piperazin-1-ylphenyl)carbonylamino)phenyl) propanoic acid,
Ethyl 2-(4-(4-(piperazin-1-yl)phenylcarbonylamino) phenoxy)propanoate
2-(4-(4-(Piperazin-1-yl)phenylcarbonylamino)phenoxy) propionic acid,
2-(4-(((2-Piperazin-1-yl)pyridin-5-yl)carbonylamino) phenoxy)acetic acid,
2-(4-(5-(4-(1,1-Dimethylethoxycarbonyl)-piperazin-1-yl)-2-thienylcarbonylamino)-3-methylphenoxy)-acetic acid,
4-((2,3,4,5-tetrahydropyrazino-[1,2-a]indole-8-yl) carbonylamino)-3-methylphenoxyacetic acid, and
or a pharmaceutically acceptable salt thereof.

3. A composition comprising a compound of claim 1 and a pharmaceutically acceptable carrier.

4. A method for inhibiting the binding of fibrinogen to blood platelets in a mammal, comprising treating the mammal in need thereof with a fibrinogen binding inhibitory amount of a composition of claim 3.

5. A method for inhibiting the aggregation of blood platelets in a mammal, by blocking fibrinogen from acting at its receptor site, comprising treating the mammal in need thereof with a fibrinogen binding inhibitory amount of a composition of claim 3.

6. A compound of claim 1, or a pharmaceutically acceptable salt thereof, wherein A is 7. A compound of claim 6 selected from the group consisting of:
3-Methyl-4-((1,2,3,4-tetrahydro-9H-pyrido[3,4-β]indol-7-yl)carbonylamino)phenoxyacetic acid,
4-(2-(1,1-dimethylethoxycarbonyl)-1,2,3,4-tetrahydro-9H-pyrido[3,4-β]benzofuran-7-yl)carbonylamino)-3-methylphenoxy acetic acid, and
(+/−) 4-((3-(1,1-Dimethylethoxycarbonyl)-1,1a,2,3,4,5-hexahydropyrazino-[1,2-α]indole-8-yl)carbonylamino)-3-methylphenoxyacetic acid,
or a pharmaceutically acceptable salt thereof.

8. A composition comprising a compound of claim 7 and a pharmaceutically acceptable carrier.

9. A method for inhibiting the binding of fibrinogen to blood platelets in a mammal, comprising treating the mammal in need thereof with a fibrinogen binding inhibitory amount of a composition of claim 8.

10. A method for inhibiting the aggregation of blood platelets in a mammal, by blocking fibrinogen from acting at its receptor site, comprising treating the mammal in need thereof with a fibrinogen binding inhibitory amount of a composition of claim 19.